US006514997B2

(12) United States Patent
Dragovich et al.

(10) Patent No.: US 6,514,997 B2
(45) Date of Patent: Feb. 4, 2003

(54) ANTIPICORNAVIRAL COMPOUNDS AND COMPOSITIONS, THEIR PHARMACEUTICAL USES, AND MATERIALS FOR THEIR SYNTHESIS

(75) Inventors: Peter S. Dragovich, Encinitas, CA (US); Thomas J. Prins, Cardiff, CA (US); Ru Zhou, Carlsbad, CA (US); Theodore O. Johnnson, Jr., San Diego, CA (US)

(73) Assignee: Agouron Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/726,376

(22) Filed: Dec. 1, 2000

(65) Prior Publication Data

US 2001/0047006 A1 Nov. 29, 2001

Related U.S. Application Data

(60) Provisional application No. 60/168,986, filed on Dec. 3, 1999, and provisional application No. 60/192,052, filed on Mar. 24, 2000.

(51) Int. Cl.$^7$ .................... A61K 31/44; C07D 401/12; C07D 413/14; C07D 471/04
(52) U.S. Cl. .................. 514/340; 514/300; 514/333; 514/299; 514/343; 546/113; 546/183; 546/256; 546/272.1; 546/278.4
(58) Field of Search ................. 546/113, 183, 546/256, 272.1, 278.4; 514/299, 300, 333, 340, 343

(56) References Cited

U.S. PATENT DOCUMENTS

| | | | | |
|---|---|---|---|---|
| 5,374,623 | A | 12/1994 | Zimmerman et al. | ......... 514/17 |
| 5,498,616 | A | 3/1996 | Mallamo et al. | ............ 514/300 |
| 5,856,530 | A | 1/1999 | Webber | ....................... 549/478 |
| 5,962,487 | A | 10/1999 | Webber et al. | ............... 514/378 |
| 6,020,371 | A | 2/2000 | Dragovich et al. | ......... 514/514 |
| 6,331,554 | B1 | 12/2001 | Dragovich et al. | ......... 514/357 |

FOREIGN PATENT DOCUMENTS

| | | |
|---|---|---|
| EP | 0 201844 | 11/1986 |
| EP | 0 632051 | 6/1994 |
| WO | WO 94/04172 | 3/1994 |
| WO | WO 95/15749 | 6/1995 |
| WO | WO 95/23222 | 8/1995 |
| WO | WO 95/31433 | 11/1995 |
| WO | WO 96/30395 | 10/1996 |
| WO | WO 97/19231 | 5/1997 |
| WO | WO 97/43305 | 11/1997 |
| WO | WO 97/49668 | 12/1997 |
| WO | WO 98/43950 | 10/1998 |
| WO | WO 99/31122 | 6/1999 |
| WO | WO 99/57135 | 11/1999 |
| WO | WO 00/78708 | 12/2000 |
| WO | WO 01/10894 | 2/2001 |
| WO | WO 01/14329 | 3/2001 |
| WO | WO 01/14576 | 3/2001 |

OTHER PUBLICATIONS

Dragovich, et al., "Structure–Based Design, Synthesis, and Biological Evaluation of Irreversible Human Rhinovirus 3C Protease Inhibitors. 3. Structure–Activity Studies of Ketomethylene–Containing Peptidomimetics", *J. Med. Chem.* (1999) vol. 42, No. 7, pp. 1203–1212, 1213–1224.

Dragovich, et al., "Solid–phase Synthesis of Irreversible Human Rhinovirus 3C Protease Inhibitors. Part 1: Optimization of Tripeptides Incorporating N–terminal Amides", *Bioorg. & Med. Chem.* (1999) (7), pp. 589–598.

Bowden et al., "Organophosphorus Chemistry. Part XIV. Reaction of Phosphorodiamidous Chlorides with Sulphonamides: a New Route to Diazadiphosphetidines", *J. Chem. Soc. Perkin Transactions I Organic and Bio–organic Chemistry* (1973) 516–520.

Dragovich, et al., "Structure–Based Design, Synthesis, and Biological Evaluation of Irreversible Human Rhinovirus 3C Protease Inhibitors. 1. Michael Acceptor Structure–Activity Studies", *J. Med. Chem.* (1998) vol. 41, No. 15, pp. 2806–2818.

(List continued on next page.)

*Primary Examiner*—Bernard Dentz
(74) *Attorney, Agent, or Firm*—Karl Neidert; Bryan Zielinski; Peter Richardson

(57) ABSTRACT

Compounds of the formula:

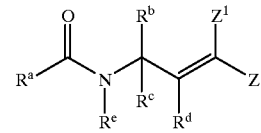

where the formula variables are as defined herein, are disclosed that advantageously inhibit or block the biological activity of the picornaviral 3C protease. Also disclosed are compounds of the formula:

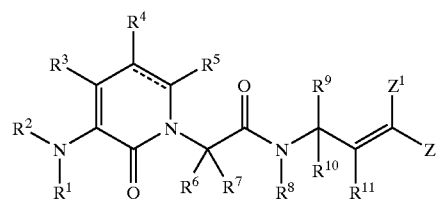

where the formula variables are as defined herein that advantageously inhibit or block the biological activity of the picornaviral 3C protease. These compounds, as well as pharmaceutical compositions containing these compounds, are useful for treating patients or hosts infected with one or more picornaviruses, such as rhinovirus 3C proteases. Intermediates and synthetic methods for preparing such compounds are also described.

28 Claims, No Drawings

OTHER PUBLICATIONS

Hartke, et al., "α,β–ungesattigte Thion– und Dithioester durch Kondensationsreaktionen", *Leibigs Ann. Chem.* (1989), pp. 321–330.

DeJohn, et al., "Functionalization of Substituted 2(1*H*)– and 4(1*H*)–Pyridones. III. The Preparation of Substituted 6–Vinyl–1,2–dihydro–2–oxo– and 1,4–Dihydro–4–oxo–3–pyridinecarboxylic Acids through the Chemistry of Pyridone Dianions", *J. Heterocyclic Chem.* (1983) vol. 20, No. 5, pp. 1295–1302.

Fasseur et al., "Studies on Pyrrolidones, Synthesis and *N*–Alkylation of β–Enaminoesters Derived from Pyroglutamic Acid", *J. Heterocyclic Chem.* (1992) vol. 29, No. 5, pp. 1285–1291.

Straub, et al., "Synthesis of the Angiotensin Converting enzyme Inhibitor (–)–A58365A via an Isomunchnone cycloaddition Reaction", *Org. Lett.* (1999) vol. 1, No. 1, pp. 83–85.

Fang et al., "Total Synthesis of the Angiotensin–Converting Enzyme Inhibitor A58365A: On the Use of Pyroglutamate as a Chiral Educt", *Tetrahedron Lett.* (1989) vol. 30, No. 28, pp. 3621–3624.

Crossley et al., "Convenient Route to γ–nitro–α–amino acids: conjugate addition of nitroalkanes to dehydroalanine derivatives", *J. Chem. Soc. Perkin Trans. I* (1998) No. 6, pp. 1113–1121.

Bellus, "Incorporation of Sulfur Dioxide into the Products of Reaction of *Schiff* Bases with Halo– or Alkylthio–ketones in Liquid $SO_2$", *Helvetica Chimica Acta* (1975) vol. 58, No. 271, pp. 2509–2511.

Hartke, "A Simple Route to 2–Alkenethiole *O*–Esters and 2–Alkenedithioic Esters", [Thiono– and Dithioesters, 37], *Synthesis* (1985) pp. 960–961.

Baldwin,, "Diarylmethylene–Tetracyanoethylene Cycloadditions", *J.Org.Chem.* (1971) vol. 36, No. 10, pp. 1441–1443.

Weislow, et al., "New Soluble–Formazan Assay for HIV–1 Cytopathic Effects: Application to High–Flux Screening of Synthetic and Natural Products for AIDS–Antiviral Activity", *J. Natl. Cancer* (1989) vol. 81, No. 8,pp. 577–586.

Diana et al., "Picornavirus Inhibitors: Trifluoromethyl Substitutions Provides a Global Protective Effect against Hepatic Metabolism", *J. Med. Chem.* (1995), vol. 38, pp. 1355–1371.

Dragovich et al. "Structure–Based Design of Irreversible, Tripeptidyl Human Rhinovirus 3C Protease Inhibitors Containing N–Methyl Amino Acids", Bioorg. & Med. Chem. Let. (1999), vol. 9, No. 15, pp. 2189–2194.

Van der Bent et al., "Synthesis and Biological Evaluation of Lorglumide–Like Hybrid Cholecystokinin–A Receptor Antagonists", *Drug Dev. Res.* (1994), vol. 31, No. 3, pp. 197–205.

Ikuta et al., "Synthesis and Anti–inflamatory Activities of 3–(3,5–Di–text–butyl–4–hydroxybenzylidene) pyrolidin–2–ones", *J. Med. Chem.* (1987), vol. 30, pp. 1995–1998.

Palmer et al., "Vinyl Sulfones as Mechanism–Based Cysteine Protease Inhibitors", *J. Med. Chem.* (1995), vol. 38, pp. 3193–3196.

Dragovich, et al., "*Structure–Based Design, Synthesis, and Biological Evaluation of Irreversible Human Rhinovirus 3C Protease Inhibitors. 2. Peptide Structure–Activity Studies*", *Med Chem.* (1998) vol. 41, No. 15, pp. 2819–2834.

Kruse, et al., "*New Methods for the Synthesis of 2–ArylPyrroles*", *Heterocycles* (1987) vol. 26, No. 12, pp. 3141–3151.

Bailey, et al., "*Ethyl Pyrrole–2–Carboxylate*", *Org. Synth.* (1971) vol. 51, 100–102.

Gonzalez–Muniz et al., "*Synthesis of 2–Substituted 8–Amino–3–oxoindolizoline–2–carboxylic Acid Derivatives as Peptide Conformation Mimetics*". *Tetrahedron* (1992) vol. 48, No. 24, pp. 5191–5198.

Garcia–Lopez, et al., "*A Simple and Versatile Route to Ketompethylene Dipeptide Analogs*". *Tetrahedron* (1988) vol. 29, No. 13, pp. 1577–1580.

Garcia–Lopez, et al., "*Synthesis of Ketomethylene Dipeptides Containing Basic Amino Acid Analogues at C–Terminus*", *Tetrahedron* (1988) vol. 44, No. 16, 5131–5138.

Charlton, et al., "*Asymmetric synthesis of lignans using oxazolidinones as chiral auxiliaries*", *NRC–CNRC Canadian Journal of Chemistry* (1997), vol. 75, No. 8, pp. 1076–1083.

Silverstein, et al., "*2–Pyrrolealdehyde*", *Org. Synth.* (1963) Coll. vol. IV, 831–833.

Sunberg, et al., "*3–(3–Pyrrolyl) thiopyrrolidones as Precursors of Benzo [1,2–b:4,3–b']dipyrroles. Synthesis of Structures Related to the Phosphodiesterase Inhibitors PDE–I and PDE–II*", *J. Org. Chem.* (1985) vol. 50, No. 4, pp. 425–432.

Wipf et al., "$S_N2$'–Reactions of Peptide Aziridenes. A Cuprate–Based Approach to (E)–Alkene Isosters", *J. Org. Chem.* 1994, vol. 59, No. 17, pp. 4875–4886.

Ming Tao et al., "Inhibition of Calpain by Peptidyl Heterocycles", Bioorg. & Med. Chem. Lett. 1996, vol. 6, No. 24, pp. 3009–3012.

Moss et al., "Peptidomimetic Inhibitors of Herpes Simplex Virus Ribonucleotide Reductase with Improved Vivo Antiviral Activity", J. Med. Chem. 1996, vol. 39, No. 21, pp. 4173–4180.

Jackson et al., Preparation of Enantiomerically Pure Protected 4–Oxo–α–amino Acids and 3–Aryl–α–amino Acids from Serine, *J. Org. Chem.* (1992), vol. 57, No. 12 pp. 3397–3404.

Askin et al., "Highly Diastereoselective Alkylations of Chiral Amide Enolates: New Routes to Hydroxyethylene Dipeptide Isostere Inhibitors of HIV–1 Protease", *J. Org. Chem.*, 57, 2771–2773 (1992).

Bradbury et al., "1,2,4–Triazolo[4,3–a]pyrazine Derivatives with Human Renin Inhibitory Activity. 2. Synthesis, Biological Properties and Molecular Modeling of Hydroxyethylene Isotere Derivatives", *J. Med. Chem.*, 33, 2335–2342 (1990).

Liu et al., "Structure–Activity Relationships for Inhibition of Papain by Peptide Michael Acceptors", J. Med. Chem., 35, 1067–1075 (1992).

Veale et al., "Nonpeptidic Inhibitors of Human Leukocyte Elastase. 5. Design, Synthesis, and X–ray Crystallography of a Series of Orally Active 5–Amino Pyrimidin–6–one Containing Trifluoromethyl Ketones", J. Med. Chem. (1995), vol. 38, pp. 98–108.

Birch et al., "Purification of Recombinant Human Rhinovirus 14 3C Protease Expressed in Escherichia coli", Protein Expression and Purification, vol. 6 (1995) pp. 609–618.

Kaldor et al., "Glutamine–Derived Aldehydes for the Inhibition of Human Rhinovirus 3C Protease", Bioorganic & Medicinal Chemistry Letters, vol. 5, No. 17 (1995) pp. 2021–2026.

Murray et al., "The enantiospecific synthesis of novel lysine analogues incorporating a pyrrolidine containing side chain", Tetrahedron Letters, vol. 39 (1998) pp. 6721–6724.

Webber et al., "Design, Synthesis, and Evaluation of Non-peptidic Inhibitors of Human Rhinovirus 3C Protease", J. Med. Chem. (1996) vol. 39, No. 26, pp. 5072–5082.

Kong et al., "Synthesis and Evaluation of Peptidyl Michael Acceptors That Inactivate Human Rhinovirus 3C Protease and Inhibit Virus Replication", J. Med. Chem. (1998) vol. 41, No. 14, pp. 2579–2587.

Webber et al., "Tripeptide Aldehyde Inhibitors of Human Rhinovirus 3C Protease: Design, Synthesis, Biological Evaluation, and Cocrystal Structure Solution of $P_1$ Glutamine Isosteric Replacements", J. Med. Chem. (1998) vol. 41, No. 15, pp. 2786–2805.

Bradbury et al., "An Efficient Synthesis of the γ–Lactone Corresponding to a Hydroxylethylene Dipeptide Isostere Using Stereoselective Bromolactonisation of a Chiral Acyloxazolidinone", Tetrahedron Letters (1989) vol. 30, No. 29, pp. 3845–3848.

Chida et al., "Total Synthesis and Absolute Configuration of Bengamide A", J. Chem. Soc., Chem. Commun. (1992) pp. 1064–1066.

Dondoni et al., "Thiazole–Based Stereoselective Routes to Leucine and Phenylalanine Hydroxyethylene Dipeptide Isostere Inhibitors of Renin and HIV–1 Aspartic Protease", J. Org. Chem. (1995) vol. 60, No. 24, pp. 7927–7933.

Herold et al., "A Versatile and Stereocontrolled Synthesis of Hydroxyethylene Dipeptide Isosteres", J. Org. Chem. (1989) vol. 54, No. 5, pp. 1178–1185.

Hanzlik et al., "Structure–Activity Relationships for Inhibition of Papain by Peptide Michael Acceptors", J. Med. Chem. (1992) vol. 35, No. 6, pp. 1067–1075.

Luly et al., "A Synthesis of Protected Aminoalkyl Epoxides from α–Amino Acids", J. Org. Chem. (1987) vol. 52, No. 8, pp. 1487–1492.

McWilliams et al., "Tandem Asymmetric Transformations: An Asymmetric 1,2–Migration from a Higher Order Zincate Coupled with a Stereoselective Homoaldol Reaction", J. Am. Chem. Soc. (1996) vol. 118, No. 47, pp. 11970–11971.

Hoffman et al., "A Simple, Stereoselective Synthesis of Ketomethylene Dipeptide Isosteres", Tetrahedron (1997) 53, pp. 7119–7126.

Jones et al., "A Short Stereocontrolled Synthesis of Hydroxyethylene Dipeptide Isosteres", J. Org. Chem. (1993) vol. 58, No. 8, pp. 2286–2290.

Pegorier et al., "A General Stereocontrolled Synthesis of Hydroxyethylene Dipeptide Isosteres", Tetrahedron Letters (1995) vol. 36, No. 16, pp. 2753–2756.

Wuts et al., "Synthesis of the Hydroxyethylene Isostere of Leu–Val", J. Org. Chem. (1992) vol. 57, No. 25, pp. 6696–6700.

Hanzlik et al., "Vinylogous Amino Acid Esters: A New Class of Inactivators for Thiol Proteases", J. Med. Chem. (1984), vol. 27, No. 6, pp. 711–712.

Venkatraman et al., "Synthesis of Potential Inhibitors for Human Rhinovirus 3C Protease", The Second Winter Conference on Medicinal and Bioorganic Chemistry, Steamboat Springs, CO, Jan. 26–31, 1997.

ANTIPICORNAVIRAL COMPOUNDS AND COMPOSITIONS, THEIR PHARMACEUTICAL USES, AND MATERIALS FOR THEIR SYNTHESIS

This application claims benefit of U.S. Provisional Patent Application No. 60/168,986, filed Dec. 3, 1999 and U.S. Provisional Patent Application No. 60/192,052, filed Mar. 24, 2000, the disclosures of which are incorporated herein by reference.

BACKGROUND OF THE INVENTION

1. Field of the Invention

The invention relates to pyridone-containing peptidomimetic compounds that advantageously inhibit the enzymatic activity of picornaviral 3C proteases, especially rhinovirus 3C proteases (RVPs), and that retard viral growth in cell culture. The invention also relates to the use of these compounds in pharmaceutical compositions, methods of treatment of rhinoviral infections using these compounds and compositions, and processes for the synthesis of these compounds and compounds useful in the syntheses thereof.

2. Related Background Art

The picornaviruses are a family of tiny non-enveloped positive-stranded RNA-containing viruses that infect humans and other animals. These viruses include the human rhinoviruses, human polioviruses, human coxsackieviruses, human echoviruses, human and bovine enteroviruses, encephalomyocarditis viruses, meningitis virus, foot and mouth viruses, hepatitis A virus, and others. The human rhinoviruses are a major cause of the common cold. To date, there are no effective therapies on the market that cure the common cold, only treatments that relieve the symptoms.

Picornaviral infections may be treated by inhibiting the proteolytic picornaviral 3C enzymes. These enzymes are required for the natural maturation of the picornaviruses. They are responsible for the autocatalytic cleavage of the genomic, large polyprotein into the essential viral proteins. Members of the 3C protease family are cysteine proteases, where the sulfhydryl group most often cleaves the glutamine-glycine amide bond. Inhibition of 3C proteases is believed to block proteolytic cleavage of the viral polyprotein, which in turn can retard the maturation and replication of the viruses by interfering with viral particle production. Therefore, inhibiting the processing of this cysteine protease with selective small molecules that are specifically recognized should represent an important and useful approach to treat and cure viral infections of this nature and, in particular, the common cold.

Some small-molecule inhibitors of the enzymatic activity of picornaviral 3C proteases (i.e., antipicornaviral compounds) have been recently discovered. See, for example: U.S. Pat. No. 5,856,530; U.S Pat. No. 5,962,487; U.S. patent application Ser. No. 08/991,282, filed Dec. 16, 1997, by Dragovich et al.; and U.S. patent application Ser. No. 09/301,977, filed Apr. 29, 1999, by Dragovich et al. See also: Dragovich et al., "Structure-Based Design, Synthesis, and Biological Evaluation of Irreversible Human Rhinovirus 3C Protease Inhibitors . . . ," *J. Med. Chem.* (1999), Vol. 42, No. 7, 1203–1212, 1213–1224; and Dragovich et al., "Solid-phase Synthesis of Irreversible Human Rhinovirus 3C Protease Inhibitors . . . ," *Bioorg. & Med. Chem.* (1999), Vol. 7, 589–598. There is still a desire, however, to discover small-molecule compounds that are especially potent antipicornaviral agents.

Inhibitors of other related cysteine proteases such as cathepsins have been described in, e.g., U.S. Pat. No. 5,374,623; U.S. Pat. No. 5,498,616; and WIPO International Publication Nos. WO 94/04172, WO 95/15749, WO 97/19231, and WO 97/49668. There yet remains a need for inhibitors targeting the picornaviral 3C cysteine protease with desirable pharmaceutical properties, such as high specificity.

SUMMARY OF THE INVENTION

This invention relates to compounds useful for inhibiting the activity of picornaviral 3C proteases having the general formula:

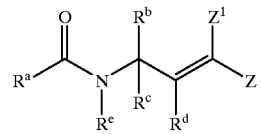

wherein:

$R^a$ is substituted or unsubstituted heterocycloalkyl or heterocycloalkylalkyl;

$R^b$ is a substituent having the formula:

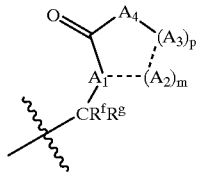

wherein:

$R^f$ and $R^g$ are independently H or lower alkyl;

m is 0 or 1;

p is an integer of from 0 to 5;

$A_1$ is CH or N;

$A_2$ is $C(R^h)(R^i)$, $N(R^j)$, S, S(O), $S(O)_2$, or O; where each $R^h$, $R^i$, and $R^j$ is independently H or lower alkyl;

each $A_3$ present is independently $C(R^h)(R^i)$, $N(R^j)$, S, S(O), $S(O)_2$, or O; where each $R^h$, $R^i$, and $R^j$ is independently H or lower alkyl;

when p is 1, 2, 3, 4, or 5, $A_4$ is $N(R^k)$, $C(R^h)(R^i)$, or O; and when p is 0 (i.e., $A_3$ is not present), $A_4$ is $N(R^k)(R^l)$, $C(R^h)(R^i)(R^j)$, and $O(R^l)$, where each $R^h$, $R^i$, and $R^j$ is independently H or lower alkyl, each $R^k$ is H, alkyl, aryl, or acyl, and each $R^l$ is H, alkyl, or aryl;

provided that no more than two heteroatoms occur consecutively in the above-depicted ring formed by $A_1$, $(A_2)_m$, $(A_3)_p$, $A_4$, and C=O, where each dotted line in the ring depicts a single bond when $A_2$ is present (i.e., m=1) and a hydrogen atom when $A_2$ is absent (i.e., m=0);

$R^c$ is H, halogen or a substituted or unsubstituted lower alkyl group;

$R^d$ is H, halogen, hydroxyl, a substituted or unsubstituted alkyl, alkoxy or alkylthio group;

$R^e$ is H or a substituted or unsubstituted alkylgroup; and

Z and $Z^1$ are independently H, F, a unsubstituted or substituted alkyl group, cycloalkyl group, heterocycloalkyl group, aryl group or heteroaryl group, —C(O)$R^n$, —CO$_2R^n$, —CN, —C(O)NR"$R^o$, —C(O)NR"OR$^o$, —C(S)$R^n$, —C(S) OR$^n$, —C(S)NR"$R^o$, —NO$_2$, —SOR$^o$, —SO$_2R^n$, —SO$_2$NR"$R^o$, —SO$_2$(NR")(OR$^o$), —SONR", —SO$_3R^n$, —PO(OR")$_2$, —PO(OR")(OR$^o$), —PO(NR"R$^o$)(OR$^p$), —PO(NR"R$^o$)(NR$^pR^q$), —C(O)NR"NR$^oR^p$, or —C(S) NR"NR$^oR^p$, wherein R", R$^o$, R$^p$, and R$^q$ are independently H, a substituted or unsubstituted alkyl group, cycloalkyl group, aryl group, heterocycloalkyl group, acyl group or thioacyl group, or wherein any two of the $R^n$, $R^o$, $R^p$, and $R^q$, taken together with the atoms to which they are bonded, form a heterocycloalkyl group, which may be optionally substituted, or Z and $R^d$, together with the atoms to which they are bonded, form a cycloalkyl or heterocycloalkyl group, where Z and $R^d$ are as defined above except for moieties that cannot form the cycloalkyl or heterocycloalkyl group, or Z and $Z^1$, together with the atom to which they are bonded, form a cycloalkyl or heterocycloalkyl group, where Z and $Z^1$ are as defined above except for moieties that cannot form the cycloalkyl or heterocycloalkyl group.

Preferably, when $R^a$ is substituted or unsubstituted heterocycloalkylalkyl, the alkyl moiety thereof is a substituted or unsubstituted saturated alkyl moiety.

Specifically, this invention relates to compounds useful for inhibiting the activity of picornaviral 3C proteases having the general Formula I:

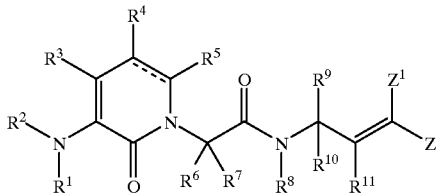

wherein:

$R^1$ is H, a substituted or unsubstituted lower alkyl group or a suitable nitrogen protecting group;

$R^2$ is an alkylcarbonyl group, an arylcarbonyl group, a cycloalkylcarbonyl group, a heterocycloalkylcarbonyl group, a heteroarylcarbonyl group, or an alkyloxycarbonyl group, wherein each of the alkyl, aryl, cycloalkyl, heterocycloalkyl or heteroaryl moieties in the above groups may be substituted or unsubstituted, or a suitable nitrogen protecting group;

$R^3$ is H or a suitable substituent; or $R^1$ together with $R^2$ form a suitable nitrogen protecting group; or $R^2$ together with $R^3$ form a heterocycloalkyl ring or heteroaryl ring, which may be optionally substituted;

$R^4$ is H or a suitable substituent;

the dotted line represents an optional bond;

$R^5$ is H or a suitable substituent;

$R^6$ is H or a substituted or unsubstituted alkyl group; or $R^5$ together with $R^6$ form a heterocycloalkyl ring, which may be optionally substituted;

$R^7$ and $R^{10}$ are independently H, halogen or a substituted or unsubstituted lower alkyl group;

$R^8$ is H or a substituted or unsubstituted lower alkyl group;

$R^{11}$ is H, halogen, hydroxyl, a substituted or unsubstituted alkyl, alkoxy or alkylthio group;

$R^9$ is a substituent having the formula:

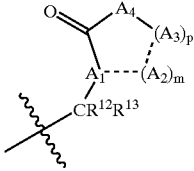

wherein:

$R^{12}$ and $R^{13}$ are independently H or lower alkyl;

m is 0 or 1;

p is an integer of from 0 to 5;

$A_1$ is CH or N;

$A_2$ is $C(R^{14})(R^{15})$, $N(R^{16})$ S, S(O), $S(O)_2$, or O; where each $R^{14}$, $R^{15}$, and $R^{16}$ is independently H or lower alkyl;

each $A_3$ present is independently $C(R^{14})(R^{15})$, $N(R^{16})$, S, S(O), $S(O)_2$, or O; where each $R^{14}$, $R^{15}$, and $R^{16}$ is independently H or lower alkyl;

when p is 1, 2, 3, 4, or 5, $A_4$ is $N(R^{17})$, $C(R^{14})(R^{15})$, or O; and when p is 0 (i.e., $A_3$ is not present), $A_4$ is $N(R^{17})(R^{18})$, $C(R^{14})(R^{15})(R^{16})$, and $O(R^{18})$, where each $R^{14}$, $R^{15}$, and $R^{16}$ is independently H or lower alkyl, each $R^{17}$ is H, alkyl, aryl, or acyl, and each $R^{18}$ is H, alkyl, or aryl;

provided that no more than two heteroatoms occur consecutively in the above-depicted ring formed by $A_1$, $(A_2)_m$, $(A_3)_p$, $A_4$, and C=O, where each dotted line in the ring depicts a single bond when $A_2$ is present (i.e., m=1) and a hydrogen atom when $A_2$ is absent (i.e., m=0); and Z and $Z^1$ are independently H, F, a unsubstituted or substituted alkyl group, cycloalkyl group, heterocycloalkyl group, aryl group or heteroaryl group, $-C(O)R^{19}$, $-CO_2R^{19}$, $-CN$, $-C(O)NR^{19}R^{20}$, $-C(O)NR^{19}OR^{20}$, $-C(S)R^{19}$, $-C(S)OR^{19}$, $-C(S)NR^{19}R^{20}$, $-NO_2$, $-SOR^{20}$, $-SO_2R^{19}$, $-SO_2NR^{19}R^{20}$, $-SO_2(NR^{19})(OR^{20})$, $-SONR^{19}$, $-SO_3R^{19}$, $-PO(OR^{19})_2$, $-PO(OR^{19})(OR^{20})$, $-PO(NR^{19}R^{20})(OR^{21})$, $-PO(NR^{19}R^{20})(NR^{21}R^{22})$, $-C(O)NR^{19}NR^{20}R^{21}$, or $-C(S)NR^{19}NR^{20}R^{21}$, wherein $R^{19}$, $R^{20}$, $R^{21}$, and $R^{22}$ are independently H, a substituted or unsubstituted alkyl group, cycloalkyl group, aryl group, heterocycloalkyl group, acyl group or thioacyl group, or wherein any two of the $R^{19}$, $R^{20}$, $R^{21}$, and $R^{22}$, taken together with the atoms to which they are bonded, form a heterocycloalkyl group, which may be optionally substituted, or Z and $R^{11}$, together with the atoms to which they are bonded, form a cycloalkyl or heterocycloalkyl group, where Z and $R^{11}$ are as defined above except for moieties that cannot form the cycloalkyl or heterocycloalkyl group, or Z and $Z^1$, together with the atom to which they are bonded, form a cycloalkyl or heterocycloalkyl group, where Z and $Z^1$ are as defined above except for moieties that cannot form the cycloalkyl or heterocycloalkyl group.

In another embodiment of the compounds of the above formulae, Z and $Z^1$ are independently H, F, a unsubstituted or substituted alkyl group, cycloalkyl group, heterocycloalkyl group, aryl group or heteroaryl group, $-C(O)R^{19}$, $-CO_2R^{19}$, $-CN$, $-C(O)NR^{19}R^{20}$, $-C(O)NR^{19}OR^{20}$, $-C(S)R^{19}$, $-C(S)NR^{19}R^{20}$, $-NO_2$, $-SOR^{20}$, $-SO_2R^{19}$, $-SO_2NR^{19}R^{20}$, $-SO_2(NR^{19})(OR^{20})$, $-SONR^{19}$, $-SO_3R^{19}$, $-PO(OR^{19})_2$, $-PO(OR^{19})(OR^{20})$ $-PO(NR^{19}R^{20})(OR^{21})$, $-PO(NR^{19}R^{20})(NR^{21}R^{22})$, $-C(O)NR^{19}NR^{20}R^{21}$, or $-C(S)NR^{19}NR^{20}R^{21}$, wherein $R^{19}$, $R^{20}$, $R^{21}$, and $R^{22}$ are independently H, a substituted or unsubstituted alkyl group, cycloalkyl group, aryl group, heterocycloalkyl group, acyl group or thioacyl group, or wherein any two of the $R^{19}$, $R^{20}$, $R^{21}$, and $R^{22}$, taken together with the atoms to which they are bonded, form a heterocycloalkyl group, which may be optionally substituted, or Z and $Z^1$, together with the atom to which they are bonded, form a cycloalkyl or heterocycloalkyl group.

In yet another embodiment of the compounds of the above formulae, Z and $Z^1$ are independently H, F, a unsubstituted or substituted alkyl group, cycloalkyl group, heterocycloalkyl group, aryl group or heteroaryl group, $-C(O)R^{19}$, $-CO_2R^{19}$, $-CN$, $-C(O)NR^{19}R^{20}$, $-C(O)NR^{19}OR^{20}$, $-C(S)R^{19}$, $-C(S)NR^{19}R^{20}$, $-NO_2$, $-SOR^{20}$, $-SO_2R^{19}$, $-SO_2NR^{19}R^{20}$, $-SO_2(NR^{19})(OR^{20})$, $-SONR^{19}$, $-SO_3R^{19}$, $-PO(OR^{19})_2$, $-PO(OR^{19})(OR^{20})$, $-PO(NR^{19}R^{20})(OR^{21})$, $-PO(NR^{19}R^{20})(NR^{21}R^{22})$, $-C(O)NR^{19}NR^{20}R^{21}$, or $-C(S)NR^{19}NR^{20}R^{21}$, wherein $R^{19}$, $R^{20}$, $R^{21}$, and $R^{22}$ are independently H, a substituted or unsubstituted alkyl group, cycloalkyl group, aryl group, heterocycloalkyl group, acyl group or thioacyl group, or wherein any two of the $R^{19}$, $R^{20}$, $R^{21}$, and $R^{22}$, taken together with the atoms to which they are bonded, form a heterocycloalkyl group, which may be optionally substituted.

In addition to compounds of the above formulae, antipicornaviral agents of the invention include prodrugs, pharmaceutically active metabolites, and pharmaceutically acceptable salts and solvates of such compounds.

DETAILED DESCRIPTION OF INVENTION AND PREFERRED EMBODIMENTS

In one embodiment, the compounds of this invention useful for inhibiting the activity of picornaviral 3C proteases have the Formula I-A:

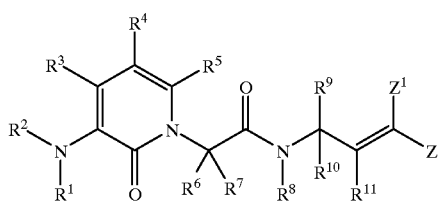

I-A wherein $R^1$, $R^2$, $R^3$, $R^4$, $R^5$, $R^6$, $R^7$, $R^8$, $R^9$, $R^{10}$, $R^{11}$, Z, and $Z^1$, and the variables contained therein, are as defined above, or a prodrug, pharmaceutically acceptable salt, pharmaceutically active metabolite, or pharmaceutically acceptable solvate thereof.

Preferably, in the compounds of Formula I-A:

$R^1$, $R^7$, $R^8$, $R^{10}$, and $R^{11}$ are independently H or a substituted or unsubstituted lower alkyl group;

$R^2$ is an alkylcarbonyl group, an arylcarbonyl group, a cycloalkylcarbonyl group, a heterocycloalkylcarbonyl group, a heteroarylcarbonyl group, an aryloxycarbonyl group or an alkyloxycarbonyl group, wherein each of the alkyl, aryl, cycloalkyl, heterocycloalkyl or heteroaryl moieties of the above groups may be substituted or unsubstituted;

$R^3$ is H or a suitable substituent; or $R^2$ together with $R^3$ form a heterocycloalkyl ring or heteroaryl ring, which may be optionally substituted;

$R^4$ is H or a suitable substituent;

$R^5$ is H or a suitable substituent;

$R^6$ is H or an unsubstituted alkyl group or a lower alkyl group optionally substituted with a cycloalkyl group, a heterocycloalkyl group, an aryl group, a heteroaryl group, an alkoxyl group, an aryloxy group, an alkylthio group, an arylthio group, wherein each alkyl, cycloalkyl, aryl, heterocycloalkyl or heteroaryl moiety thereof may be optionally substituted; or $R^5$ together with $R^6$ form a substituted or unsubstituted five- or six-membered heterocycloalkyl ring;

wherein when $R^3$, $R^4$, and $R^5$ are suitable substituents, said suitable substituents may be independently selected from alkyl, aryl, cycloalkyl, heterocycloalkyl, heteroaryl, nitro, amino, cyano, halogen, haloalkyl (trifluoromethyl), hydroxyl, alkoxy, alkylenedioxy, aryloxy, cycloalkoxy, heterocycloalkoxy, heteroaryloxy, alkylcarbonyl, alkyloxycarbonyl, alkylcarbonyloxy, arylcarbonyl, arylcarbonyloxy, aryloxycarbonyl, cycloalkylcarbonyl, cycloalkylcarbonyloxy, cycloalkyoxycarbonyl, heteroarylcarbonyl, heteroarylcarbonyloxy, heteroaryloxycarbonyl, heterocycloalkylcarbonyl, heterocycloalkylcarbonyloxy, heterocycloalkyloxycarbonyl, carboxyl, carbamoyl, formyl, keto (oxo), thioketo, sulfo, alkylamino, cycloalkylamino, arylamino, heterocycloalkylamino, heteroarylamino, dialkylamino, alkylaminocarbonyl, cycloalkylaminocarbonyl, arylaminocarbonyl, heterocycloalkylaminocarbonyl, heteroarylaminocarbonyl, dialkylaminocarbonyl, alkylaminothiocarbonyl, cycloalkylaminothiocarbonyl, arylaminothiocarbonyl, heterocycloalkylaminothiocarbonyl, heteroarylaminothiocarbonyl, dialkylaminothiocarbonyl, alkylsulfonyl, arylsulfonyl, alkylsulfenyl, arylsulfenyl, alkylcarbonylamino, cycloalkylcarbonylamino, arylcarbonylamino, heterocycloalkylcarbonylamino, heteroarylcarbonylamino, alkylthiocarbonylamino, cycloalkylthiocarbonylamino, arylthiocarbonylamino, heterocycloalkylthiocarbonylamino, heteroarylthiocarbonylamino, alkylsulfonyloxy, arylsulfonyloxy, alkylsulfonylamino, arylsulfonylamino, mercapto, alkylthio, arylthio, and heteroarylthio, wherein any of the alkyl, aryl, cycloalkyl, heterocycloalkyl, heteroaryl moieties present in the above substituents may be further substituted with one or more suitable substituents, preferably selected from nitro, amino, cyano, halogen, haloalkyl, hydroxyl, keto, and unsubstituted alkyl, aryl, cycloalkyl, heterocycloalkyl, heteroaryl, alkoxy, or aryloxy;

$R^9$ is an aminocarbonylalkyl group, an alkylcarbonylaminoalkyl group, an alkylaminocarbonylalkyl group or a substituent having the formula:

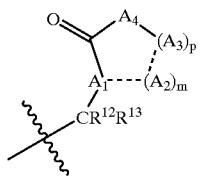

wherein:
$R^{12}$ and $R^{13}$ are independently H or lower alkyl;
m is 1;
p is 1 or 2;
$A_1$ is CH or N;
$A_2$ is $C(R^{14})(R^{15})$, $N(R^{16})$, S, (O), $S(O)_2$, or O;
each $A_3$ present is independently $C(R^{14})(R^{15})$, $N(R^{16})$, S, S(O), $S(O)_2$, or O;
$A_4$ is $N(R^{17})$, $C(R^{14})(R^{15})$, or O;
wherein each $R^{14}$, $R^{15}$, and $R^{16}$ is independently H or lower alkyl, and each $R^{17}$ is H, alkyl, aryl, or acyl;
provided that no more than two heteroatoms occur consecutively in the above-depicted ring formed by $A_1$, $(A_2)_m$, $(A_3)_p$, $A_4$, and C=O, where each dotted line in the ring depicts a single bond; and
Z and $Z^1$ are independently H, F, a unsubstituted or substituted alkyl group, cycloalkyl group, heterocycloalkyl group, aryl group or heteroaryl group, —C(O)R$^{19}$, —CO$_2$R$^{19}$, —CN, —C(O)NR$^{19}$R$^{20}$, —C(O)NR$^{19}$OR$^{20}$, —C(S)R$^{19}$, —C(S)NR$^{19}$R$^{20}$, —NO$_2$, —SOR$^{20}$, —SO$_2$R$^{19}$, —SO$_2$NR$^{19}$R$^{20}$, —SO$_2$(NR$^{19}$)(OR$^{20}$), —SONR$^{19}$, —SO$_3$R$^{19}$, —PO(OR$^{19}$)$_2$, —PO(OR$^{19}$)(OR$^{20}$), —PO(NR$^{19}$R$^{20}$)(OR$^{21}$), —PO(NR$^{19}$R$^{20}$)(NR$^{21}$R$^{22}$), —C(O)NR$^{19}$NR$^{20}$R$^{21}$, or —C(S)NR$^{19}$NR$^{20}$R$^{21}$, wherein R$^{19}$, R$^{20}$, R$^{21}$, and R$^{22}$ are independently H, a substituted or unsubstituted alkyl group, cycloalkyl group, aryl group, heterocycloalkyl group, acyl group or thioacyl group, or wherein any two of the R$^{19}$, R$^{20}$, R$^{21}$, and R$^{22}$, taken together with the atoms to which they are bonded, form a heterocycloalkyl group, which may be optionally substituted, or Z and Z$^1$, together with the atom to which they are bonded, form a cycloalkyl or heterocycloalkyl group, where Z and Z$^1$ are as defined above except for moieties that cannot form the cycloalkyl or heterocycloalkyl group.

Preferably, R$^3$, R$^4$ and R$^5$ may be independently selected from H, alkyl, aryl, cycloalkyl, heterocycloalkyl, heteroaryl, amino, cyano, halogen, haloalkyl (trifluoromethyl), hydroxyl, keto, alkoxy, aryloxy, cycloalkoxy, heterocycloalkoxy, alkyloxycarbonyl, aryloxycarbonyl, cycloalkyoxycarbonyl, heteroarylcarbonyl, heteroaryloxycarbonyl, heteroaryl carbonyloxy, heterocycloalkyloxycarbonyl, carboxyl, alkylamino, arylamino, dialkylamino, alkylaminocarbonyl, alkylsulfonyl, or arylsulfonyl, wherein the alkyl, cycloalkyl, heterocycloalkyl, aryl, and heteroaryl moieties of any of the above substituents may be optionally substituted by one or more of haloalkyl, nitro, amino, cyano, halogen, hydroxyl, haloalkoxy, mercapto, keto or unsubstituted alkyl (except for alkyl), cycloalkyl, heterocycloalkyl, heteroaryl, alkoxy, aryloxy, alkylamino, dialkylamino, alkylthio or arylthio groups.

In accordance with a convention used in the art,

is used in structural formulas herein to depict the bond that is the point of attachment of the moiety or substituent to the core or backbone structure.

As used herein, the term "alkyl" represents a straight- or branched-chain saturated or unsaturated hydrocarbon, containing 1 to 10 carbon atoms which may be unsubstituted or substituted by one or more of the substituents described below. Exemplary alkyl substituents include, but are not limited to methyl (Me), ethyl (Et), propyl, isopropyl, butyl, isobutyl, t-butyl, ethenyl, propenyl, butenyl, pentenyl, ethynyl, butynyl, propynyl (propargyl, isopropynyl), pentynyl, hexynyl, and the like. The term "lower alkyl" refers to an alkyl group containing from 1 to 4 carbon atoms.

"Cycloalkyl" represents a group comprising a non-aromatic monocyclic, bicyclic, or tricyclic hydrocarbon containing from 3 to 14 carbon atoms which may be unsubstituted or substituted by one or more of the substituents described below and may be saturated or unsaturated. Exemplary cycloalkyls include monocyclic rings having from 3–7, preferably 3–6, carbon atoms, such as cyclopropyl, cyclobutyl, cyclopentyl, cyclohexyl, cycloheptyl and the like, that may be fully saturated or partially unsaturated. Illustrative examples of cycloalkyl groups include the following:

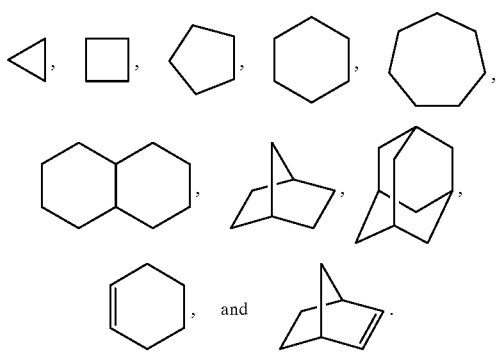

"Heterocycloalkyl" represents a group comprising a non-aromatic, monovalent monocyclic, bicyclic, or tricyclic radical, which is saturated or partially unsaturated, containing 3 to 18 ring atoms, which includes 1 to 5 heteroatoms selected from nitrogen, oxygen and sulfur, and which may be unsubstituted or substituted by one or more of the substituents described below. Illustrative examples of heterocycloalkyl groups include, but are not limited to, azetidinyl, pyrrolidyl, piperidyl, piperazinyl, morpholinyl, tetrahydro-2H-1,4-thiazinyl, tetrahydrofuryl, dihydrofuryl, tetrahydropyranyl, dihydropyranyl, 1,3-dioxolanyl, 1,3-dioxanyl, 1,4-dioxanyl, 1,3-oxathiolanyl, 1,3-oxathianyl, 1,3-dithianyl, azabicylo[3.2.1]octyl, azabicylo[3.3.1]nonyl, azabicylo[4.3.0]nonyl, oxabicylo[2.2.1]heptyl, 1,5,9-triazacyclododecyl, and the like. Illustrative examples of heterocycloalkyl groups include the following moieties:

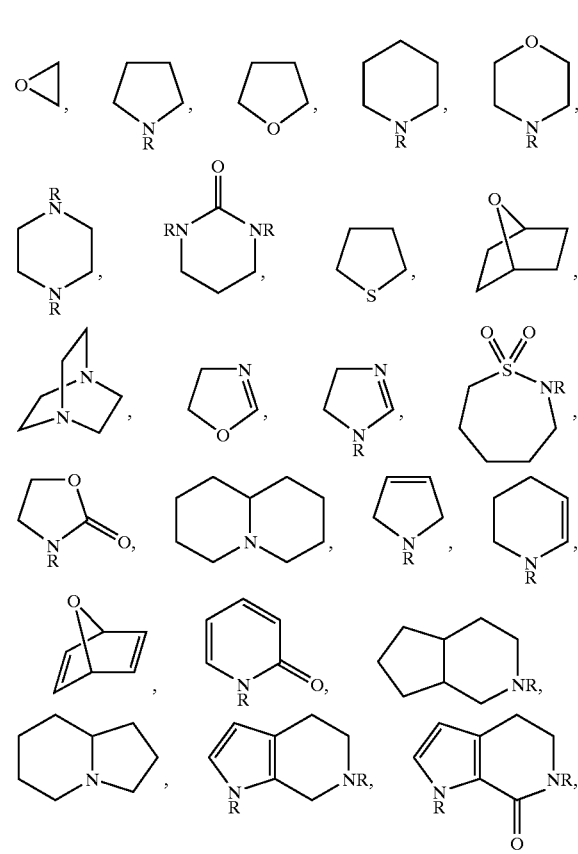

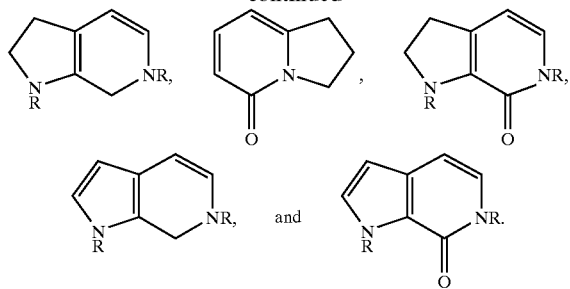

"Aryl" represents a group comprising an aromatic, monovalent monocyclic, bicyclic, or tricyclic radical containing from 6 to 18 carbon ring atoms, which may be unsubstituted or substituted by one or more of the substituents described below, and to which may be fused one or more cycloalkyl groups, heterocycloalkyl groups or heteroaryl groups, which themselves may be unsubstituted or substituted by one or more suitable substituents. Illustrative examples of aryl groups include the following moieties:

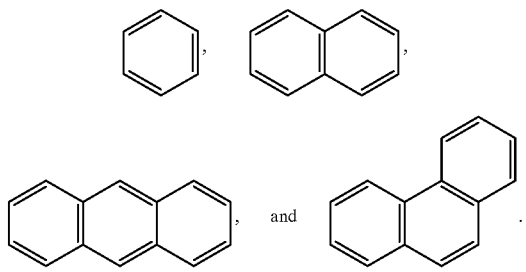

"Heteroaryl" represents a group comprising an aromatic monovalent monocyclic, bicyclic, or tricyclic radical, containing 5 to 18 ring atoms, including 1 to 5 heteroatoms selected from nitrogen, oxygen and sulfur, which may be unsubstituted or substituted by one or more of the substituents described below. Illustrative examples of heteroaryl groups include, but are not limited to, thienyl, pyrrolyl, imidazolyl, pyrazolyl, furyl, isothiazolyl, furazanyl, isoxazolyl, thiazolyl, pyridyl, pyrazinyl, pyrimidinyl, pyridazinyl, triazinyl, benzo[b]thienyl, naphtho[2,3-b]thianthrenyl, isobenzofuranyl, chromenyl, xanthenyl, phenoxathienyl, indolizinyl, isoindolyl, indolyl, indazolyl, purinyl, isoquinolyl, quinolyl, phthalazinyl, naphthyridinyl, quinoxyalinyl, quinzolinyl, benzothiazolyl, benzimidazolyl, tetrahydroquinolinyl, cinnolinyl, pteridinyl, carbazolyl, beta-carbolinyl, phenanthridinyl, acridinyl, perimidinyl, phenanthrolinyl, phenazinyl, isothiazolyl, phenothiazinyl, and phenoxazinyl. Further examples of heteroaryl groups include the following moieties:

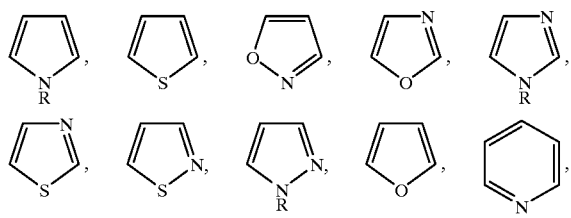

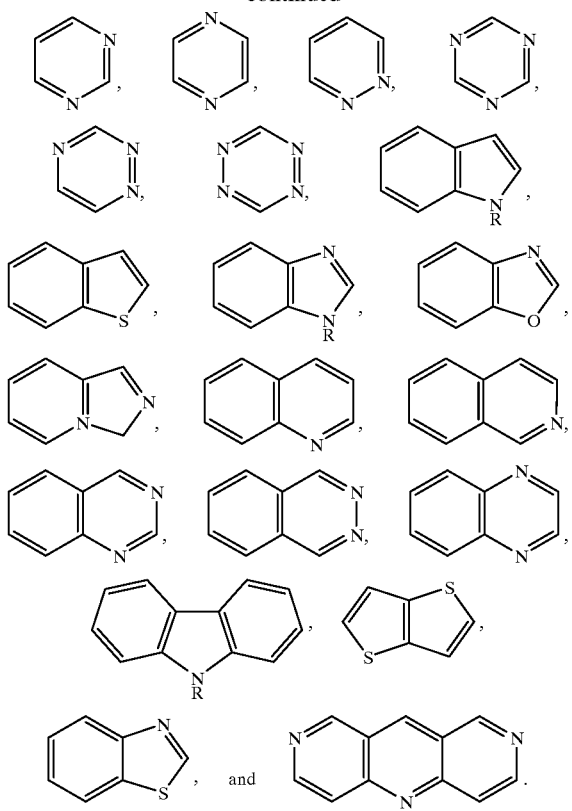

Exemplary "suitable substituents" that may be present on any of the above alkyl, aryl, cycloalkyl, heterocycloalkyl or heteroaryl groups are described herein and include alkyl (except for alkyl), aryl, cycloalkyl, heterocycloalkyl, heteroaryl, nitro, amino, cyano, halogen, hydroxyl, alkoxy, alkylenedioxy, aryloxy, cycloalkoxy, heterocycloalkoxy, heteroaryloxy, alkylcarbonyl, alkyloxycarbonyl, alkylcarbonyloxy, arylcarbonyl, arylcarbonyloxy, aryloxycarbonyl, cycloalkylcarbonyl, cycloalkylcarbonyloxy, cycloalkyoxycarbonyl, heteroarylcarbonyl, heteroarylcarbonyloxy, heteroaryloxycarbonyl, heterocycloalkylcarbonyl, heterocycloalkylcarbonyloxy, heterocycloalkyoxycarbonyl, carboxyl, carbamoyl, formyl, keto (oxo), thioketo, sulfo, alkylamino, cycloalkylamino, arylamino, heterocycloalkylamino, heteroarylamino, dialkylamino, alkylaminocarbonyl, cycloalkylaminocarbonyl, arylaminocarbonyl, heterocycloalkylaminocarbonyl, heteroarylaminocarbonyl, dialkylaminocarbonyl, alkylaminothiocarbonyl, cycloalkylaminothiocarbonyl, arylaminothiocarbonyl, heterocycloalkylaminothiocarbonyl, heteroarylaminothiocarbonyl, dialkylaminothiocarbonyl, alkylsulfonyl, arylsulfonyl, alkylsulfenyl, arylsulfenyl, alkylcarbonylamino, cycloalkylcarbonylamino, arylcarbonylamino, heterocycloalkylcarbonylamino, heteroarylcarbonylamino, alkylthiocarbonylamino, cycloalkylthiocarbonylamino, arylthiocarbonylamino, heterocycloalkylthiocarbonylamino, heteroarylthiocarbonylamino, alkylsulfonyloxy, arylsulfonyloxy, alkylsulfonylamino, arylsulfonylamino, mercapto, alkylthio, arylthio, heteroarylthio, wherein any of the alkyl, alkylene, aryl, cycloalkyl, heterocycloalkyl, heteroaryl moieties present in the above substituents may be further substituted. Preferred "suitable substituents" include alkyl, aryl, cycloalkyl, heterocycloalkyl, heteroaryl, halogen, hydroxyl, alkoxy, alkylenedioxy, aryloxy, cycloalkoxy, heteroaryloxy, and carboxyl. The alkyl, alkylene, cycloalkyl, heterocycloalkyl, aryl, and heteroaryl moieties of any of the above substituents may be optionally substituted by one or more of alkyl (except for alkyl), haloalkyl, aryl, nitro, amino, alkylamino, dialkylamino, halogen, hydroxyl, alkoxy, haloalkoxy, aryloxy, mercapto, alkylthio or arylthio groups.

If the substituents themselves are not compatible with the synthetic methods of this invention, the substituent may be protected with a suitable protecting group that is stable to the reaction conditions used in these methods. The protecting group may be removed at a suitable point in the reaction sequence of the method to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Chemical Synthesis* ($3^{rd}$ ed.), John Wiley & Sons, NY (1999), which is incorporated herein by reference in its entirety. In some instances, a substituent may be specifically selected to be reactive under the reaction conditions used in the methods of this invention. Under these circumstances, the reaction conditions convert the selected substituent into another substituent that is either useful in an intermediate compound in the methods of this invention or is a desired substituent in a target compound.

In the compounds of this invention, $R^1$ and $R^2$, independently or taken together, may be a suitable nitrogen protecting group. As indicated above, nitrogen protecting groups are well known in the art and any nitrogen protecting group that is useful in the methods of preparing the compounds of this invention or may be useful in the antipicornaviral compounds of this invention may be used. Exemplary nitrogen protecting groups include alkyl, substituted alkyl, carbamate, urea, amide, imide, enamine, sulfenyl, sulfonyl, nitro, nitroso, oxide, phosphinyl, phosphoryl, silyl, organometallic, borinic acid and boronic acid groups. Examples of each of these groups, methods for protecting nitrogen moieties using these groups and methods for removing these groups from nitrogen moieties are disclosed in T. Greene and P. Wuts, supra. Preferably, when $R^1$ and/or $R^2$ are independently suitable nitrogen protecting groups, suitable $R^1$ and $R^2$ substituents include, but are not limited to, carbamate protecting groups such as alkyloxycarbonyl (e.g., Boc: t-butyloxycarbonyl) and aryloxycarbonyl (e.g., Cbz: benzyloxycarbonyl, or FMOC: fluorene-9-methyloxycarbonyl), alkyloxycarbonyls (e.g., methyloxycarbonyl), alkyl or arylcarbonyl, substituted alkyl, especially arylalkyl (e.g., trityl (triphenylmethyl), benzyl and substituted benzyl), and the like. When $R^1$ and $R^2$ taken together are a suitable nitrogen protecting group, suitable $R^1/R^2$ substituents include phthalimido and a stabase (1,2-bis (dialkylsilyl))ethylene).

The terms "halogen" and "halo" represent chloro, fluoro, bromo or iodo substituents. "Heterocycle" is intended to mean a heteroaryl or heterocycloalkyl group. "Acyl" is intended to mean a —C(O)—R radical, where R is a substituted or unsubstituted alkyl, cycloalkyl, aryl, heterocycloalkyl or heteroaryl group. "Acyloxy" is intended to mean an —OC(O)—R radical, where R is a substituted or unsubstituted alkyl, cycloalkyl, aryl, heterocycloalkyl or heteroaryl group. "Thioacyl" is intended to mean a —C(S)—R radical, where R is a substituted or unsubstituted alkyl, cycloalkyl, aryl, heterocycloalkyl or heteroaryl group. "Sulfonyl" is intended to mean an —SO$_2$— biradical. "Sulfenyl" is intended to mean an —SO— biradical. "Sulfo" is intended to mean an —SO$_2$H radical. "Hydroxy" is intended to mean the radical —OH. "Amine" or "amino" is intended to mean the radical —NH$_2$. "Alkylamino" is intended to mean the radical —NHR$_a$, where R$_a$ is an alkyl group. "Dialkylamino" is intended to mean the radical —NR$_a$R$_b$, where R$_a$ and R$_b$ are each independently an alkyl group, and is intended to include heterocycloalkyl groups, wherein R$_a$ and R$_b$, taken together, form a heterocyclic ring that includes the amine nitrogen. "Alkoxy" is intended to mean the radical —OR$_a$, where R$_a$ is an alkyl group. Exemplary alkoxy groups include methoxy, ethoxy, propoxy, and the like. "Lower alkoxy" groups have alkyl moieties having from 1 to 4 carbons. "Alkoxycarbonyl" is intended to mean the radical —C(O)OR$_a$, where R$_a$ is an alkyl group. "Alkylsulfonyl" is intended to mean the radical —SO$_2$R$_a$, where R$_a$ is an alkyl group. "Alkylenedioxy" is intended to mean the divalent radical —OR$_a$O— which is bonded to adjacent atoms (e.g., adjacent atoms on a phenyl or naphthyl ring), wherein R$_a$ is a lower alkyl group. "Alkylaminocarbonyl" is intended to mean the radical —C(O)NHR$_a$, where R$_a$ is an alkyl group. "Dialkylaminocarbonyl" is intended to mean the radical —C(O)NR$_a$R$_b$, where R$_a$ and R$_b$ are each independently an alkyl group. "Mercapto" is intended to mean the radical —SH. "Alkylthio" is intended to mean the radical —SR$_a$, where R$_a$ is an alkyl group. "Carboxy" is intended to mean the radical —C(O)OH. "Keto" or "oxo" is intended to mean the diradical=O. "Thioketo" is intended to mean the diradical=S. "Carbamoyl" is intended to mean the radical —C(O)NH$_2$. "Cycloalkylalkyl" is intended to mean the radical -alkyl-cycloalkyl, wherein alkyl and cycloalkyl are defined as above, and is represented by the bonding arrangement present in the groups —CH$_2$-cyclohexane or —CH$_2$-cyclohexene. "Arylalkyl" is intended to mean the radical -alkylaryl, wherein alkyl and aryl are defined as above, and is represented by the bonding arrangement present in a benzyl group. "Aminocarbonylalkyl" is intended to mean the radical -alkylC(O) NH$_2$ and is represented by the bonding arrangement present in the group —CH$_2$CH$_2$C(O)NH$_2$. "Alkylaminocarbonylalkyl" is intended to mean the radical -alkylC(O)NHR$_a$, where R$_a$ is an alkyl group and is represented by the bonding arrangement present in the group —CH$_2$CH$_2$C(O)NHCH$_3$. "Alkylcarbonylaminoalkyl is intended to mean the radical -alkylNHC(O)-alkyl and is represented by the bonding arrangement present in the group —CH$_2$NHC(O)CH$_3$. "Dialkylaminocarbonylalkyl" is intended to mean the radical -alkylC(O)NR$_a$R$_b$, where R$_a$ and R$_b$ are each independently an alkyl group. "Aryloxy" is intended to mean the radical —OR$_c$, where R$_c$ is an aryl group. "Heteroaryloxy" is intended to mean the radical —OR$_d$, where R$_d$ is a heteroaryl group. "Arylthio" is intended to mean the radical —SR$_c$, where R$_c$ is an aryl group. "Heteroarylthio" is intended to mean the radical —SR$_d$, where R$_d$ is a heteroaryl group.

If an inventive compound is a base, a desired salt may be prepared by any suitable method known in the art, including treatment of the free base with an inorganic acid, such as hydrochloric acid, hydrobromic acid, sulfuric acid, nitric acid, phosphoric acid, and the like, or with an organic acid, such as acetic acid, maleic acid, succinic acid, mandelic acid, fumaric acid, malonic acid, pyruvic acid, oxalic acid, glycolic acid, salicylic acid, pyranosidyl acid, such as glucuronic acid or galacturonic acid, alpha-hydroxy acid, such as citric acid or tartaric acid, amino acid, such as aspartic acid or glutamic acid, aromatic acid, such as benzoic acid or cinnamic acid, sulfonic acid, such as p-toluenesulfonic acid or ethanesulfonic acid, or the like.

If an inventive compound is an acid, a desired salt may be prepared by any suitable method known to the art, including treatment of the free acid with an inorganic or organic base, such as an amine (primary, secondary, or tertiary); an alkali metal or alkaline earth metal hydroxide; or the like. Illustrative examples of suitable salts include organic salts derived from amino acids such as glycine and arginine; ammonia; primary, secondary, and tertiary amines; and cyclic amines, such as piperidine, morpholine, and piperazine; as well as inorganic salts derived from sodium, calcium, potassium, magnesium, manganese, iron, copper, zinc, aluminum, and lithium.

All compounds of this invention contain at least one chiral center and may exist as single stereoisomers (e.g., single enantiomers or single diastereomers), any mixture of stereoisomers (e.g., any mixture of enantiomers or diastereomers) or racemic mixtures thereof. All such single stereoisomers, mixtures and racemates are intended to be encompassed within the broad scope of the present invention. Compounds identified herein as single stereoisomers are meant to describe compounds that are present in a form that contains at least 90% of a single stereoisomer of each chiral center present in the compounds. Where the stereochemistry of the chiral carbons present in the chemical structures illustrated herein is not specified, the chemical structure is intended to encompass compounds containing either stereoisomer of each chiral center present in the compound. Preferably, however, the inventive compounds are used in optically pure, that is, stereoisomerically pure, form or substantially optically pure (substantially stereoisomerically pure) form. As used herein, the term "stereoisomeric" purity (or "optical" purity) refers to the "enantiomeric" purity and/or "diastereomeric" purity of a compound. Compounds that are substantially enatiomerically pure contain at least 90% of a single isomer and preferably contain at least 95% of a single isomer of each chiral center present in the enantiomer. Compounds that are substantially diastereomerically pure contain at least 90% of a single isomer of each chiral center present in the diastereomer, and preferably contain at least 95% of a single isomer of each chiral center. More preferably, the substantially enantiomerically and diasteriomerically pure compounds in this invention contain at least 97.5% of a single isomer and most preferably contain at least 99% of a single isomer of each chiral center in the compound. The term "racemic" or "racemic mixture" refers to a mixture of equal amounts of enantiomeric compounds, which encompasses mixtures of enantiomers and mixtures of enantiomeric diastereomers. The compounds of this invention may be obtained in stereoisomerically pure (i.e., enantiomerically and/or diastereomerically pure) or substantially stereoisomerically pure (i.e., substantially enantiomerically and/or diastereomerically pure) form. Such compounds may be obtained synthetically, according to the procedures described herein using optically pure or substantially optically pure materials. Alternatively, these compounds may be obtained by resolution/separation of a mixture of stereoisomers, including racemic mixtures, using conventional procedures. Exemplary methods that may be useful for the resolution/separation of stereoisomeric mixtures include chromatography and crystallization/recrystallization. Other useful methods may be found in *"Enantiomers, Racemates, and Resolutions,"* J. Jacques et al., 1981, John Wiley and Sons, New York, N.Y., the disclosure of which is incorporated herein by reference.

Preferred stereoisomers of the compounds of this invention are described herein.

Another embodiment of this invention comprises the compounds depicted by Formula I-a (as represented by Formula I, wherein the dotted line represents a bond):

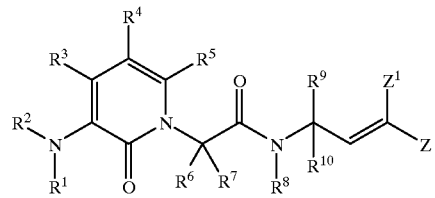

I-a wherein:

$R^2$ is an alkylcarbonyl group, an arylcarbonyl group, a cycloalkylcarbonyl group, a heterocycloalkylcarbonyl group, a heteroarylcarbonyl group, an aryloxycarbonyl group or an alkyloxycarbonyl group, wherein each of the alkyl, aryl, cycloalkyl, heterocycloalkyl or heteroaryl moieties of the above groups may be substituted or unsubstituted;

$R^3$, $R^4$, $R^5$ are independently H or a suitable substituent described above, and $R^1$, $R^6$, $R^7$, $R^8$, $R^9$, $R^{10}$, Z and $Z^1$, and the variables contained therein, are as defined above.

Yet another embodiment of this invention comprises the compounds depicted by Formula I-b:

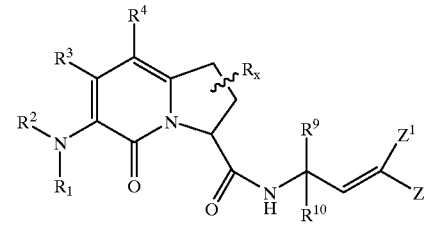

I-b wherein:

$R^2$ is an alkylcarbonyl group, an arylcarbonyl group, a cycloalkylcarbonyl group, a heterocycloalkylcarbonyl group, a heteroarylcarbonyl group, an aryloxycarbonyl group or an alkyloxycarbonyl group, wherein each of the alkyl, aryl, cycloalkyl, heterocycloalkyl or heteroaryl moieties of the above groups may be substituted or unsubstituted;

$R_x$ represents H or one or more suitable substituents;

$R^3$ and $R^4$ are independently H or a suitable substituent described above; and $R^1$, $R^9$, $R^{10}$, Z, and $Z^1$, and the variables contained therein, are as defined above.

A further embodiment of this invention comprises the compounds depicted by Formula I-c:

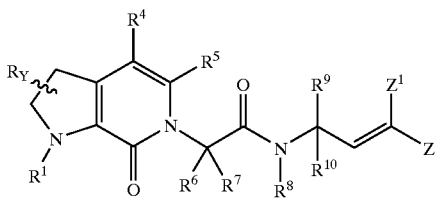

I-c wherein:

$R^7$, $R^8$, and $R^{10}$ are independently H or a substituted or unsubstituted lower alkyl group;

$R_Y$ represents H or one or more suitable substituents;

$R^4$ and $R^5$ are independently H or a suitable substituent described above; and $R^1$, $R^6$, $R^9$, Z, and $Z^1$, and the variables contained therein, are as defined above.

Another embodiment of this invention comprises the compounds depicted by Formula I-d:

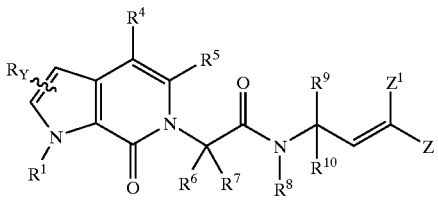

I-d wherein:

$R^7$, $R^8$, and $R^{10}$ are independently H or a substituted or unsubstituted lower alkyl group;

$R_Y$ represents H or one or more suitable substituents;

$R^4$ and $R^5$ are independently H or a suitable substituent described above; and $R^1$, $R^6$, $R^9$, Z, and $Z^1$, and the variables contained therein, are as defined above.

Yet another embodiment of this invention comprises the compounds depicted by Formula I-e (as represented by Formula I, wherein the dotted line does not represent a bond):

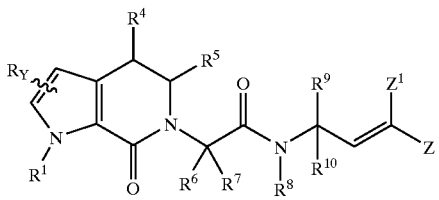

I-e wherein:

$R^7$, $R^8$, and $R^{10}$ are independently H or a substituted or unsubstituted lower alkyl group;

$R_Y$ represents H or one or more suitable substituents;

$R^4$ and $R^5$ are independently H or a suitable substituent described above; and $R^1$, $R^6$, $R^9$, Z, and $Z^1$, and the variables contained therein, are as defined above.

In preferred embodiments of Formulas I-a and I-b, $R^2$ is selected from a substituted or unsubstituted alkyloxycarbonyl group, alkylcarbonyl, cycloalkylcarbonyl, arylcarbonyl, heterocycloalkylcarbonyl or heteroarylcarbonyl group. Preferably, when $R^2$ is a substituted alkyloxycarbonyl group, $R^2$ is an unsubstituted or substituted arylalkyloxycarbonyl group. Exemplary $R^2$ groups include, but are not limited to benzyloxycarbonyl, methylcarbonyl, t-butylcarbonyl, trifluoromethylcarbonyl, cyclopentylcarbonyl, tetrahydrofuran-2-carbonyl, 1,3-dithiolane-2-carbonyl and the like. Preferably, $R^2$ is a substituted or unsubstituted benzyloxycarbonyl, arylcarbonyl, or heteroarylcarbonyl group. Even more preferably, $R^2$ is an unsubstituted or substituted benzyloxycarbonyl or heteroarylcarbonyl group, wherein the heteroaryl moiety is a five-membered heterocycle having from one to three heteroatoms selected from O, N, and S, more preferably a five-membered heterocycle having at least one nitrogen heteroatom and at least one oxygen heteroatom (e.g., unsubstituted or substituted 1,2-oxazolyl (i.e., isoxazolyl), 1,3-oxazolyl (i.e., oxazolyl), or oxadiazolyl (1,2,3-oxadiazolyl, 1,2,4-oxadiazolyl, or 1,2,5-oxadiazolyl). When the heteroaryl moiety is oxadiazolyl, unsubstituted and monomethyl-substituted 1,2,4-oxadiazolyl are preferred. In especially preferred embodiments, the heteroaryl moiety is 3-isoxazolyl or 5-isoxazolyl, either unsubstituted or substituted with one or two methyl groups and/or halogens (F, Cl, Br or I), with chlorine and fluorine being preferred. Accordingly, the heteroarylcarbonylgroup in the especially preferred embodiments is an unsubstituted or substituted 3-carbonyl-1,2-oxazolyl group (i.e., 3-carbonyl-isoxazolyl) or a 5-carbonyl-1,2-oxazolyl group (i.e., 5-carbonyl-isoxazolyl).

In preferred embodiments of the compounds of this invention, the substituent variables $R^3$, $R^4$, and $R^5$, as present in the compounds of Formulas I-a, I-b, I-c, I-d, and I-e, are selected from H, alkyl, aryl, cycloalkyl, heterocycloalkyl, heteroaryl, nitro, amino, cyano, halogen, haloalkyl, hydroxyl, keto, alkoxy, aryloxy, wherein any of the alkyl, aryl, cycloalkyl, heterocycloalkyl, heteroaryl moieties present in the above substituents may be further substituted with one or more substituents selected from nitro, amino, cyano, halogen, haloalkyl, hydroxyl, keto, and unsubstituted alkyl, aryl, cycloalkyl, heterocycloalkyl, heteroaryl, alkoxy, or aryloxy.

In preferred embodiments of the compounds of this invention, the substituent variables $R_x$ in the compounds of Formula I-b are selected from H, alkyl, aryl, cycloalkyl, heterocycloalkyl, heteroaryl, nitro, amino, cyano, halogen, haloalkyl, hydroxyl, alkoxy, alkylenedioxy, aryloxy, cycloalkoxy, heterocycloalkoxy, heteroaryloxy, alkylcarbonyl, alkyloxycarbonyl, alkylcarbonyloxy, arylcarbonyl, arylcarbonyloxy, aryloxycarbonyl, cycloalkylcarbonyl, cycloalkylcarbonyloxy, cycloalkyoxycarbonyl, heteroarylcarbonyl, heteroarylcarbonyloxy, heteroaryloxycarbonyl, heterocycloalkylcarbonyl, heterocycloalkylcarbonyloxy, heterocycloalkyloxycarbonyl, carboxyl, carbamoyl, formyl, keto, thioketo, sulfo, alkylamino, cycloalkylamino, arylamino, heterocycloalkylamino, heteroarylamino, dialkylamino, alkylaminocarbonyl, cycloalkylaminocarbonyl, arylaminocarbonyl, heterocycloalkylaminocarbonyl, heteroarylaminocarbonyl, dialkylaminocarbonyl, alkylaminothiocarbonyl, cycloalkylaminothiocarbonyl, arylaminothiocarbonyl, heterocycloalkylaminothiocarbonyl, heteroarylaminothiocarbonyl, dialkylaminothiocarbonyl, alkylsulfonyl, arylsulfonyl, alkylsulfenyl, arylsulfenyl, alkylcarbonylamino, cycloalkylcarbonylamino, arylcarbonylamino, heterocycloalkylcarbonylamino, heteroarylcarbonylamino, alkylthiocarbonylamino, cycloalkylthiocarbonylamino, arylthiocarbonylamino, heterocycloalkylthiocarbonylamino, heteroarylthiocarbonylamino, alkylsulfonyloxy, arylsulfonyloxy, alkylsulfonylamino, arylsulfonylamino, mercapto, alkylthio, arylthio, and heteroarylthio, wherein any of the alkyl, aryl, cycloalkyl, heterocycloalkyl, heteroaryl moieties present in the above substituents may be further substituted with one or more substituents selected from nitro, amino, cyano, halogen, haloalkyl, hydroxyl, keto, and unsubstituted alkyl, aryl, cycloalkyl, heterocycloalkyl, heteroaryl, alkoxy, or aryloxy.

In preferred embodiments of the compounds of this invention, the substituent variable $R_y$ in the compounds of formula Formulas I-c, I-d, and I-e, are selected from H, alkyl, aryl, cycloalkyl, heterocycloalkyl, heteroaryl, nitro, amino, cyano, halogen, haloalkyl, hydroxyl, alkoxy, alkylenedioxy, aryloxy, cycloalkoxy, heterocycloalkoxy, heteroaryloxy, alkylcarbonyl, alkyloxycarbonyl, alkylcarbonyloxy, arylcarbonyl, arylcarbonyloxy, aryloxycarbonyl, cycloalkylcarbonyl, cycloalkylcarbonyloxy, cycloalkyoxycarbonyl, heteroarylcarbonyl, heteroarylcarbonyloxy, heteroaryloxycarbonyl, heterocycloalkylcarbonyl, heterocycloalkylcarbonyloxy, heterocycloalkyloxycarbonyl, carboxyl, carbamoyl, formyl, keto, thioketo, sulfo, alkylamino, cycloalkylamino, arylamino, heterocycloalkylamino, heteroarylamino, dialkylamino, alkylaminocarbonyl, cycloalkylaminocarbonyl, arylaminocarbonyl, heterocycloalkylaminocarbonyl, heteroarylaminocarbonyl, dialkylaminocarbonyl, alkylaminothiocarbonyl, cycloalkylaminothiocarbonyl, arylaminothiocarbonyl, heterocycloalkylaminothiocarbonyl, heteroarylaminothiocarbonyl, dialkylaminothiocarbonyl, alkylsulfonyl, arylsulfonyl, alkylsulfenyl, arylsulfenyl, alkylcarbonylamino, cycloalkylcarbonylamino, arylcarbonylamino, heterocycloalkylcarbonylamino, heteroarylcarbonylamino, alkylthiocarbonylamino, cycloalkylthiocarbonylamino, arylthiocarbonylamino, heterocycloalkylthiocarbonylamino, heteroarylthiocarbonylamino, alkylsulfonyloxy, arylsulfonyloxy, alkylsulfonylamino, arylsulfonylamino, mercapto, alkylthio, arylthio, and heteroarylthio, wherein any of the alkyl, aryl, cycloalkyl, heterocycloalkyl, heteroaryl moieties present in the above substituents may be further substituted with one or more substituents selected from nitro, amino, cyano, halogen, haloalkyl, hydroxyl, keto, and unsubstituted alkyl, aryl, cycloalkyl, heterocycloalkyl, heteroaryl, alkoxy, or aryloxy.

In especially preferred embodiments of Formulas I-a, I-c, I-d, and I-e, $R^6$ is H or an unsubstituted alkyl group or an optionally substituted lower alkyl group, wherein these groups are comprised of a straight- or branched-chain saturated hydrocarbon group, a straight- or branched-chain substituted saturated hydrocarbon group, or group comprised of a straight- or branched-chain saturated hydrocarbon moiety and an unsaturated hydrocarbon moiety. When $R^6$ is a substituted alkyl group, the point of attachment of $R^6$ is via a saturated hydrocarbon moiety. When $R^6$ is a substituted saturated hydrocarbon group, the saturated hydrocarbon group may be optionally substituted with a cycloalkyl group, a heterocycloalkyl group, an aryl group, a heteroaryl group, an alkoxy group, an aryloxy group, an alkylthio group, an arylthio group, wherein each alkyl, cycloalkyl, aryl, heterocycloalkyl or heteroaryl moiety thereof may be optionally substituted. When $R^6$ is comprised of a saturated hydrocarbon moiety and an unsaturated hydrocarbon moiety, the saturated hydrocarbon moiety may be bound to an unsaturated hydrocarbon moiety containing one or more double-bonds or triple-bonds, the terminal positions of which may be substituted by the substituents described above, or may contain additional straight- or branched-chain saturated hydrocarbon moieties. Preferably, the unsaturated hydrocarbon moiety contains one double-bond or one triple-bond, the terminal position(s) of which may optionally contain a straight- or branched-chain saturated hydrocarbon moiety. Preferably, if the unsaturated hydrocarbon moiety contains a double-bond, both terminal positions of the double bond contain a straight- or branched-chain saturated hydrocarbon moiety. In especially preferred embodiments, $R^6$ is H or a substituted or unsubstituted lower alkyl, arylalkyl, heteroarylalkyl, cycloalkylalkyl group, or a group comprised of a straight-chain saturated hydrocarbon moiety and an unsaturated hydrocarbon moiety. Preferably, $R^6$ is H, methyl, substituted methyl, ethyl, n-propyl, n-butyl, sec-butyl, 2-propyn-1-yl, 3-methyl-3-buten-1-yl, -methylcyclohexyl, substituted or unsubstituted -methylthienyl or substituted or unsubstituted benzyl, wherein the phenyl moiety of the substituted benzyl is substituted by one or more substituents independently selected from lower alkyl, lower alkoxy, hydroxy, amino, alkylamino or dialkylamino or halogen and the thienyl moiety of the substituted -methylthienyl is substituted by one or more substituents independently selected from lower alkyl, lower alkoxy, hydroxy, amino, alkylamino or dialkylamino or halogen. When $R^6$ is substituted methyl, the methyl (methylene) moiety may be substituted with an alkoxy group, an aryloxy group, an alkylthio group or an arylthio group. Most preferably, $R^6$ is H, ethyl, 2-propyn-1-yl, -methylcyclohexyl, or substituted or unsubstituted benzyl, wherein the phenyl moiety of the substituted benzyl is substituted by one or more substituents independently selected from lower alkyl, lower alkoxy and halogen.

In the preferred embodiments of the compounds, prodrugs, pharmaceutically acceptable salts, pharmaceutically active metabolites, or pharmaceutically acceptable solvates of this invention $R^b$ and $R^9$ are defined as above and m is 1 and p is 1 or 2 (i.e., both $A_2$ and $A_3$ are present) or when p is 0, m is 0 (i.e, both $A_2$ and $A_3$ are absent). More preferably, in $R^b$ and $R^9$, when m is 1 and p is 1 or 2, $A_2$ and $A_3$ are both $C(R^h)(R^i)$ or $C(R^{14})(R^{15})$, respectively. More preferably, when m is 1, p is 1.

In especially preferred embodiments of Formulas I-a, I-b, I-c, I-d, and I-e, $R^9$ is selected from —CH$_2$CH$_2$C(O)NH$_2$; —CH$_2$CH$_2$C(O)NH-alkyl; —CH$_2$NHC(O)CH$_3$; and

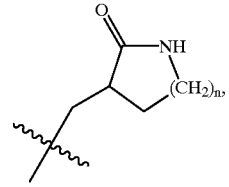

where n is 1 or 2. More preferably, $R^9$ is

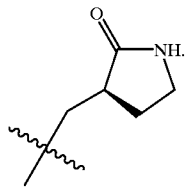

In the preferred embodiments of the compounds prodrugs, pharmaceutically acceptable salts, pharmaceutically active metabolites, or pharmaceutically acceptable solvates of this invention, Z and $Z^1$ are independently H, substituted or unsubstituted alkyl, —$CO_2R''$ or —$CO_2R^{19}$, as appropriate, wherein $R''$ and $R^{19}$ are as defined above, or Z and $Z^1$, taken together with the atom to which they are attached, form a heterocycloalkyl group, as defined above. In another useful embodiment of the compounds of this invention, Z and/or $Z^1$ may be —$C(S)OR''$ or —$C(S)OR^{19}$, wherein $R''$ and $R^{19}$ are as defined above. Such compounds may be prepared using procedures described in K. Hartke, et al., *Leibigs Ann. Chem.*, 321–330 (1989) and K. Hartke, et al., *Synthesis*, 960–961 (1985). Preferably, in the compounds of Formulas I-a, I-b, I-c, I-d, and I-e, Z, and $Z^1$ are independently H, substituted or unsubstituted alkyl, —$CO_2R^{19}$, or taken together with the atom to which they are attached, form a heterocycloalkyl group, which may be optionally substituted. More preferably, Z and $Z^1$ are independently selected from H, —$CO_2H$, substituted or unsubstituted lower alkyl, —$CO_2$-alkyl, —$CO_2$-cycloalkyl, —$CO_2$-alkylaryl (e.g., —$CO_2$-benzyl), —$CO_2$-alkylheteroaryl (e.g., —$CO_2$-$(CH_2)_n$pyridyl) or taken together with the atom to which they are attached form a heterocycloalkyl group, which may be optionally substituted. The heterocycloalkyl group may optionally contain O, N, S, and/or P and may be substituted by one or more of oxo (keto) or thioketo. In preferred embodiments of this invention, Z and $Z^1$ are not both H. Most preferably, $Z^1$ is H or lower alkyl and Z is —$CO_2H$, substituted or unsubstituted—$CO_2$-alkyl, —$CO_2$-alkylaryl, —$CO_2$-alkylheteroaryl, —$CO_2$-cycloalkyl, or or taken together with the atom to which they are attached form a heterocycloalkyl group, which may be optionally substituted. Exemplary Z groups include, but are not limited to substituted and unsubstituted —$CO_2$-alkyl groups, which include straight- and branched-chain alkyl groups such as ethoxycarbonyl, t-butoxycarbonyl, isopropoxycarbonyl, (2,2-dimethylpropyl)-oxycarbonyl, and the like, and which include straight and branched-chain arylalkyl and heteroarylalkyl groups, such as benzyloxycarbonyl, pyridylmethyleneoxycarbonyl, and the like, substituted and unsubstituted —$CO_2$-cycloalkyl groups such as cyclobutyloxycarbonyl, cyclopentyloxycarbonyl, cyclohexyloxycarbonyl, cycloheptyloxycarbonyl, and the like, or taken together with $Z^1$ and the atom to which they are

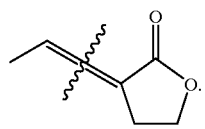

attached form

A preferred embodiment of this invention comprises stereoisomers of the subject compounds having the formula:

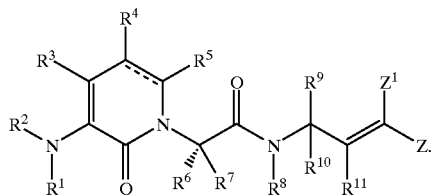

Another preferred embodiment of this invention comprises stereoisomers of the subject compounds having the formula:

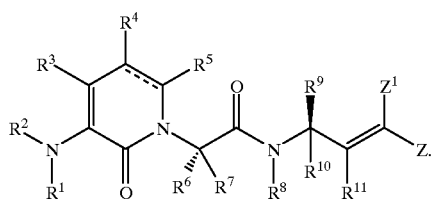

Especially preferred embodiments of this invention comprise stereoisomers of the subject compounds having the formula:

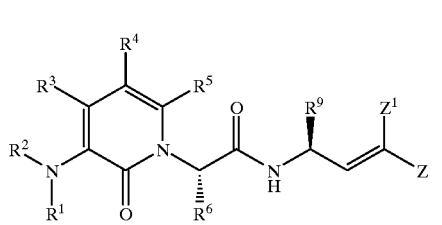

Specific especially preferred embodiments of this invention comprise compounds of Formulas I-a', I-b', I-c', I-d', and I-e' as follows:

I-a'

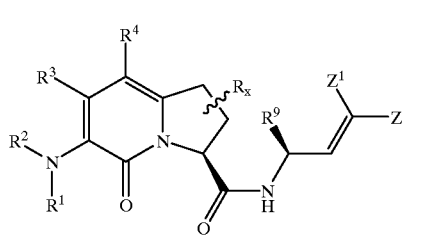

wherein $R^1$, $R^2$, $R^3$, $R^4$, $R^5$, $R^6$, $R^9$, Z, and $Z^1$ are as previously defined;

I-b'

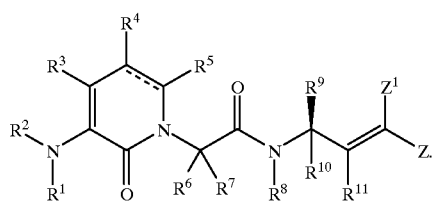

wherein $R^1$, $R^2$, $R^3$, $R^4$, $R^9$, $R_x$, Z, and $Z^1$ are as previously defined;

I-c'

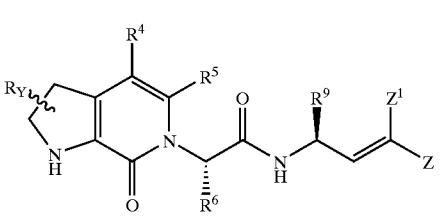

wherein $R^4$, $R^5$, $R^6$, $R^9$, $R_y$, Z, and $Z^1$ are as previously defined;

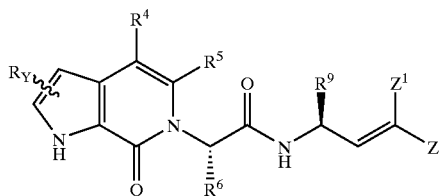

I-d' wherein $R^4$, $R^5$, $R^6$, $R^9$, $R_y$, Z, and $Z^1$ are as previously defined; and

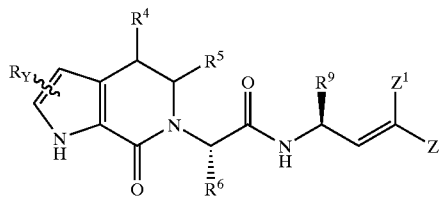

I-e' wherein $R^4$, $R^5$, $R^6$, $R^9$, $R_y$, Z, and $Z^1$ are as previously defined.

In especially preferred embodiments of Formulas I-a' and I-b', $R^2$ is unsubstituted or substituted benzyloxycarbonyl, arylcarbonyl, or heteroarylcarbonyl, more preferably heteroarylcarbonyl, where the heteroaryl moiety is a five-membered heterocycle having from one to three heteroatoms selected from O, N, and S. More preferably $R^2$ is heteroarylcarbonyl wherein the heteroaryl moiety is a five-membered heterocycle having at least one nitrogen heteroatom and at least one oxygen heteroatom (e.g., unsubstituted or substituted 1,2-oxazolyl (i.e., isoxazolyl), 1,3-oxazolyl (i.e., oxazolyl), or oxadiazolyl (1,2,3-oxadiazolyl, 1,2,4-oxadiazolyl, or 1,2,5-oxadiazolyl); preferred oxadiazolyls are unsubstituted and monomethyl-substituted 1,2,4-oxadiazolyl. In especially preferred embodiments, the heteroaryl moiety is 3-isoxazolyl or 5-isoxazolyl, either unsubstituted or substituted with one or two substituents selected from methyl and halogen, with chloro and fluoro being preferred halogen substituents.

In the especially preferred embodiments of Formulas I-a', I-b', I-c', I-d', and I-e', $R^6$ is selected from H or:

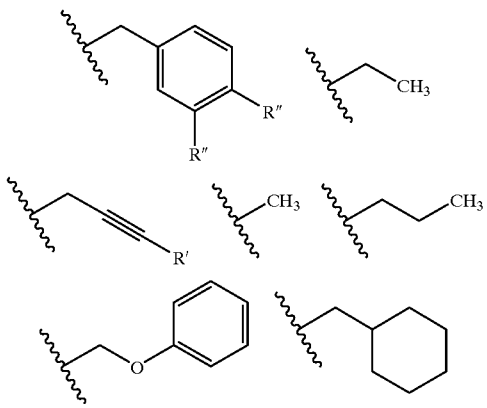

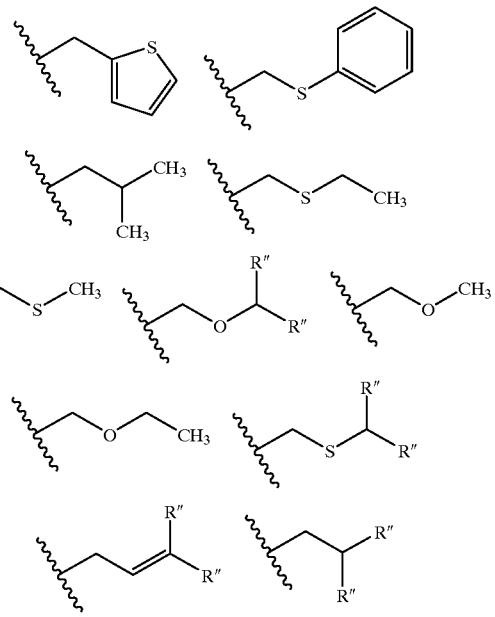

wherein R' may be H or alkyl and R" may be H or independently selected from lower alkyl, lower alkoxy, hydroxy, amino, alkylamino or dialkylamino, and halogen.

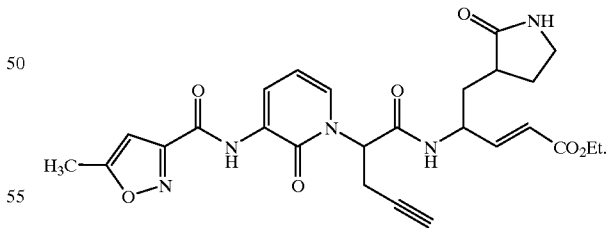

A particularly preferred embodiment of this invention comprises a compound having the formula:

and prodrugs, pharmaceutically active metabolites, and pharmaceutically acceptable salts and solvates thereof. Other useful embodiments of this invention comprise any stereoisomer or mixture of stereoisomers of the above-noted compound.

One preferred stereoisomer of this compound may be represented by the formula:

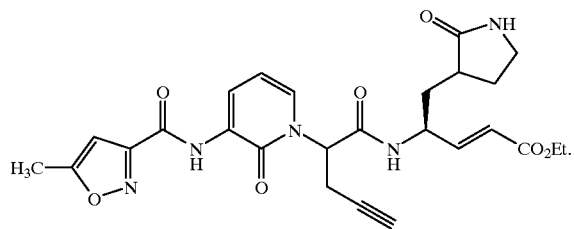
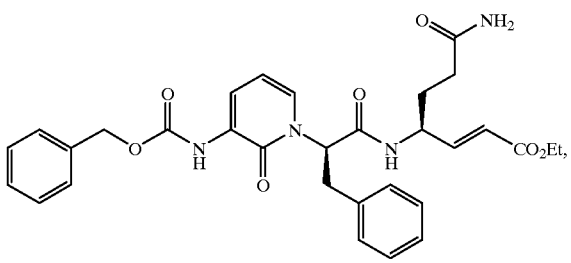
Another preferred stereoisomer of this compound may be represented by the formula:
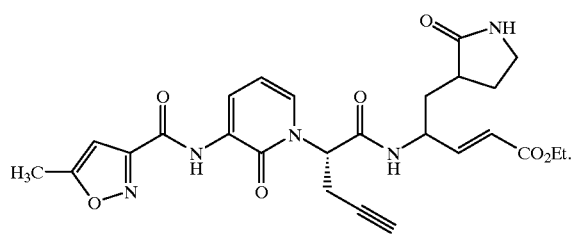
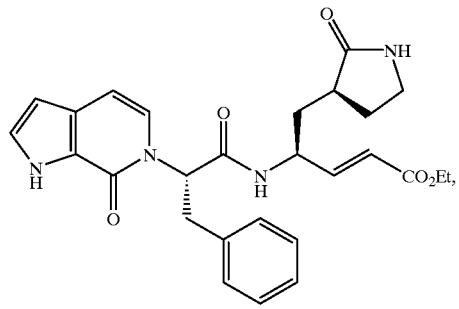
An especially preferred stereoisomer of this compound may be represented by the formula:
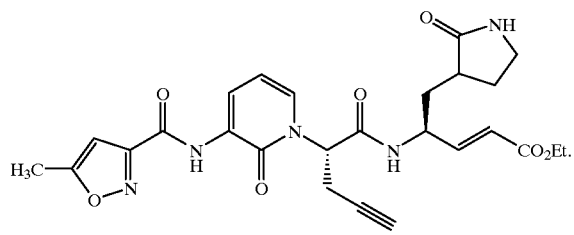
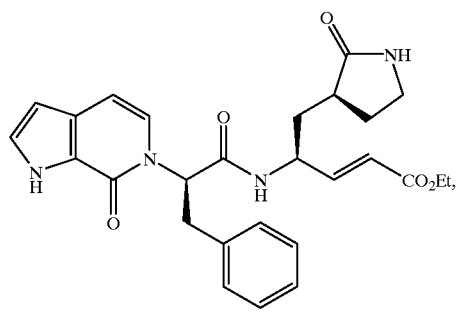
Preferred specific compounds include those of the Examples below, especially:
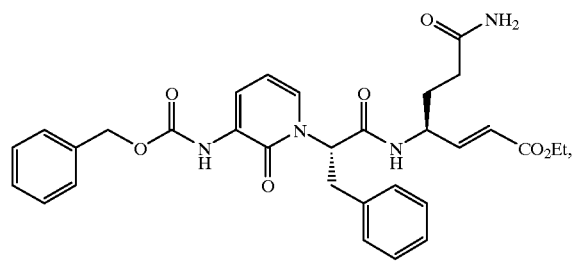
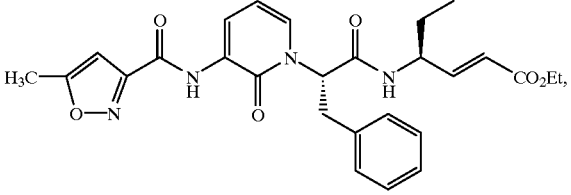
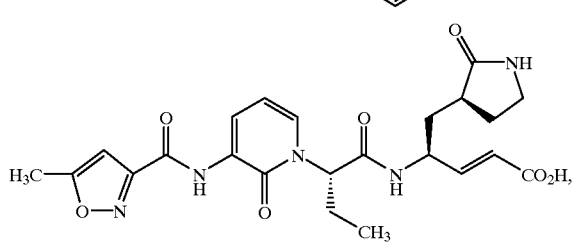
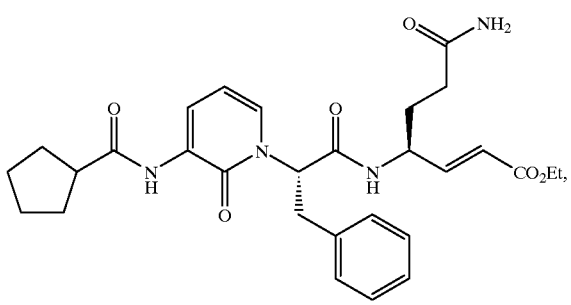

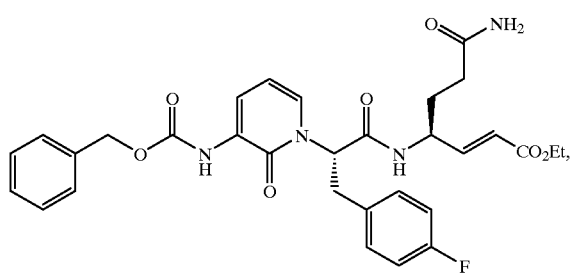
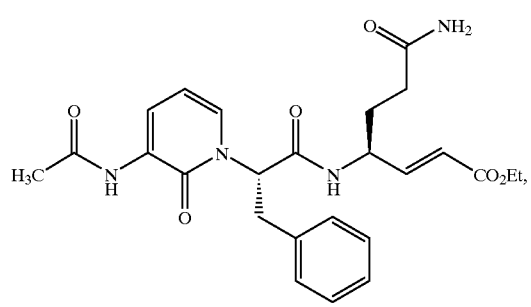
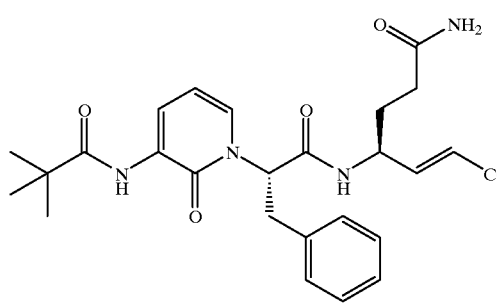
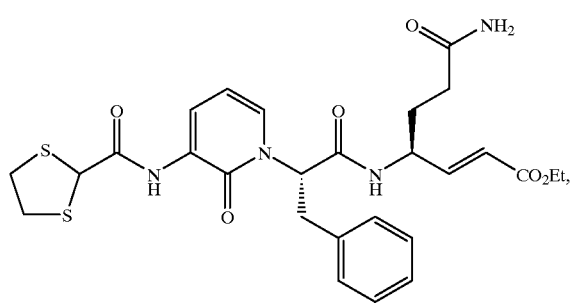
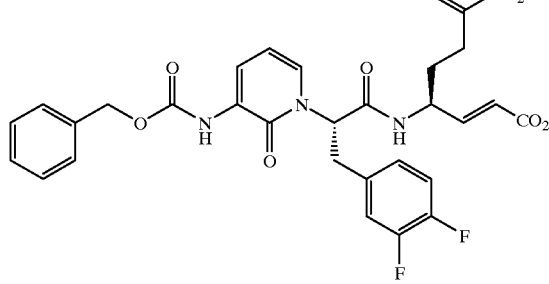
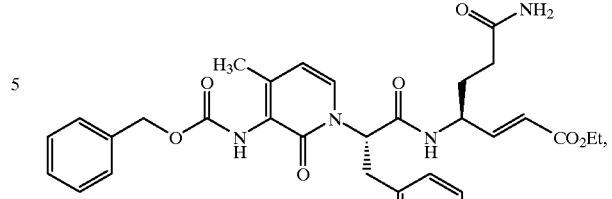
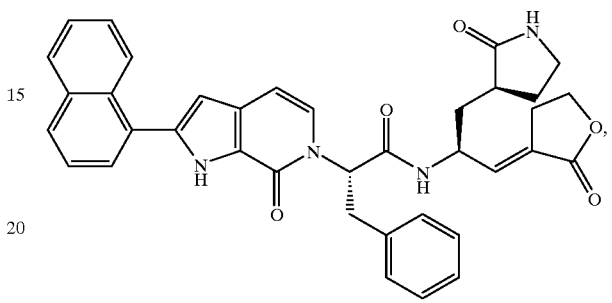
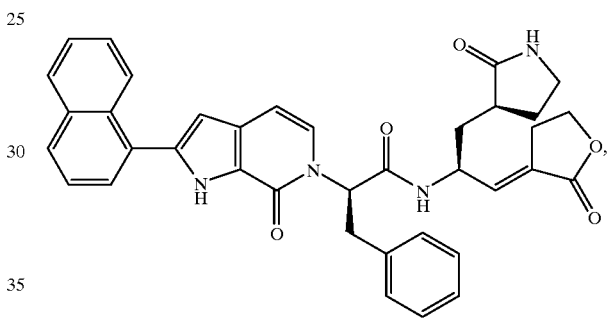
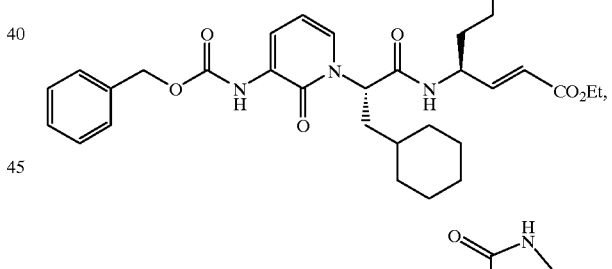
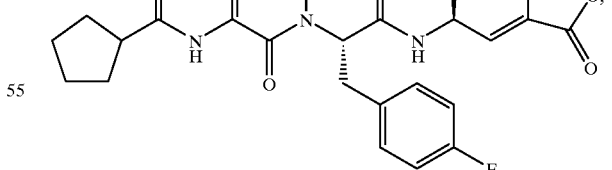
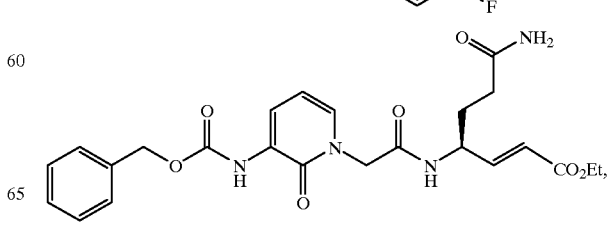

-continued
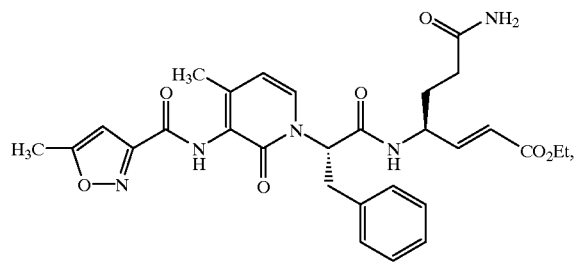
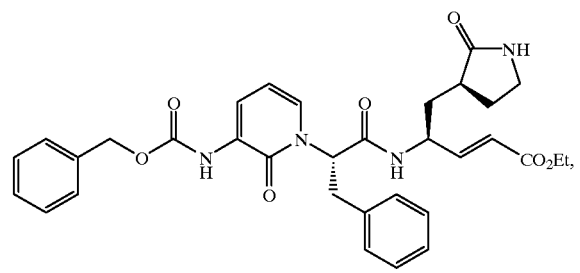
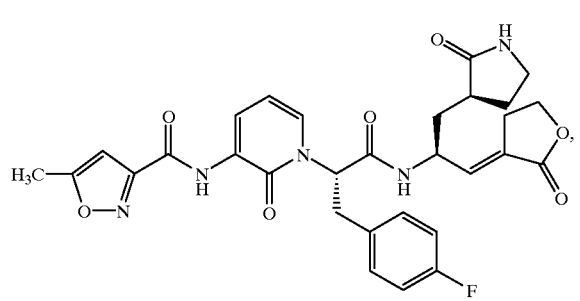
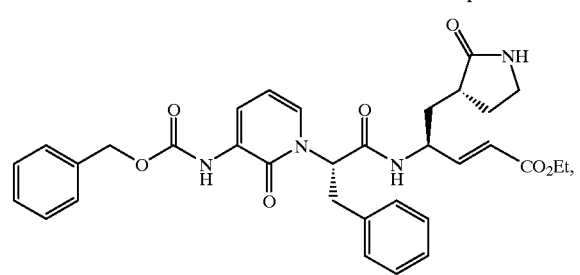
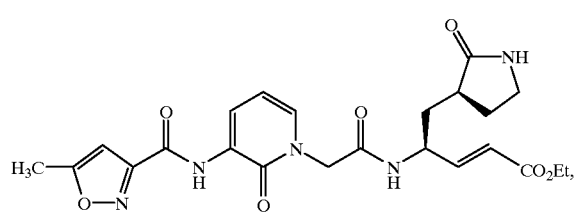
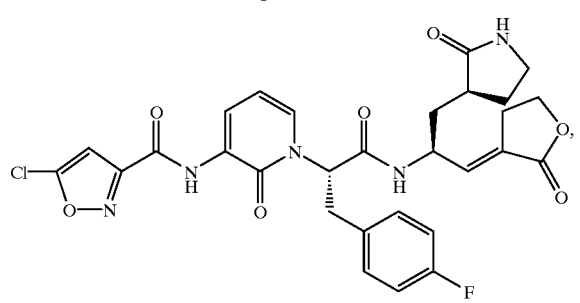
-continued
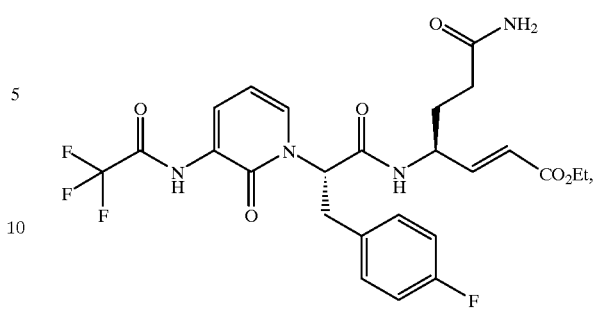
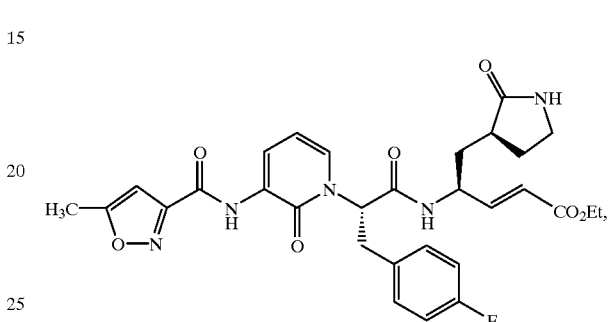
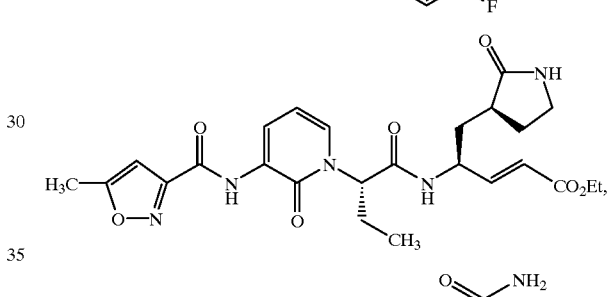
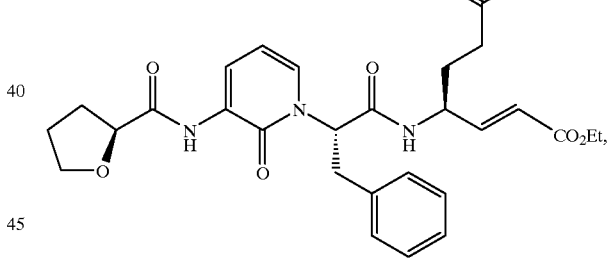
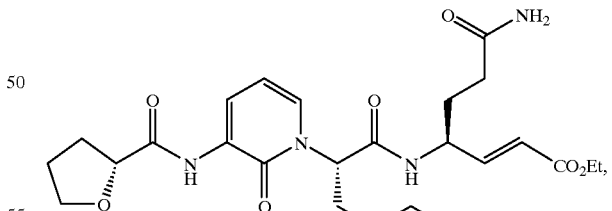
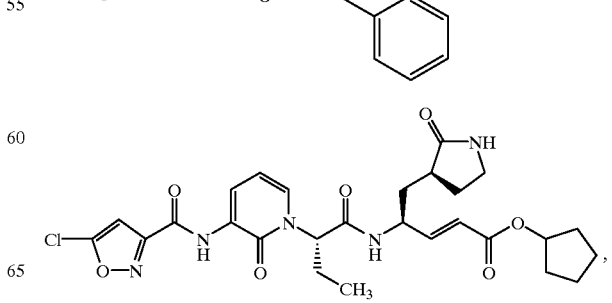

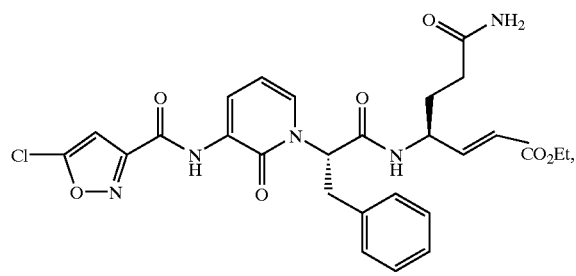
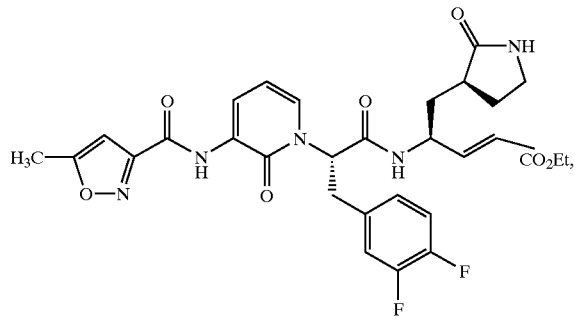
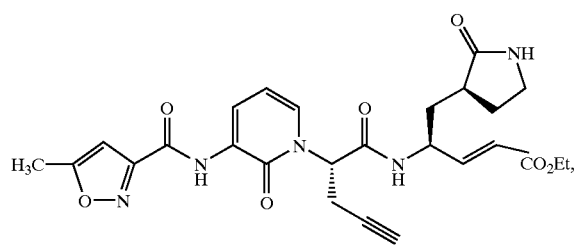
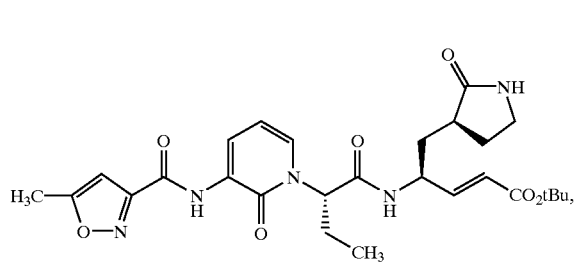
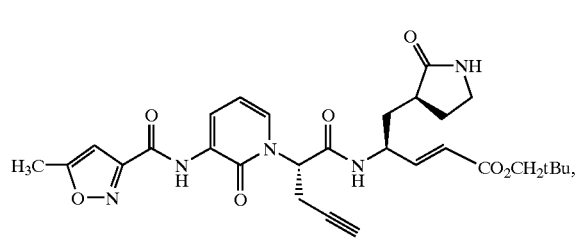
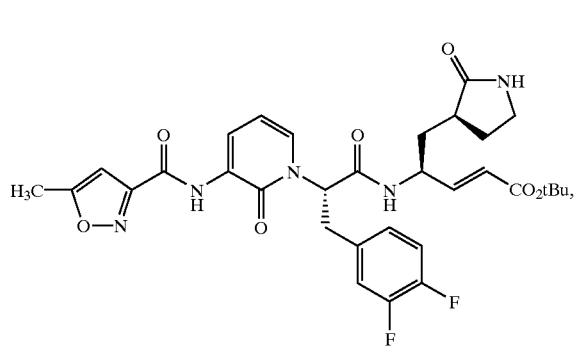
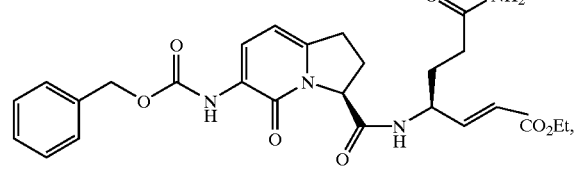
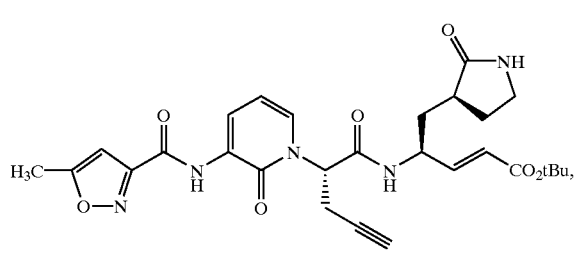
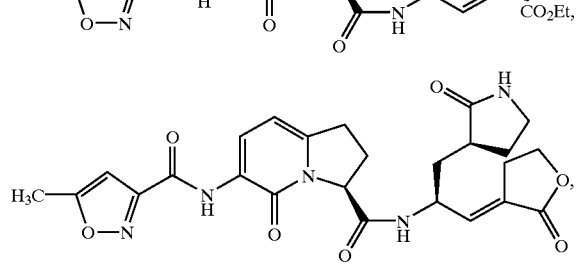
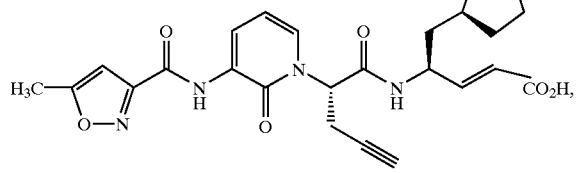
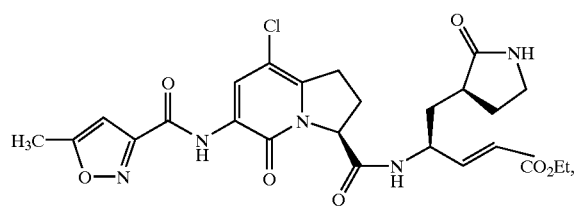
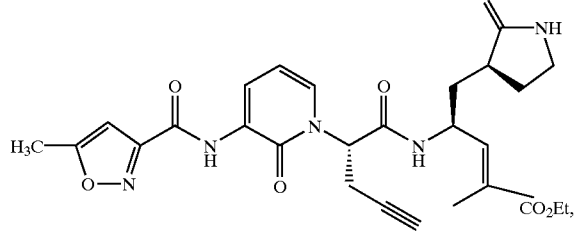

31
-continued
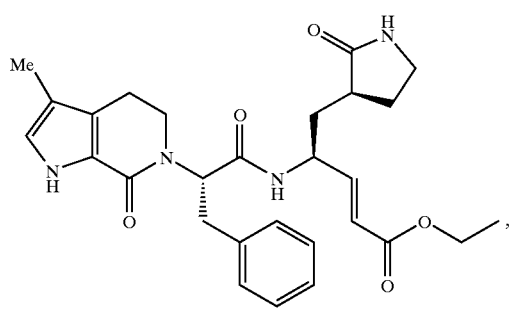
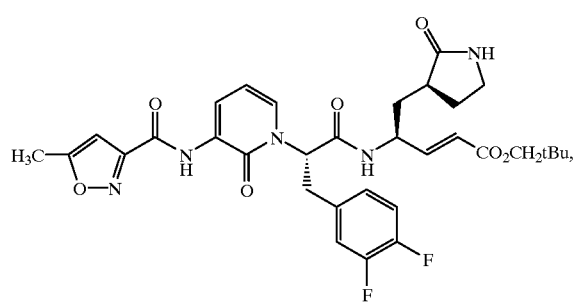
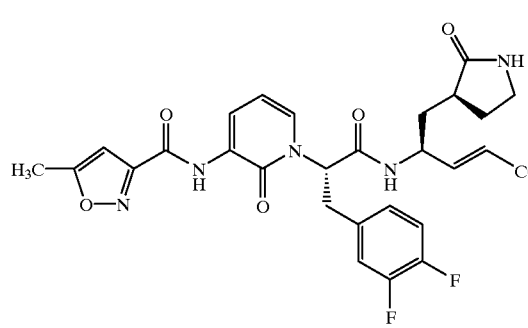
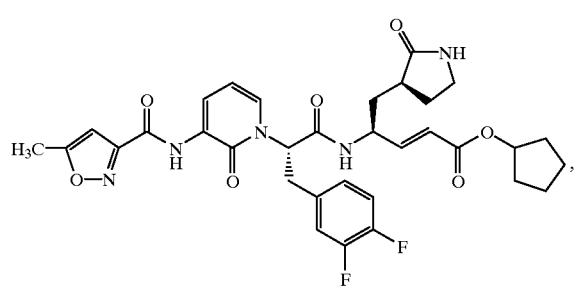
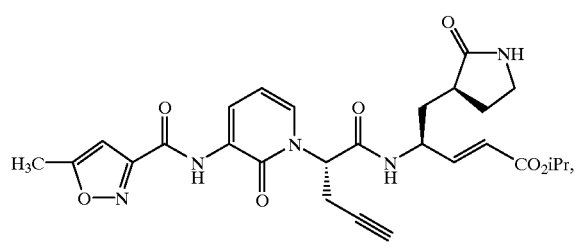
32
-continued
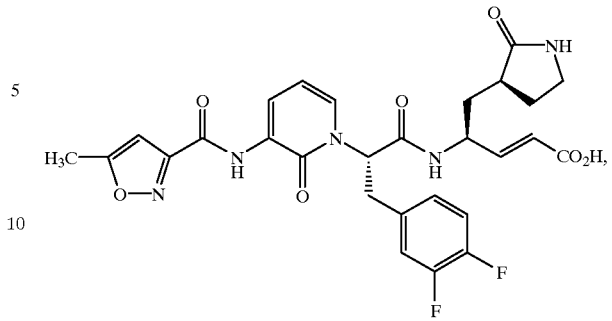
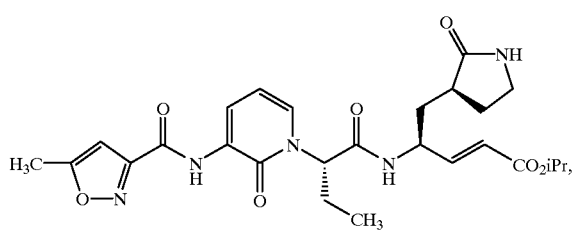
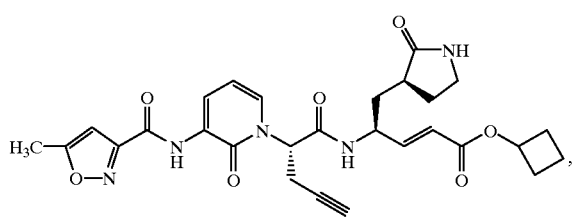
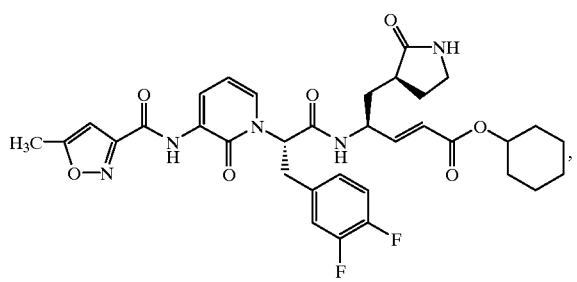
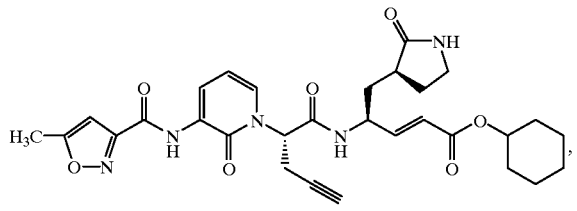
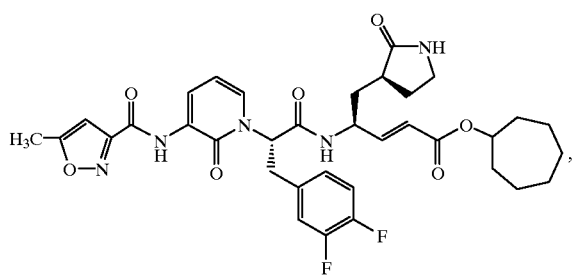

-continued
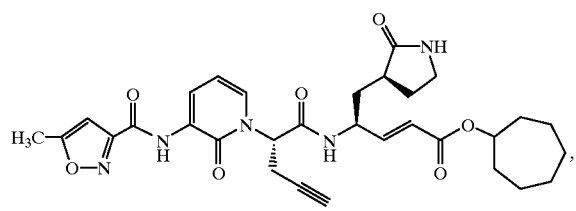
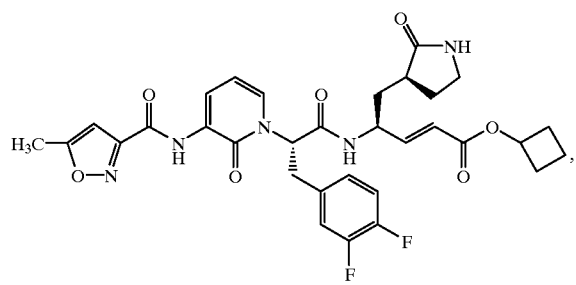
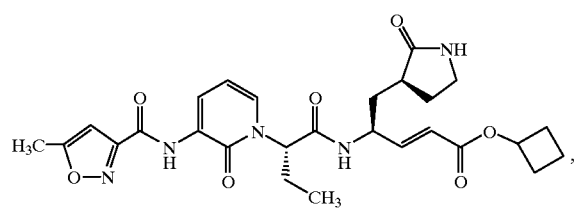
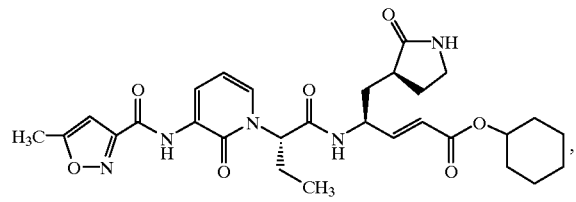
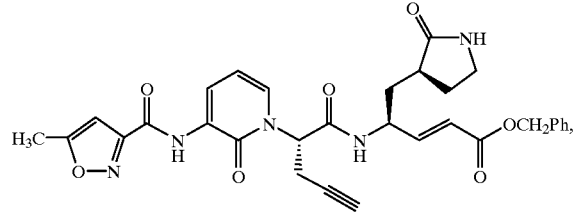
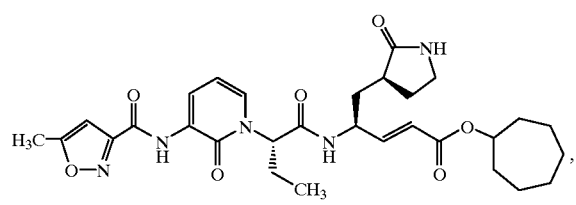
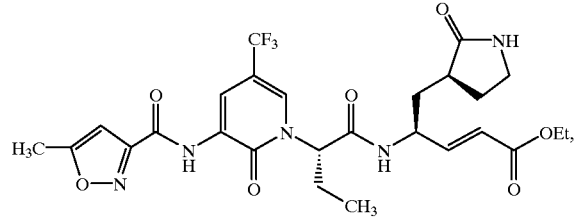
-continued
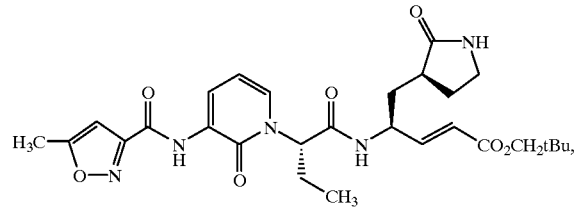
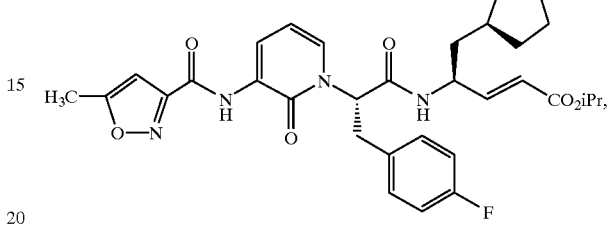
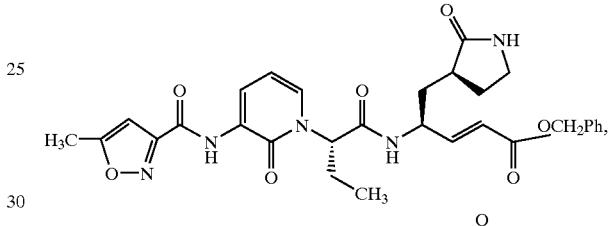
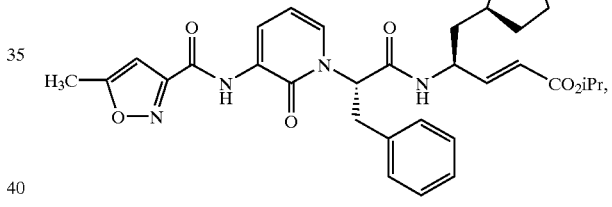
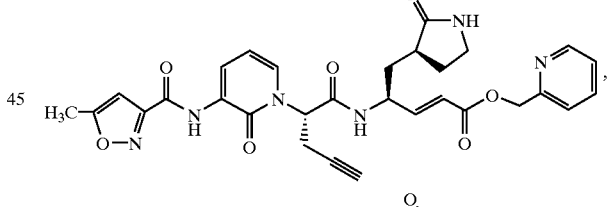
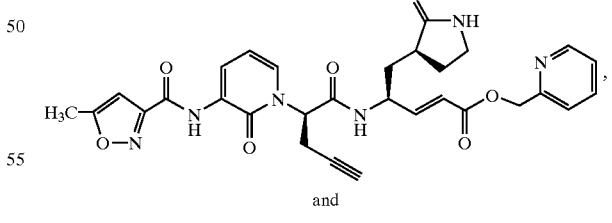
and
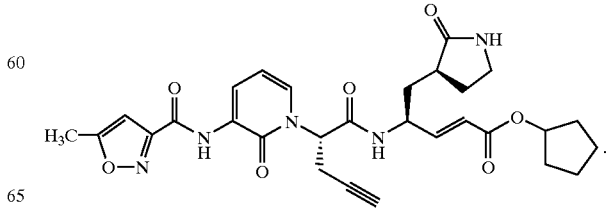

The invention is also directed to the intermediates of Formula II, which are useful in the synthesis of certain compounds of Formula I:

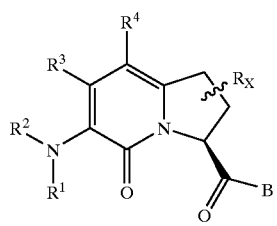

II wherein the variables $R^1$, $R^2$, $R^3$, $R^4$, and $R_x$ are as defined above, and B is H, —$OR^{24}$ When $R^1$ and/or $R^2$ are independently suitable nitrogen protecting groups, any suitable nitrogen-protecting group known in the art may be used (see, e.g., Greene & Wuts, supra). Suitable $R^1$ and $R^2$ substituents include, but are not limited to, carbamate protecting groups such as alkyloxycarbonyl (e.g., Boc) and aryloxycarbonyl (e.g., Cbz or FMOC), alkyloxycarbonyls (e.g., methyloxycarbonyl), alkyl or arylcarbonyl, substituted alkyl, especially arylalkyl (e.g., trityl (triphenylmethyl), benzyl and substituted benzyl) and the like. Preferably, when $R^1$ and $R^2$ are independently suitable nitrogen protecting groups, suitable $R^1$ and $R^2$ substituents include, but are not limited to, Boc, Cbz, FMOC, methyloxycarbonyl and trityl. When $R^1$ and $R^2$ taken together are a suitable nitrogen protecting group, suitable $R^1/R^2$ substituents include phthalimido and a stabase (1,2-bis (dialkylsilyl))ethylene). $R^{24}$ may be H or a suitable protecting group for a carboxyl moiety. Suitable carboxyl protecting groups are also well known in the art, examples of which may be found in Greene and Wuts, supra, and include, but are not limited to, protecting groups where $R^{24}$ is alkyl, substituted or unsubstituted aryl, alkyl and/or aryl substituted silyl (e.g., t-butyldimethylsilyl (TBS)), and the like.

The invention is also directed to pharmaceutically acceptable salts of the compounds of Formula II. Preferred examples of the Formula II useful as intermediates include the following:

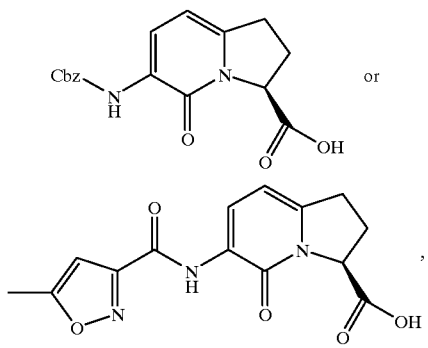

and pharmaceutically acceptable salts thereof.

The antipicornaviral compounds of this invention include prodrugs, the pharmaceutically active metabolites, and the pharmaceutically acceptable salts and solvates thereof. In preferred embodiments, the compounds of Formula I, prodrugs, pharmaceutically acceptable salts, and pharmaceutically active metabolites and solvates thereof have an antipicornaviral activity, more preferably antirhinoviral activity, corresponding to an $EC_{50}$ less than or equal to 100 $\mu$M in the H1-HeLa cell culture assay.

A "prodrug" is intended to mean a compound that is converted under physiological conditions or by solvolysis or metabolically to a specified compound that is pharmaceutically active. A prodrug may be a derivative of one of the compounds of this invention that contains a moiety, such as for example —$CO_2R$, or —$PO(OR)_2$, that may be cleaved under physiological conditions or by solvolysis. Any suitable R substituent may be used that provides a pharmaceutically acceptable solvolysis or cleavage product. A prodrug containing such a moiety may be prepared according to conventional procedures by treatment of a compound of this invention containing, for example, an amido, carboxylic acid, or hydroxyl moiety with a suitable reagent. A "pharmaceutically active metabolite" is intended to mean a pharmacologically active compound produced through metabolism in the body of a specified compound. A "pharmaceutically acceptable salt" is intended to mean a salt that retains the biological effectiveness of the free acids and bases of a specified compound and that is not biologically or otherwise undesirable. Examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methanesulfonates, propanesulfonates, naphthalene-1-sulfonates, naphthalene-2-sulfonates, and mandelates. A "solvate" is intended to mean a pharmaceutically acceptable solvate form of a specified compound that retains the biological effectiveness of such compound. Examples of solvates include compounds of the invention in combination with water, isopropanol, ethanol, methanol, DMSO, ethyl acetate, acetic acid, or ethanolamine. In the case of compounds, salts, or solvates that are solids, it is understood by those skilled in the art that the inventive compounds, salts, and solvates may exist in different crystal forms, all of which are intended to be within the scope of the present invention and specified formulas.

The present invention is also directed to a method of inhibiting picornaviral 3C protease activity, comprising contacting the protease with an effective amount of a compound of Formula I, or a pharmaceutically acceptable salt, prodrug, pharmaceutically active metabolite, or solvate thereof. For example, picornaviral 3C protease activity may be inhibited in mammalian tissue by administering a compound of Formula I or a pharmaceutically acceptable salt, prodrug, pharmaceutically active metabolite, or solvate thereof. More preferably, the present method is directed at inhibiting rhinviral protease activity. "Treating" or "treatment" is intended to mean at least the mitigation of a disease condition in a mammal, such as a human, that is alleviated by the inhibition of the activity of one or more picornaviral 3C proteases, including, but not limited to human rhinoviruses, human poliovirus, human coxsackieviruses, encephalomyocarditis viruses, meningitis virus, and hepatitis A virus. The methods of treatment for mitigation of a disease condition include the use of the compounds in this invention in any conventionally acceptable manner, for example, as a prophylactic. The activity of the inventive compounds as inhibitors of picornaviral 3C protease activity may be measured by any of the suitable methods known to those skilled in the art, including in vivo and in vitro assays. An example of a suitable assay for activity measurements is the antiviral H1-HeLa cell culture assay described herein.

Administration of the compounds of the Formula I and their pharmaceutically acceptable prodrugs, salts, active metabolites, and solvates may be performed according to any of the generally accepted modes of administration available to those skilled in the art. Illustrative examples of suitable modes of administration include oral, nasal, parenteral, topical, transdermal, and rectal.

An inventive compound of Formula I or a pharmaceutically acceptable salt, prodrug, active metabolite, or solvate thereof may be administered as a pharmaceutical composition in any pharmaceutical form recognizable to the skilled artisan as being suitable. Suitable pharmaceutical forms include solid, semisolid, liquid, or lyophilized formulations, such as tablets, powders, capsules, suppositories, suspensions, liposomes, and aerosols. Pharmaceutical compositions of the invention may also include suitable excipients, diluents, vehicles, and carriers, as well as other pharmaceutically active agents, depending upon the intended use or mode of administration. In preferred embodiments, the inventive pharmaceutical compositions are delivered orally, or intranasally in the form of suspensions. Acceptable methods of preparing suitable pharmaceutical forms of the pharmaceutical compositions may be routinely determined by those skilled in the art. For example, pharmaceutical preparations may be prepared following conventional techniques of the pharmaceutical chemist involving steps such as mixing, granulating, and compressing when necessary for tablet forms, or mixing, filling, and dissolving the ingredients as appropriate, to give the desired products for oral, parenteral, topical, intravaginal, intranasal, intrabronchial, intraocular, intraaural, and/or rectal administration.

Solid or liquid pharmaceutically acceptable carriers, diluents, vehicles, or excipients may be employed in the pharmaceutical compositions. Illustrative solid carriers include starch, lactose, calcium sulfate dihydrate, terra alba, sucrose, talc, gelatin, pectin, acacia, magnesium stearate, and stearic acid. Illustrative liquid carriers include syrup, peanut oil, olive oil, saline solution, and water. The carrier or diluent may include a suitable prolonged-release material, such as glyceryl monostearate or glyceryl distearate, alone or with a wax. When a liquid carrier is used, the preparation may be in the form of a syrup, elixir, emulsion, soft gelatin capsule, sterile injectable liquid (e.g., solution), or a nonaqueous or aqueous liquid suspension. A dose of the pharmaceutical composition contains at least a therapeutically effective amount of the active compound (i.e., a compound of Formula I or a pharmaceutically acceptable salt, prodrug, active metabolite, or solvate thereof), and preferably is made up of one or more pharmaceutical dosage units. The selected dose may be administered to a mammal, for example, a human patient, in need of treatment mediated by inhibition of picornaviral 3C protease activity, by any known or suitable method of administering the dose, including: topically, for example, as an ointment or cream; orally; rectally, for example, as a suppository; parenterally by injection; or continuously by intravaginal, intranasal, intrabronchial, intraaural, or intraocular infusion. A "therapeutically effective amount" is intended to mean the amount of an inventive agent that, when administered to a mammal in need thereof, is sufficient to effect treatment for disease conditions alleviated by the inhibition of the activity of one or more picornaviral 3C proteases, such as human rhinoviruses, human poliovirus, human coxsackieviruses, encephalomyocarditis viruses, menigovirus, and hepatitis A virus. The amount of a given compound of the invention that will be therapeutically effective will vary depending upon factors such as the particular compound, the disease condition and the severity thereof, the identity of the mammal in need thereof, which amount may be routinely determined by artisans.

GENERAL SYNTHETIC METHODS

Preferably, the inventive compounds of Formulas I and II are prepared by the methods of the present invention, including the General Methods shown below. When stereochemistry is not specified in chemical structures, either stereocenter may be utilized. Although several intermediates are described and depicted as 2-hydroxypyridines, it is understood that such entities may also exist as the corresponding 2-pyridone tautomers. The following abbreviations also apply: Boc (tert-butoxycarbonyl), Ac (acetyl), Cbz (benzyloxycarbonyl), DMB (2,4-dimethoxybenzyl), TBS (tert-butyldimethylsilyl), TBDPS (tert-butyldiphenylsilyl), Ms (methanesulfonate), Ts (toluenesulfonate), Bn (benzyl), and Tr (triphenylmethyl).

General Method 1

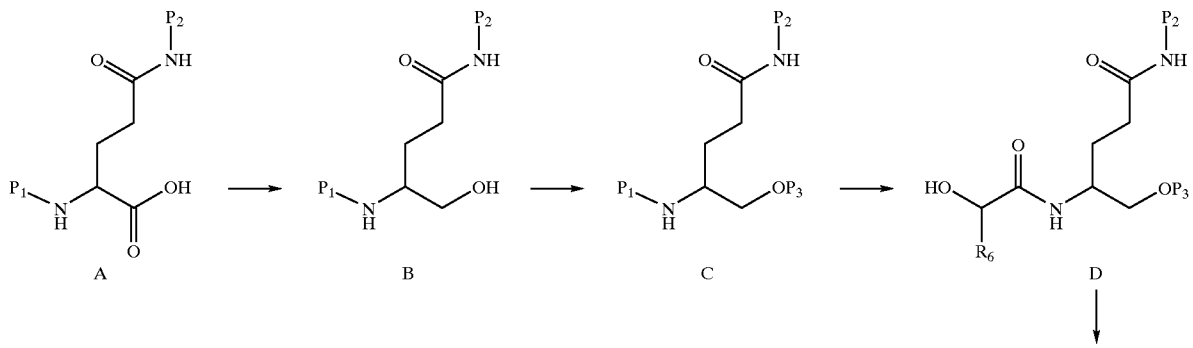

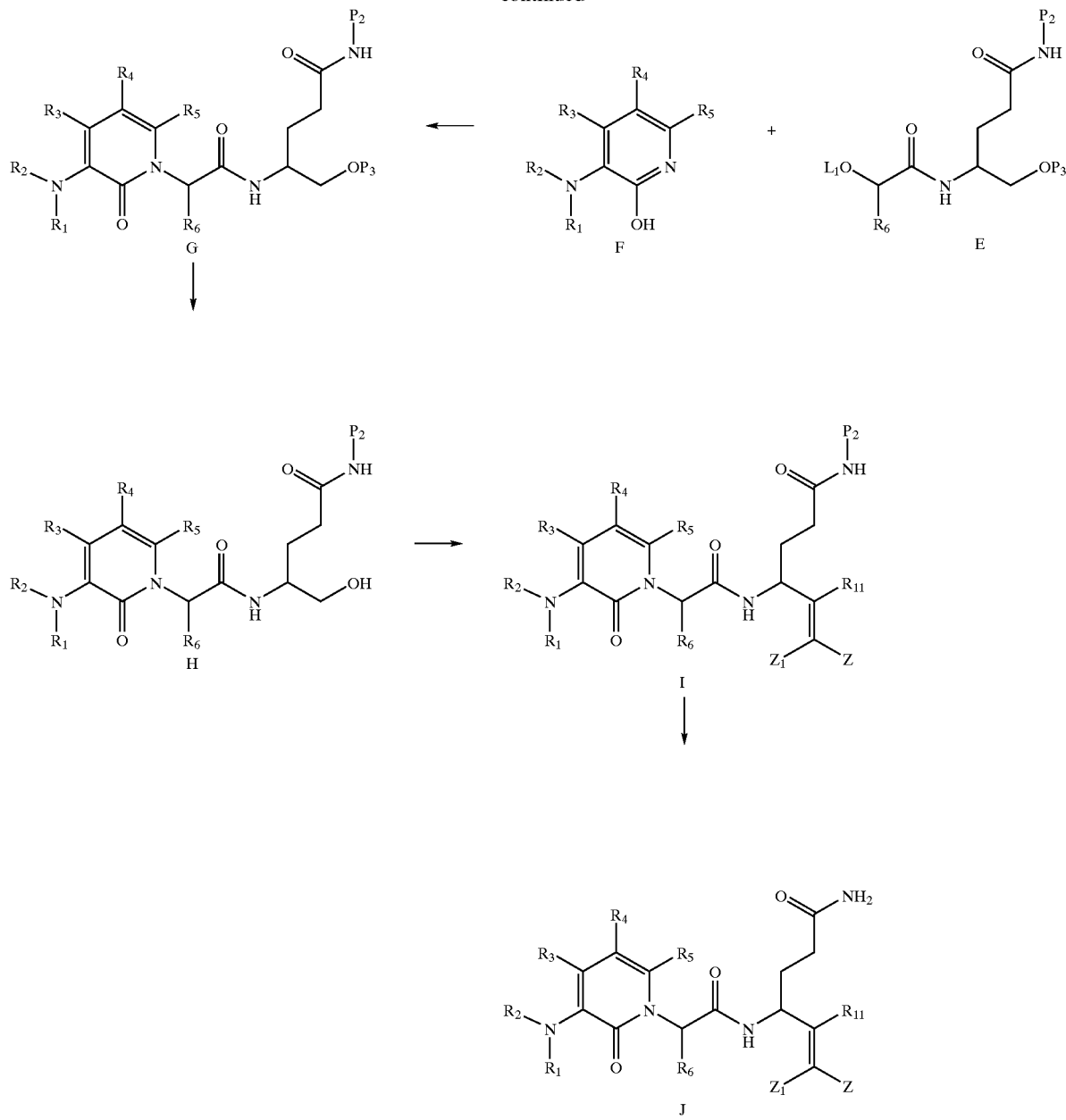

In General Method 1, an amino acid A (commercially available or prepared by methods described in the chemical literature) where $P_1$ is an appropriate protecting group for the amine functionality (e.g, Cbz, Boc, or Ac), and $P_2$ is an appropriate protecting group for the amide nitrogen (e.g, Tr), is reductively transformed into alcohol B. Compound B is subsequently converted to compound C where $P_3$ is an appropriate protecting group for the alcohol functionality (e.g., TBS). At this point, the $P_1$ protecting group present in C is removed and the resulting amine or salt thereof (not shown) is subjected to an amide bond forming reaction with an appropriate α-hydroxycarboxylic acid (which incorporates $R_6$ and in which $R_7$ is H; also not shown) to provide imtermediate D. The alcohol functionality present in D is then converted to an appropriate leaving group (e.g., mesylate, tosylate) E and is coupled with 2-hydroxypyridine F (which incorporates $R_1$, $R_2$, $R_3$, $R_4$, and $R_5$) to give intermediate G. Note that the $R_1$ and $R_2$ moieties present in F may be an appropriate protecting groups for the amine functionality. The $P_3$ protecting group is subsequently removed from G and the resulting alcohol (H) is oxidized to the corresponding aldehyde (not shown) and subjected to an olefin-forming reaction to afford intermediate I (which incorporates $R_{11}$, Z, and $Z_1$). The $P_2$ protecting group present in I is then removed to give product J. If $R_1$ and/or $R_2$ is/are initially a protecting group for the amine functionality, it/they may be removed from intermediates G, H, or I or product J and replaced with a different $R_1$ and/or $R_2$ substituent to afford alternate intermediates G, H, or I or products J.

General Method 2

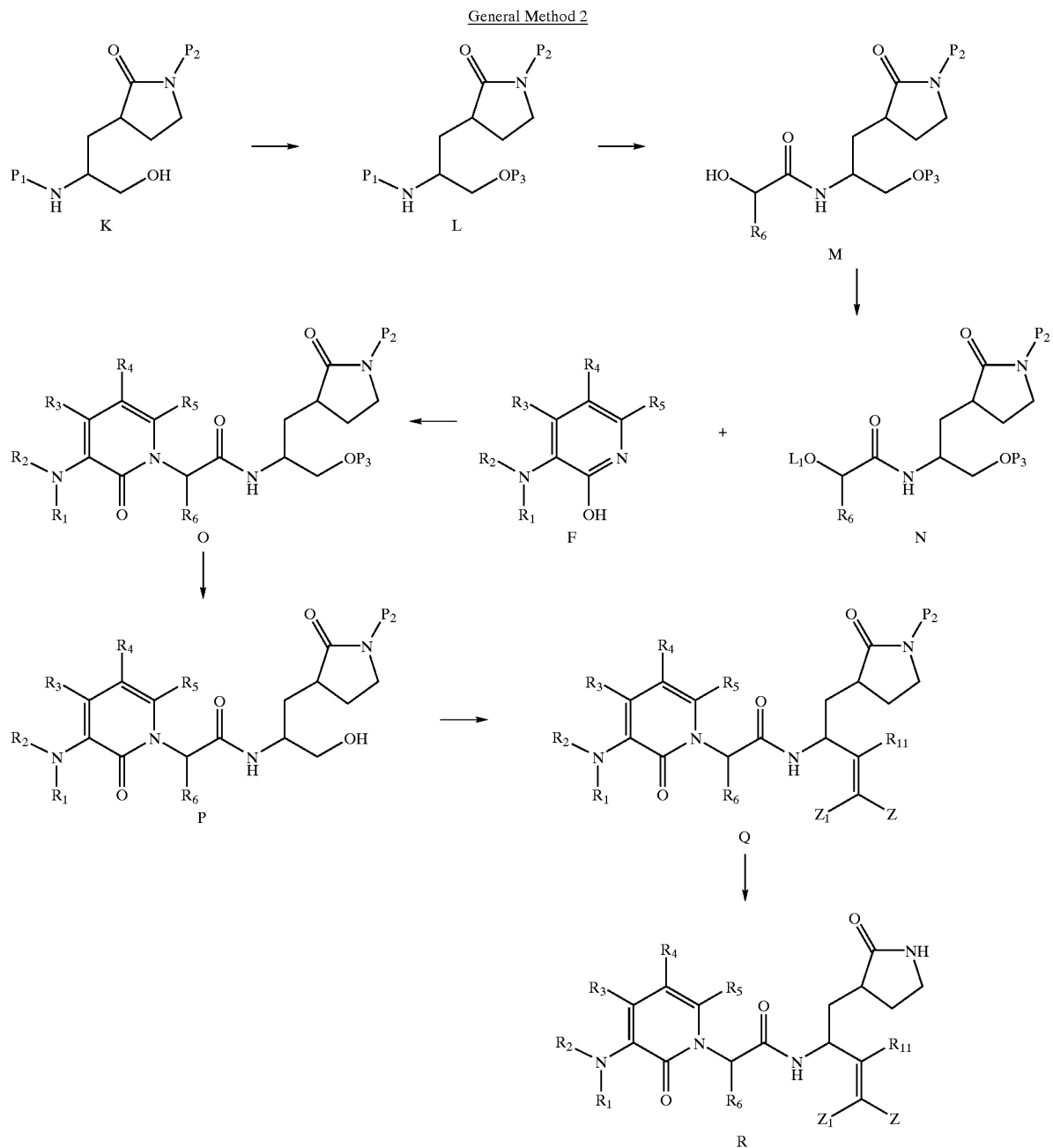

In General Method 2, amino alcohol K (prepared by methods described in the chemical literature), which incorporates $R_9$ and in which $R_{10}$ is H, $P_1$ is an appropriate protecting group for amine functionality (e.g, Cbz, Boc, or Ac), and $P_2$ is an appropriate protecting group for the amide nitrogen (e.g. DMB), is converted to compound L where $P_3$ is an appropriate protecting group for the alcohol functionality (e.g., TBDPS). The $P_1$ protecting group present in L is then removed and the resulting amine or salt thereof (not shown) is subjected to an amide bond forming reaction with an appropriate α-hydroxycarboxylic acid (which incorporates $R_6$ and in which $R_7$ is H; also not shown) to provide intermediate M. The alcohol functionality present in M is then converted to an appropriate leaving group (e.g., mesylate, tosylate) N and is coupled with 2-hydroxypyridine F (which incorporates $R_1$, $R_2$, $R_3$, $R_4$, and $R_5$) to give intermediate O. Note that the $R_1$ and $R_2$ moieties present in F may be an appropriate protecting group for the amine functionality. The $P_3$ protecting group is subsequently removed from O and the resulting alcohol (P) is oxidized to the corresponding aldehyde (not shown) and subjected to an olefin-forming reaction to afford intermediate Q (which incorporates $R_{11}$, Z, and $Z_1$). The $P_2$ protecting group present in Q is then removed to give product R. If $R_1$ and/or $R_2$ is/are initially a protecting group for the amine functionality, it/they may be removed from intermediates O, P, or Q or product R and replaced with a different $R_1$ and/or $R_2$ substituent to afford alternate intermediates O, P, or Q or products R.

General Method 3
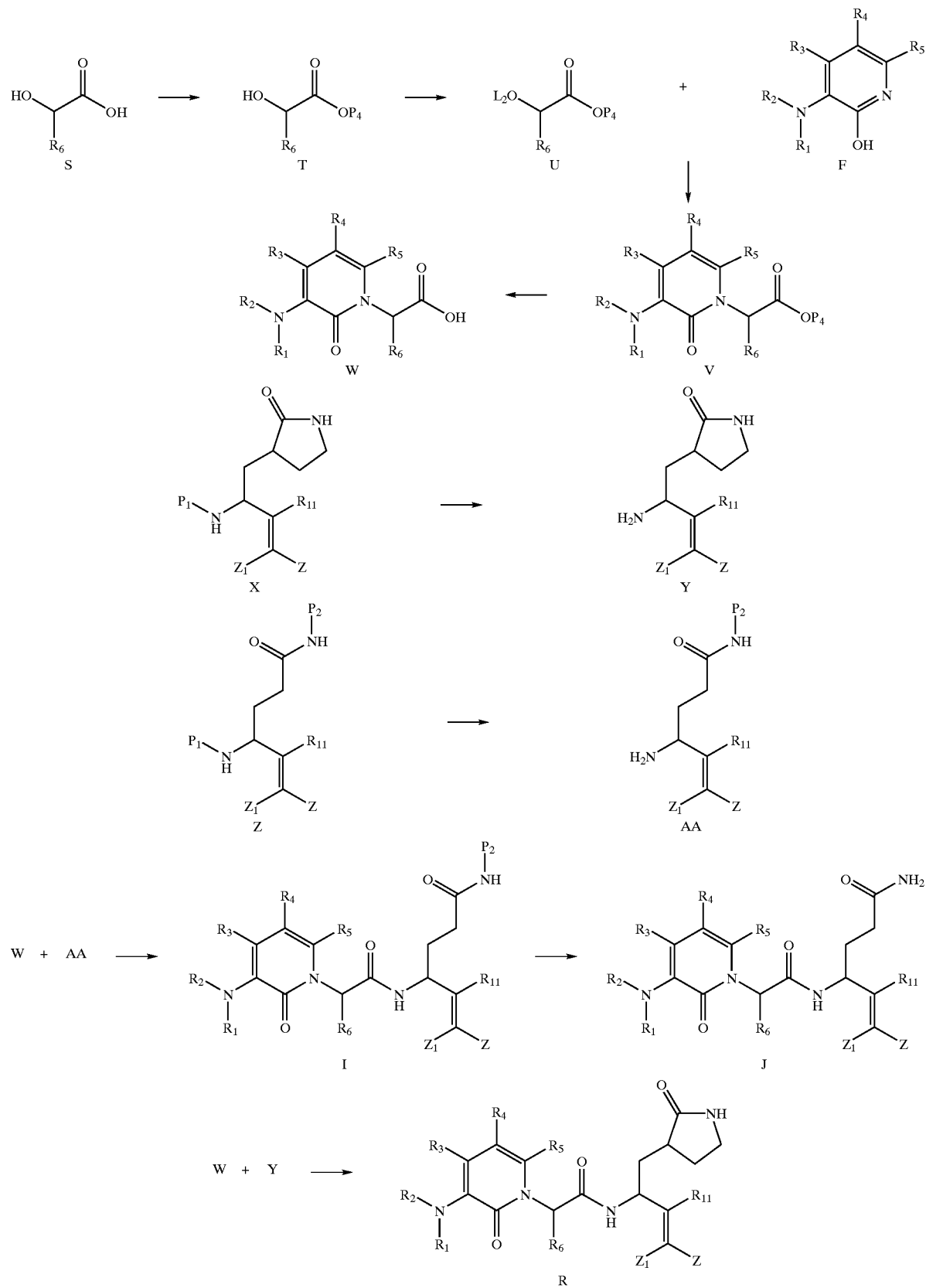

An alternate method for preparing either product J or product R is illustrated in General Method 3. An α-hydroxycarboxylic acid S (either commercially available or prepared by methods described in the chemical literature) which incorporates $R_6$ and in which $R_7$ is H is converted to α-hydroxyester T where $P_4$ is an appropriate protecting group for the carboxylic acid functional group (e.g, methyl, benzyl, or tert-butyl). The alcohol functionality present in T is then converted to an appropriate leaving group (e.g., mesylate, tosylate, triflate) U and is coupled with 2-hydroxypyridine F (which incorporates $R_1$, $R_2$, $R_3$, $R_4$, and $R_5$) to give intermediate V. Note that the $R_1$ and $R_2$ moieties present in F may be an appropriate protecting group for the amine functionality. The $P_4$ protecting group is subsequently removed from V to afford carboxylic acid W.

Independently, intermediates X and Z (prepared by methods described in the chemical literature) which incorporate $R_{11}$, Z, and $Z_1$ and in which $P_1$ is an appropriate protecting group for the amine functionality (e.g., Cbz, Boc, or Ac) and $P_2$ is an appropriate protecting group for the amide nitrogen (e.g., Tr), are converted to their corresponding amines Y and AA (or salts thereof), respectively. Amines AA and Y are then independently coupled with carboxylic acid W to afford intermediate I and product R, respectively. The $P_2$ protecting group present in intermediate I is subsequently removed to afford product J. Note that, although not depicted in General Method 3, the lactam nitrogen present in intermediate X may be protected with a suitable protecting group (e.g., DMB). If such a moiety is present in X, it may be removed after coupling of W with Y to afford product R.

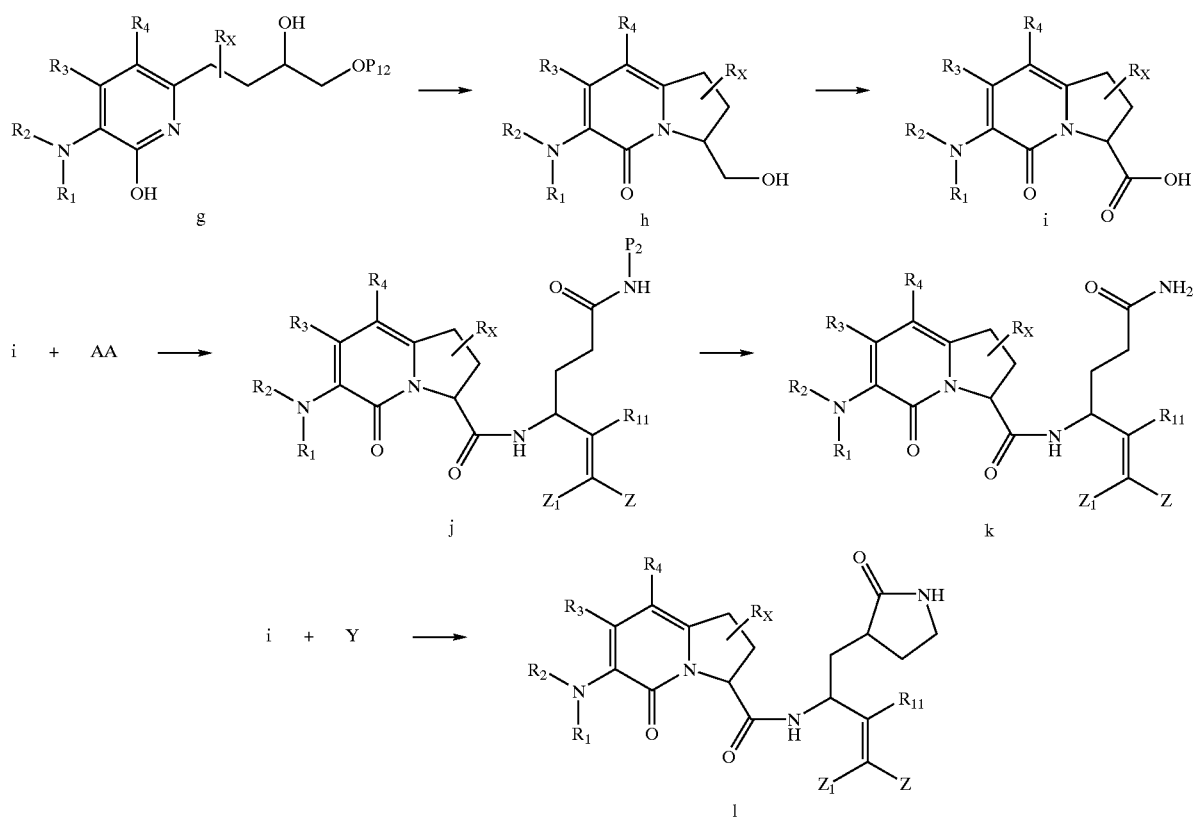

General Method 4

A method for preparing bicyclic products k and l is illustrated in General Method 4. Thus, an appropriate pyridine g (which incorporates $R_1$, $R_2$, $R_3$, and $R_4$, and which may be optionally substituted with $R_x$ as shown) (an example of which may prepared as described in Specific Method 7 below) in which $P_{11}$ and $P_{12}$ are protecting groups for the alcohol functionality (e.g., silyl ether, methyl) is subjected to an intramolecular cyclization/deprotection protocol in which both $P_{11}$ and $P_{12}$ are removed to give pyridone h. Note that the $R_1$ and $R_2$ moieties present in g may be an appropriate protecting group for the amine functionality (e.g., Cbz). The alcohol moiety present in h is then oxidized to the corresponding carboxylic acid i. This oxidation may be accomplished via an aldehyde intermediate (not shown). Carboxylic acid i is then independently coupled with amines AA and Y (or salts thereof) (prepared as described in General Method 3 above) to afford intermediate j and product l, respectively. The $P_2$ protecting group present in intermediate j is subsequently removed to afford product k. Note that, although not depicted in General Method 4, the lactam nitrogen present in intermediate Y may be protected with a suitable protecting group (e.g., DMB). If such a moiety is present in Y, it may be removed after coupling of i with Y to afford product l. In addition, if $R_1$ and/or $R_2$ is/are initially a protecting group for the amine functionality, it/they may be removed from intermediates g, h, i, or j or products k or l and replaced with a different $R_1$ and/or $R_2$ substituent to afford alternate intermediates g, h, i, or j or products k or l.

in Org. Lett. 1999, 1, 83) in which $R_x$ is/are H and $P_{13}$ is an appropriate protecting group for the carboxylic acid functionality (e.g., methyl, ethyl, benzyl, or tert-butyl ester) is transformed into diazo compound n. This intermediate is subjected to a rhodium-catalyzed cyclization reaction involving phenylvinyl sulfone to give intermediate o (in which $R_3$ is H). The hydroxyl group present in o is converted to the corresponding trifluoromethane sulfonate (OTf) p, and this intermediate is further transformed to the amine r via imine q. The amine present in r is derivatized with an appropriate moiety to afford intermediate s (which contains the $R_2$ functional group and in which $R_1$ is H). Intermediate s is subjected to a desulfurization reaction to give intermediate t and this entity is deprotected to give carboxylic acid i (in which $R_1$, $R_3$, $R_4$, and $R_x$ are H). Alternatively,

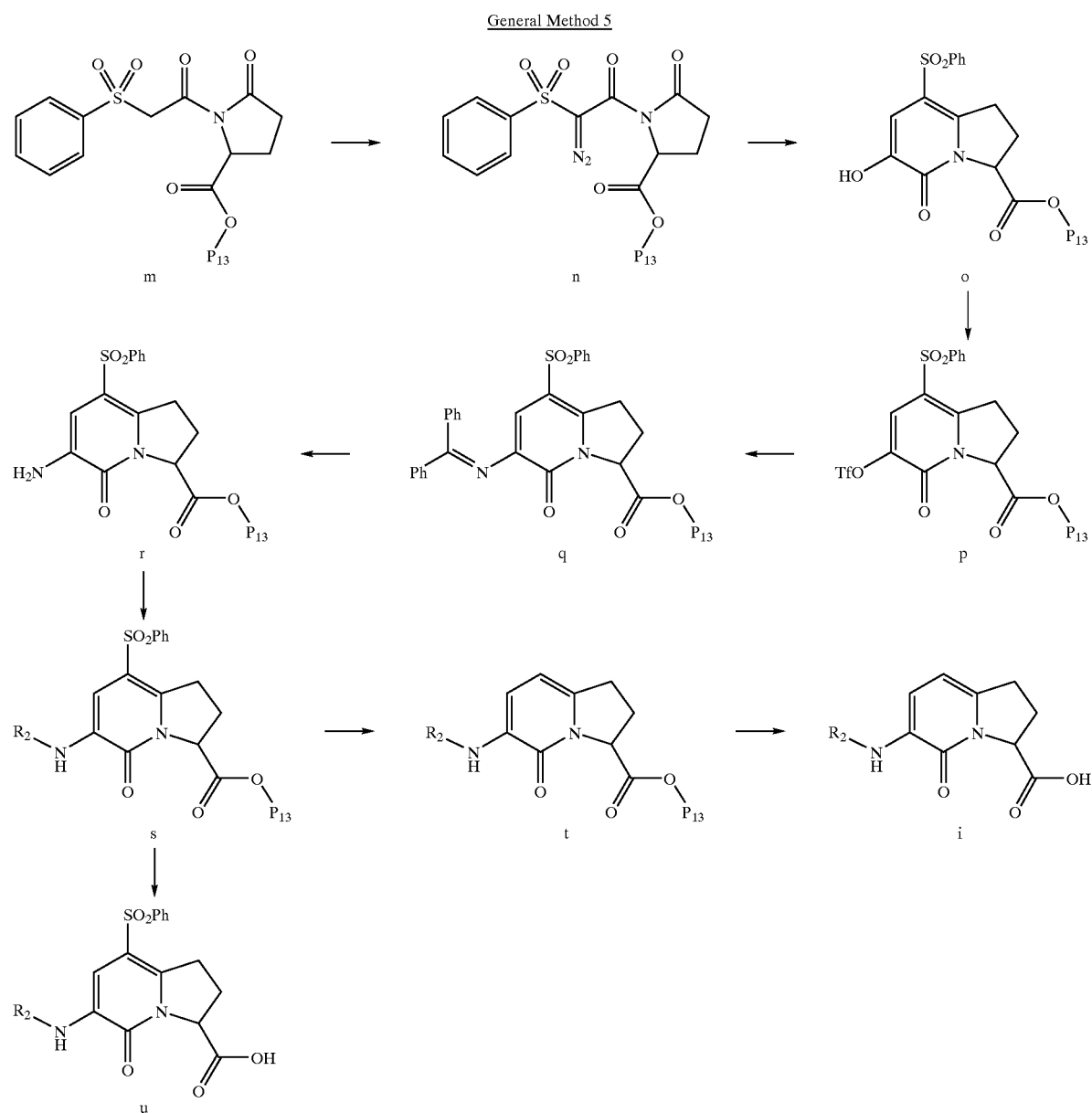

General Method 5

An alternate method for preparing a particular type of intermediate is illustrated in General Method 5. Thus, the sulfone m (which may be prepared by the method described in intermediate s may be deprotected to give carboxylic acid u (in which $R_1$, $R_3$, and $R_x$ are H) which may be utilized in place of i in General Method 4 above.

General Method 6

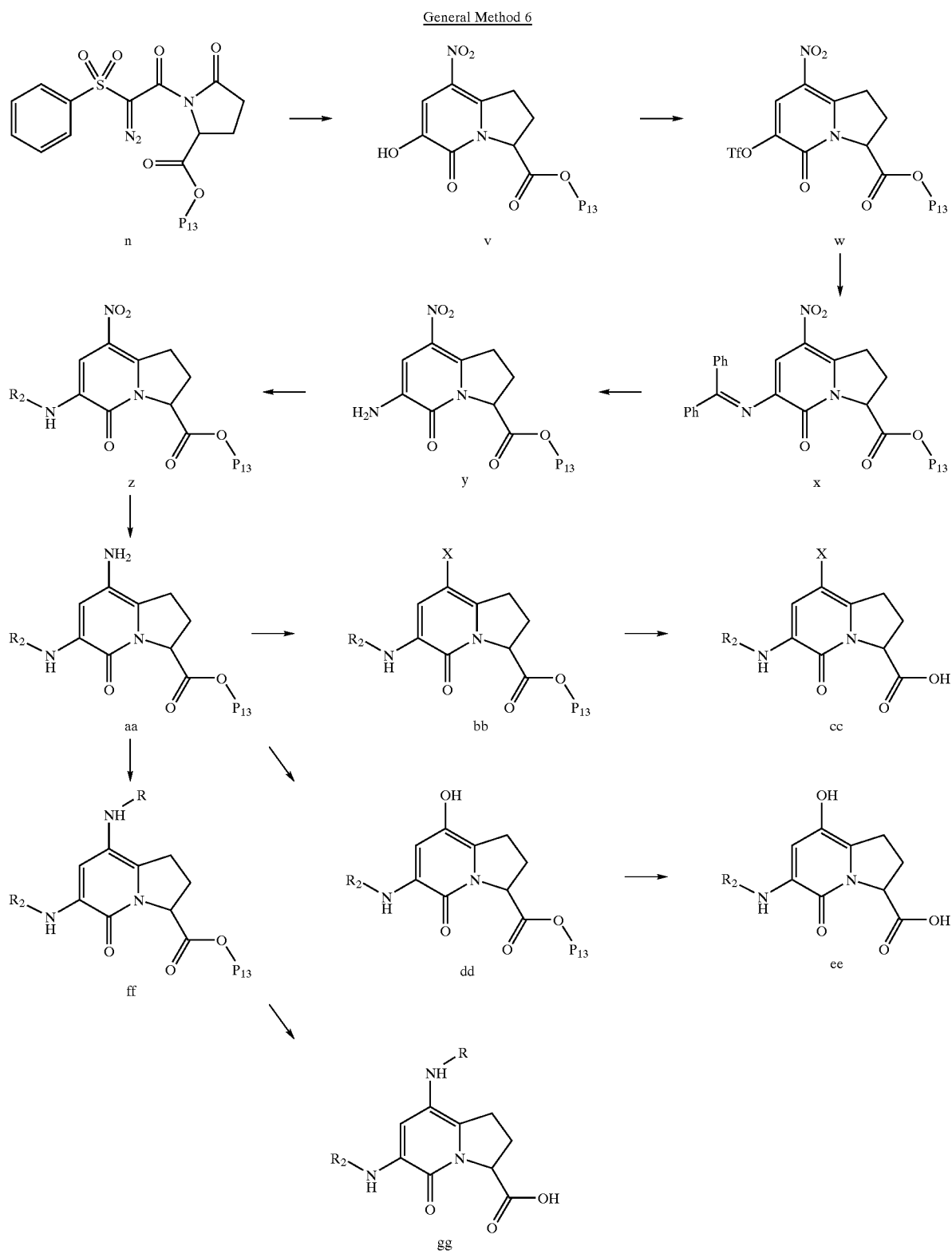

An additional method for preparing intermediates related to i is illustrated in General Method 6. Thus, the diazo compound n (prepared in General Method 5 above) in which $R_x$ is/are H and in which $P_{13}$ is an appropriate protecting group for the carboxylic acid functionality (e.g., methyl, ethyl, benzyl, or tert-butyl ester) is subjected to a rhodium-catalyzed cyclization reaction involving nitroethylene to give intermediate v (in which $R_3$ is H). The hydroxyl group present in v is converted to the corresponding trifluoromethane sulfonate (OTf) w, and this intermediate is further transformed to the amine y via imine x. The amine present in y is derivatized with an appropriate moiety to afford intermediate z (which contains the $R_2$ functional group and in which $R_1$ is H). Intermediate z is reduced to give intermediate aa and this entity is transformed to intermediate bb in which X is a halogen. Intermediate bb is subsequently deprotected to give carboxylic acid cc. If desired, intermediate aa may also be transformed into intermediate t (General Method 5 above). Alternatively, intermediate aa is transformed to intermediate dd which is subsequently deprotected to give carboxylic acid ee. Alternatively, intermediate aa is transformed to intermediate ff in which R is alkyl, acyl, sulfonyl, or acyloxy. Intermediate ff is subsequently deprotected to give carboxylic acid gg. Carboxylic acids cc, ee, and gg may each be utilized in place of i in General Method 4 above.

trifluoromethane sulfonate (OTf) ii, and this intermediate is further transformed to the amine kk via imine jj. The amine present in kk is derivatized with an appropriate moiety to afford intermediate ll (which contains the $R_2$ functional group and in which $R_1$ is H). Intermediate ll is subsequently deprotected to give carboxylic acid mm which may be utilized in place of i in General Method 4 above. At any point in the above sequence, if $Z_2$ is alkoxy or benzyloxy it may be replaced with a hydroxyl functionality. The resulting carboxylic acid may subsequently be rearranged to the corresponding amine using established methods and the amine-containing intermediates may be utilized as depicted in General Method 6. For example, intermediate ll (when $Z_2$ is OH) may be rearranged to intermediate aa (General Method 6).

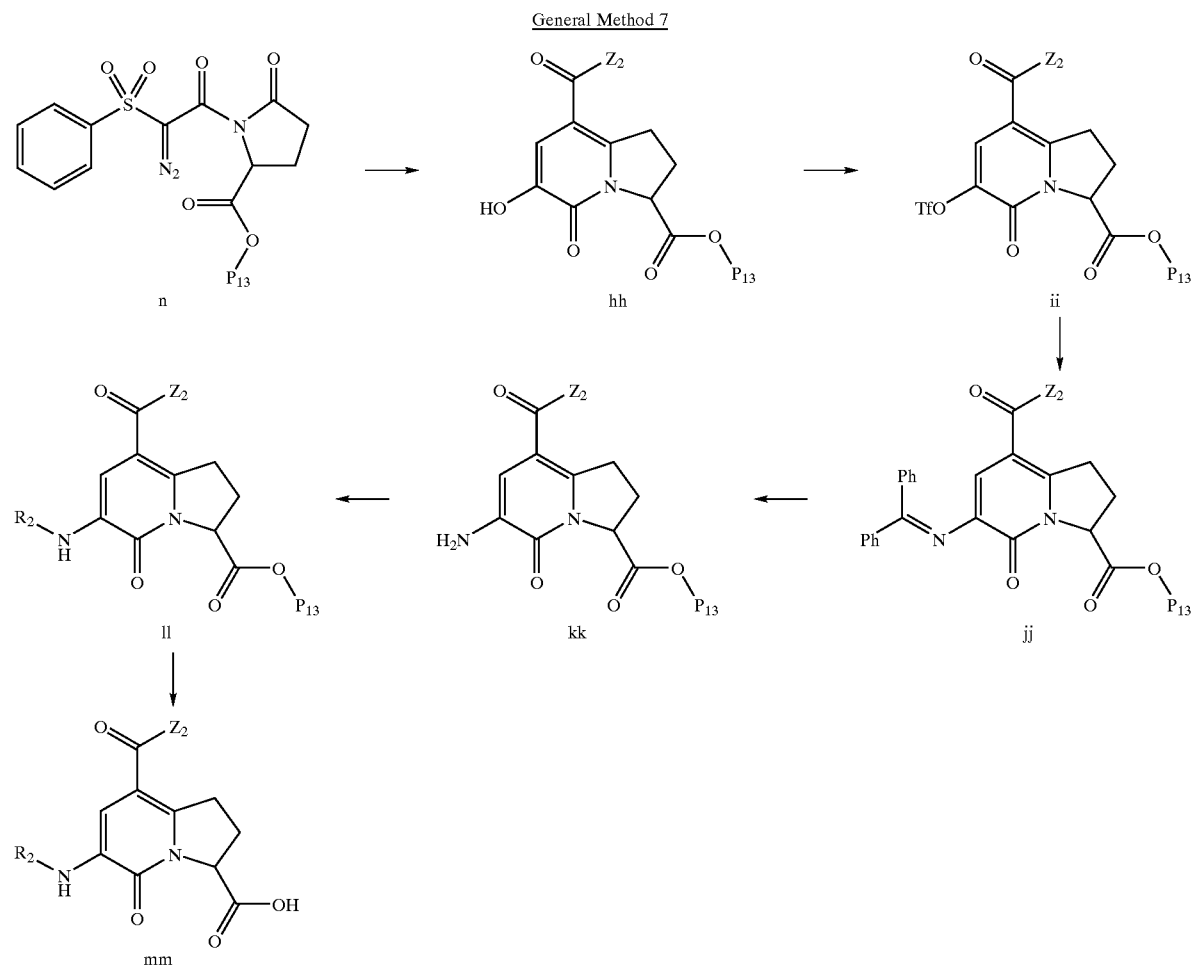

An additional method for preparing intermediates related to i is illustrated in General Method 7. Thus, the diazo compound n (prepared in General Method 5 above) in which $R_x$ is/are H and in which $P_{13}$ is an appropriate protecting group for the carboxylic acid functionality (e.g., methyl, ethyl, benzyl, or tert-butyl ester) is subjected to a rhodium-catalyzed cyclization reaction involving acrylate esters or vinyl ketones to give intermediate hh (in which $R_3$ is H and $Z_2$ is alkyl, aryl, alkoxy, and benzyloxy). The hydroxyl group present in hh is converted to the corresponding General Method 8

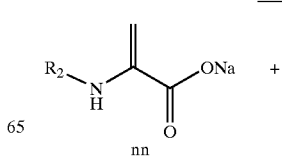

53
-continued

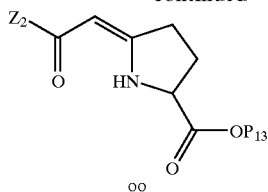
oo

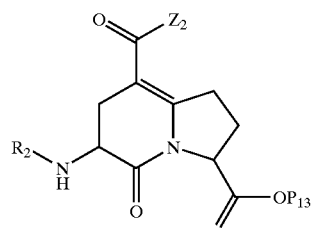
pp

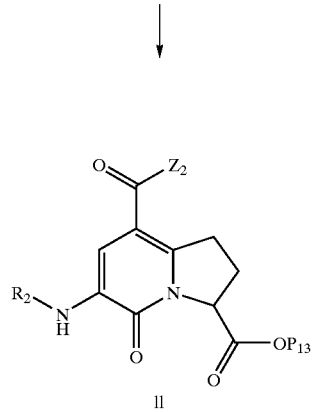
ll

Yet another method for preparing intermediate ll is depicted in General Method 8. Thus the sodium salt of α-dehydroalanine derivative nn (which incorporates $R_2$ and in which $R_1$ is H) (which is either commercially available or may be prepared from serine by a variety of literature techniques) is condensed with intermediate oo (which may be prepared as described in *Tetrahedron Lett.* 1989, 30, 3621) in which $R_x$ is/are H and $P_{13}$ is an appropriate protecting group for the carboxylic acid functionality (e.g., methyl, ethyl, benzyl, or tert-butyl ester) and in which $Z_2$ is alkyl, aryl, alkoxy, or benzyloxy to give intermediate pp. Intermediate pp is subsequently oxidized (by a variety of literature methods) to afford intermediate ll which may be utilized as described above in General Method 7.

General Method 9

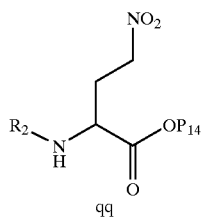 + 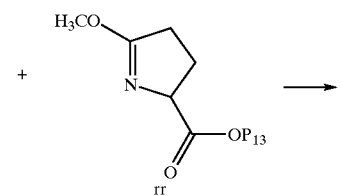
qq                    rr

54
-continued

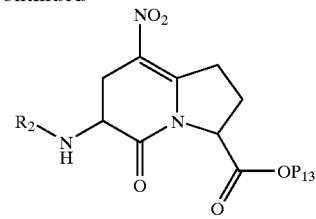
ss

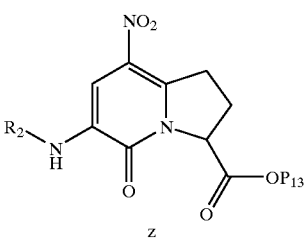
z

An alternate method for preparing intermediate z (from General Method 6 above) is depicted in General Method 9. Thus the nitro compound qq (prepared by analogy with the method described in: *J. Chem. Soc., Perkin Trans.* 1 1998, 1113) which incorporates $R_2$ and in which $R_1$ is H and $P_{14}$ is a suitable protecting group for the carboxylic acid functionality (e.g., methyl or ethyl) is condensed with intermediate rr (prepared according to: *J. Heterocyclic Chem.* 1992, 29, 1285) in which $R_x$ is/are H and $P_{13}$ is a suitable protecting group for the carboxylic acid functionality (e.g., methyl, ethyl, benzyl, or tert-butyl) to give intermediate ss. Intermediate ss is subsequently oxidized (by a variety of literature methods) to afford intermediate z which may be utilized as described above in General Method 6.

General Method 10

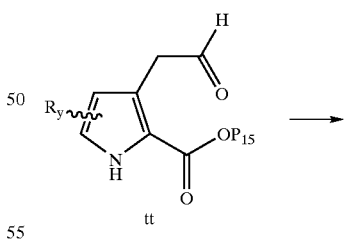
tt

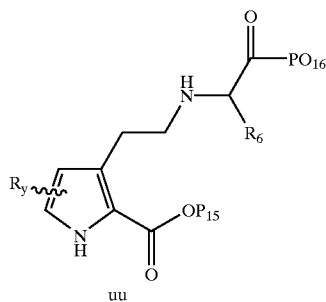
uu

General Method 10 depicts the preparation of the bicyclic pyrrole vv, starting with aldehyde tt, prepared according to the procedure described in Smith, K. M., *J. Chem. Soc.,* *Perkin Trans. I,* 1973, p. 516. This compound is subjected to reductive amination conditions with an amine to give compound uu. The carboxylic acid protecting group $P_{16}$ is removed, and the resulting acid is condensed intramolecularly with the secondary amine to give bicycle vv. This bicyclic compound may be coupled to amine Y or AA according to the method described in General Method 3.

SPECIFIC METHODS

The following Specific Methods may also be utilized to prepare some of the compounds described in this invention.

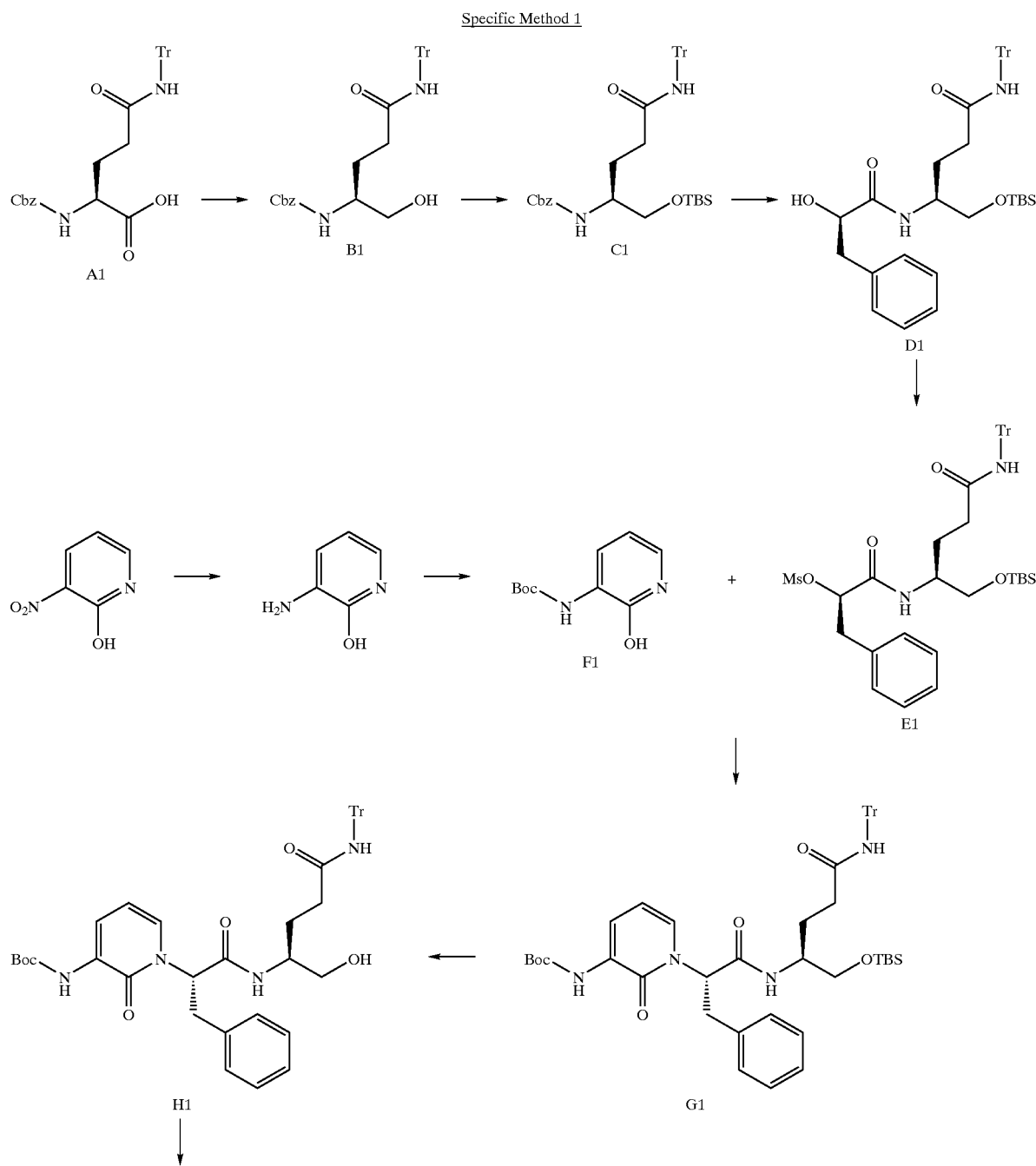

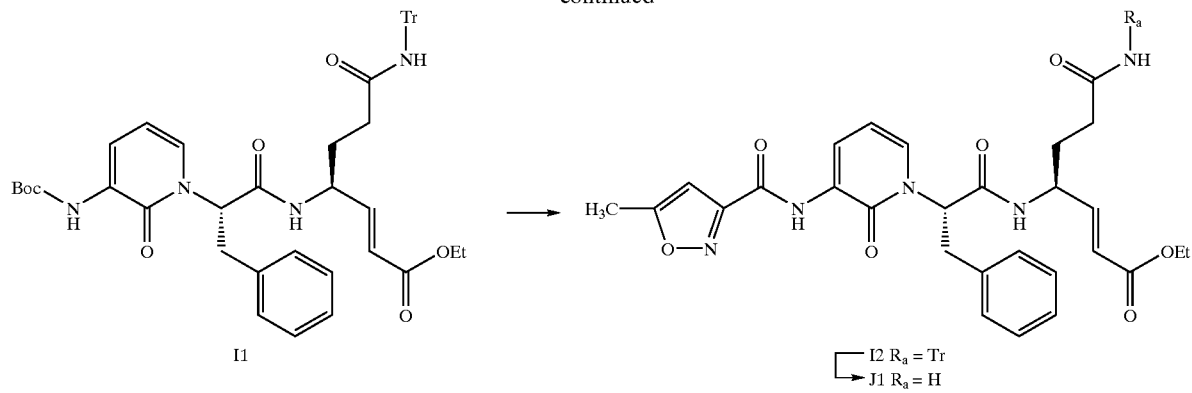

Specific Method 1 describes the preparation of specific compound J1 (compound 5). Thus, commercially available amino acid A1 was reduced to alcohol B1 which, in turn, was transformed into compound C1. The Cbz moiety present in C1 was removed by hydrogenation and the resulting amine (not shown) was coupled with D-3-phenyllactic acid (commercially available) to afford intermediate D1. This latter entity was subsequently transformed to the corresponding methanesulfonate (mesylate) (E1) and was coupled with the sodium salt of 2-hydroxypyridine F1 to provide intermediate G1. The 2-hydroxypyridine F1 was prepared from commercially available 2-hydroxy-3-nitropyridine by reduction and subsequent Boc protection of the resulting amine. The silyl protecting group present in G1 was removed and the alcohol thus obtained (H1) was oxidized to the corresponding aldehyde (not shown) and subjected to an olefin-forming reaction to give intermediate I1. The Boc moiety contained in I1 was then thermally deprotected and the resulting amine (not shown) was derivatized with commercially available 5-methylisoxazole-3-carbonyl chloride to give intermediate I2. The trityl protecting group present in I2 was subsequently removed under acidic conditions to complete the preparation of specific compound J1 (compound 5).

Specific Method 2

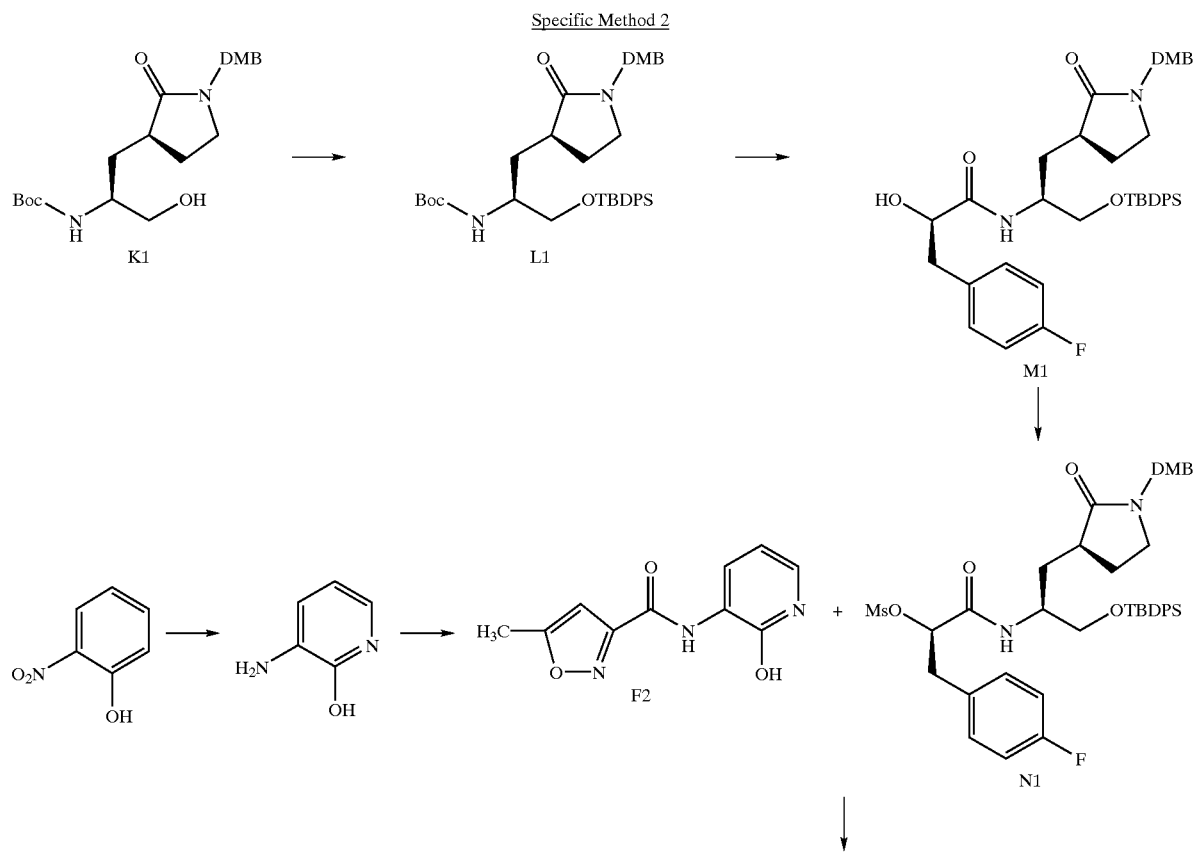

-continued

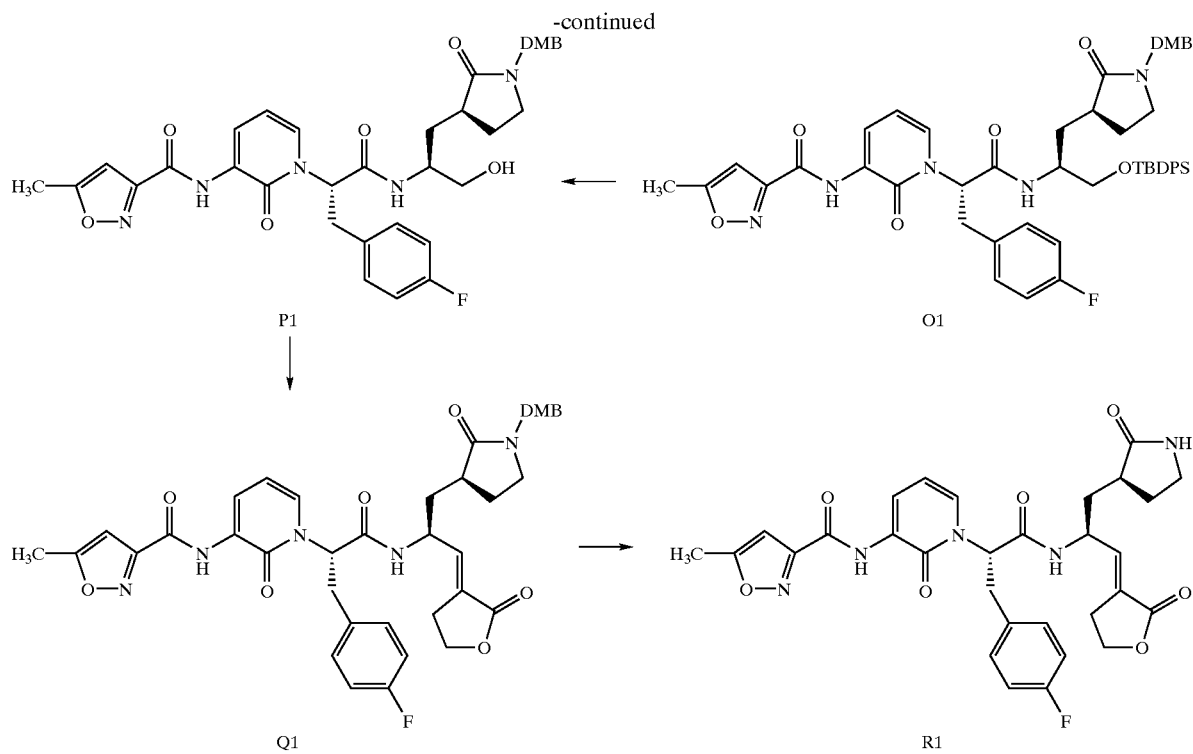

Specific Method 2 describes the preparation of specific compound R1 (compound 20). Thus, alcohol K1 (prepared as described in Dragovich, et al., *J. Med Chem.* 1999, 42, 1213) was protected to give intermediate L1. The Boc protecting group present in L1 was removed under acidic conditions and the resulting amine salt (not shown) was coupled with (2R)-3-(4'-fluorophenyl)-2-hydroxypropionic acid (S1, prepared as described in Specific Method 3 below) to afford intermediate M1. This latter entity was subsequently transformed to the corresponding methanesulfonate (mesylate) (N1) and was coupled with the sodium salt of 2-hydroxypyridine F2 to provide intermediate O1. The 2-hydroxypyridine F2 was prepared from commercially available 2-hydroxy-3-nitropyridine by reduction and subsequent derivatization of the resulting amine with commercially available 5-methylisoxazole-3-carbonyl chloride. The silyl protecting group present in O1 was removed and the alcohol thus obtained (P1) was oxidized to the corresponding aldehyde (not shown) and subjected to an olefin-forming reaction to give intermediate Q1. The DMB moiety contained in Q1 was then deprotected to complete the preparation of specific compound R1 (compound 20).

Specific Method 3

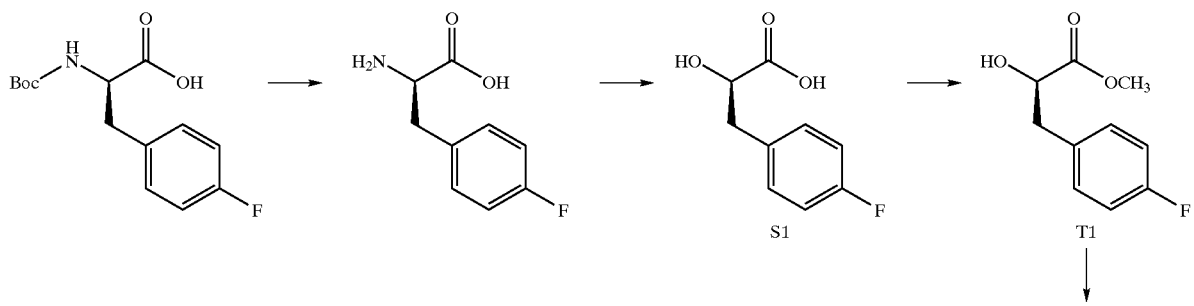

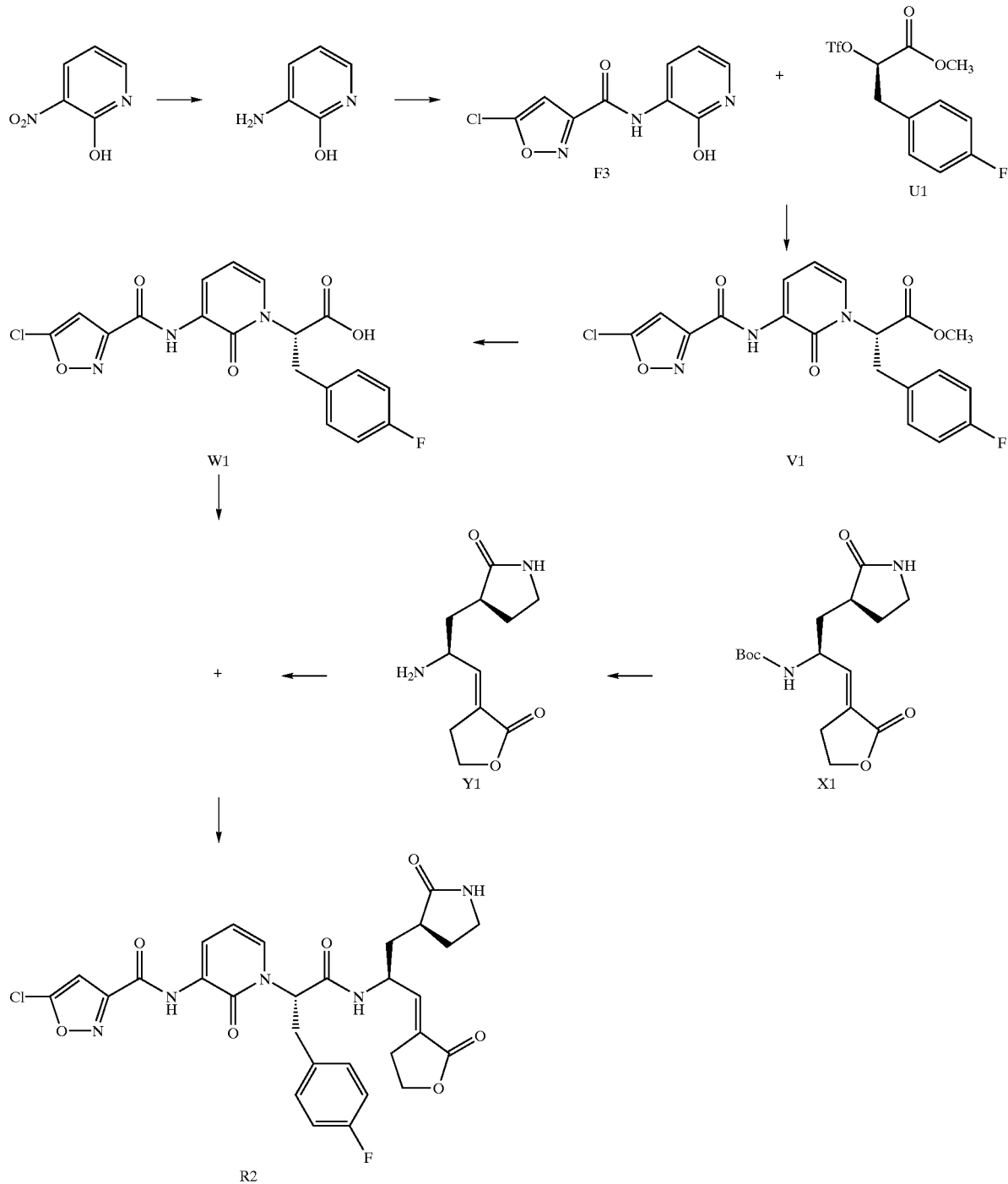

Specific Method 3 describes the preparation of specific compound R2 (compound 23). Thus, commercially available Boc-D-(4-F)Phe-OH was deprotected under acidic conditions and the resulting amine salt was subjected to a diazotization/displacement protocol to provide (2R)-3-(4'-fluorophenyl)-2-hydroxypropionic acid (S1). This material was subsequently transformed into the corresponding trifluoromethane sulfonate (triflate) U1 via the methyl ester T1 and was coupled with the sodium salt of 2-hydroxypyridine F3 to provide intermediate V1. The 2-hydroxypyridine F3 was prepared from commercially available 2-hydroxy-3-nitropyridine by reduction and subsequent derivatization of the resulting amine with 5-chloroisoxazole-3-carbonyl chloride (prepared as described in the Experimental Section of this work). The methyl ester present in V1 was subsequently hydrolyzed under basic conditions and the resulting carboxylic acid (W1) was coupled with amine Y1 (or salt thereof) to complete the preparation of specific compound R2 (compound 23). Amine Y1 (or salt thereof) was prepared by deprotection of intermediate X1 (prepared in a manner analogous to that described in Baldwin et al., *J. Org. Chem.* 1971, 36, 1441).

Specific Method 4
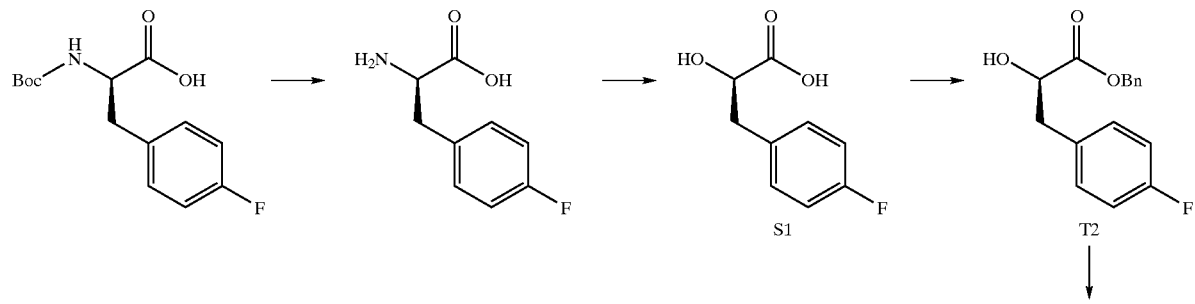
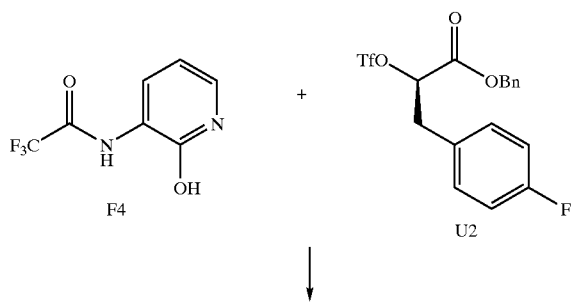
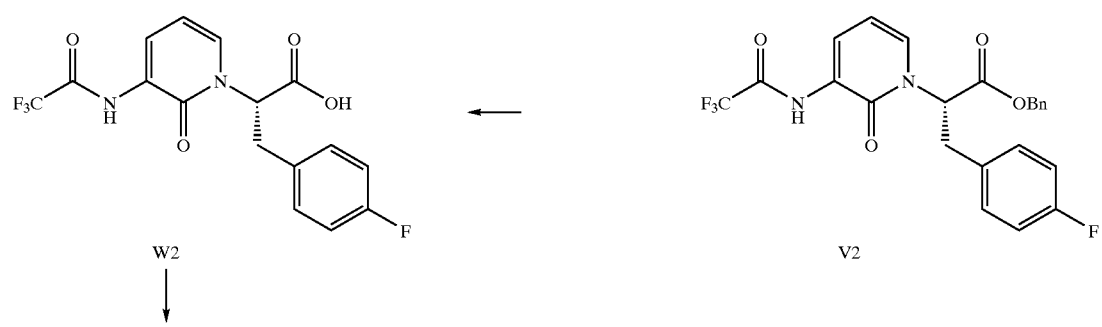
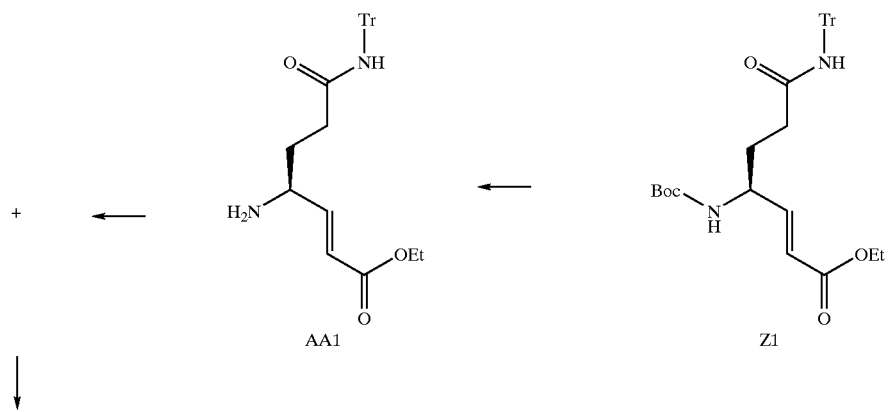

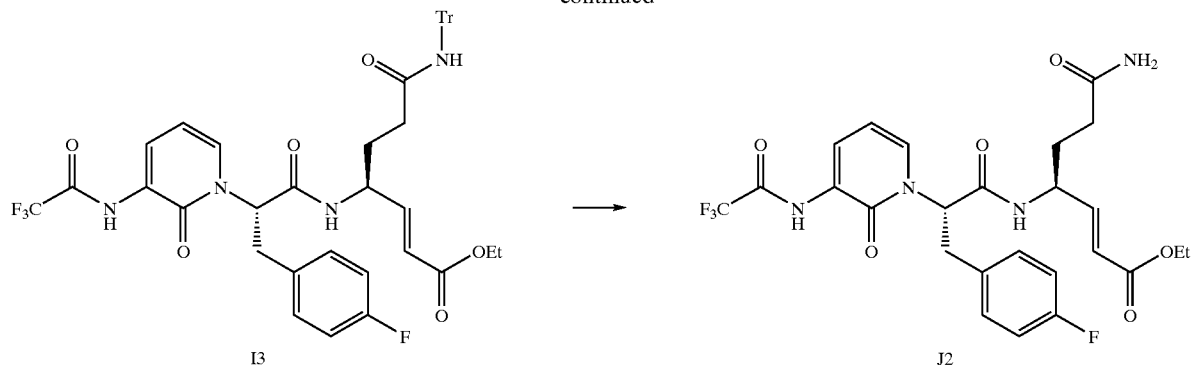

Specific Method 4 describes the preparation of specific compound J2 (compound 24). Thus, (2R)-3-(4'-fluorophenyl)-2-hydroxypropionic acid (S1, prepared as described above in Specific Method 3) was transformed into the corresponding trifluoromethane sulfonate (triflate) U2 via the benzyl ester T2 and was coupled with the sodium salt of 2-hydroxypyridine F4 to provide intermediate V2. The 2-hydroxypyridine F4 was prepared from commercially available 2-hydroxy-3-nitropyridine by reduction and subsequent derivatization of the resulting amine with trifluoroacetic anhydride. The benzyl ester present in V2 was subsequently removed by hydrogenation and the resulting carboxylic acid (W2) was coupled with amine AA1 (or salt thereof) to give intermediate I3. The trityl protecting group present in I3 was then removed under acidic conditions to complete the preparation of specific compound J2 (compound 24). Amine AA1 (or salt thereof) was prepared by deprotection of intermediate Z1 (prepared as described in Dragovich, et al. *J. Med. Chem.* 1998, 41, 2806).

Specific Method 5

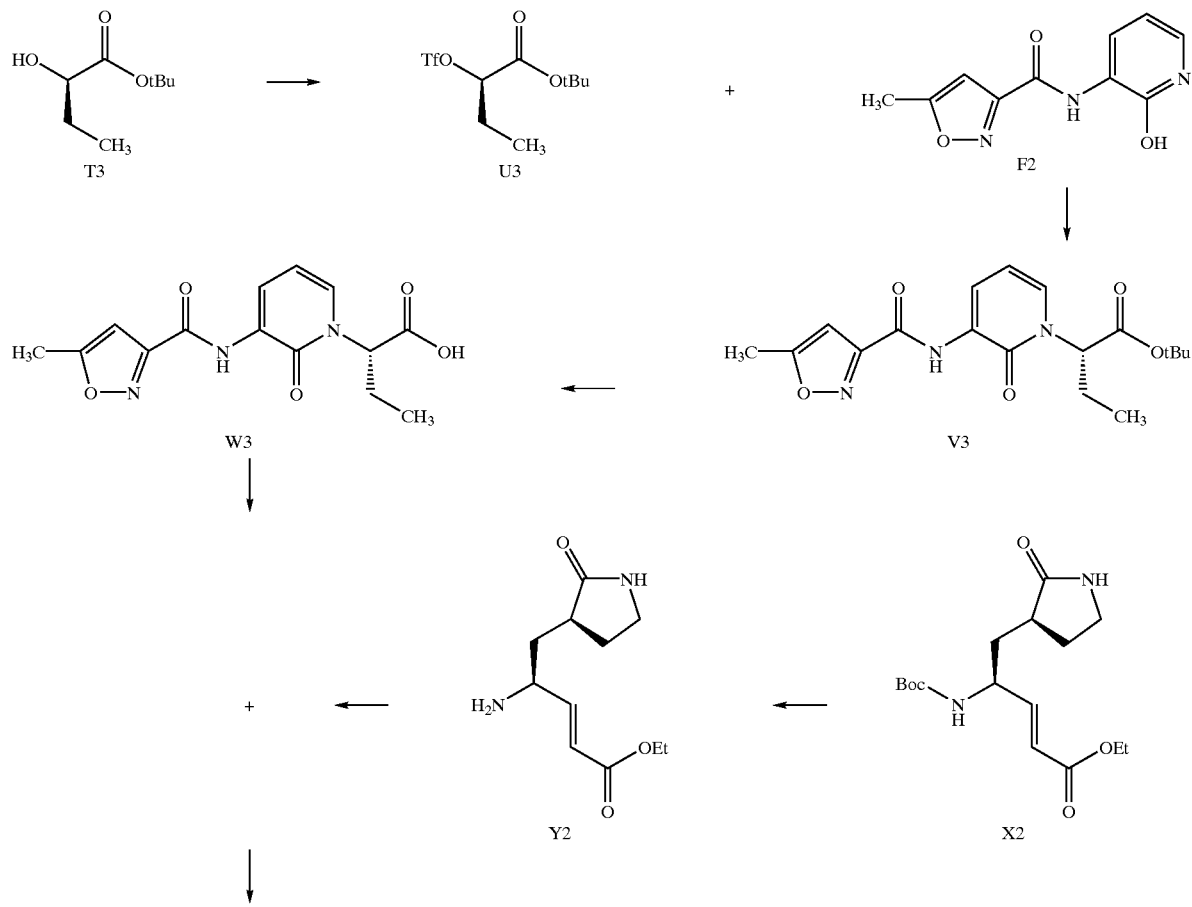

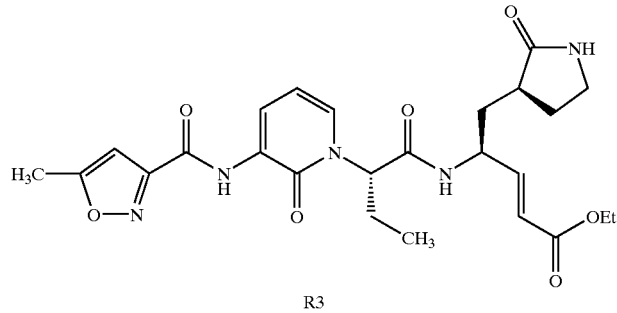

R3

Specific Method 5 describes the preparation of specific compound R3 (compound 26). Thus, commercially available tert-butyl (R)-2-hydroxybutyrate (T3) was transformed into the corresponding trifluoromethane sulfonate (triflate) U3 and was coupled with the sodium salt of 2-hydroxypyridine F2 (prepared as described in Specific Method 2 above) to provide intermediate V3. The tert-butyl ester present in V3 was subsequently hydrolyzed under acidic conditions and the resulting carboxylic acid (W3) was coupled with amine Y2 (or salt thereof) to complete the preparation of specific compound R3 (compound 26). Amine Y2 (or salt thereof) was prepared by deprotection of intermediate X2, prepared according to the method disclosed in the co-pending application, U.S. Provisional Patent Application No. 60/150,358, filed Aug. 24, 1999, the disclosure of which is incorporated herein by reference.

Specific Method 6

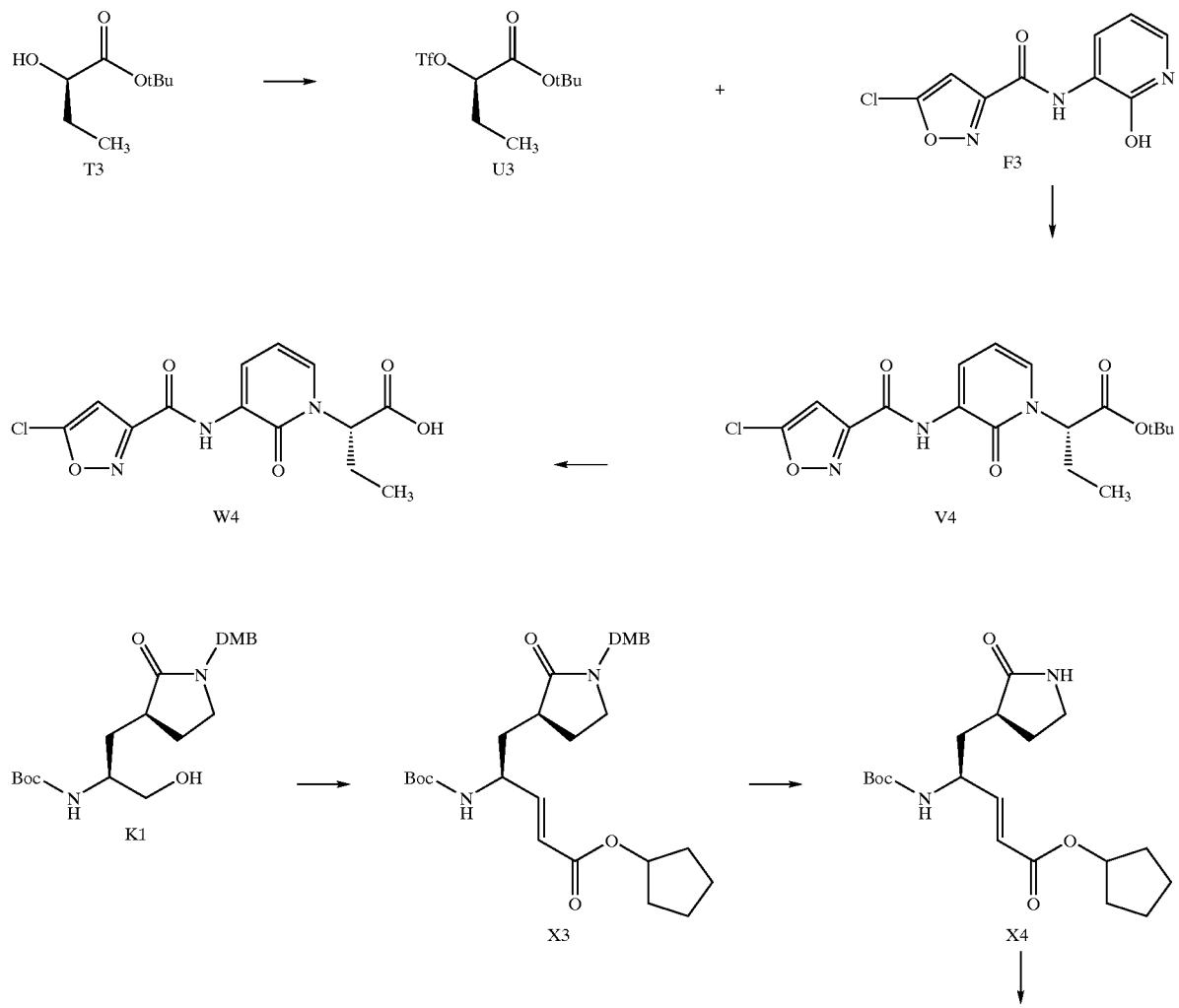

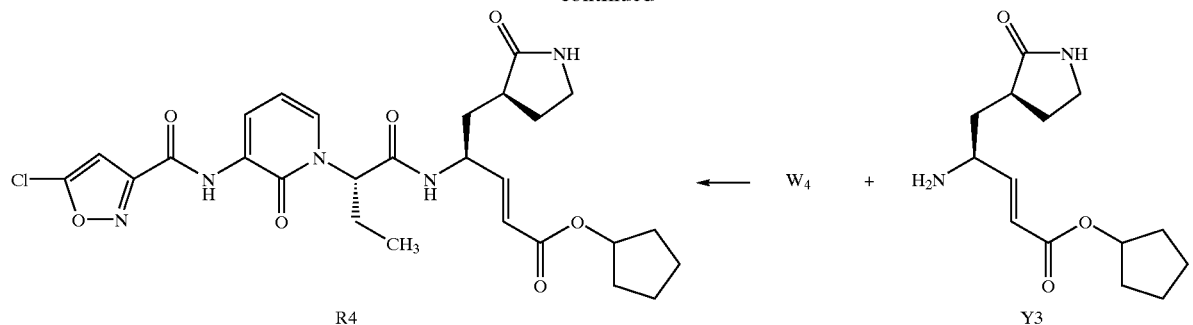

Specific Method 6 describes the preparation of specific compound R4 (compound 29). Thus, trifluoromethane sulfonate (triflate) U3 (prepared as described in Specific method 5 above) was coupled with the sodium salt of 2-hydroxypyridine F3 (prepared as described in Specific Method 3 above) to provide intermediate V4. The tert-butyl ester present in V4 was subsequently hydrolyzed under acidic conditions and the resulting carboxylic acid (W4) was coupled with amine Y3 (or salt thereof) to complete the preparation of specific compound R4 (compound 29). Amine Y3 (or salt thereof) was synthesized from alcohol K1 (prepared as described in Dragovich, et al., *J. Med Chem.* 1999, 42, 1213) by the following method. Alcohol K1 was oxidized to the corresponding aldehyde (not shown) and subjected to an olefin-forming reaction to give intermediate X3. The DMB moiety contained in X3 was then deprotected to provide intermediate X4, and this entity was deprotected under acidic conditions to afford amine Y3 (or salt thereof).

Specific Method 7

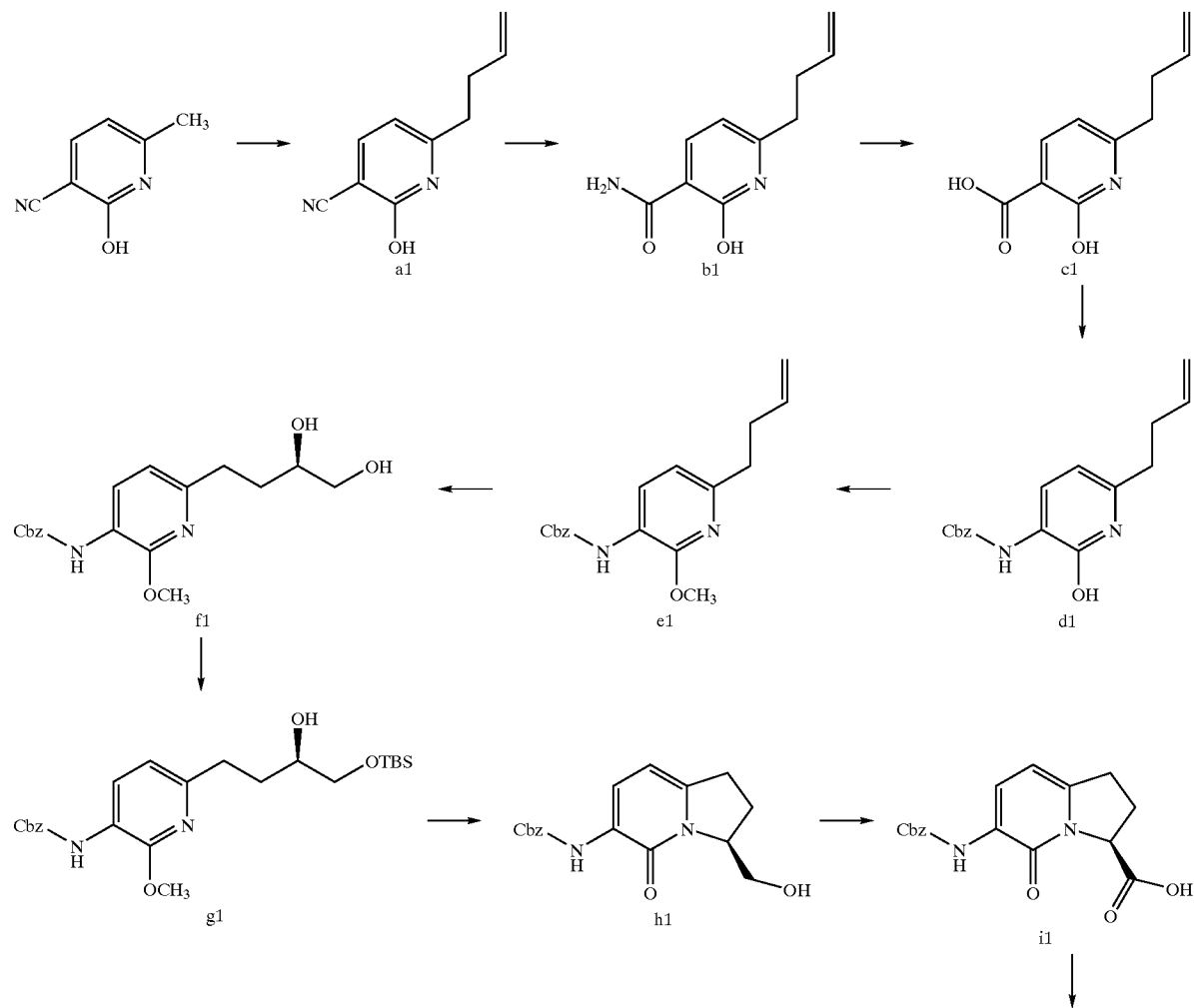

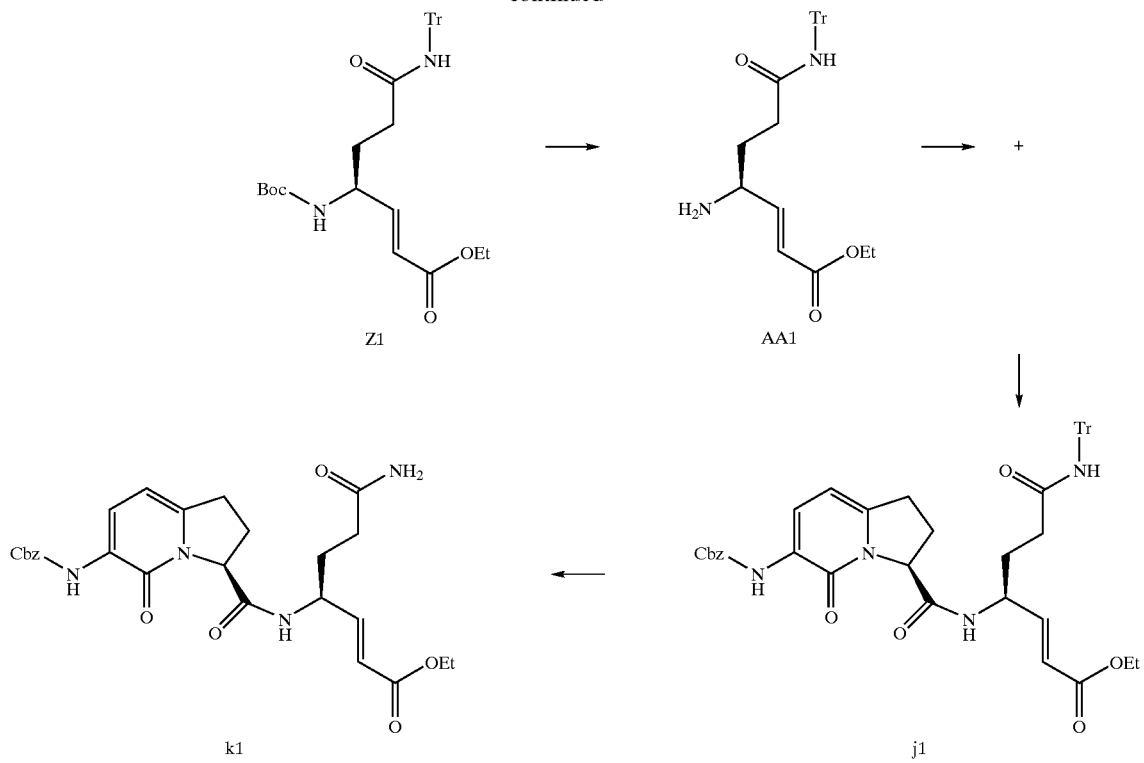

Specific Method 7 describes the preparation of specific compound k1 (compound 36). Thus, the dianion of commercially available 2-hydroxy-6-methylnicotinonitrile was converted to intermediate a1 by methods related to those described in the literature (DeJohn, D.; Domagala, J. M.; Kaltenbronn, J. S.; Krolls, U. *J. Heterocyclic Chem.* 1983, 20, 1295). The nitrile functionality present in this intermediate was then converted to the corresponding carboxylic acid c1 via the primary amide b1. Intermediate c1 was subjected to a Curtius rearrangement and the resulting isocyanate was trapped with benzyl alcohol to provide carbamate d1. The hydroxyl moiety contained in d1 was selectively methylated and the resulting methyl ether (e1) was subjected to an asymmetric dihydroxylation reaction to give diol f1. This asymmetric dihydroxylation reaction can be effected utilizing a variety of commercial and non-commercial chiral additives. The primary hydroxyl moiety contained in f1 was selectively protected as the corresponding tert-butyldimethylsilyl ether (g1). This intermediate was treated with trifluoromethanesulfonic anhydride in the presence of 2,6-lutidine at low temperature followed by exposure to tetrabutylammonium fluoride to effect (i) intramolecular cyclization and (ii) silyl ether deprotection and afford alcohol h1. Alcohol h1 was oxidized to the corresponding aldehyde (not shown), and this intermediate was further oxidized to the corresponding carboxylic acid i1. Acid i1 was coupled with amine AA1 (or salt thereof) to give intermediate j1. The trityl protecting group present in j1 was then removed under acidic conditions to complete the preparation of specific compound k1 (compound 36). Amine AA1 (or salt thereof) was prepared by deprotection of intermediate Z1 (prepared as described in Dragovich, et al. *J. Med. Chem.* 1998, 41, 2806).

Specific Method 8

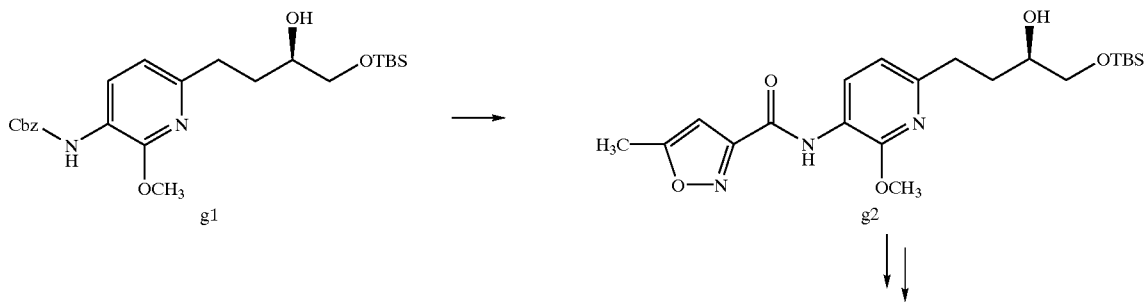

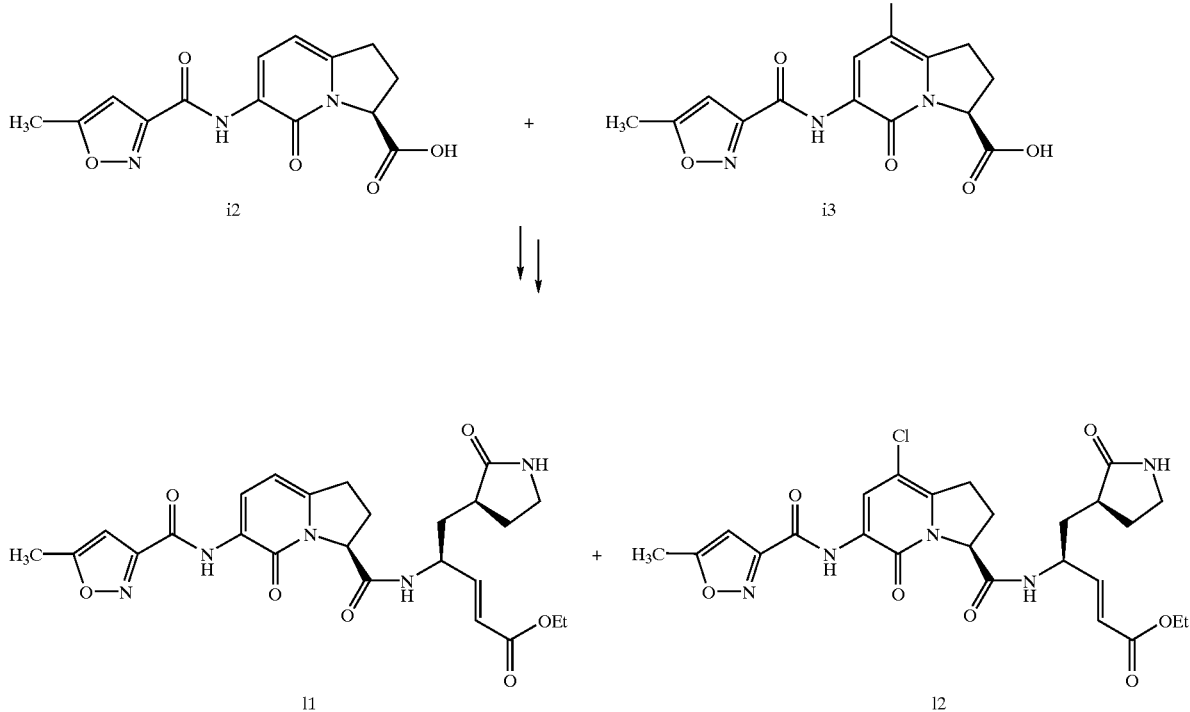

Specific Method 8 describes the preparation of specific compounds 11 and 12 (compounds 37 and 39, respectively). Thus, the Cbz moiety present in intermediate g1 (prepared as described in Specific Method 7 above) was removed and the resulting amine (not shown) was derivatized with commercially available 5-methylisoxazole-3-carbonyl chloride to provide intermediate g2. This intermediate was converted to specific compound 11 (compound 37) by a process analogous to that described in Specific Method 7 for the conversion of intermediate g1 to intermediate j1 utilizing amine Y2 (Specific Method 5) where appropriate. During this process, a small amount of intermediate i3 was also serendipitously generated. This intermediate was transformed to specific compound 12 (compound 39) by a process analogous to that described in Specific Method 7 for the conversion of intermediate g1 to intermediate j1 utilizing amine Y2 (Specific Method 5) where appropriate.

Specific Method 9

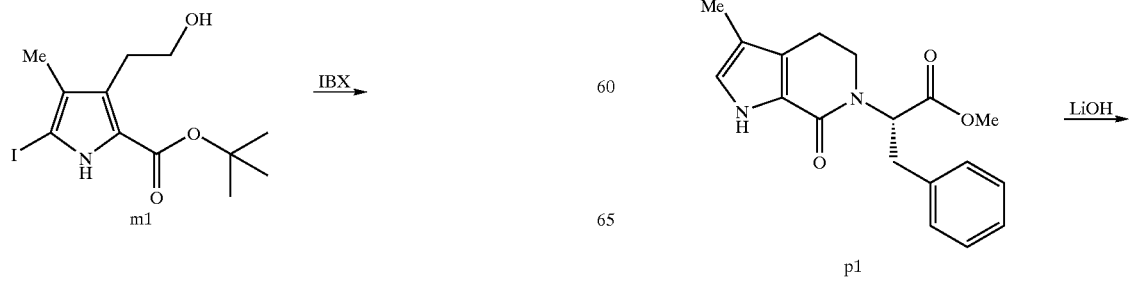

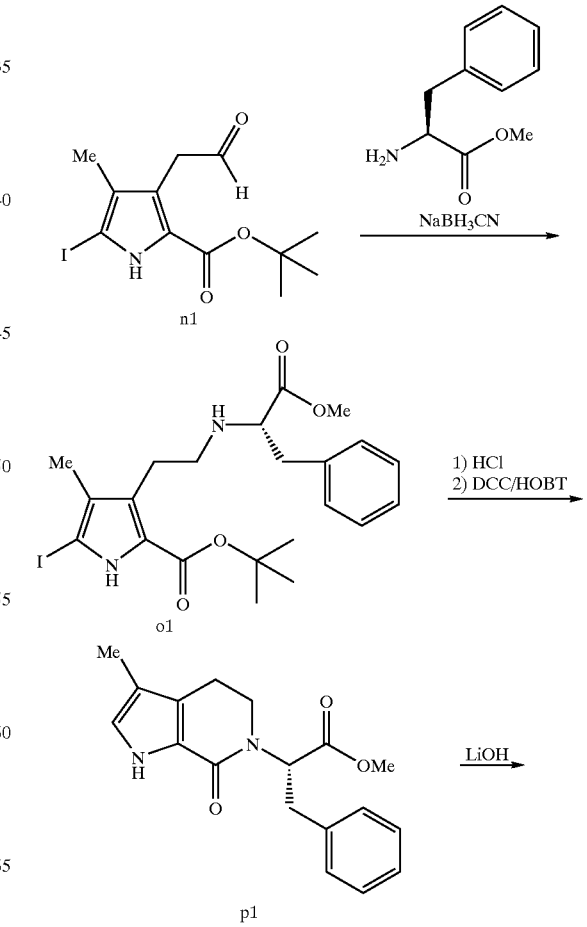

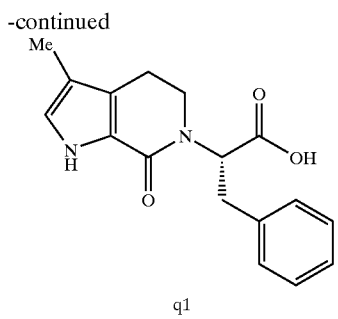

q1

Specific Method 9 describes the synthesis of a bicyclic pyrrole. Alcohol m1 was oxidized with 2-iodoxybenzoic acid to give aldehyde n1, then reductively aminated with phenylalanine methyl ester and sodium cyanoborohydride to give amine o1. The t-butyl-protecting group was selectively removed, and the resulting amino acid was cyclized with DCC-HOBT to give p1. The methyl ester was cleaved with lithium hydroxide to give acid q1. Boc-protected 4S-amino-5-(2-oxo-pyrrolidin-3S-yl)-pent-2(trans)-enoic acid ethyl ester X2 was deprotected with HCl, then coupled to acid q1, using HATU, to complete the preparation of compound 43.

EXAMPLES

Examples of the processes used to make several of the compounds of Formulas I and II are set forth below. The structures of the compounds of the following examples were confirmed by one or more of the following: proton magnetic resonance spectroscopy, infrared spectroscopy, elemental microanalysis and melting point. Proton magnetic resonance ($^1$H NMR) spectra were determined using either a Varian UNITYplus 300 or a General Electric QE-300 spectrometer operating at a field strength of 300 megahertz (MHz). Chemical shifts are reported in parts per million (ppm, δ) downfield from an internal tetramethylsilane standard. Alternatively, $^1$H NMR spectra were referenced to residual protic solvent signals as follows: $CHCl_3$=7.26 ppm; DMSO=2.49 ppm, $C_6HD_5$=7.15 ppm. Peak multiplicities are designated as follows: s, singlet; d, doublet; dd, doublet of doublets; t, triplet; q, quartet; br, broad resonance; m, multiplet. Coupling constants are given in Hertz. Infrared absorption (IR) spectra were obtained using a Perkin-Elmer 1600 series FTIR spectrometer. Elemental microanalyses were performed by Atlantic Microlab Inc., Norcross, Ga. and gave results for the elements stated within ±0.4% of the theoretical values. Flash column chromatography was performed using Silica gel 60 (Merck Art 9385). Analytical thin layer chromatography (TLC) was performed using pre-coated sheets of Silica 60 $F_{254}$ (Merck Art 5719). Melting points were determined on a Mel-Temp apparatus and are uncorrected. All reactions were performed in septum-sealed flasks under a slight positive pressure of argon unless otherwise noted. All commercial reagents were used as received from their respective suppliers with the following exceptions. Tetrahydrofuran (THF) was distilled from sodium-benzophenone ketyl prior to use. Dichloromethane ($CH_2Cl_2$) was distilled from calcium hydride prior to use. $Et_2O$ refers to diethyl ether. DMF refers to N,N-dimethylformamide. DMSO refers to dimethylsulfoxide. MTBE refers to tert-butyl methyl ether. Other abbreviations include: $CH_3OH$ (methanol), EtOH (ethanol), EtOAc (ethyl acetate), DME (ethylene glycol dimethyl ether) Ac (acetyl), Me (methyl), Ph (phenyl), Tr (triphenylmethyl), Cbz (benzyloxycarbonyl), Boc (tert-butoxycarbonyl), TFA (trifluoroacetic acid), DIEA (N,N-diisopropylethylamine), TMEDA (N,N,N',N'-tetramethylethylenediamine), AcOH (acetic acid), $Ac_2O$ (acetic anhydride), NMM (4-methylmorpholine), HOBt (1-hydroxybenzotriazole hydrate), HATU [O-(7-azabenzotriazol-1-yl)-N,N,N',N'-tetramethyluronium hexafluorophosphate], EDC [1-(3-dimethylaminopropyl)-3-ethylcarbarbodiimide hydrochloride], DCC (dicyclohexyl-carbodiimide), DDQ (2,3-dichloro-5,6-dicyano-1,4-benzoquinone), DMAP (4-dimethylaminopyridine), Gln (glutamine), Leu (leucine), Phe (phenylalanine), Phe(4-F) (4-fluorophenylalanine), Val (valine), amino-Ala (2,3-diaminopropionic acid), and (S)-Pyrrol-Ala [(2S,3'S)-2-amino-3-(2'-oxopyrrolidin-3'-yl)-propionic acid]. Additionally, "L" represents the configuration of naturally occurring amino acids.

Example 1

Preparation of Compound 1: trans-(2'S,4S)-4-[2'-(3"-Benzyloxycarbonylamino-2"-oxo-2"H-pyridin-1"-yl)-3'-phenylpropionylamino]-6-carbamoylhex-2-enoic Acid Ethyl Ester

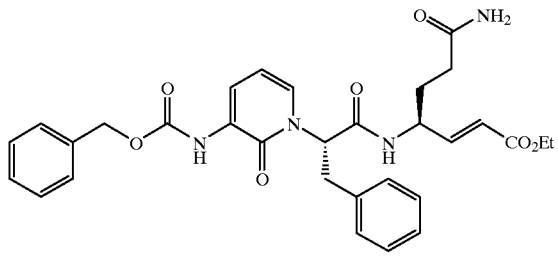

Preparation of Intermediate (2-Hydroxypyridin-3-yl)carbamic Acid Benzyl Ester

A suspension of 10% palladium on carbon (0.20 g) and 2-hydroxy-3-nitropyridine (3.00 g, 21.4 mmol, 1 equiv) in EtOH (100 mL) was subjected to one atmosphere of hydrogen for 4 hours. After purging the reaction vessel with argon, the mixture was filtered and the filtrate evaporated to give 2-hydroxy-3-aminopyridine which was used without further purification. This crude material was stirred in THF (70 mL) at 23° C. Benzyl chloroformate (3.37 mL, 23.6 mmol, 1.1 equiv) and $Na_2CO_3$ (5.00 g, 47.2 mmol, 2.2 equiv) were added and the reaction mixture was stirred for 60 h then diluted with EtOAc (250 mL) and washed sequentially with saturated $NaHCO_3$ and brine (50 mL each). The organic phase was dried over $MgSO_4$, filtered, and concentrated. The residue was purified by flash column chromatography (gradient elution, 3→5% $CH_3OH$ in $CH_2Cl_2$) to provide the title intermediate (3.69 g, 71%) as a white solid: $^1$H NMR ($CDCl_3$) δ 5.21 (s, 2H), 6.33 (t, 1H, J=6.8), 7.00 (dd, 1H, J=6.8, 1.6), 7.31–7.43 (m, 5H), 7.80 (s, 1H), 8.12–8.17 (m, 1H), 12.97 (s, 1H).

Preparation of Intermediate 5-(3-Benzyloxycarbonylamino-2-oxo-2H-pyridin-1-yl)-6-phenyl-4-[2-(tritylcarbamoyl)ethyl]hex-2-enoic Acid Ethyl Ester (2-Hydroxypyridin-3-yl)carbamic acid benzyl ester was converted to the title intermediate via condensation with E1 (see Example 5) by a process analogous to that described in Example 5 for the conversion of F1 to intermediate I1: $1^1$H NMR ($CDCl_3$) δ 1.28 (t, 3H, J=7.2), 1.55–1.69 (m, 1H), 1.86–2.00 (m, 1H), 2.06–2.23 (m, 2H), 3.12 (dd, 1H, J=13.6, 7.8), 3.46 (dd, 1H, J=13.6, 8.2), 4.17 (q, 2H, J=7.2), 4.43–4.54 (m, 1H), 5.14 (d, 1H, J=12.1), 5.18 (d, 1H, J=12.1), 5.49–5.57 (m, 1H), 5.62 (dd, 1H, J=15.7, 1.7), 6.14 (t, 1H, J=7.3), 6.59–6.75 (m, 3H), 7.08–7.41 (m, 26H), 7.73 (s, 1H), 7.93–7.98 (m, 1H).

Preparation of Compound 1

The preceding intermediate was converted to compound 1 by a process analogous to that described in Example 5 for the conversion of I2 to product J1: IR (cm-$^1$) 3298, 1713, 1655, 1590, 1508, 1196; $^1$H NMR (CDCl$_3$) δ 1.30 (t, 3H, J=7.1), 1.65–1.96 (m, 2H), 2.02–2.19 (m, 2H), 3.15 (dd, 1H, J=13.8, 7.6), 3.49 (dd, 1H, J=13.8, 8.3), 4.18 (q, 2H, J=7.1), 4.42–4.53 (m, 1H), 5.17 (s, 2H), 5.62–5.81 (m, 4H), 6.28 (t, 1H, J=7.2), 6.66 (dd, 1H, J=15.6, 5.4), 7.12–7.40 (m, 12H), 7.81 (s, 1H), 7.97–8.04 (m, 1H); Anal. C$_{31}$H$_{34}$N$_4$O$_7$·0.25H$_2$O: C, H, N.

Example 2

Preparation of a 1:1 mixture of Compound 1 (above) and Compound 2: trans-(2'R,4S)-4-[2'-(3"-Benzyloxycarbonylamino-2"-oxo-2"H-pyridin-1"-yl)-3'-phenylpropionylamino]-6-carbamoylhex-2-enoic Acid Ethyl Ester

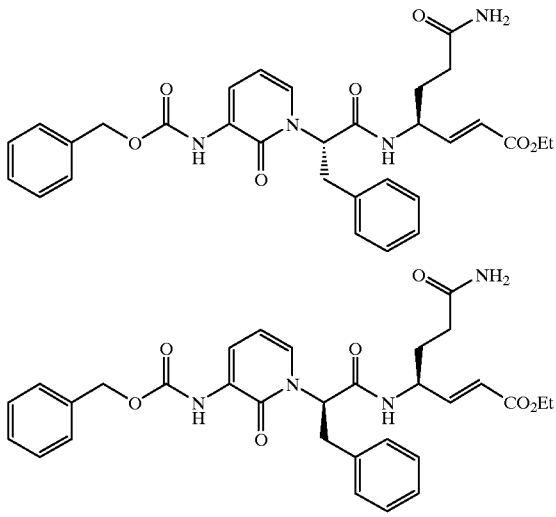

The title products were prepared from commercially available (2R)-2-hydroxy-3-phenylpropionic acid by a process analogous to that described in Example 22 for the conversion of S1 to product R2 utilizing intermediates (2-hydroxypyridin-3-yl)carbamic acid benzyl ester (Example 1) and AA1 (Example 23) where appropriate: $^1$H NMR (CDCl$_3$) (mixture of isomers) δ 1.20 (t, J=7.0), 1.29 (t, J=7.2), 1.64–2.25 (m), 3.08 (dd, J=13.6, 6.4), 3.14 (dd, J=13.6, 7.8), 3.41–3.52 (m), 4.09 (q, J=7.2), 4.18 (q, J=7.0), 4.39–4.50 (m), 5.16 (s), 5.18 (s), 5.59–5.82 (m), 6.12–6.22 (m), 6.25–6.34 (m), 6.65 (dd, J=15.6, 5.6), 6.70 (dd, J=15.6, 5.3), 7.10–7.41 (m), 7.47–7.58 (m), 7.79–7.86 (m), 7.97–8.07 (m).

Example 3

Preparation of Compound 3: trans-(2'S,3'''S,4S)-4-[2'-(7"-Oxo-1",∂"-dihydropyrrolo[2",3"-c-pyridin-6"-yl)-3'-phenylpropionylamino]-5-(2'''-oxopyrrolidin-3'''-yl)pent-2-enoic Acid Ethyl Ester

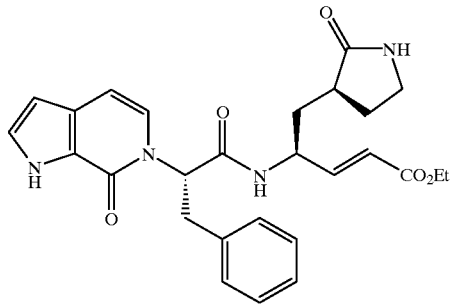

Preparation of Intermediate (2S)-2-(2',2'-Diethyloxyethylamino)-3-phenylpropionic Acid Ethyl Ester A solution of L-phenylalanine ethyl ester (8.37 g, 46.8 mmol, 1 equiv), bromoacetaldehyde diethyl acetal (10.6 mL, 70.1 mmol, 1.5 equiv), and DIEA (16.2 mL, 93.4 mmol, 2.0 equiv) in DMF (100 mL) was heated at 80° C. for 2 d. The resulting solution was cooled to 23° C., taken up in chloroform (200 mL), washed with 10% aqueous potassium carbonate (3×50 mL), dried over potassium carbonate, and concentrated. Purification of the residue by silica gel chromatography yield 7.4 g (54%) of product. $^1$H NMR (CDCl$_3$) δ 1.13–1.23 (m, 9H), 2.61 (dd, 1H, J=11.8, 5.9), 2.78 (dd, 1H, J=11.8, 5.9), 2.96–3.03 (m, 2H), 3.46–3.53 (m, 1H), 3.55–3.70 (m, 4H), 4.18 (q, 2H, J=7.1), 4.57 (t, 1H, J=5.5), 7.19–7.33 (m, 5H).

Preparation of Intermediate (2S)-2-[(2,2-Diethoxyethyl)-(1H-pyrrole-2-carbonyl)-amino]-3-phenylpropionic Acid Ethyl Ester Pyrrole-2-carboxylic acid (0.82 g, 7.41 mmol, 1.42 equiv) in CH$_2$Cl$_2$ (30 mL) was treated with oxalyl chloride (1.0 mL, 11.1 mmol, 2.13 equiv), followed by DMF (1 drop). The reaction mixture was held at 23° C. overnight, then was concentrated under reduced pressure. The resulting solid was taken up in CH$_2$Cl$_2$ (30 mL), and was treated with the preceding intermediate (1.60 g, 5.2 mmol, 1 equiv), and collidine (1.96 mL, 14.8 mmol, 2.85 equiv). The resulting solution was held at 23° C. overnight, then was taken up in EtOAc (100 mL), and washed sequentially with saturated aqueous citric acid (20 mL), saturated aqueous sodium bicarbonate (20 mL), and brine (2×20 mL). The organic layer was dried over MgSO$_4$, then was concentrated to yield 2.18 g of crude product. The product was purified by silica gel chromatography to give 1.42 g (68%) of product. $^1$H NMR (CDCl$_3$) δ 1.15–1.30 (m, 9H), 3.24 (d, 2H, J=5.8), 3.75–4.43 (m, 2H), 4.15–4.28 (m, 6H), 4.50–4.57 (m, 1H), 5.05 (dd, 1H, J=13.6, 5.8), 6.22–6.24 (m, 1H), 6.56–6.59 (m, 1H), 6.94–6.96 (m, 1H), 7.19–7.33 (m, 5H), 9.76 (s, 1H).

Preparation of Intermediate (2S)-(7-Oxo-1,7-dihydropyrrolo[2,3-c]pyridin-6-yl)-3-phenylpropionic Acid Ethyl Ester A solution of the preceding intermediate (1.04 g, 2.59 mmol) in toluene (30 mL) was treated with PTSA (5 mg), then heated to reflux for 1 h. The solution was taken up in EtOAc (100 mL), washed with saturated aqueous sodium bicarbonate (30 mL), then brine (30 mL), then concentrated. Purification of the residue by silica gel chromatography gave 0.14 g (18%) of product. $^1$H NMR (CDCl$_3$) δ 1.11 (t, 3H, J=7.1), 3.25 (dd, 1H, J=14.2, 9.8), 3.49 (dd, 1H, J=14.2, 5.7), 4.11 (q, 2H, J=7.1), 5.57 (dd, 1H, J=9.6, 5.7), 6.26 (t, 1H, J=2.3), 6.42 (d, 1H, J=7.2), 6.70 (d, 1H, J=7.2), 7.00–7.20 (m, 6H), 10.33 (s, 1H),.

Preparation of Compound 3

A solution of the preceding intermediate (0.14 g, 0.45 mmol, 1 equiv) in 1:1 1,4-dioxane-water (5 mL) was treated with LiOH-hydrate (28 mg, 0.68 mmol, 1.42 equiv), and heated to reflux for 30 min. The resulting solution was taken up in ethyl acetate (50 mL), washed with saturated aqueous citric acid (10 mL), followed by brine (2×15 mL), dried over MgSO$_4$, then evaporated to yield 61 mg of the corresponding acid. This was taken up in DMF (5 mL), treated with intermediate Y2 (Example 25, 49 mg, 0.22 mmol, 0.48 equiv), DIEA (0.07 mL, 0.43 mmol, 0.95 equiv), and HATU (82 mg, 0.22 mmol, 0.49 equiv), then held at 23° C. overnight. The solution was taken up in ethyl acetate (30 mL), washed with brine (10 mL), then evaporated. Purification of the residue by silica gel chromatography yielded 0.12 g (56%) of product as a 2:1 mixture of 2S:2R diastereomers (Compounds 3 and 4, respectively). The diastereomers were separated by preparative reverse phase HPLC (acetonitrile-H$_2$O gradient). Compound 3: $^1$H NMR (CDCl$_3$) δ 1.28 (t, 3H, J=7.1), 1.42–1.65 (m, 2H), 1.90–2.10 (m, 2H), 2.20–2.35 (m, 1H), 2.82–2.95 (m, 1H), 3.05–3.25 (m, 2H), 3.53 (dd, 1H, J=13.8, 7.8), 4.17 (q, 2H, J=7.1), 4.45–4.58 (m, 1H), 5.76–5.90 (m, 2H), 6.32 (t, 1H, J=2.1), 6.63 (d, 1H, J=7.3), 6.69–6.78 (m, 2H), 7.08–7.35 (m, 7H), 8.11 (d, 1H, J=7.1), 11.22 (s, 1H).

Example 4

Preparation of Compound 4: trans-(2'R,3'''S,4S)-4-[2'-(7''-Oxo-1'',7''-dihydropyrrolo[2'',3''-c-pyridin-6''-yl)-3'-phenylpropionylamino]-5-(2'''-oxopyrrolidin-3'''-yl)pent-2-enoic Acid Ethyl Ester

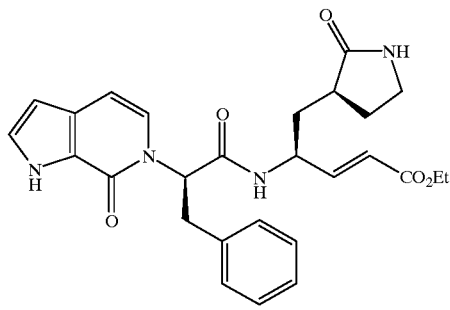

See Preceding Example for preparation: $^1$H NMR (CDCl$_3$) δ 1.18 (t, 3H, J=7.1), 1.42–1.52 (m, 1H), 1.58–1.70 (m, 1H), 1.90–2.28 (m, 3H), 3.12 (dd, 1H, J=13.3, 7.1), 3.20–3.28 (m, 2H), 3.57 (dd, 1H, J=13.3, 9.0), 4.07 (q, 2H, J=7.0), 4.45–4.58 (m, 1H), 5.80 (d, 1H, J=15.7), 6.04 (t, 1H, J=7.7), 6.37 (t, 1H, J=2.3), 6.48 (s, br, 1H), 6.60–6.80 (m, 2H), 7.00–7.40 (m, 6H), 8.11 (d, 1H, J=7.8), 10.61 (s, 1H).

Example 5

Preparation of Compound 5: trans-(2'S,4S)-6-Carbamoyl-4-(2'-{3''-[(5'''-methylisoxazole-3'''-carbonyl)amino]-2''-oxo-2''H-pyridin-1''-yl}-3'-phenylpropionylamino)hex-2-enoic Acid Ethyl Ester (J1)

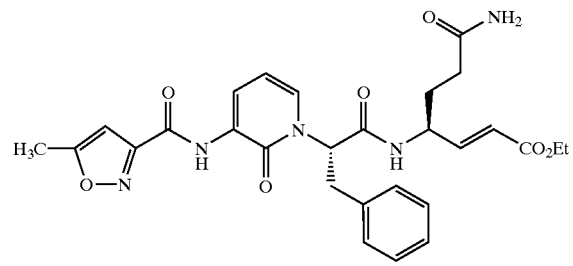

Preparation of Intermediate (1S)-[1-Hydroxymethyl-3-(tritylcarbamoyl)propyl]carbamic Acid Benzyl Ester (B1)

4-Methylmorpholine (1.89 mL, 17.2 mmol, 1 equiv) and ethyl chloroformate (1.65 mL, 17.3 mmol, 1 equiv) were added to a mixture of commercially available Cbz-Gln(Trt)-OH (9.00 g, 17.2 mmol, 1 equiv) in THF (23 mL) at −10° C. After stirring 20 min, the reaction mixture was filtered and the filtrate was added dropwise to a suspension of NaBH$_4$ (1.47 g, 38.9 mmol, 2.25 equiv) in H$_2$O (10 mL) at 0° C. The resulting mixture was allowed to warm to 23° C. and stirred for 5 h. It was then cooled again to 0° C., quenched by the careful addition of 1 N HCl (30 mL) and then partitioned between MTBE (500 mL) and brine (2×100 mL). The organic phase was dried over Na$_2$SO$_4$ and evaporated to provide the title intermediate which was used without further purification.

Preparation of Intermediate (1S)-[1-(tert-Butyldimethylsilanyloxymethyl)-3-(tritylcarbamoyl)propyl]carbamic Acid Benzyl Ester (C1)

Intermediate B1, prepared above, was dissolved in DMF (10 mL). Imidazole (2.69 g, 39.5 mmol, 2.3 equiv) and tert-butyldimethylsilyl chloride (2.86 g, 19.0 mmol, 1.1 equiv) were added. The reaction mixture was stirred overnight, then diluted with MTBE (500 mL) and washed sequentially with 2.5% KHSO$_4$, H$_2$O, NaHCO$_3$, H$_2$O, and brine (100 mL each). The organic phase was dried over MgSO$_4$ and evaporated. The residue was purified by flash column chromatography (gradient elution, 25→40% EtOAc in hexanes) to provide the title intermediate (7.6 g, 71%) as a white amorphous solid: IR (cm$^{-1}$) 3307, 1708, 1660, 1496, 1249; $^1$H NMR (CDCl$_3$) δ-0.01–0.05 (m, 6H), 0.89 (s, 9H), 1.76–1.93 (m. 2H), 2.29–2.40 (m, 2H), 3.56–3.77 (m, 3H), 5.03–5.16 (m, 3H), 7.00 (s, 1H), 7.18–7.39 (m, 20 H); Anal. C$_{38}$H$_{46}$N$_2$O$_4$Si: C, H, N.

Preparation of Intermediate (2'R,4S)-5-(tert-Butyldimethylsilanyloxy)-4-(2'-hydroxy-3'-phenylpropionylamino)pentanoic Acid Tritylamide (D1)

Intermediate C1 from above (7.6 g, 12 mmol, 1 equiv) and 10% palladium on carbon (0.45 g) were suspended in EtOH (140 mL) and hydrogenated at 50 psi overnight. The reaction mixture was filtered through Whatman #3 paper, the paper was washed with EtOH (120 mL) and the combined filtrates were evaporated. The residue was combined with D-3-phenyllactic acid (1.42 g, 12.2 mmol, 1 equiv), iPr$_2$NEt (4.25 mL, 24.4 mmol, 2 equiv) and HATU (4.64 g, 12.2 mmol, 1 equiv) in DMF (35 mL) at 0° C. After stirring 1 h, the reaction mixture was allowed to warm to 23° C. and stirred 20 min more. Then 5% KHSO$_4$ (80 mL) and MTBE (600 mL) were added and the phases were separated. The organic phase was washed with H$_2$O (80 mL) and brine (70 mL), dried over Na$_2$SO$_4$ and evaporated. The residue was purified by flash column chromatography (50% EtOAc in hexanes) to provide the title intermediate as a white foam (4.85 g, 62%): IR (cm$^{-1}$) 3394, 3295, 1666, 1649, 1519, 1255, 1114, 1085; $^1$H NMR (CDCl$_3$) δ 0.03–0.02 (m, 6H), 0.85 (s, 9H), 1.70–1.89 (m, 2H), 2.18–2.42 (m, 3H), 2.83 (dd, 1H, J=13.8, 8.1), 3.15 (dd, 1H, J=13.8, 4.0), 3.40 (dd, 1H, J=10.0, 4.7), 3.51 (dd, 1H, J=10.0, 3.1), 3.83–3.94 (m, 1H), 4.17–4.23 (m, 1H), 6.79 (d, 1H, J=8.7), 7.09 (s, 1H), 7.17–7.32 (m, 20H); Anal. C$_{39}$H$_{48}$N$_2$O$_4$Si·0.30H$_2$O: C, H, N.

Preparation of Intermediate (1'S,2R)-Methanesulfonic Acid 1-[1'-(tert-butyldimethylsilanyloxymethyl)-3'-(tritylcarbamoyl)propylcarbamoyl]-2-phenylethyl Ester (E1)

Intermediate D1 from above (1.96 g, 3.08 mmol, 1 equiv) and iPr$_2$NEt (0.752 mL, 4.32 mmol, 1.4 equiv) were dissolved in CH$_2$Cl$_2$ (30 mL) and cooled to –10° C. Methanesulfonyl chloride (0.286 mL, 3.70 mmol, 1.2 equiv) was added dropwise, slowly, with vigorous stirring. After 30 min, the reaction mixture was diluted with CH$_2$Cl$_2$ (200 mL), washed with brine (50 mL), dried over Na$_2$SO$_4$ and evaporated to provide the title intermediate which was used without further purification.

Preparation of Intermediate (2-Hydroxypyridin-3-yl)carbamic acid tert-Butyl Ester (F1)

A suspension of 10% palladium on carbon (0.35 g) and 2-hydroxy-3-nitropyridine (5.00 g, 35.7 mmol, 1 equiv) in EtOH (170 mL) was subjected to one atmosphere of hydrogen for 16 hours. After purging the reaction vessel with argon, the mixture was filtered through Whatman #3 paper and the filtrate was evaporated to give 2-hydroxy-3-aminopyridine which was used without further purification. This crude material was stirred in THF (100 mL) at 23° C. Di-tert-butyl dicarbonate (7.79 g, 35.7 mmol, 1 equiv) was added and the reaction mixture was heated to reflux for 4 h. More di-tert-butyl dicarbonate (6.0 g, 27 mmol, 0.8 equiv) was added and the reaction mixture was heated to reflux overnight. The solvent was evaporated and the residue was purified by flash column chromatography (gradient elution, 50→60% EtOAc in hexanes) to provide the title intermediate as a white solid (6.48 g, 83%): IR (cm$^{-1}$) 3225, 1725, 1649, 1514; $^1$H NMR (CDCl$_3$) δ 1.52 (s, 9H), 6.33 (dd, 1H, J=7.4, 6.6), 7.01 (dd, 1H, J=6.6, 1.8), 7.56 (s, 1H), 8.11 (d, 1H, J=7.1), 12.61 (s, 1H); Anal. C$_{10}$H$_{14}$N$_2$O$_3$: C, H, N.

Preparation of Intermediate (1"S,2'S)-(1-{1'-[1"-(tert-Butyldimethylsilanyloxymethyl)-3"-(tritylcarbamoyl)propylcarbamoyl]-2'-phenylethyl}-2-oxo-1,2-dihydropyridin-3-yl)-carbamic Acid tert-Butyl Ester (G1)

Intermediate F1 from above (0.838 g, 3.99 mmol, 1.3 equiv) was stirred in THF (20 mL). Sodium hydride (60% dispersion in mineral oil, 0.148 g, 3.70 mmol, 1.2 equiv) was added. After stirring 20 min, a solution of intermediate E1 from above (1 equiv based on D1) in THF (15 mL) was added. The resulting mixture was heated to reflux for 40 h, but thin layer chromatography showed the reaction to be only 50% complete. In a separate flask, more sodium hydride (60% dispersion in mineral oil, 0.111 g, 2.78 mmol, 0.9 equiv) was added to a suspension of F1 (0.647 g, 3.08 mmol, 1 equiv) in THF (10 mL). After stirring 20 min, this mixture was added to original reaction vessel and the resulting mixture was heated to reflux for 21 h. After stirring at 23° C. over the weekend, the crude reaction mixture was diluted with MTBE (600 mL) and washed with a mixture of brine and 10% KHSO$_4$ (3:1, 80 mL) and brine (80 mL), then dried over Na$_2$SO$_4$ and evaporated. The residue was purified by flash column chromatography (gradient elution, 30→35% EtOAc in hexanes) to provide the desired intermediate G1 as a white foam (1.98 g, 77%): IR (cm$^{-1}$) 3389, 3307, 1725, 1678, 1649, 1590, 1502; $^1$H NMR (CDCl$_3$) δ-0.02–0.04 (m, 6H), 0.86 (s, 9H), 1.52 (s, 9H), 1.55–1.88 (m, 2H), 2.08–2.14 (m, 2H), 3.19 (dd, 1H, J=13.7, 8.1), 3.39–3.51 (m, 2H), 3.53 (dd, 1H, J=14.2, 7.8), 3.82–3.93 (m, 1H), 5.60–5.67 (m, 1H), 6.17 (t, 1H, J=7.3), 6.44 (d, 1H, J=8.3), 7.04 (s, 1H), 7.12–7.36 (m, 21H), 7.59 (s, 1H), 7.94 (d, 1H, J=7.1); Anal. C$_{49}$H$_{60}$N$_4$O$_6$Si: C, H, N.

Preparation of Intermediate (1"S,2'S)(1-{1'-[1"-Hydroxymethyl-3"-(tritylcarbamoyl)propylcarbamoyl]-2'-phenylethyl}-2-oxo-1,2-dihydropyridin-3-yl)carbamic Acid tert-Butyl Ester (H1)

Intermediate G1 from above (1.92 g, 2.32 mmol, 1 equiv) was dissolved in a mixture of CH$_3$CN (30 mL) and H$_2$O (3 mL) in a plastic tube. Triethylamine trihydrofluoride (21 drops) was added and the reaction solution was stirred overnight. It was then diluted with EtOAc (750 mL), washed with brine (3×80 mL), dried over MgSO$_4$ and evaporated to provide the title intermediate which was used without further purification.

Preparation of Intermediate trans-(2'S,4S)-4-[2'-(3"-tert-Butoxycarbonylamino-2"-oxo-2"H-pyridin-1"-yl)-3'-phenylpropionylamino]-6-(tritylcarbamoyl)-hex-2-enoic Acid Ethyl Ester (I1)

Intermediate H1 from above (1 equiv based on G1) was dissolved in CH$_2$Cl$_2$ (20 mL). Commercially available Dess-Martin periodinane (1.09 g, 2.55 mmol, 1.1 equiv) was added. After stirring 2 h, the solvent was evaporated and the residue was suspended in toluene and again evaporated (70 mL, then 2×20 mL) to give a yellow foam. One half of this material (1.16 mmol based on GI) was dissolved in THF (17 mL). (Carbethoxymethylene) triphenylphosphorane (0.563 g, 1.62 mmol, 1.4 equiv) was added and the reaction mixture was heated to reflux for 1 h and then stirred at 23° C. overnight. After evaporating the solvent, the residue was purified by flash column chromatography (gradient elution, 40→50% EtOAc in hexanes) to provide the title intermediate (0.710 g, 77%): IR (cm$^{-1}$) 3378, 3284, 1719, 1649, 1596, 1508, 1267; $^1$H NMR (CDCl$_3$) δ 1.28 (t, 3H, J=7.1), 1.47 (s, 9H), 1.54–1.69 (m, 1H), 1.87–2.02 (m, 1H), 2.09–2.22 (m, 2H), 3.12 (dd, 1H, J=13.7, 7.7), 3.47 (dd, 1H, J=13.7, 8.1), 4.17 (q, 2H, J=7.1), 4.43–4.54 (m, 1H), 5.51–5.58 (m, 1H), 5.64 (dd, 1H, J=15.7, 1.6), 6.12 (t, 1H, J=7.2), 6.60–6.68 (m, 3H), 7.08–7.31 (m, 21H), 7.51 (s, 1H), 7.90 (d, 1H, J=7.1); Anal. C$_{47}$H$_{50}$N$_4$O$_7$·0.50H$_2$O: C, H, N.

Preparation of Intermediate trans-(2'S,4S)-4-(2'-{3"-[(5"'-Methylisoxazole-3"'-carbonyl)amino]-2"-oxo-2"H-pyridin-1"-yl}-3'-phenylpropionylamino)-6-(tritylcarbamoyl)hex-2-enoic Acid Ethyl Ester (I2)

Intermediate I1 from above (0.088 g, 0.11 mmol, 1 equiv) was heated (neat) to between 190 and 200° C. for 65 minutes, then allowed to cool providing the crude amine as a dark residue which was dissolved in CH$_3$CN (2 mL) and cooled to 0° C. 5-Methylisoxazole-3-carbonyl chloride (0.033 g, 0.23 mmol, 2 equiv) and 4-methylmorpholine (0.025 mL, 0.23 mmol, 2 equiv) were added and the reaction mixture was allowed to warm to 23° C. After stirring 40 min, a mixture of 10% KHSO$_4$ and brine (1:1, 15 mL) and EtOAc (70 mL) were added. The phases were separated and the organic phase was washed with brine, dried over Na$_2$SO$_4$ and evaporated. The residue was purified by flash column chromatography (50% EtOAc in hexanes) to provide the title intermediate (0.049 g, 55%): IR (cm$^{-1}$) 3331, 1678 (br), 1590, 1525; $^1$H NMR (CDCl$_3$) δ 1.28 (t, 3H, J=7.1), 1.58–1.72 (m, 1H), 1.87–2.03 (m, 1H), 2.10–2.26 (m, 2H), 2.48 (s, 3H), 3.15 (dd, 1H, J=13.7, 7.8), 3.47 (dd, 1H, J=13.7, 8.1), 4.17 (q, 2H, J=7.1), 4.43–4.55 (m, 1H), 5.54–5.61 (m, 1H), 5.65 (dd, 1H, J=15.8, 1.5), 6.17 (t, 1H, J=7.3), 6.45 (s, 1H), 6.65 (dd, 1H, J=15.8, 5.4), 6.72 (s, 1H), 6.84 (d, 1H, J=8.0), 7.08–7.32 (m., 22 H), 8.35 (dd, 1H, J=7.3, 1.5), 9.49 (s, 1H); Anal. C$_{47}$H$_{46}$N$_5$O$_7$·0.25H$_2$O: C, H, N.

Preparation of Product J1 (Compound 5)

Intermediate I2 from above (0.047 g, 0.059 mmol, 1 equiv) was dissolved in CH$_2$Cl$_2$ (3 mL). Triisopropylsilane (0.036 mL, 0.176 mmol, 3 equiv) and TFA (2 mL) were added. The bright yellow solution was stirred 25 min, then diluted with CCl$_4$ (3 mL) and all the volatiles were evaporated. The residue was purified by flash column chromatography (3% CH$_3$OH in CH$_2$Cl$_2$) to give the desired product J1 (0.028 g, 85%): IR (cm$^{-1}$) 3342, 1666 (br), 1590, 1531, 1455; $^1$H NMR (CDCl$_3$) δ 1.30 (t, 3H, J=7.1), 1.70–1.84 (m, 1H), 1.85–1.99 (m, 1H), 2.17–2.24 (m, 2H), 2.48 (s, 3H), 3.18 (dd, 1H, J=13.7, 7.8), 3.50 (dd, 1H, J=13.7, 8.1), 4.19 (q, 2H, J=7.1), 4.43–4.54 (m, 1H), 5.68 (dd, 1H, J=15.7, 1.3), 5.74–5.82 (m, 1H), 6.00 (s, 1H), 6.19 (s, 1H), 6.32 (t, 1H, J=7.3), 6.46 (s, 1H), 6.69 (dd, 1H, J=15.7, 5.5), 7.13–7.30 (m, 5H), 7.48 (dd, 1H, J=7.3, 1.6), 7.62 (d, 1H, J=7.6), 8.39 (dd, 1H, J=7.3, 1.6), 9.46 (s, 1H); Anal. C$_{28}$H$_{31}$N$_5$O$_7$·0.50H$_2$O: C, H, N.

Example 6

Preparation of Compound 6: trans-(2'S,4S)-6-Carbamoyl-4-{2'-[3"-cyclopentanecarbonylamino-2"-oxo-2"H-pyridin-1"-yl]-3'-phenylpropionylamino}hex-2-enoic Acid Ethyl Ester

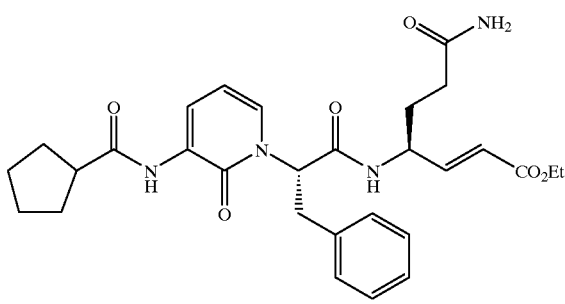

The title compound was prepared from I1 (Example 5) by a process analogous to that described in Example 5 for the conversion of I1 to product J1 utilizing intermediate cyclopentanecarbonyl chloride where appropriate: IR (cm$^{-1}$) 3319, 1713, 1666, 1590, 1514; $^1$H NMR (CDCl$_3$) δ 1.31 (t, 3H, J=7.1), 1.55–2.02 (m, 10H), 2.04–2.22 (m, 2H)2.68–2.80 (m, 1H), 3.16 (dd, 1H, J=13.7, 7.7), 3.51 (dd, J=13.7, 8.1), 4.19 (q, 2H, J=7.1), 4.45–4.56 (m, 1H), 5.57–5.74 (m, 4H), 6.29 (t, 1H, J=7.4), 6.68 (dd, 1H, J=15.8, 5.5), 7.10–7.32 (m, 7H), 8.30 (s, 1H), 8.35 (dd, 1H, J=7.4, 1.7); Anal. C$_{29}$H$_{36}$N$_4$O$_6$·0.50H$_2$O: C, H, N.

Example 7

Preparation of Compound 7: trans-(2'S,4S)-4-[2'-(3"-Benzyloxycarbonylamino-2"-oxo-2"H-pyridin-1"-yl)-3'-(4'"-fluorophenyl)propionylamino]-6-carbamoylhex-2-enoic Acid Ethyl Ester

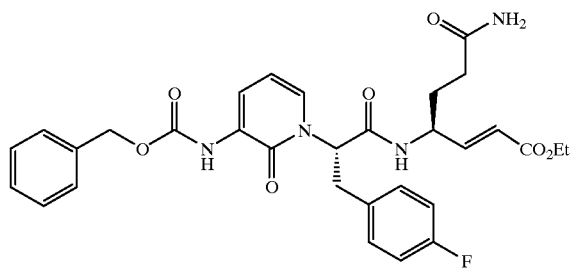

Preparation of Intermediate trans-(2'S,4S)-4-[2'-(3"-Benzyloxycarbonylamino-2"-oxo-2"H-pyridin-1"-yl)-3'-(4'"-fluorophenyl)propionylamino]-6-(tritylcarbamoyl)hex-2-enoic Acid Ethyl Ester Intermediate C1 (Example 5) was converted to the title intermediate by a process analogous to that described in Example 5 for the conversion of C1 to intermediate I1 utilizing S1 (Example 22) where appropriate: IR (cm$^{-1}$) 3283, 1722, 1651, 1604, 1513; $^1$H NMR (CDCl$_3$) δ 1.32 (t, 3H, J=6.9), 1.62–1.71 (m, 1H), 1.94–2.01 (m, 1H), 2.17–2.24 (m, 2H), 3.06–3.13 (m, 1H), 3.43–3.50 (m, 1H), 4.21 (q, 2H, J=6.9), 4.50–4.57 (m, 1H), 5.16–5.25 (m, 2H), 5.52 (t, 1H, J=8.1), 5.63 (dd, 1H, J=15.6, 1.5), 6.18 (t, 1H, J=7.2), 6.65 (s, br. 1H), 6.69 (dd, 1H, J=15.6, 5.4), 6.84 (d, 1H, J=8.4), 6.96 (t, 2H, J=8.4), 7.09–7.18 (m, 7H), 7.21–7.33 (m, 12H), 7.38–7.42 (m, 4H), 7.76 (s, br. 1H), 7.99 (d, 1H, J=7.5); Anal. C$_{50}$H$_{47}$N$_4$O$_7$·0.5H$_2$O: C, H, N.

Preparation of Compound 7

The preceding intermediate was converted to compound 7 by a process analogous to that described in Example 5 for the conversion of I2 to product J1: mp=99–101° C.; IR (cm$^{-1}$) 3308, 1714, 1650, 1511, 1199; $^1$H NMR (CDCl$_3$) δ 1.33 (t, 3H, J=6.9), 1.72–1.82 (m, 1H), 1.86–1.96 (m, 1H), 2.10–2.18 (m, 2H), 3.10–3.17 (m, 2H), 3.10–3.17 (m, 2H), 3.46–3.53 (m, 1H), 3.63–3.74 (m, 2H), 4.22 (q, 2H, J=6.9), 4.48–4.57 (m, 1H), 5.21 (s, 2H), 5.58–5.65 (m, 2H), 5.91–5.97 (m, 1H), 6.19–6.22 (m, 1H), 6.35 (t, 1H, J=7.2), 6.69 (dd, 1H, J=15.6, 5.1), 6.98 (t, 2H, J=8.7), 7.13–7.18 (m, 2H), 7.36–7.40 (m, 5H), 7.85 (s, br. 1H), 8.06–8.09 (m, 1H); Anal. C$_{33}$H$_{33}$N$_4$O$_7$·1.25H$_2$O: C, H, N.

Example 8

Preparation of Compound 8: trans-(2'S,4S)-4-[2'-(3"-Acetylamino-2"-oxo-2"H-pyridin-1"-yl)-3'-phenypropionylamino]-6-carbamoylhex-2-enoic Acid Ethyl Ester

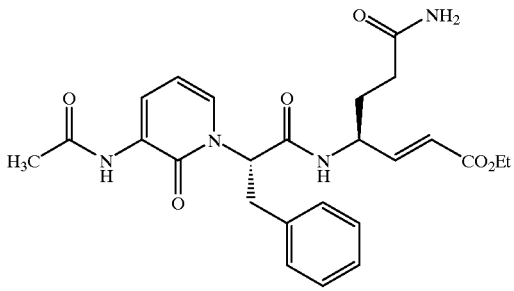

The title compound was prepared from I1 (Example 5) by a process analogous to that described in Example 5 for the conversion of I1 to product J1 utilizing intermediate acetyl chloride where appropriate: IR (cm$^{-1}$) 3307, 1708, 1666, 1643, 1590, 1519; $^1$H NMR (CDCl$_3$) δ 1.30 (t, 3H, J=7.1), 1.70–1.86 (m, 2H), 2.05–2.24 (m, 5H), 3.15 (dd, 1H, J=13.7, 8.1), 3.50 (dd, 1H, J=13.7, 7.8), 4.19 (q, 2H, J=7.1), 4.45–4.56 (m, 1H), 5.66–5.77 (m, 2H), 5.82 (s, 1H), 5.94 (s, 1H), 6.28 (t, 1H, J=7.2), 6.69 (dd, 1H, J=15.7, 5.6), 7.10–7.29 (m, 5H), 7.32–7.45 (m, 2H), 8.28–8.36 (m, 2H); Anal. C$_{25}$H$_{30}$N$_4$O$_6$·0.5H$_2$O: C, H, N.

Example 9

Preparation of Compound 9: trans-(2'S,4S)-6-Carbamoyl-4-{2'-[3"-(2'",2'"-dimethylpropionylamino)-2"-oxo-2"H-pyridin-1"-yl]-3'-phenylpropionylamino}hex-2-enoic Acid Ethyl Ester

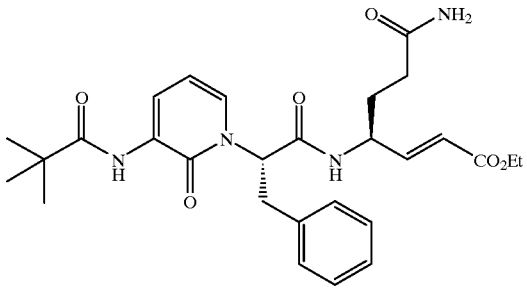

The title compound was prepared from I1 (Example 5) by a process analogous to that described in Example 5 for the conversion of I1 to product J1 utilizing intermediate 2,2-dimethylpropionyl chloride where appropriate: IR (cm$^{-1}$) 3378, 3307, 3213, 1713, 1666, 1643, 1590, 1514, 1273; $^1$H NMR (CDCl$_3$) δ 1.18–1.37 (m, 12H), 1.67–1.98 (m, 2H), 2.05–2.20 (m, 2H), 3.17 (dd, 1H, J=13.6, 7.7), 3.50 (dd, 1H, J=13.6, 8.2), 4.19 (q, 2H, J=7.1), 4.43–4.54 2(m, 1H), 5.62–5.72 (m, 2H), 5.81–5.92 (m, 2H), 6.29 (t, 1H, J=7.2), 6.66 (dd, 1H, J=15.8, 5.7), 7.13–7.39 (m, 7H), 8.33–8.38 (m, 1H), 8.59 (s, 1H); Anal. C$_{28}$H$_{36}$N$_4$O$_6$·0.50H$_2$O: C, H,

Example 10

Preparation of Compound 10: trans-(2'S,4S)-6-Carbamoyl-4-(2'- {3"-[([1'",3'"]dithiolane-2'"-carbonyl)amino]-2"-oxo-2"H-pyridin-1"-yl}-3'-phenylpropionylamino)hex-2-enoic Acid Ethyl Ester

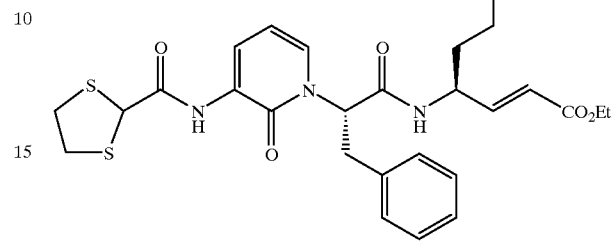

The title compound was prepared from I1 (Example 5) by a process analogous to that described in Example 5 for the conversion of I1 to product J1 utilizing intermediate [1,3]dithiolane-2-carbonyl chloride (prepared as described in *Helv. Chim. Acta* 1975, 58, 2509) where appropriate: IR (cm$^{-1}$) 3295, 1672 (br), 1590, 1519 (br), 1273; $^1$H NMR (CDCl$_3$) δ 1.30 (t, 3H, J=7.1), 1.66–2.22 (m, 4H), 3.17 (dd, 1H, J=13.7, 7.8), 3.28–3.45 (m, 4H), 3.52 (dd, 1H, J=13.7, 8.1), 4.19 (q, 2H, J=7.1), 4.43–4.55 (m, 1H), 5.01 (s, 1H), 5.66 (dd, 1H, J=15.8, 1.5), 5.67 (s, 1H), 5.86 (s, 2H), 6.29 (t, 1H, J=7.3), 6.67 (dd, 1H, J=15.8, 5.5), 7.12–7.40 (m, 7H), 8.31 (dd, 1H, J=7.3, 1.6), 9.57 (s, 1H); Anal. C$_{27}$H$_{32}$N$_4$O$_6$S$_4$·0.50H$_2$O: C, H, N.

Example 11

Preparation of Compound 11: trans-(2'S,4S)-4-[2'-(3"-Benzyloxycarbonylamino-2"-oxo-2"H-pyridin-1"-yl)-3'-(3'",4'"-difluorophenyl)propionylamino]-6-carbamoylhex-2-enoic Acid Ethyl Ester

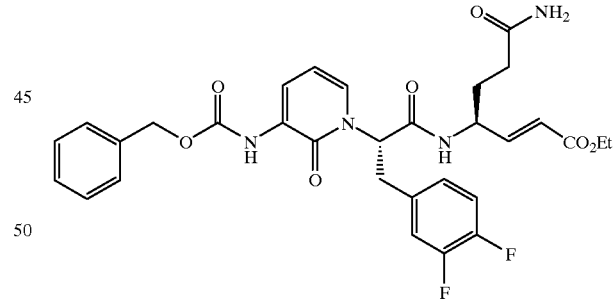

Preparation of Intermediate (2R)-3-(3',4'-Difluorophenyl)-2-hydroxypropionic Acid Boc-D-3,4-Difluorophenylalanine (3.05 g, 11.0 mmol, 1 equiv) was dissolved in 1,4-dioxane (10 mL), and a solution of HCl in 1,4-dioxane (4.0 M, 10 mL) was added. The reaction was stirred at 23° C. for 5 h, then the solvent was removed under reduced pressure. The residue was dissolved in 1 M H$_2$SO$_4$ (22 mL), cooled to 0° C. and 2 N NaNO$_2$ (22 mL) was added via addition funnel under argon. The reaction mixture was stirred at 0° C. for 3 h and warmed to room temperature overnight. The resulting mixture was extracted with MTBE (3×40 mL), dried over Na$_2$SO$_4$ and concentrated. The residue was recrystallized from ether/petroleum ether to afford the title intermediate (1.29 g, 58%) as off-white solid. $^1$H NMR (DMSO-$d_6$) δ 0.82–0.86 (m, 2H), 1.10–1.27 (m, 4H), 1.40–1.48 (m, 2H), 1.63–1.78 (m, 5H), 3.95–4.00 (m, 1H).

Preparation of Compound 11

Intermediate C1 (Example 5) was converted to compound 11 by a process analogous to that described in Example 7 for the conversion of C1 to compound 7 utilizing (2R)-3-(3',4'-difluorophenyl)-2-hydroxypropionic acid (Example 11) where appropriate: mp=175–178° C.; IR (cm$^{-1}$) 3298, 1661, 1516, 1266; $^1$H NMR (CDCl$_3$) δ 1.32 (t, 3H, J=7.2), 1.74–1.95 (m, 2H), 2.12–2.20 (m, 2H), 3.05–3.12 (m, 1H), 3.42–3.50 (m, 1H), 4.21 (q, 2H, J=7.2), 4.45–4.56 (m, 1H), 5.21 (s, 2H), 5.58–5.71 (m, 3H), 6.07–6.10 (m, 1H), 6.32–6.34 (m, 1H), 6.71 (dd, 1H, J=15.6, 5.1), 6.88–6.91 (m, 1H), 6.99–7.11 (m, 2H), 7.30–7.33 (m, 1H), 7.36–7.39 (m, 5H), 7.53 (s, br. 1H), 7.86 (s, br. 1H), 8.04 (s, br. 1H); Anal. $C_{31}H_{32}N_4O_7 \cdot 0.50H_2O$: C, H, N.

Example 12

Preparation of Compound 12: trans-(2'S,4S)-4-[2''-(3''-Benzyloxycarbonylamino-4''-methyl-2''-oxo-2''H-pyridin-1''-yl)-3'-phenylpropionylamino]-6-carbamoylhex-2-enoic Acid Ethyl Ester

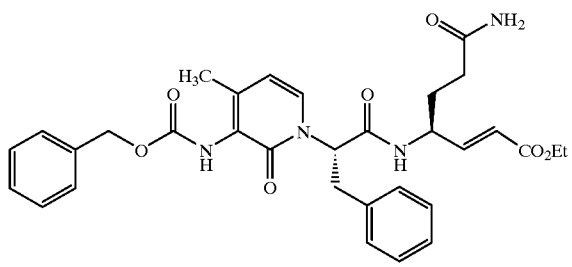

Preparation of Intermediate (2-Hydroxy-6-methylphenyl)carbamic Acid Benzyl Ester A suspension of 10% palladium on carbon (0.045 g) and 2-hydroxy-4-methyl-3-nitropyridine (0.600 g, 3.89 mmol, 1 equiv) in EtOH (20 mL) was subjected to one atmosphere of hydrogen for 16 hours. After purging the reaction vessel with argon, the mixture was filtered through Whatman #3 paper and the filtrate was evaporated to give 2-hydroxy-4-methyl-3-aminopyridine which was used without further purification. This crude material was stirred in THF (18 mL) at 23° C. Benzyl chloroformate (0.611 mL, 4.28 mmol, 1.1 equiv) and Na$_2$CO$_3$ (0.907 g, 8.56 mmol, 2.2 equiv) were added and the reaction mixture was stirred for 60 h, but TLC showed the reaction to be only 25% complete. The reaction mixture was heated to reflux for 24 h. More benzyl chloroformate (0.611 mL, 4.28 mmol, 1.1 equiv) and Na$_2$CO$_3$ (0.454 g, 4.28 mmol, 1.1 equiv) were added. The reaction mixture was heated to reflux for 24 h more, allowed to cool, diluted with EtOAc (200 mL), washed with half-saturated brine (2×40 mL), dried over MgSO$_4$, filtered and evaporated. The residue was purified by flash column chromatography (gradient elution, 3→5% CH$_3$OH in CH$_2$Cl$_2$) to provide the title intermediate (0.363 g, 35%) as a white solid: $^1$H NMR (DMSO-$d_6$) δ 2.02 (s, 3H), 3.31–3.35 (m, 2H), 5.06 (s, 2H), 6.83 (d, 1H, J=6.7), 7.17 (d, 1H, J=6.7), 7.28–7.39 (m, 5H); Anal. $C_{14}H_{14}N_2O_3$: C, H, N.

Preparation of Compound 12

The preceding intermediate was converted to compound 12 by a process analogous to that described in Example 7 for the conversion of C1 to compound 7 utilizing commercially available (2R)-2-hydroxy-3-phenylpropionic acid and C1 (Example 5) where appropriate: IR (cm$^{-1}$) 3284, 1684 (br), 1596, 1327, (br), 1308, 1267, 1237; $^1$H NMR (CDCl$_3$) δ 1.29 (t, 3H, J=7.1), 1.55–1.68 (m, 1H), 1.82–2.07 (m, 4H), 2.14 (s, 3H), 3.08 (dd, 1H, J=13.6, 7.1), 3.47 (dd, J=13.6, 8.8), 4.17 (q, 2H, J=7.1), 4.41–4.52 (m, 1H), 5.06 (d, 1H, J=12.3), 5.12 (d, 1H, J=12.3), 5.59 (dd, 1H, J=15.7, 1.6), 5.67–5.74 (m, 1H), 5.90 (s, 1H), 6.02 (s, 1H), 6.17 (d, 1H, J=7.3), 6.68 (dd, 1H, J=15.7, 5.1), 7.01 (s, 1H), 7.13–7.38 (m, 10H), 7.48 (d, 1H, J=7.3); Anal. $C_{32}H_{36}N_4O_7 \cdot 0.75H_2O$: C, H, N.

Example 13

Preparation of a 1:1 mixture of Compound 13: trans-(2S,2''S,3S)-2-(2'-Naphthalen-1'-yl-7'-oxo-1',7'-dihydropyrrolo[2',3'-c]pyridin-6'-yl)-N-[2'''-(2'''-oxodihydrofuran-3'''-ylidene)-1''-(2'''-oxopyrrolidin-3'''-ylmethyl)ethyl]-3-phenylpropionamide and Compound 14: trans-(2R,2''S,3S)-2-(2'-Naphthalen-1'-yl-7'-oxo-1',7'-dihydropyrrolo[2',3'-c]pyridin-6'-yl)-N-[2''-(2'''-oxodihydrofuran-3'''-ylidene)-1''-(2'''-oxopyrrolidin-3''''-ylmethyl)ethyl]-3-phenylpropionamide

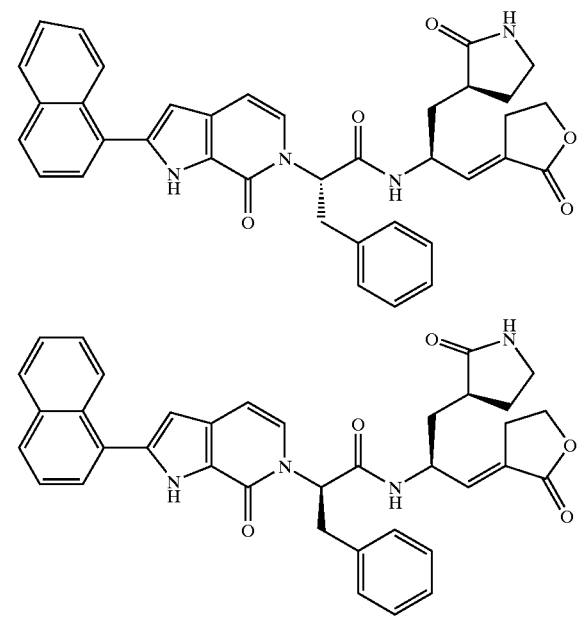

Preparation of Intermediate Pyrrole-2-carboxylic Acid Methyl Ester

Pyrrole-2-carboxylic acid (10.0 g, 90.0 mmol) in diethyl ether (200 mL) was treated with diazomethane (270 mmol, generated from N-nitroso-N-methyl urea), then back titrated with acetic acid until the yellow color dissipated. The solution was washed with saturated aqueous sodium bicarbonate (3×20 mL), followed by brine (3×20 mL), then was evaporated to obtain 10 g (88%) of product. $^1$H NMR (CDCl$_3$) δ 3.86 (s, 3H), 6.26–6.29 (m, 1H), 6.91–6.94 (m, 1H), 6.65–6.98 (m, 1H), 9.14 (s, 1H).

Preparation of Intermediate 5-Bromo-1H-pyrrole-2-carboxylic Acid Methyl Ester A solution of the preceding intermediate (10.0 g, 79.9 mmol, 1 equiv) in carbon tetrachloride (300 mL) was heated to 70° C., then treated dropwise with a solution of bromine (126.0 mL, 99.9 mmol, 1.25 equiv) in carbon tetrachloride (200 mL). The reaction was initiated by the addition of iodine (40 mg). After the addition was complete, the reaction was held at 70° C. for 10 min, then cooled to 23° C. using an ice bath. The mixture was washed with 10% aqueous sodium carbonate (100 mL), followed by water (100 mL). The volatiles were evaporated, and the residue was purified by silica gel chromatography to obtain 4.5 g (27%) of product: $^1$H NMR (CDCl$_3$) δ 3.88 (s, 3H), 6.23 (dd, 1H, J=3.8, 2.6), 6.80 (dd, 1H, J=3.9, 2.7), 9.29 (s, 1H).

Preparation of Intermediate 5-Naphthalene-1-yl-1H-pyrrole-2-carboxylic Acid Methyl Ester Argon gas was bubbled for 15 min through a solution of the preceding intermediate (2.04 g, 10.0 mmol, 1 equiv) in 2 M aqueous sodium carbonate (20 mL), and DMF (150 mL). The mixture was then treated with tris(dibenzylidienacetone)dipalladium (O) (0.46 g, 0.50 mmol, 0.05 equiv), and triphenylarsine (0.61 g, 2.0 mmol, 0.20 equiv), then heated to reflux, under argon, for 12 h. The mixture was taken up in ethyl acetate (500 mL) and water (150 mL), then filtered through celite. The organic layer was washed with brine (3×50 mL), then evaporated. Purification of the residue by silica gel chromatography yielded 2.05 g (81%) of product. $^1$H NMR (CDCl$_3$) δ 3.88 (s, 3H), 6.22 (dd, 1H, J=3.8. 2.6), 7.50–7.59 (m, 4H), 7.88 (dd, 1H, J=3.9, 2.7), 7.89–8.16 (m, 2H), 8.17–8.22 (m, 1H), 9.37 (s, 1H). This material was taken up in 1:1 1,4-dioxane-water (30 mL), and treated with lithium hydroxide hydrate (1.02 g, 24.4 mmol, 2.4 equiv), then heated to reflux for 15 min. The solution was acidified with 20% aqueous citric acid (30 mL), then extracted with ethyl acetate (75 mL). The organic layer was washed with brine (2×20 mL), then evaporated. The residue was taken up in CH$_2$Cl$_2$, (30 mL), and treated with oxalyl chloride (2.10 mL, 24.0 mmol, 2.4 equiv), and DMF (one drop), then heated to reflux for 30 min. Evaporation yielded 5-naphthalen-1-yl-1H-pyrrole-2-carboxylic acid chloride which was used in the subsequent procedure without additional purification.

Preparation of Products 13 and 14

The preceding intermediate was converted to an inseparable 1:1 mixture of the title compounds by a process that was analogous to that described in Example 3 for the conversion of pyrrole-2-carbonyl chloride to compounds 3 and 4 and utilizing intermediate Y1 (Example 22) in lieu of Y2 where appropriate. $^1$H NMR (CDCl$_3$) δ 1.55–2.00 (m, 6H), 2.50–3.50 (m, 7H), 4.00–4.50 (m, 3H), 4.42–5.60 (m, 1H), 5.90–8.40 (m, 15H), 10.49 (s, 0.5H), 11.54 (s, 0.5H).

Example 14

Preparation of Compound 15: trans-(2'S,4S)-4-[2'-(3"-Benzyloxycarbonylamino-2"-oxo-2"H-pyridin-1"-yl)-3'-cyclohexylpropionylamino]-6-carbamoyl-hex-2-enoic Acid Ethyl Ester

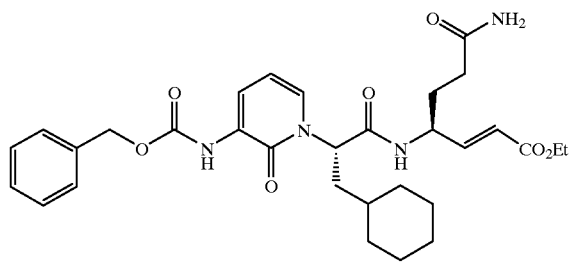

Preparation of Intermediate (2R)-3-Cyclohexyl-2-hydroxypropionic Acid

Boc-D-Cyclohexylalanine-OH (3.00 g, 11.1 mmol, 1 equiv) was dissolved in 1,4-dioxane (10 mL), and a solution of HCl in 1,4-dioxane (4.0 M, 10 mL) was added. The reaction was stirred at 23° C. for 5 h, then the solvent was removed under reduced pressure. The residue was dissolved in 1 M H$_2$SO$_4$ (22 mL), cooled to 0° C. and 2 N NaNO$_2$ (22 mL) was added via addition funnel under argon. The reaction mixture was stirred at 0° C. for 3 h and warmed to room temperature overnight. The resulting mixture was extracted with MTBE (3×40 mL), dried over Na$_2$SO$_4$ and concentrated. The residue was triturated with petroleum ether, filtered and dried in the air to afford the title intermediate (0.6 g, 31%) as off-white solid. $^1$H NMR (DMSO-d$_6$) δ 3.09–3.24 (m, 2H), 4.20–4.24 (m, 1H), 7.13–7.18 (m, 1H), 7.38–7.47 (m, 2H), 8.49 (s, br. 1H).

Preparation of Compound 15

Intermediate C1 (Example 5) was converted to product 15 by a process analogous to that described in Example 7 for the conversion of C1 to compound 7 utilizing (2R)-3-cyclohexyl-2-hydroxypropionic acid (Example 14) where appropriate: mp=64–66° C.; IR (cm$^{-1}$) 3302, 2925, 1721, 1651, 1197; $^1$H NMR (CDCl$_3$) δ 0.93–1.05 (m, 2H), 1.18–1.22 (m, 4H), 1.32 (t, 3H, J=7.2), 1.66–1.75 (m, 4H), 1.82–1.91 (m, 2H), 1.94–2.06 (m, 2H), 2.10–2.17 (m, 2H), 2.90–2.92 (m, 2H), 4.23 (q, 2H, J=7.2), 4.52–4.60 (m, 1H), 5.23 (s, 2H), 5.65 (t, 1H, J=8.1), 5.82–5.86 (m, 1H), 5.62 (dd, 1H, J=15.9, 1.8), 6.01–6.05 (m, 1H), 6.37 (t, 1H, J=7.2), 6.85 (dd, 1H, J=15.9, 5.7), 7.25–7.29 (m, 1H), 7.36–7.43 (m, 5H), 7.88 (s, br. 1H), 8.09 (d, 1H, J=6.9); Anal. C$_{31}$H$_{40}$N$_4$O$_7$·1.0H$_2$O: C, H, N.

Example 15

Preparation of Compound 16: trans-(2'''S,2'''S, 3''''S)-Cyclopentanecarboxylic acid(1-{2'-(4''-fluorophenyl)-1'-[2'-(2''''-oxo-dihydrofuran-3''''-ylidene)-1-(2''''-oxopyrrolidin-3''''-ylmethyl) ethylcarbamoyl]ethyl}-2-oxo-1,2-dihydropyridin-3-yl)amide

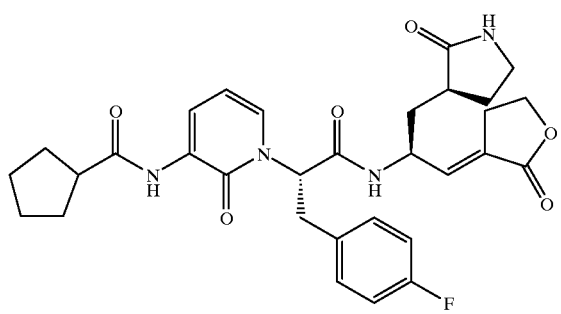

Preparation of Intermediate Cyclopentanecarboxylic Acid (2-Hydroxypyridin-3-yl)amide A sample of 10% Pd on C (0.40 g) was added to a solution of 2-hydroxy-3-nitropyridine (3.52 g, 25.0 mmol, 1 equiv) in EtOH. The reaction mixture was stirred at room temperature under $H_2$ atmosphere (balloon) overnight and then was filtered through Celite. The filtrate was concentrated under reduced pressure. The residue was dissolved in $CH_3CN$ (100 mL), cooled to 0° C., and cyclopentanecarbonyl chloride (25 mmol, 3.04 mL, 1 equiv) and NMM (2.75 mL, 25 mmol, 1 equiv) were added sequentially. The resulting mixture was stirred at 0° C. for 20 min, then was partitioned between water (400 mL) and 10% $CH_3OH$ in $CH_2Cl_2$ (2×400 mL). The organic layers were dried over $Na_2SO_4$, concentrated, and the resulting residue recrystallized from $CH_2Cl_2$/hexanes to afford the title intermediate as a off-white solid (3.36 g, 65%); mp=242–243° C.; IR (cm$^{-1}$) 3263, 1644, 1605, 1521, 1199; $^1$H NMR (DMSO-d$_6$) δ 1.51–1.57 (m, 2H), 1.60–1.72 (m, 4H), 1.79–1.88 (m, 2H), 2.98–3.08 (m, 1H), 6.20 (t, 1H, J=6.9), 7.08 (d, 1H, J=6.6), 8.23 (d, 1H, J=7.5), 9.02 (s, br. 1H), 11.95 (s, br. 1H); Anal. $C_{11}H_{14}N_2O_2$: C, H, N.

Preparation of Compound 16

The preceding intermediate was converted to compound 16 by a process that was analogous to that described in Example 19 for the conversion of F2 to R1: mp=135–137° C.; IR (cm$^{-1}$) 3288, 2954, 1754, 1682, 1511, 1219; $^1$H NMR (CDCl$_3$) δ 0.84–0.93 (m, 2H), 1.55–1.66 (m, 4H), 1.82–2.02 (m, 5H), 2.27–3.22 (m, 2H), 2.70–2.89 (m, 3H), 3.09–3.17 (m, 1H), 3.20–3.37 (m, 2H), 3.42–3.39 (m, 1H), 5.63 (t, 1H, J=7.2), 6.03 (s, br. 1H), 6.25–6.35 (m, 2H), 6.94 (t, 2H, J=8.7), 7.08–7.12 (m, 2H), 7.25 (d, 1H, J=9.0), 8.30–8.35 (m, 2H), 8.44 (d, 1H, J=6.0); Anal. $C_{31}H_{35}FN_4O_6$·1.0H$_2$O: C, H, N.

Example 16

Preparation of Compound 17: trans-(4S)-4-[2'-(3''-Benzyloxycarbonylamino-2''-oxo-2''H-pyridin-1''-yl) acetylamino]-6-carbamoylhex-2-enoic Acid Ethyl Ester

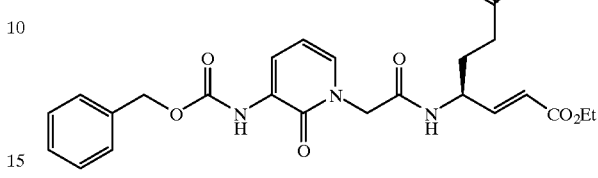

Preparation of intermediate (3-benzyloxycarbonylamino-2-oxo-2h-pyridin-1-yl) acetic acid tert-butyl ester Sodium hydride (0.070 g of a 60% suspension in mineral oil, 1.75 mmol, 1.0 equiv) was added to a solution of (2-hydroxypyridin-3-yl)carbamic acid benzyl ester prepared as described in Example 1) (0.415 g, 1.70 mmol, 1 equiv) in THF (20 mL) at 0° C. The reaction mixture was stirred for 20 min at 0° C., then tert-butyl bromoacetate (0.275 mL, 1.86 mmol, 1.1 equiv) was added. The reaction mixture was warmed to 23° C. for 45 min, then was partitioned between 0.5 M HCl (150 mL) and EtOAc (2×100 mL). The organic layers were dried over $Na_2SO_4$ and were concentrated. Purification of the residue by flash column chromatography (30% EtOAc in hexanes) provided the title compound (0.485 g, 85%) as an off-white solid: mp=88–90° C.; IR (cm$^{-1}$) 3380, 1739, 1652, 1604; $^1$H NMR (CDCl$_3$) δ 1.48 (s, 9H), 4.57 (s, 2H), 5.20 (s, 2H), 6.25 (t, 1H, J=7.1), 6.87 (dd, 1H, J=6.9, 1.7), 7.27–7.41 (m, 5H), 7.86 (s, br, 1H), 8.05 (d, br, 1H J=6.8); Anal. $C_{19}H_{22}N_2O_5$: C, H, N.

Preparation of Intermediate (3-Benzyloxycarbonylamino-2-oxo-2H-pyridin-1-yl) acetic Acid (3-Benzyloxycarbonylamino-2-oxo-2H-pyridin-1-yl) acetic acid tert-butyl ester (0.485 g, 1.35 mmol) was stirred in a 1:1 mixture of trifluoroacetic acid and $CH_2Cl_2$ at 23° C. for 1 h. The volatiles were then removed under reduced pressure and the residue was triturated with Et$_2$O (40 mL). The resulting solid was filtered through a medium frit, washed with Et$_2$O (20 mL) and air-dried to give the title intermediate (0.315 g, 77%): mp=171–173° C.; $^1$H NMR (DMSO-d$_6$) δ 4.67 (s, 2H), 5.15 (s, 2H), 6.28 (t, 1H, J=7.1), 7.29–7.43 (m, 7H), 7.85 (dd, 1H, J=7.4, 1.7), 8.47 (s, 1H).

Preparation of Compound 17

The preceding intermediate was converted to compound 17 by a process analogous to that described in Example 23 for the conversion of W2 to J2: mp=169–174° C.; IR (cm$^{-1}$) 3273, 1719, 1649; $^1$H NMR (DMSO-d$_6$) δ 1.19 (t, 3H, J=7.1), 1.64–1.85 (m, 2H), 2.10 (t, 2H, J=7.6), 4.11 (q, 2H, J=7.1), 4.38–4.41 (m, 1H), 4.60 (d, 1H, J=15.5), 4.67 (d, 1H, J=15.5), 5.15 (s, 2H), 5.92 (dd, 1H, J=15.8, 1.3), 6.26 (t, 1H, J=7.1), 6.76–6.83 (m, 2H), 7.09–7.42 (m, 7H), 7.84 (d, 1H, J=7.3), 8.41–8.44 (m, 2H); Anal. $C_{24}H_{28}N_4O_7$·0.50H$_2$O: C, H, N.

Example 17

Preparation of Compound 18: trans-(2'S,4S)-6-Carbamoyl-4-(2'-{4"-methyl-3"-[(5'''-methylisoxazole-3'''-carbonyl)amino]-2"-oxo-2"H-pyridin-1"-yl}-3'-phenylpropionylamino)hex-2-enoic Acid Ethyl Ester

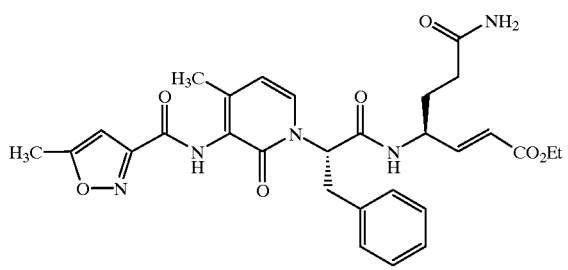

Preparation of Intermediate 5-Methylisoxazole-3-carboxylic Acid (2'-hydroxy-4'-methylpyridin-3'-yl)amide A sample of 10% Pd on C (0.35 g) was added to a solution of 2-hydroxy-3-nitropyridine (2.03 g, 14.5 mmol, 1 equiv) in EtOH. The reaction mixture was stirred at room temperature under $H_2$ atmosphere (balloon) overnight and then was filtered through Celite. The filtrate was concentrated under reduced pressure. The residue was dissolved in $CH_3CN$ (100 mL), cooled to 0° C., and 5-methylisoxazole-3-carbonyl chloride (2.11 g, 14.5 mmol, 1 equiv) and NMM (1.51 mL, 14.5 mmol, 1 equiv) were added sequentially. The resulting mixture was stirred at 0° C. for 20 min, and then was partitioned between water (400 mL) and 10% $CH_3OH$ in $CH_2Cl_2$ (2×400 mL). The organic layers were dried over $Na_2SO_4$, concentrated and the resulting residue was recrystallized from $CH_2Cl_2$/hexanes to afford the title intermediate as an off-white solid (2.42 g, 76%): IR (cm$^{-1}$) 3330, 1650, 1536; $^1$H NMR (DMSO-d$_6$) δ 3.34 (s, 3H), 6.31 (t, 1H, J=6.6), 6.73 (s, 1H), 7.21 (d, 1H, J=7.2), 8.29 (s, 1H, J=7.2), 9.46 (s, br. 1H), 12.23 (s, br. 1H).

Preparation of Compound 18

The preceding intermediate was converted to Compound 18 by a process analogous to that described in Example 7 for the conversion of C1 to Compound 7 utilizing (2R)-2-hydroxy-3-phenylpropionic acid where appropriate: mp=138–141° C.; IR (cm$^{-1}$) 3289, 1663, 1542, 1203; $^1$H NMR (CDCl$_3$) δ 1.22 (t, 3H, J=7.2), 1.62–1.89 (m, 2H), 1.99 (s, 3H), 2.02–2.07 (m, 1H), 2.47 (s, 3H), 3.03–3.39 (m, 5H), 4.12 (q, 2H, J=7.2), 4.32–4.41 (m, 1H), 5.76 (dd, 1H, J=15.6, 1.5), 5.80–5.83 (m, 1H), 6.13 (d, 1H, J=7.5), 6.60 (s, br. 1H), 6.75 (dd, 1H, J=15.6, 5.4), 7.15–7.24 (m, 5H), 7.76 (d, 1H, J=7.2), 8.65 (d, 1H, J=7.8), 9.59 (s, br. 1H); Anal. $C_{29}H_{33}N_5O_7 \cdot 1.5TFA$: C, H, N.

Example 18

Preparation of Compound 19: trans-(2'S,3'''S,4S)-4-[2'-(3"-Benzyloxy-carbonylamino-2"-oxo-2"H-pyridin-1"-yl)-3'-phenylpropionylamino]-5-(2'''-oxopyrrolidin-3'''-yl)pent-2-enoic Acid Ethyl Ester

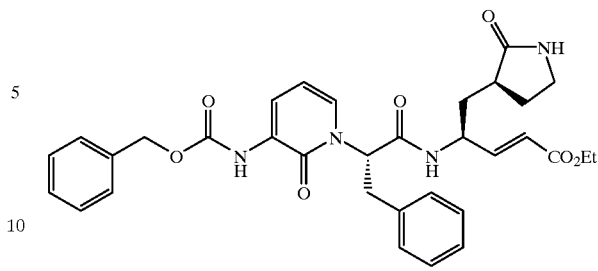

The title compound was prepared from K1 (Example 19) by a process analogous to that described in Example 19 for the conversion of K1 to R1 utilizing commercially available (2R)-2-hydroxy-3-phenylpropionic acid, (2-hydroxypyridin-3-yl)carbamic acid benzyl ester (Example 2), and commercially available (carbethoxymethylene)-triphenylphosphorane where appropriate: IR (cm$^{-1}$) 3272, 1684 (br), 1590, 1514, 1273, 1196; $^1$H NMR (CDCl$_3$) δ 1.30 (t, 3H, J=7.1), 1.42–1.55 (m, 1H), 1.59–1.75 (m, 1H), 2.00–2.27 (m, 3H), 3.07–3.28 (m, 3H), 3.43 (dd, 1H, J=13.7, 7.3), 4.19 (q, 2H, J=7.1), 4.36–4.47 (m, 1H), 5.12–5.21 (m, 2H), 5.75 (dd, 1H, J=15.6, 1.2), 5.85–5.94 (m, 1H), 6.26 (t, 1H, J=7.2), 6.58 (s, 1H), 6.70 (dd, 1H, J=15.6, 5.7), 7.10–7.41 (m, 10H), 7.44–7.50 (m, 1H), 7.71 (s, 1H), 7.97 (d, 1H J=6.2), 8.28 (d, 1H, J=6.8); Anal. $C_{33}H_{36}N_4O_7 \cdot 0.25H_2O$: C, H, N.

Example 19

Preparation of Compound 20: trans-(2"S,2""S, 3""S)-5-Methylisoxazole-3-carboxylic Acid (1'-{2"-(4'''-fluorophenyl)-1"-[2""-(2""-oxodihydrofuran-3""-ylidene)-1""-(2"""oxopyrrolidin-3"""-ylmethyl)ethylcarbamoyl]ethyl}-2'-oxo-1',2'-dihydropyridin-3'-yl)amide (R1)

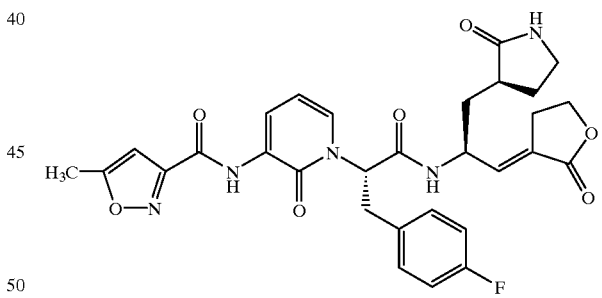

Preparation of Intermediate (1S,3'S)-{2-(tert-Butyldiphenylsilanyloxy)-1-[1'-(2",4"-dimethoxybenzyl)-2'-oxopyrrolidin-3'-ylmethyl]ethyl}carbamic Acid tert-Butyl Ester (L1)

Intermediate K1 (4.41 g, 10.8 mmol, 1 equiv) was stirred in $CH_2Cl_2$ (50 mL) and the mixture was cooled to 0° C. Triethylamine (7.52 mL, 54.0 mmol, 5 equiv), tert-butylchlorodiphenylsilane (5.53 mL, 21.6 mmol, 2 equiv) and 4-(dimethylamino)pyridine (0.330 g, 2.70 mmol, 0.25 equiv) were added successively. The mixture was allowed to warm to 23° C. and was stirred for 2 h. It was then diluted with MTBE (400 mL), washed with brine (2×100 mL), dried over $MgSO_4$ and evaporated. The residue was purified by flash column chromatography to provide the title intermediate (3.51 g, 50%) as a white foam: IR (cm$^{-1}$) 3319, 1678, 1508; $^1$H NMR (CDCl$_3$) δ 1.05 (s, 9H), 1.42 (s, 9H), 1.44–1.65 (m, 2H), 2.05–2.17 (m, 1H), 2.23–2.35 (m, 1H), 2.44–2.56 (m, 1H), 3.14–3.21 (m, 2H), 3.55–3.68 (m, 2H), 3.69–3.81 (m, 1H), 3.79 (s, 3H), 3.79 (s, 3H), 4.42 (s, 2H), 4.77 (d, 1H, J=9.3), 6.41–6.46 (m, 2H), 7.09–7.13 (m, 1H), 7.34–7.46 (m, 6H), 7.61–7.67 (m, 4H); Anal. C$_{37}$H$_{50}$N$_2$O$_6$Si: C, H, N.

Preparation of Intermediate (1'S,2R,3"S)-N-{2'-(tert-Butyldiphenylsilanyloxy)-1'-[1"-(2'",4'"-dimethoxybenzyl)-2"-oxopyrrolidin-3"-ylmethyl]ethyl}-2-hydroxy-3-(4""-fluorophenyl)propionamide (M1)

Intermediate L1 from above (3.4 g, 5.26 mmol, 1 equiv) was dissolved in 1,4-dioxane (20 mL) at 23° C. A solution of HCl in the same solvent (4.0 M, 20 mL) was added. After stirring 75 min, the volatiles were evaporated to provide a residue which was dissolved in CH$_3$CN (25 mL) and cooled to 0° C. (2R)-3-(4'-Fluorophenyl)-2-hydroxypropionic acid (intermediate S1, see below, 0.968 g, 5.26 mmol, 1 equiv), 4-methylmorpholine (1.91 mL, 17.4 mmol, 3.3 equiv) and HATU (2.20 g, 5.79 mmol, 1.1 equiv) were added successively and the reaction mixture was allowed to warm to 23° C. and stirred 2.5 h. It was then diluted with EtOAc (500 mL) and washed with a mixture of brine and 10% KHSO$_4$ (3:1, 100 mL) and a mixture of brine and NaHCO$_3$ (1:1, 100 mL). The organic phase was dried over MgSO$_4$ and evaporated. The residue was purified by flash column chromatography (first in 5% CH$_3$OH in CH$_2$Cl$_2$, then in 3% CH$_3$OH in CH$_2$Cl$_2$) to provide the title intermediate (0.90 g, 51%) as a white foam: IR (cm$^{-1}$) 3389, 3319, 1660, 1508; $^1$H NMR (CDCl$_3$) δ 1.04 (s, 9H), 1.52–1.66 (m, 2H), 2.02–2.13 (m, 2H), 2.20–2.39 (m, 2H), 2.77–2.86 (m, 1H), 3.07–3.23 (m, 3H), 3.47 (dd, 1H, J=9.9, 5.9), 3.59 (dd, 1H, J=9.9, 3.6), 3.77 (s, 3H), 3.78 (s, 3H), 3.99–4.11 (m, 1H), 4.22–4.29 (m, 1H), 4.31–4.41 (m, 2H), 6.36–6.45 (m, 2H), 6.81–6.89 (m, 2H), 7.05 (d, 1H, J=8.0), 7.13–7.22 (m, 3H), 7.34–7.46 (m, 6H), 7.59–7.67 (m, 4H); Anal. C$_{41}$H$_{49}$FN$_2$O$_6$Si·0.25H$_2$O: C, H, N.

Preparation of Intermediate (1'S,2R,3"S)-Methanesulfonic Acid 1-{2'-(tert-butyldiphenylsilanyloxy)-1'-[1"-(2'",4'"-dimethoxybenzyl)-2"-oxopyrrolidin-3"-ylmethyl]ethylcarbamoyl}-2-(4""-fluorophenyl)ethyl Ester (N1)

Intermediate M1 from above (2.13 g, 2.99 mmol, 1 equiv) and iPr$_2$NEt (0.729 mL, 4.19 mmol, 1.4 equiv) were dissolved in CH$_2$Cl$_2$ (35 mL) and cooled to –10° C. Methanesulfonyl chloride (0.277 mL, 3.58 mmol, 1.2 equiv) was added dropwise, slowly, with vigorous stirring. After 30 min, the reaction mixture was diluted with MTBE (500 mL), washed with a mixture of brine and 10% KHSO$_4$ (2:1, 100 mL) and brine (100 mL), dried over Na$_2$SO$_4$ and evaporated to provide the title intermediate which was used without further purification.

Preparation of Intermediate 5-Methylisoxazole-3-carboxylic Acid(2'-hydroxypyridin-3'-yl)amide (F2)

A suspension of 10% palladium on carbon (0.45 g) and 2-hydroxy-3-nitropyridine (7.00 g, 50.0 mmol, 1 equiv) in EtOH (210 mL) was subjected to one atmosphere of hydrogen for 16 hours. After purging the reaction vessel with argon, the mixture was filtered through Whatman #3 paper and the filtrate was evaporated to give 2-hydroxy-3-aminopyridine which was used without further purification. This crude material was suspended in CH$_3$CN (170 mL) and cooled to 0° C. 5-Methylisoxazole-3-carbonyl chloride (8.00 g, 55.0 mmol, 1 equiv) was added in one portion. After 25 min at 0° C., the reaction mixture was allowed to warm to 23° C. and stirred for an additional 75 min. The thick mixture was then poured into dilute HCl (0.02 M, 150 mL) and mixed thoroughly. The undissolved solid was collected by filtration and washed with H$_2$O (2×20 mL) then dried under vacuum overnight to provide the title intermediate (7.1 g, 65%): $^1$H NMR (DMSO-d$_6$) δ 2.48 (s, 3H), 6.29 (dd, 1H, J=7.2, 6.6), 6.69 (s, 1H), 7.19 (dd, 1H, J=6.6, 1.8), 8.26 (dd, 1H, J=7.2, 1.8), 9.43 (s, 1H), 12.20 (s, 1H).

Preparation of Intermediate (1'''S,2"S,3""S)-5-Methylisoxazole-3-carboxylic Acid{1'-[1"-{2'"-(tert-butyldiphenylsilanyloxy)-1'''-[1""-(2''''',4'''''-dimethoxybenzyl)-2''''-oxopyrrolidin-3''''-ylmethyl]ethylcarbamoyl}-2"-(4''''''-fluorophenyl)ethyl]-2'-oxo-1',2'-dihydropyridin-3'-yl}amide (O1)

Intermediate F2 from above (1.11 g, 5.06 mmol, 1.7 equiv) was stirred in THF (14 mL). Sodium hydride (60% dispersion in mineral oil, 0.173 g, 4.32 mmol, 1.45 equiv) was added. After stirring 30 min, a solution of intermediate N1 from above (1 equiv based on M1) in THF (11 mL) was added. The resulting mixture was heated to reflux overnight, then diluted with EtOAc (500 mL) and washed with a mixture of brine and 10% KHSO$_4$ (3:1, 100 mL) and brine and NaHCO$_3$ (3:1, 100 mL). The organic phase was dried over Na$_2$SO$_4$ and evaporated. The residue was purified by flash column chromatography (gradient elution, 2→3% CH$_3$OH in CH$_2$Cl$_2$) to provide the desired intermediate O1 as a white foam (2.58 g, 95%): IR (cm$^{-1}$) 3331, 3284, 1666, 1596, 1531, 1455; $^1$H NMR (CDCl$_3$) δ 1.06 (s, 9H), 1.45–1.71 (m, 2H), 1.94–2.32 (m, 3H), 2.52 (s, 3H), 3.07–3.19 (m, 3H), 3.42–3.52 (m, 2H), 3.67–3.74 (m, 1H), 3.79 (s, 3H), 3.81 (s, 3H), 3.99–4.10 (m, 1H), 4.30 (d, 1H, J=14.6), 4.39 (d, 1H, J=14.6), 5.54–5.63 (m, 1H), 6.25 (t, 1H, J=7.3), 6.42–6.50 (m, 3H), 6.81–6.88 (m, 2H), 7.04–7.13 (m, 3H), 7.20–7.26 (m, 1H), 7.36–7.48 (m, 7H), 7.60–7.68 (m, 4H), 8.40 (dd, 1H, J=7.3, 1.6), 9.60 (s, 1H); Anal. C$_{51}$H$_{56}$FN$_5$O$_8$Si: C, H, N.

Preparation of Intermediate (2"S,2'''S,3""S)-5-Methylisoxazole-3-carboxylic Acid {1'-[1"-{1'''-[1''''-(2''''',4'''''-dimethoxybenzyl)-2'''''-oxopyrrolidin-3'''''-ylmethyl]-2"-2"-hydroxyethylcarbamoyl}-2"-(4''''''-fluorophenyl)ethyl]-2'-oxo-1',2'-dihydropyridin-3'-yl}amide (P1)

Intermediate O1 from above (2.51 g, 2.75 mmol, 1 equiv) was dissolved in a mixture of CH$_3$CN (30 mL) and H$_2$O (1 mL) in a plastic tube. Hydrofluoric acid (48%, 5 mL) was added dropwise. After 1 h and 1.5 h, more hydrofluoric acid (2.5 mL and 2 mL respectively) was added. After 3.5 h total, the reaction mixture was poured into saturated aqueous NaHCO$_3$ (250 mL), extracted with CH$_2$Cl$_2$ (3×400 mL), dried over Na$_2$SO$_4$ and evaporated. The residue was purified by flash column chromatography (5% CH$_3$OH in CH$_2$Cl$_2$) to provide the title intermediate (1.84 g, 99%) as a white foam: IR (cm$^{-1}$) 3401 (br), 3331, 1655, 1590, 1531, 1508, 1455, 1208; $^1$H NMR (CDCl$_3$) δ 1.47–1.63 (m, 2H), 1.87–1.99 (m, 1H), 2.07–2.18 (m, 1H), 2.33–2.44 (m, 1H), 2.49 (s, 3H), 3.10–3.24 (m, 3H), 3.46–3.56 (m, 3H), 3.76 (s, 3H), 3.78 (s, 3H), 3.84–3.89 (m, 1H), 3.92–4.03 (m, 1H), 4.19 (d, 1H, J=14.5), 4.39 (d, 1H, J=14.5), 5.54–5.61 (m, 1H), 6.22 (t, 1H, J=7.2), 6.38–6.46 (m, 3H), 6.85–6.93 (m, 2H), 6.99–7.04 (m, 1H), 7.06–7.13 (m, 2H), 7.24 (dd, 1H, J=7.2, 1.7), 8.33 (d, 1H, J=7.3), 8.38 (dd, 1H, J=7.2, 1.7), 9.54 (s, 1H); Anal. $C_{35}H_{38}FN_5O_8 \cdot 0.50H_2O$: C, H, N.

Preparation of Intermediate trans-(2"S,2'"S,3'"S)-5-Methylisoxazole-3-carboxylic Acid {1'-[1"-[1'"-[1""-(2"",4""-dimethoxybenzyl)-2""-oxopyrrolidin-3""-ylmethyl]-2'"-(2-oxocyclopentylidene)ethylcarbamoyl,-2"-(4""'-fluorophenyl)ethyl]-2'-oxo-1',2'-dihydropyridin-3'-yl}amide (Q1)

Intermediate P1 from above (1.76 g, 2.60 mmol, 1 equiv) and commercially available Dess-Martin periodinane (1.11 g, 2.60 mmol, 1 equiv) were combined in $CH_2Cl_2$ (20 mL) at 23° C. and stirred 2 h. The volatiles were evaporated. The residue was suspended in toluene and concentrated to dryness (2×25 mL). The resulting residue was dissolved in a mixture of ethylene glycol dimethyl ether and DMF (5:1, 24 mL). 3-(triphenyl-$1^5$-phosphanylidene)-dihydrofuran-2-one (prepared in a manner analogous to that described in Baldwin et al., *J. Org. Chem.* 1971, vol. 36, 1441) (0.902 g, 2.60 mmol, 1 equiv) was added and the reaction mixture was heated to 100° C. for 1.5 h. It was then allowed to cool, diluted with EtOAc (500 mL), washed with brine (200 mL, 100 mL), dried over $MgSO_4$ and evaporated. The residue was chromatographed (gradient elution, 2→3% $CH_3OH$ in $CH_2CH_2Cl_2$) then rechromatographed (50% EtOAc in $CH_2Cl_2$) to give the title intermediate (1.46 g) contaminated with triphenylphosphine oxide (approximately 35% by weight): $^1$H NMR ($CDCl_3$) δ 1.47–1.62 (m, 2H), 1.87–1.98 (m, 1H), 2.21–2.31 (m, 1H), 2.38–2.52 (m, 1H), 2.50 (s, 3H), 2.81–2.93 (m, 1H), 3.10–3.33 (m, 4H), 3.50 (dd, 1H, J=14.1, 7.0), 3.76 (s, 3H), 3.77 (s, 3H), 4.19 (d, 1H, J=14.3), 4.29–4.52 (m, 3H), 4.38 (d, 1H, J=14.3), 5.42–5.49 (m, 1H), 6.23 (t, 1H, J=7.2), 6.27–6.33 (m, 1H), 6.40–6.48 (m, 3H), 6.90–6.97 (m, 2H), 7.00–7.12 (m, 3H), 7.15 (dd, 1H, J=7.2, 1.6), 8.39 (dd, 1H, J=7.2, 1.6), 8.83 (d, 1H, J=5.7), 9.56 (s, 1H).

Preparation of Product R1 (Compound 20)

Intermediate Q1, prepared above, was dissolved in a mixture of $CHCl_3$ (30 mL) and $H_2O$ (3 mL). DDQ (0.390 g, 1.72 mmol, 1.4 equiv) was added and the reaction mixture was warmed in a 60° C. oil bath for 1.5 h. More DDQ (0.390 g, 1.72 mmol, 1.4 equiv) was added and the reaction vessel was held in the 60° C. oil bath for 1.5 h more. DDQ (0.390 g, 1.72 mmol, 1.4 equiv) was again added. After stirring 2 h more, the reaction mixture was allowed to cool, diluted with $CH_2Cl_2$ (250 mL), and washed sequentially with a mixture of brine and 1 N HCl (2:1, 80 mL), a mixture of brine and $NaHCO_3$ (2:1, 80 mL) and brine (80 mL). The organic phase was dried over $MgSO_4$ and evaporated. The residue was purified by flash column chromatography (2.5% $CH_3OH$ in $CH_2Cl_2$) to provide the desired product (0.530 g, 73%) as an off-white amorphous solid: IR (cm$^{-1}$) 3336, 1750, 1682, 1530; $^1$H NMR ($CDCl_3$) δ 1.39–1.49 (m, 1H), 1.63–1.80 (m, 1H), 2.09–2.37 (m, 3H), 2.49 (s, 3H), 2.74–2.86 (m, 1H), 3.11 (dd, 1H, J=13.8, 8.5), 3.14–3.38 (m, 3H), 3.39 (dd, 1H, J=13.8, 7.5), 4.30–4.46 (m, 3H), 5.72–5.79 (m, 1H), 6.29 (t, 1H, J=7.2), 6.30–6.36 (m, 1H), 6.44–6.47 (m, 1H), 6.77 (s, 1H), 6.88–6.97 (m, 2H), 7.04–7.11 (m, 2H), 7.44–7.50 (m, 1H), 8.37 (dd, 1H, J=7.2, 1.6), 8.66 (d, 1H, J=6.2), 9.47 (s, 1H); Anal. $C_{30}H_{30}FN_5O_7 \cdot 0.25H_2O$: C, H, N.

Example 20

Preparation of Compound 21: trans-(2'S,3'"R,4S)-4-[2'-(3"-Benzyloxycarbonylamino-2"-oxo-2"H-pyridin-1"-yl)-3'-phenylpropionylamino]-5-(2'"-oxopyrrolidin-3'"-yl)pent-2-enoic Acid Ethyl Ester

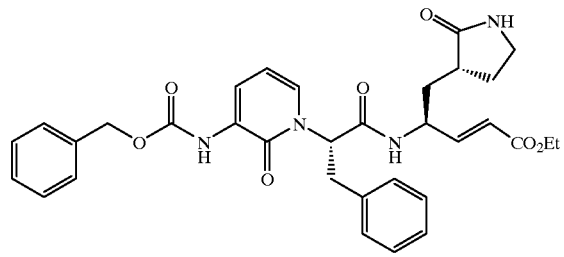

The title compound was prepared from (2S,3'R)-{1-[1'-(2",4"-dimethoxybenzyl)-2'-oxopyrrolidin-3'-ylmethyl]-2-hydroxyethyl}carbamic acid tert-butyl ester (prepared as described in Dragovich, et al. *J. Med. Chem.* 1999, 42, 1213) by a process analogous to that described in Example 19 for the conversion of K1 to R1 utilizing commercially available (2R)-2-hydroxy-3-phenylpropionic acid, (2-hydroxypyridin-3-yl)carbamic acid benzyl ester (Example 2), and commercially available (triphenyl-$1^5$-phosphanylidene)acetic acid ethyl ester where appropriate: IR (cm$^{-1}$) 3483, 3272, 1684 (br), 1514, 1267, 1196; $^1$H NMR ($CDCl_3$) δ 1.31 (t, 3H, J=7.1), 1.48–1.79 (m, 2H), 2.02–2.24 (m, 2H), 2.27–2.39 (m, 1H), 3.12 (dd, 1H, J=13.7, 8.2), 3.19–3.34 (m, 2H), 3.48 (dd, 1H, J=13.7, 7.8), 4.19 (q, 2H, J=7.1), 4.43–4.53 (m, 1H), 5.17 (s, 2H), 5.73 (dd, 1H, J=15.6, 1.3), 5.90–5.98 (m, 1H), 6.27 (t, 1H, J=7.1), 6.63 (dd, 1H, J=15.6, 6.0), 6.65–6.71 (m, 1H), 7.13–7.27 (m, 6H), 7.31–7.40 (m, 4H), 7.50 (dd, 1H, J=7.1, 1.6), 7.75 (s, 1H), 7.97 (d, 1H, J=6.6), 8.69 (d, 1H, J=7.0); Anal. $C_{33}H_{36}N_4O_7 \cdot 0.50H_2O$: C, H, N.

Example 21

Preparation of Compound 22: trans-(4S,3""S)-4-(2'-{3"-[(5'"-Methylisoxazole-3'"-carbonyl)amino]-2"-oxo-2"H-pyridin-1"-yl}acetylamino)-5-(2""-oxopyrrilidin-3""-yl)pent-2-enoic Acid Ethyl Ester

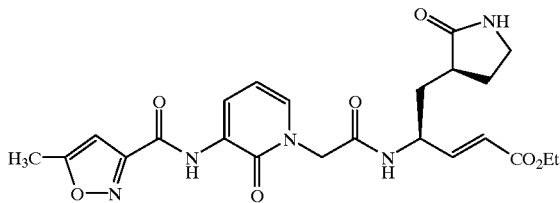

Preparation of Intermediate {3-[(5'-Methylisoxazole-3'-carbonyl)amino]-2-oxo-2H-pyridin-1-yl}acetic Acid tert-Butyl Ester To a solution of 5-methylisoxazole-3-carboxylic acid (2'-hydroxy-4'-methylpyridin-3'-yl)amide (F2, Example 19) (0.520 g, 2.37 mmol, 1 equiv) in THF (20 mL) at 0° C. was added NaH (0.095 g, 2.37 mmol, 1.0 equiv). The resulting mixture was stirred at 0° C. for 20 min, and then t-butyl bromoacetate (0.385 mL, 2.61 mmol, 1.1 equiv) was added. The reaction mixture was stirred and warmed to room temperature for 30 min, then was partitioned between 0.5 N HCl (100 mL) and EtOAc (2×100 mL). The combined organic layers were dried over $Na_2SO_4$ and were concentrated. Purification of the residue by flash column chromatography (30% EtOAc in hexanes) provided the title intermediate (0.628 g, 79%) as a white solid: IR ($cm^{-1}$) 3343, 1743, 1651, 1581, 1156; $^1$H NMR ($CDCl_3$) δ 1.52 (s, 9H), 2.53 (s, 3H), 4.65 (s, 2H), 6.32 (t, 1H, J=7.2), 6.51 (s, 1H), 7.01 (dd, 1H, J=6.9, 1.8), 8.50 (dd, 1H, J=7.5, 1.8), 9.63 (s, br. 1H); Anal. $C_{16}H_{19}N_3O_5$: C, H, N.

Preparation of Compound 22

The preceding intermediate was transformed into Compound 22 by a process that was analogous to that described in Example 25 for the transformation of V3 to product R3: mp=102–106° C.; IR ($cm^{-1}$) 3336, 1684, 1534, 1457; $^1$H NMR ($CDCl_3$) δ 1.27 (t, 3H, J=7.2), 1.67–1.75 (m, 1H), 1.98–2.09 (m, 1H), 2.37–2.49 (m, 1H), 2.53 (s, 3H), 2.55–2.61 (m, 1H), 3.34–3.46 (m, 2H), 3.51–3.52 (m, 1H), 4.17 (q, 2H, J=7.2), 4.61–4.78 (m, 3H), 5.98 (dd, 1H, J=15.6, 1.5), 6.20 (s, br. 1H), 6.35 (t, 1H, J=7.8), 6.51 (s, 1H), 6.85 (dd, 1H, J=15.6, 5.1), 7.17 (d, 1H, J=7.2), 8.33 (d, 1H, J=7.2), 8.49 (d, 1H, J=7.5), 9.57 (s, br. 1H); Anal. $C_{23}H_{27}N_5O_7$: C, H, N.

Example 22

Preparation of Compound 23: trans-(2"S,2"S, 3""'S)-5-Chloroisoxazole-3-carboxylic Acid (1'-{2"-(4'"-fluorophenyl)-1"-[2""-(2""'-oxodihydrofuran-3""'-ylidene)-1""-(2""'-oxopyrrolidin-3""'-ylmethyl)ethylcarbamoyl]ethyl}-2'-oxo-1',2"-dihydropyridin-3'-yl)amide (R2)

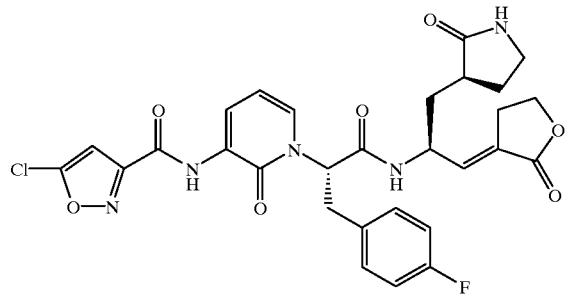

Preparation of Intermediate (2R)-3-(4'-Fluorophenyl)-2-hydroxypropionic Acid (S1)

This intermediate was prepared according to the method disclosed in the co-pending application, U.S. Provisional Patent Application No.60/150,365, filed Aug. 24, 1999.

Preparation of Intermediate (2R)-3-(4'-Fluorophenyl)-2-hydroxypropionic Acid Methyl Ester (T1)

This intermediate was prepared as described in co-pending U.S. Provisional Patent Application No. 60/150, 365, filed Aug. 24, 1999.

Preparation of Intermediate (2R)-3-(4-Fluorophenyl)-2-trifluoromethane-sulfonyloxypropionic Acid Methyl Ester (U1)

Intermediate T1 from above (0.198 g, 1.00 mmol, 1 equiv) was dissolved in $CH_2Cl_2$ (6 mL) and cooled in an ice bath. 2,6-Lutidine (0.198 mL, 1.70 mmol, 1.7 equiv) and trifluoromethanesulfonic anhydride (0.269 mL, 1.60 mmol, 1.6 equiv) were added and the reaction mixture was stirred 30 min. It was then diluted with MTBE (200 mL), washed with a mixture of brine and 1 N HCl (2:1, 75 mL) and brine (75 mL), dried over $Na_2SO_4$ and evaporated to provide the title intermediate which was used without further purification.

Preparation of Intermediate 5-Chloroisoxazole-3-carboxylic Acid Ethyl Ester

To a solution of ethyl chlorooximidoacetate (11.0 g, 72.6 mmol, 1 equiv) in 1,1-dichloroethylene (350 mL) was added $Et_3N$ (25.3 mL, 181 mmol, 2.5 equiv) in 1,1-dichloroethylene (100 mL) via addition funnel over 30 min. The reaction mixture was stirred at room temperature for 23 h, then was partitioned between water (150 mL) and $CH_2Cl_2$ (2×150 mL). The combined organic layers were dried over $Na_2SO_4$ and were concentrated. The residue was purified by flash column chromatography (10% EtOAc in hexanes) to give the title intermediate (4.49 g, 35%) as a pale yellow oil: IR ($cm^{-1}$) 1735, 1436, 1253; $^1$H NMR ($CDCl_3$) δ 1.45 (t, 3H, J=7.2), 4.49 (q, 2H, J=7.2), 7.29 (s, 1H).

Preparation of Intermediate 5-Chloroisoxazole-3-carboxylic Acid

An aqueous solution of LiOH (2.0 M, 22.5 mL, 45.0 mmol, 2.0 equiv) was added to a solution of the preceding intermediate (3.95 g, 22.5 mmol, 1 equiv) in EtOH (80 mL) at 23° C. The resulting mixture was stirred at room temperature for 45 min, then the volatiles were removed under reduced pressure. The residue thus obtained was partitioned between 1.0 N HCl (150 mL) and EtOAc (2×150 mL). The combined organic layers were dried over $Na_2SO_4$ and were concentrated to give the title intermediate (crude) (2.84 g, 86%) as a off-white solid which was used without further purification: $^1$H NMR (DMSO-$d_6$) δ 7.15 (s, 1H).

Preparation of Intermediate 5-Chloroisoxazole-3-carbonyl Chloride

A solution of 5-chloroisoxazole-3-carboxylic acid (0.750 g, 4.32 mmol, 1 equiv) and thionyl chloride (9.0 mL, 120 mmol, 28 equiv) in $CHCl_3$ (21 mL) was heated to reflux for 28 h. The volatiles were evaporated to provide a residue which was dissolved in benzene (40 mL), which was subsequently evaporated to give the title intermediate as a yellow oil which was used without further purification.

Preparation of Intermediate 5-Chloroisoxazole-3-carboxylic Acid (2'-hydroxypyridin-3'-yl)amide (F3)

A suspension of 10% palladium on carbon (0.15 g) and 2-hydroxy-3-nitropyridine (1.70 g, 12.1 mmol, 2.8 equiv) in EtOH (60 mL) was subjected to one atmosphere of hydrogen for 16 hours. After purging the reaction vessel with argon, the mixture was filtered through Whatman #3 paper and the filtrate was evaporated to give 2-hydroxy-3-aminopyridine (1.33 g, 99%) which was used without further purification. A portion of this material (0.524 g, 4.76 mmol, 1.1 equiv) was combined with the 5-chloroisoxazole-3-carbonyl chloride prepared above (4.32 mmol, 1 equiv based on theoretical yield) in THF (50 mL) and stirred 60 min. The volatiles were evaporated and the residue was stirred in half saturated $NaHCO_3$ (20 mL) for 30 min. The undissolved solid was collected by filtration, washed with $H_2O$ (3×5 mL) and dried under vacuum overnight to provide the title intermediate (0.900 g, 87%) as a tan solid which was used without further purification. $^1$H NMR (DMSO-d$_6$) δ 6.30 (t, 1H, J=6.9), 7.22 (dd, 1H, J=6.9, 1.7), 7.25 (s, 1H), 8.24 (dd, 1H, J=6.9, 1.7), 9.47 (s, 1H), 12.22 (s, 1H).

Preparation of Intermediate (2S)-2-{3'-[(5"-Chloroisoxazole-3"-carbonyl)amino]-2'-oxo-2H-pyridin-1'-yl}-3-(4'''-fluorophenyl)propionic Acid Methyl Ester (V1)

Intermediate F3 from above (0.280 g, 1.17 mmol, 1.17 equiv) was suspended in THF (7 mL). Sodium hydride (60% dispersion in mineral oil, 0.044 g, 1.1 mmol, 1.1 equiv) was added in one portion. After stirring 30 min, a solution of intermediate U1 from above (1.00 mmol, 1 equiv, based on T1) in THF (10 mL) was added dropwise. The resulting mixture was stirred 16 hours, then diluted with MTBE (250 mL) and washed with brine (2×80 mL). The organic phase was dried over MgSO$_4$ and evaporated. The residue was purified by flash column chromatography (33% EtOAc in hexanes) to provide the title intermediate (0.316 g, 75%) as a white foam: IR (cm$^{-1}$) 3331, 1743, 1690, 1643, 1602, 1531, 1437; $^1$H NMR (CDCl$_3$) δ 3.33 (dd, 1H, J=14.5, 10.3), 3.53 (dd, 1H, J=14.5, 5.5), 3.78 (s, 3H), 5.36 (dd, 1H, J=10.3, 5.5), 6.18 (t, 1H, J=7.2), 6.67 (s, 1H), 6.82 (dd, 1H, J=7.2, 1.7), 6.89–6.97 (m, 2H), 7.01–7.07 (m, 2H), 8.38 (dd, 1H, J=7.2, 1.7), 9.52 (s, 1H); Anal. C$_{19}$H$_{15}$ClFN$_3$O$_5$: C, H, N.

Preparation of Intermediate (2S)-2- {3'-[(5"-Chloroisoxazole-3"-carbonyl)amino]-2'-oxo-2H-pyridin-1'-yl}-3-(4'''-fluorophenyl)propionic Acid (W1)

Intermediate V1 from above (0.445 g, 1.06 mmol, 1 equiv) was dissolved in CH$_3$OH (10 mL). An aqueous solution of NaOH (1.0 M, 4.2 mL, 4.2 mmol, 4 equiv) was added dropwise. The reaction mixture was stirred 2 h, then poured into a mixture of brine and 10% KHSO$_4$ (1:1, 50 mL) and extracted with CH$_2$Cl$_2$ (3×100 mL). The combined organic phases were dried over MgSO$_4$ and evaporated to provide the title intermediate as a yellow foam which was used without further purification.

Preparation of Intermediate trans-(2'S,3"S)-3-[2'-Amino-3'-(2"-oxodihydrofuran-3"-ylidene)propyl]pyrrolidin-2-one (Y1)

Intermediate X1 (prepared in a manner analogous to that described in Baldwin et al., *J. Org. Chem.* 1971, 36, 1441) (0.413 g, 1.27 mmol, 1.2 equiv) was stirred for 45 min in a mixture of TFA (5 mL) in CH$_2$Cl$_2$ (10 mL). Then the volatiles were evaporated to provide the title intermediate which was used without purification.

Preparation of Product R2 (Compound 23)

Intermediates W1 (1.06 mmol, 1 equiv based on V1) and Y1 (1.27 mmol, 1.2 equiv based on X1) were combined in CH$_3$CN (14 mL) and cooled in an ice bath. 4-Methylmorpholine (0.583 mL, 5.30 mmol, 5 equiv) and HATU (0.403 g, 1.06 mmol, 1 equiv) were added and the reaction mixture was allowed to warm to 23° C. and stirred 1.5 h. It was then diluted with EtOAc (500 mL) and washed with a mixture of brine and 10% KHSO$_4$ (3:1, 80 mL), a mixture of brine and NaHCO$_3$ (3:1, 80 mL) and brine (80 mL). The organic phase was dried over Na$_2$SO$_4$ and evaporated. The residue was chromatographed (5% CH$_3$OH in CH$_2$Cl$_2$) then rechromatographed (2.5% CH$_3$OH in CH$_2$Cl$_2$) to provide the desired product R2 (0.418 g, 64%) contaminated with a diastereomer (approximately 30%, presumably the 2"R epimer): $^1$H NMR (CDCl$_3$) (mixture of isomers) δ 1.33–1.51 (m), 1.62–1.88 (m), 2.06–2.39 (m), 2.73–2.88 (m), 2.98–3.45 (mn), 4.27–4.44 (m), 5.71–5.88 (m), 6.27–6.43 (m), 6.66 (s), 6.68 (s), 6.81 (s), 6.88–6.98 (m), 7.03–7.24 (m), 7.48 (d, J=7.3), 7.55–7.62 (m), 8.34–8.42 (m), 8.65 (d, J=6.2), 8.77 (d, J=7.0), 9.41–9.48 (m).

Example 23

Preparation of Compound 24: trans-(2'S,4S)-6-Carbamoyl-4- {3'-(4"-fluorophenyl)-2'-[2"'-oxo-3"'-(2"",2"",2""-trifluoroacetylamino)-2"'H-pyridin-1"'-yl]propionylamino }hex-2-enoic Acid Ethyl Ester (J2)

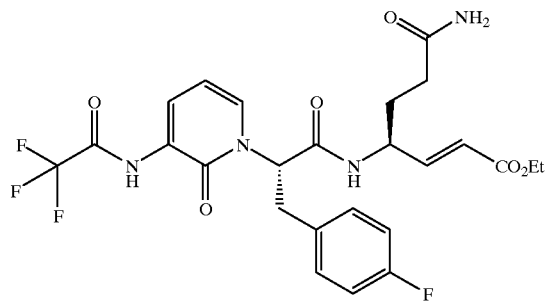

Preparation of Intermediate (2R)-3-(4'-Fluorophenyl)-2-hydroxypropionic Acid Benzyl Ester (T2)

Intermediate S1 (1.00 g, 5.43 mmol, 1 equiv) was dissolved in CH$_3$CN (8 mL). 1,8-Diazabicyclo[5.4.0]undec-7-ene (0.812 mL, 5.43 mmol, 1 equiv) and benzyl bromide (0.646 mL, 5.43 mmol, 1 equiv) were added successively. The resulting solution was stirred 40 h, then diluted with MTBE (250 mL) and washed with 5% KHSO$_4$ and brine (75 mL each). The organic phase was dried over Na$_2$SO$_4$ and evaporated. The residue was purified by flash column chromatography (25% EtOAc in hexanes) to provide the title intermediate (1.25 g, 84%) as a colorless oil which solidified over several days: IR (cm$^{-1}$) 3450, 1954, 1890, 1725, 1602; $^1$H NMR (CDCl$_3$) δ 2.76–2.81 (m, 1H), 2.94 (dd, 1H, J=14.1, 6.2), 3.08 (dd, 1H, J=14.1, 4.6), 4.42–4.49 (m, 1H), 5.14 (d, 1H, J=12.1), 5.21 (d, 1H, J=12.1), 6.86–6.94 (m, 2H), 7.03–7.11 (m, 2H), 7.29–7.42 (m, 5H); Anal. C$_{16}$H$_{15}$FO$_3$: C, H.

Preparation of Intermediate (2R)-3-(4-Fluorophenyl)-2-trifluoromethane-sulfonyloxypropionic Acid Benzyl Ester (U2)

Intermediate T2 from above (0.134 g, 0.489 mmol, 1 equiv) was dissolved in CH$_2$Cl$_2$ (5 mL) and cooled in an ice bath. 2,6-Lutidine (0.114 mL, 0.979 mmol, 2 equiv) and trifluoromethanesulfonic anhydride (0.156 mL, 0.927 mmol, 1.9 equiv) were added and the reaction mixture was stirred 30 min. It was then diluted with MTBE (150 mL), washed with a mixture of brine and 1 N HCl (2:1, 75 mL) and brine (50 mL), dried over Na$_2$SO$_4$ and evaporated to provide the title intermediate which was used without further purification.

Preparation of Intermediate 2,2,2-Trifluoro-N-(2'-hydroxypyridin-3'-yl)acetamide (F4)

TFA (4 mL) was added to a solution of intermediate F1 (0.700 g, 3.33 mmol, 1 equiv) in CH$_2$Cl$_2$ (6 mL). After stirring 30 min, the volatiles were evaporated. The residue was suspended in toluene and concentrated to dryness to provide crude 2-hydroxy-3-aminopyridine which was (without further purification) suspended in $CH_2Cl_2$ (14 mL) and cooled in an ice bath. 4-Methylmorpholine (1.10 mL, 10.0 mmol, 3 equiv) and trifluoroacetic anhydride (0.471 mL, 3.33 mmol, 1 equiv) were added successively. After 30 min, more 4-methylmorpholine (0.550 mL, 5 mmol, 1.5 equiv) was added. The reaction mixture was stirred an additional 1.5 h, then diluted with EtOAc (250 mL) and washed with brine, $H_2O$ and brine (25 mL each). The organic phase was dried over $MgSO_4$ and evaporated. The residue was purified by flash column chromatography (5% $CH_3OH$ in $CH_2Cl_2$) to provide the title intermediate (0.173 g, 25%) as a white amorphous solid: $^1H$ NMR (DMSO-$d_6$) δ 6.27 (t, 1H, J=6.9), 7.32 (dd, 1H, J=6.9, 1.8), 7.94 (dd, 1H, J=6.9, 1.8), 10.16 (s, 1H), 12.20 (s, 1H); Anal. $C_7H_5F_3N_2O_2$: C, H, N.

Preparation of Intermediate (2S)-3-(4'-Fluorophenyl)-2-[2"-oxo-3"-(2'",2'",2'"-trifluoroacetylamino)-2"H-pyridin-1"-yl]propionic Acid Benzyl Ester (V2)

Intermediate F4 from above (0.111 g, 0.539 mmol, 1.1 equiv) was suspended in THF (3 mL). Sodium hydride (60% dispersion in mineral oil, 0.020 g, 0.50 mmol, 1 equiv) was added in one portion. After stirring 30 min, a solution of intermediate U2 (0.489 mmol, 1 equiv, based on T2) in THF (5 mL) was added dropwise. The resulting mixture was stirred 2 hours, then diluted with MTBE (150 mL) and washed with brine (2×50 mL). The organic phase was dried over $MgSO_4$ and evaporated. The residue was purified by flash column chromatography (25% EtOAc in hexanes) to provide the title intermediate (0.190 g, 84%) as a thick oil: IR(cm$^{-1}$) 3343, 1743, 1727, 1655, 1602, 1296, 1214, 1161; $^1H$ NMR (CDCl$_3$) δ 3.31 (dd, 1H, J=14.4, 10.0), 3.52 (dd, 1H, J=14.4, 5.4), 5.21 (s, 2H), 5.39 (dd, 1H, J=10.0, 5.4), 6.18 (t, 1H, J=7.3), 6.85 (dd, 1H, J=7.3, 1.7), 6.87–7.04 (m, 4H), 7.25–7.38 (m, 5H), 8.31 (dd, 1H, J=7.3, 1.7), 9.03 (s, 1H); Anal. $C_{23}H_{18}F_4N_2O_4$: C, H, N.

Preparation of Intermediate (2S)-3-(4'-Fluorophenyl)-2-[2"-oxo-3"-(2'",2'",2'"-trifluoroacetylamino)-2"H-pyridin-1"-yl]propionic Acid (W2)

A suspension of 10% palladium on carbon (0.030 g) and intermediate V2 from above (0.151 g, 0.327 mmol, 1 equiv) in EtOH (5 mL) was subjected to one atmosphere of hydrogen for 16 hours. After purging the reaction vessel with argon, the mixture was filtered through Whatman #3 paper and the filtrate was evaporated to give the title intermediate which was used without further purification.

Preparation of Intermediate trans-(4S)-4-Amino-6-(tritylcarbamoyl)hex-2-enoic Acid Ethyl Ester (AA1)

Intermediate Z1 (prepared according to Dragovich, et al., J. Med. Chem. 1998, 41, 2806) (0.177 g, 0.326 mmol, 1 equiv) was stirred for 2 h in a solution of HCl in 1,4-dioxane (2.0 M, 8 mL). Then the volatiles were evaporated to provide the title intermediate which was used without further purification.

Preparation of Intermediate trans-(2'S,4S)-4-{3'-(4"-Fluorophenyl)-2'-[2'"-oxo-3'"-(2"",2"",2""-trifluoroacetylamino)-2'"H-pyridin-1'"-yl]propionylamino}-6-(tritylcarbamoyl)hex-2-enoic Acid Ethyl Ester (I3)

Intermediates W2 and AA1 (as prepared above) were combined in $CH_2Cl_2$ (5 mL) and cooled in an ice bath. HOBt (0.049 g, 0.36 mmol, 1.1 equiv), $iPr_2NEt$ (0.171 mL, 0.982 mmol, 3 equiv) and EDC (0.063 g, 0.33 mmol, 1 equiv) were added sequentially. The reaction mixture was allowed to warm to 23° C. overnight, then diluted with EtOAc (200 mL) and washed with 5% $KHSO_4$ and brine (50 mL each). The organic phase was dried over $MgSO_4$ and evaporated. The residue was purified by flash column chromatography (44% EtOAc in hexanes) to provide the title intermediate (0.138 g, 53%) as a white amorphous solid: $^1H$ NMR (CDCl$_3$) δ 1.30 (t, 3H, J=7.1), 1.70–1.84 (m, 1H), 1.85–1.99 (m, 1H), 2.26–2.34 (m, 2H), 3.01–3.10 (m, 1H), 3.31–3.40 (m, 1H), 4.19 (q, 2H, J=7.1), 4.46–4.56 (m, 1H), 5.42–5.49 (m, 1H), 5.63 (dd, 1H, J=15.7, 1.6), 6.18 (t, 1H, J=7.3), 6.62–6.71 (m, 2H), 6.88–6.96 (m, 2H), 7.00–7.06 (m, 2H), 7.10–7.34 (m, 17H), 8.25 (dd, 1H, J=7.3, 1.6), 9.02 (s, 1H); Anal. $C_{44}H_{40}F_4N_4O_6$: C, H, N.

Preparation of Product J2 (Compound 24)

Intermediate I3 from above (0.112 g, 0.141 mmol, 1 equiv) and triisopropylsilane (0.086 mL, 0.420 mmol, 3 equiv) were combined in $CH_2Cl_2$ (4 mL). TFA (2 mL) was added. After stirring 30 min, $CCl_4$ (4 mL) was added and the volatiles were evaporated. The residue was purified by flash column chromatography (5% $CH_3OH$ in $CH_2Cl_2$) to provide the desired product (0.078 g, 100%) as a tan amorphous powder: $^1H$ NMR (CDCl$_3$) δ 1.31 (t, 3H, J=7.1), 1.75–1.96 (m, 2H), 2.13–2.30 (m, 2H), 3.12 (dd, 1H, J=13.7, 7.5), 3.46 (dd, 1H, J=13.7, 8.5), 4.20 (d, 2H, J=7.1), 4.45–4.55 (m, 1H), 5.63 (dd, 1H, J=15.7, 1.6), 5.66–5.74 (m, 1H), 5.92 (s, 1H), 6.28 (s, 1H), 6.37 (t, 1H, J=7.3), 6.67 (dd, 1H, J=15.7, 5.7), 6.92–7.00 (m, 2H), 7.09–7.17 (m, 2H), 7.54 (dd, 1H, J=7.3, 1.6), 7.60 (d, 1H, J=7.5), 8.34 (dd, 1H, J=7.3, 1.6), 9.04 (s, 1H); Anal. $C_{25}H_{26}F_4N_4O_6 \cdot 1.25H_2O$: C, H, N.

Example 24

Preparation of Compound 25: trans-(2'S,3'""S,4S)-4-(3'-(4"-Fluorophenyl)-2'-{3'"-[(5""-methylisoxazole-3""-carbonyl)amino]-2'-oxo-2'"H-pyridin-1'"-yl}propionylamino)-5-(2""-oxopyrrolidin-3""-yl)pent-2-enoic Acid Ethyl Ester

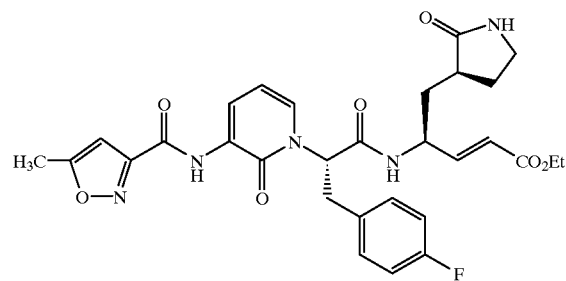

The title compound was prepared from F2 (Example 19) in a manner analogous to that described for the conversion of U2 to I3 in Example 23 utilizing intermediate Y2 (Example 25) where appropriate: IR (cm$^{-1}$) 3331, 1690, 1590, 1531, 1455; $^1H$ NMR (CDCl$_3$) δ 1.30 (t, 3H, J=7.0), 1.45–1.55 (m, 1H), 1.64–1.75 (m, 1H), 2.03–2.31 (m, 3H), 2.49 (s, 3H), 3.10 (dd, 1H, J=13.7, 7.9), 3.20–3.46 (m, 3H), 4.20 (q, 2H, J=7.0), 4.36–4.47 (m, 1H), 5.67 (dd, 1H, J=15.7, 1.4), 5.85–5.92 (m, 1H), 6.29 (t, 1H, J=7.2), 6.45 (s, 1H), 6.70 (dd, 1H, J=15.7, 5.7), 6.86 (s, 1H), 6.90–6.97 (m, 2H), 7.10–7.16 (m, 2H), 7.60 (dd, 1H, J=7.2, 1.6), 8.37 (dd, 1H, J=7.2, 1.6), 8.51 (d, 1H, J=6.6), 9.47 (s, 1H).

Example 25

Preparation of Compound 26: trans-(2'S,3'"S,4S)-4-(2'-{3"-[(5'''-Methylisoxazole-3'''-carbonyl)amino]-2"-oxo-2"H-pyridin-1"-yl}butyrylamino)-5-(2'''-oxopyrrolidin-3'''-yl)pent-2-enoic Acid Ethyl Ester (R3)

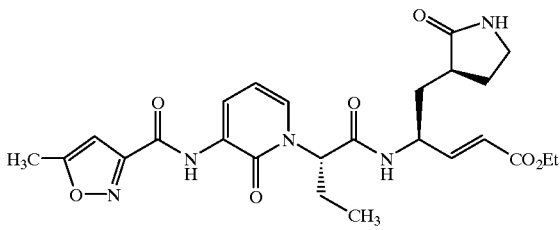

Preparation of Intermediate (2R)-2-Trifluoromethanesulfonyl-oxybutyric acid tert-butyl ester (U3)

Commercially available T3 (0.575 g, 3.59 mmol, 1 equiv) was dissolved in $CH_2Cl_2$ (25 mL) and cooled in an ice bath. 2,6-Lutidine (0.836 mL, 7.18 mmol, 2 equiv) and trifluoromethanesulfonic anhydride (1.15 mL, 6.84 mmol, 1.9 equiv) were added and the reaction mixture was stirred 30 min. It was then diluted with MTBE (400 mL), washed with a mixture of brine and 1 N HCl (2: 1, 100 mL) and brine (100 mL), dried over $Na_2SO_4$ and evaporated to provide the title intermediate which was used without further purification.

Preparation of Intermediate (2S)-2-{3'-[(5"-Methylisoxazole-3"-carbonyl)amino]-2'-oxo-2'H-pyridin-1'-yl}butyric Acid tert-Butyl Ester (V3)

Intermediate F2 from above (0.200 g, 0.912 mmol, 1.1 equiv) was suspended in THF (6 mL). Sodium hydride (60% dispersion in mineral oil, 0.0332 g, 0.830 mmol, 1 equiv) was added in one portion. After stirring 30 min, a solution of intermediate U3 (0.830 mmol, 1 equiv, based on T3) in THF (7 mL) was added dropwise. The resulting mixture was stirred 2 hours, then diluted with EtOAc (200 mL) and washed with brine (2×50 mL). The organic phase was dried over $MgSO_4$ and evaporated. The residue was purified by flash column chromatography (25% EtOAc in hexanes) to provide the title intermediate (0.178 g, 59%) as an oil: $R_f$=0.30(25% EtOAc in hexanes); IR ($cm^{-1}$) 3331, 1731, 1690, 1649, 1602, 1531; $^1$H NMR ($CDCl_3$) δ 0.93 (t, 3H, J=7.3), 1.45 (s, 9H), 1.83–2.01 (m, 1H), 2.17–2.31 (m, 1H), 2.50 (s, 3H), 5.44–5.51 (m, 1H), 6.32 (t, 1H, J=7.2), 6.48 (s, 1H), 7.10 (dd, 1H, J=7.2, 1.8), 8.45 (dd, 1H, J=7.2, 1.8), 9.64 (s, 1H); Anal. $C_{18}H_{23}N_3O_5$: C, H, N.

Preparation of Intermediate (2S)-2- {3'-[(5"-Methylisoxazole-3"-carbonyl)amino]-2'-oxo-2H-pyridin-1'-yl}butyric Acid (W3)

Intermediate V3 from above (0.143 g, 0.397 mmol, 1 equiv) was stirred for 1 h in a solution of TFA (2 mL) in $CH_2Cl_2$ (3 mL). The volatiles were evaporated. The residue was suspended in toluene (10 mL) and concentrated to dryness, providing the title intermediate which was used without further purification.

Preparation of Intermediate trans-(3'S,4S)-4-Amino-5-(2'-oxopyrrolidin-3'-yl)pent-2-enoic Acid Ethyl Ester (Y2)

Intermediate X2, prepared according to the method disclosed in the co-pending application, U.S. Provisional Patent Application No. 60/150,358, filed Aug. 24, 1999(0.130 g, 0.398 mmol, 1 equiv), was stirred for 30 min in a solution of TFA (2 mL) in $CH_2Cl_2$ (3 mL). The volatiles were evaporated. The residue was suspended in toluene (10 mL) and concentrated to dryness, providing the title intermediate which was used without further purification.

Preparation of Product R3 (Compound 26)

Intermediates W3 and Y2 (as prepared above) were combined in $CH_2Cl_2$ (7 mL) and cooled in an ice bath. HOBt (0.064 g, 0.47 mmol, 1.2 equiv), $iPr_2NEt$ (0.484 mL, 2.78 mmol, 20 7 equiv) and EDC (0.084 g, 0.44 mmol, 1.1 equiv) were added sequentially. The reaction mixture was allowed to warm to 23° C. overnight, then diluted with EtOAc (500 mL) and washed with 5% $KHSO_4$, half saturated $NaHCO_3$, and brine (100 mL each). The organic phase was dried over $MgSO_4$ and evaporated. The residue was purified by flash column chromatography (gradient elution, 2→3% $CH_3OH$ in $CH_2Cl_2$) to provide the title intermediate (0.119 g, 58%) as a white foam: IR ($cm^{-1}$) 3331, 1684, 1649, 1590, 1531; $^1$H NMR ($CDCl_3$) δ 0.92 (t, 3H, J=7.3), 1.29 (t, 3H, J=7.1), 1.47–1.58 (m, 1H), 1.62–1.77 (m, 1H), 1.85–2.00 (m, 1H), 2.08–2.33 (m, 4H), 2.49 (s, 3H), 3.25–3.42 (m, 2H), 4.19 (q, 2H, J=7.1), 4.39–4.50 (m, 1H), 5.73 (dd, 1H, J=8.8, 6.8), 5.97 (dd, 1H, J=15.7, 1.4), 6.34 (t, 1H, J=7.2), 6.46 (s, 1H), 6.86 (dd, 1H, J=15.7, 5.9), 7.18 (s, 1H), 7.59 (dd, 1H, J=7.2, 1.8), 8.42 (dd, 1H, J=7.2, 1.8), 8.58–8.62 (m, 1H), 9.56 (s, 1); Anal. $C_{25}H_{31}N_5O_7 \cdot 0.50H_2O$: C, H, N.

Example 26

Preparation of a 1:1 Mixture of Compound 27: trans-(2'S,2'''S,4S)-6-Carbamoyl-4-(2'- {2"-oxo-3"-[(tetrahydrofuran-2'''-carbonyl)amino]-2"H-pyridin-1"-yl}-3'-phenylpropionylamino)hex-2-enoic Acid Ethyl Ester and Compound 28: trans-(2'S,2R,4S)-6-Carbamoyl-4-(2'-{2"-oxo-3"[(tetrahydrofuran-2'''-carbonyl)amino]-2"H-pyridin-1"-yl}-3'-phenylpropionylamino)hex-2-enoic Acid Ethyl Ester

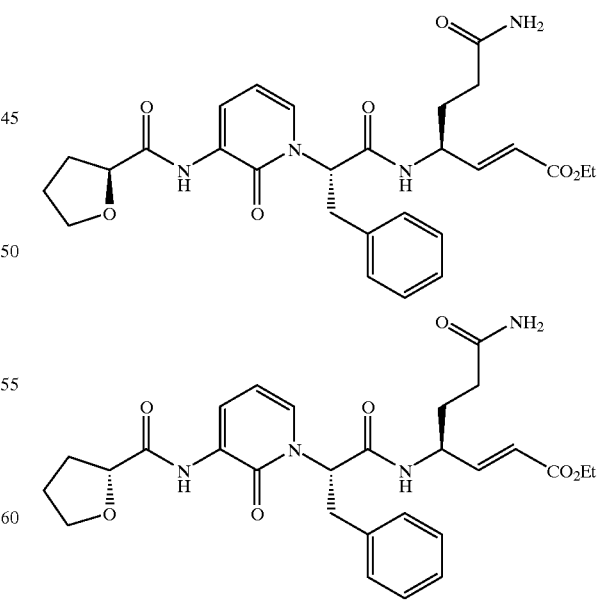

The title compounds were prepared from I1 (Example 5) by a process analogous to that described in Example 5 for the conversion of I1 to product J1 utilizing intermediate tetrahydrofuran-2-carbonyl chloride (racemic, Aldrich) where appropriate: IR (cm$^{-1}$) 3344, 1646, 1519, 1178; $^1$H NMR (CDCl$_3$) δ 1.34 (t, 3H, J=7.2), 1.72–1.82 (m, 1H), 1.95–2.04 (m, 2H), 2.16–2.23 (m, 2H), 2.32–2.43 (m, 1H), 3.18–3.27 (m, 1H), 3.51–3.60 (m, 5H), 3.93–4.00 (m, 1H), 4.05–4.12 (m, 1H), 4.22 (q, 2H, J=7.20, 4.46–4.55 (m, 2H), 5.54–5.69 (m, 2H), 6.34–6.41 (m, 2H), 6.68 (dd, 1H, J=15.6, 5.4), 6.86–6.93 (m, 1H), 7.17–7.41 (m, 5H), 8.42–8.45 (m, 1H), 9.37 (d, 1H, J=10.2); Anal. C$_{28}$H$_{34}$N$_4$O$_7$·1.5TFA: C, H, N.

Example 27

Preparation of Compound 29: trans-(2'S,3'''S,4S)-4-(2'-{3''-[(5'''-Chloroisoxazole-3'''-carbonyl)amino]-2''-oxo-2''H-pyridin-1''-yl}butyrylamino)-5-(2''''-oxopyrroldin-3''''-yl)pent-2-enoic Acid Cyclopentyl Ester (R4)

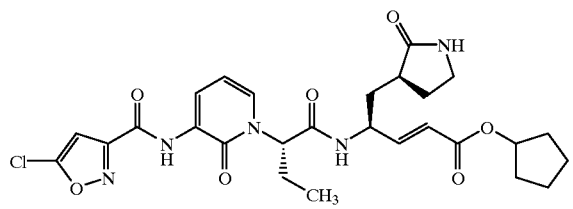

Preparation of Intermediate (2S)-2-{3'-[(5''-Chloroisoxazole-3''-carbonyl)amino]-2'-oxo-2'H-pyridin-1'-yl}butyric Acid tert-Butyl Ester (V4)

Intermediate F3 from above (0.781 g, 3.26 mmol, 1.1 equiv) was suspended in THF (10 mL). Sodium hydride (60% dispersion in mineral oil, 0.119 g, 2.98 mmol, 1 equiv) was added in one portion. After stirring 30 min, a solution of intermediate U3 (2.96 mmol, 1 equiv, based on T3) in THF (15 mL) was by syringe. The resulting mixture was stirred 2 hours, then diluted with EtOAc (500 mL) and washed with brine (2×100 mL). The organic phase was dried over MgSO$_4$ and evaporated. The residue was purified by flash column chromatography (20% EtOAc in hexanes) to provide the title intermediate (0.834 g, 74%): R$_f$=0.33 (20% EtOAc in hexanes); IR (cm$^{-1}$) 3334, 1732, 1694, 1650, 1603, 1537; $^1$H NMR (CDCl$_3$) δ 0.93 (t, 3H, J=7.4), 1.46 (s, 9H), 1.85–2.00 (m, 1H), 2.17–2.32 (m, 1H), 5.44–5.50 (m, 1H), 6.33 (t, 1H, J=7.3), 6.68 (s, 1H), 7.12 (dd, 1H, J=7.3, 1.7), 8.43 (dd, 1H, J=7.3, 1.7), 9.61 (s, 1H); Anal. C$_{17}$H$_{20}$ClN$_3$O$_5$: C, H, N.

Preparation of Intermediate (2S)-2- {3'-[(5''-Chloroisoxazole-3''-carbonyl)amino]-2'-oxo-2'H-pyridin-1'-yl}butyric Acid (W4)

Intermediate V4 from above (0.544 g, 1.42 mmol, 1 equiv) was stirred for 1 h in a mixture of TFA (9 mL) and CH$_2$Cl$_2$ (9 mL). The volatiles were evaporated. The residue was suspended in CCl$_4$ and concentrated to dryness (2×10 mL), providing the title intermediate which was used without further purification.

Preparation of Intermediate trans-(3'S,4S)-4-tert-Butoxycarbonylamino-5-[1'-(2'',4''-dimethoxybenzyl)-2'-oxopyrrolidin-3'-yl]pent-2-enoic Acid Cyclopentyl Ester (X3)

Intermediate K1 (prepared according to Dragovich, et al., J. Med. Chem. 1999, 42, 1213) (2.00 g, 4.90 mmol, 1 equiv) and commercially available Dess-Martin periodinane (2.30 g, 5.38 mmol, 1.1 equiv) were combined in CH$_2$Cl$_2$ (50 mL) and stirred 2 h. The solvent was evaporated and the residue was suspended in and then evaporated from toluene (2×25 mL). The resulting residue was dissolved in THF (100 mL). (Triphenyl-1$^5$-phosphanylidene)acetic acid cyclopentyl ester (prepared in a manner analogous to that described in Baldwin, et al. J. Org. Chem. 1971, 36, 1441) (2.28 g, 5.87 mmol, 1.2 equiv) was added. The reaction mixture was heated to reflux for 100 min, allowed to cool, diluted with EtOAc (300 mL) and washed with a mixture of brine and NaHCO$_3$ (1:1, 100 mL). The organic phase was dried over MgSO$_4$ and evaporated. The residue was purified by flash column chromatography (gradient elution, 44→50% EtOAc in hexanes) to provide the title intermediate (1.58 g, 62%) as a foam: IR (cm$^{-1}$) 3307, 1708, 1678, 1508; $^1$H NMR (CDCl$_3$) δ 1.43 (s, 9H), 1.50–1.93 (m, 10H), 1.97–2.08 (m, 1H), 2.21–2.33 (m, 1H), 2.48–2.60 (m, 1H), 3.17–3.23 (m, 2H), 3.80 (s, 6H), 4.26–4.40 (m, 1H), 4.41 (s, 2H), 5.18–5.24 (m, 1H), 5.26–5.33 (m, 1H), 5.92 (dd, 1H, J=15.6, 1.6), 6.41–6.47 (m, 2H), 6.82 (dd, 1H, J=15.6, 5.2), 7.08–7.13 (m, 1H); Anal. C$_{28}$H$_{40}$N$_2$O$_7$·0.75H$_2$O: C, H, N.

Preparation of Intermediate trans-(3'S,4S)-4-tert-Butoxycarbonylamino-5-(2'-oxopyrrolidin-3'-yl)pent-2-enoic Acid Cyclopentyl Ester (X4)

Intermediate X3 from above (1.54 g, 2.98 mmol, 1 equiv) was dissolved in a mixture of H$_2$O (5 mL) and CHCl$_3$ (50 mL). DDQ (0.947 g, 4.17 mmol, 1.4 equiv) was added and the reaction mixture was heated in a 60° C. oil bath for 1.5 h. More DDQ (0.90 g, 3.96 mmol, 1.3 equiv) was added and heating at 60° C. was continued for 2 h more. After cooling to 23° C., the reaction mixture was diluted with CH$_2$Cl$_2$ (600 mL) and washed with a mixture of brine and 10% KHSO$_4$ (1:1, 150 mL) and a mixture of brine and NaHCO$_3$ (2×200 mL). The organic phase was dried over MgSO$_4$ and evaporated. The residue was purified by flash column chromatography (gradient elution, 2→3% CH$_3$OH in CH$_2$Cl$_2$) to provide the title intermediate (0.850 g, 78%) as a tan foam: IR (cm$^{-1}$) 3305, 1698, 1522, 1279, 1165; $^1$H NMR (CDCl$_3$) δ 1.44 (s, 9H), 1.52–2.05 (m, 1H), 2.38–2.54 (m, 2H), 3.29–3.40 (m, 2H), 4.29–4.41 (m, 1H), 5.17–5.27 (m, 2H), 5.93 (dd, 1H, J=15.7, 1.6), 5.96–6.40 (m, 1H), 6.82 (dd, 1H, J=15.7, 5.3); Anal. C$_{19}$H$_{30}$N$_2$O$_5$·0.30H$_2$O: C, H, N.

Preparation of Intermediate trans-(3'S,4S)-4-Amino-5-(2'-oxo-pyrrolidin-3'-yl)pent-2-enoic acid Cyclopentyl Ester (Y3)

Intermediate X4 (0.522 g, 1.42 mmol, 1 equiv) was stirred for 40 min in a solution of TFA (7 mL) in CH$_2$Cl$_2$ (10 mL). The volatiles were evaporated. The residue was suspended in CCl$_4$ and concentrated to dryness (2×20 mL), providing the title intermediate which was used without further purification.

Preparation of Product R4 (Compound 29)

Intermediates W4 and Y3 (as prepared above) were combined in CH$_2$Cl$_2$ (25 mL) and cooled in an ice bath. HOBt (0.269 g, 1.99 mmol, 1.4 equiv), iPr$_2$NEt (1.74 mL, 9.99 mmol, 7 equiv) and EDC (0.341 g, 0.1.78 mmol, 1.25 equiv) were added sequentially. The reaction mixture was allowed to warm to 23° C. over the weekend. It was then diluted with EtOAc (500 mL) and washed with a mixture of brine and 10% KHSO$_4$ (1:1, 100 mL) and brine (100 mL). The organic phase was dried over Na$_2$SO$_4$ and evaporated. The residue was purified by flash column chromatography (2% CH₃OH in CH₂Cl₂) to provide the title intermediate (0.590 g, 72%) as a white foam: IR (cm⁻¹) 3295, 1690, 1649, 1590, 1531; ¹H NMR (CDCl₃) δ 0.92 (t, 3H, J=7.3), 1.50–2.02 (m, 10H), 2.11–2.37 (m, 4H), 3.25–3.44 (m, 2H), 3.64–3.74 (m, 1H), 4.41–4.52 (m, 1H), 5.18–5.24 (m, 1H), 5.69 (dd, 1H, J=9.0, 6.6), 5.94 (dd, 1H, J=15.6, 1.4), 6.36 (t, 1H, J=7.3), 6.67 (s, 1H), 6.82 (dd, 1H, J=15.6, 5.9), 7.15 (s, 1H), 7.58 (dd, 1H, J=7.3, 1.7), 8.42 (dd, 1H, J=7.3, 1.7), 8.49 (m, 1H), 9.52 (s, 1H); Anal. C₂₇H₃₂ClN₅O₇·0.50H₂O: C, H, N.

Example 28

Preparation of Compound 30: trans-(2'S,4S)-6-Carbamoyl-4-(2'-{3"-[(5'''-chloroisoxazole-3'''-carbonyl)amino]-2"-oxo-2"H-pyridin-1"-yl}-3'-phenylpropionylamino)hex-2-enoic Acid Ethyl Ester

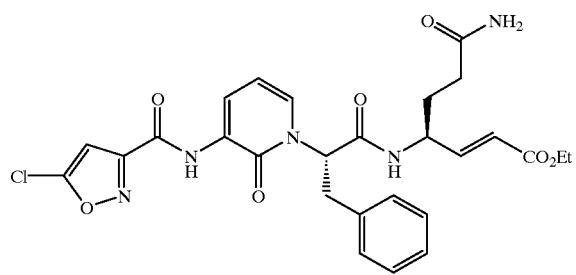

Preparation of Intermediate (1'S,4"S)-5-Chloroisoxazole-3-carboxylic Acid {1'-[1"-Benzyl-4"-(tert-butyldimethylsilanyloxymethyl)-2"-oxo-6"-(tritylcarbamoyl)hexyl]-2'-oxo-1',2'-dihydropyridin-3'-yl}amide To solution of 5-chloroisoxazole-3-carboxylic acid (Example 22, 0.253 g, 1.71 mmol, 2.0 equiv) in CHCl₃ (21 mL) was added SOCl₂ (9 mL). The reaction mixture was heated to reflux for 26 h. The volatiles were removed under reduced pressure to give crude 5-chloroisoxazole-3-carbonyl chloride.

A sample of 10% Pd on C (0.070 g) was added to a solution of (1'S,4"S)-5-chloroisoxazole-3-carboxylic acid {1'-[1"-Benzyl-4"-(tert-butyldimethylsilanyloxy-methyl)-2"-oxo-6"-(tritylcarbamoyl)hexyl]-2'-oxo-1',2'-dihydropyridin-3'-yl}amide (Example 1, 0.74 g, 0.855 mmol, 1 equiv) in EtOAc (15 mL). The reaction mixture was stirred at room temperature under H₂ atmosphere (balloon) for 4 h, and then was filtered through Celite. The filtrate was concentrated under reduced pressure. The residue was dissolved in THF (15 mL), cooled to 0° C., and 5-chloroisoxazole-3-carbonyl chloride (1.71 mmol, 2.0 equiv) and NMM (0.188 mL, 1.71 mmol, 2.0 equiv) were added sequentially. The resulting mixture was stirred at 0° C. for 1 h, then was partitioned between water (100 mL) and EtOAc (2×100 mL). The organic layers were dried over Na₂SO₄ and concentrated. The residue was purified by flash column chromatography (35% EtOAc in hexanes) to afford the title intermediate (0.666 g, 90%): IR (cm⁻¹) 3332, 1684, 1531; ¹H NMR (CDCl₃) δ 0.01 (s, 6H), 0.86 (s, 9H), 1.60–1.71 (m, 1H), 1.80–1.83 (m, 1H), 2.12–2.16 (m, 2H), 3.16–3.23 (m, 1H), 3.36–3.41 (m, 1H), 3.47–3.55 (m, 2H), 3.81–3.90 (m, 1H), 5.64–5.70 (m, 1H), 6.26 (t, 1H, J=7.2), 6.47 (d, 1H, J=8.7), 6.70 (s, 1H), 7.02 (s, br. 1H), 7.17–7.33 (m, 20H), 7.37 (d, 1H, J=7.2), 8.40 (d, J=7.8), 9.56 s, br. 1H).

Preparation of Compound 30

The preceding intermediate was converted into compound 30 by a process that was analogous to that described in Example 7 for the conversion of intermediate C1 to compound 7: mp=163–165° C.; IR (cm⁻¹) 3335, 1648, 1533, 1179; ¹H NMR (CDCl₃) δ 0.34 (t, 3H, J=7.2), 1.76–1.86 (m, 1H), 1.94–2.00 (m, 1H), 2.23 (t, 2H, J=6.9), 3.20–3.27 (m, 1H), 3.35–3.42 m, 2H), 3.51–3.58 (m, 1H), 4.22 (q, 2H, J=7.2), 4.52–4.57 (m, 1H), 5.69 (dd, 1H, J=15.6, 1.5), 6.70 (s, br. 1H), 6.14 (s, br. 1H), 6.32 (s, br. 1H), 6.39 (t, 1H, J=7.2), 6.69 (dd, 1H, J=15.6, 5.4), 7.21–7.33 (m, 4H), 7.47 (d, 1H, J=7.2), 8.44 (d, 1H, J=7.5), 9.47 (s, br. 1H); Anal. C₂₇H₂₈ClN₅O₇·0.6H₂O: C, H, N.

Example 29

Preparation of Compound 31: trans-(2'S,3'"S,4S)-4-(2'-{3"-[(5'"-Methyl-isoxazole-3'"-carbonyl)amino]-2"-oxo-2"H-pyridin-1"-yl}pent-4'-ynoyl-amino)-5-(2""-oxopyrrolidin-3""-yl)pent-2-enoic Acid Ethyl Ester

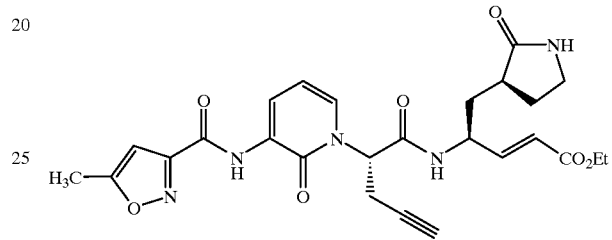

The title compound was prepared from D-propargylalanine by a process analogous to that described in Example 22 for the conversion of D-(4-fluorophenylalanine) to product R2 utilizing intermediates F2 and Y2 and an alternate deprotection of the intermediate corresponding to V1 (LiI in pyridine) where appropriate: IR (cm⁻¹) 3295, 1684, 1649, 1596, 1531; ¹H NMR (CDCl₃) δ 1.27 (t, 3H, J=7.1), 1.52–1.62 (m, 1H), 1.64–1.80 (m, 1H), 2.04 (t, 1H, J=2.6), 2.08–2.38 (m, 3H), 2.49 (s, 3H), 2.91 (ddd, 1H, J=17.0, 8.4, 2.6), 3.01 (ddd, 1H, J=17.0, 6.8, 2.6), 3.22–3.39 (m, 2H), 4.18 (q, 2H, J=7.1), 4.44–4.55 (m, 1H), 5.71–5.78 (m, 1H), 6.03 (dd, 1H, J=15.6, 1.5), 6.32 (t, 1H, J=7.2), 6.46 (s, 1H), 6.85 (dd, 1H, J=15.6, 5.4), 6.89 (s, 1H), 7.49 (dd, 1H, J=7.2, 1.7), 8.41 (dd, 1H, J=7.2, 1.7), 8.68 (d, 1H, J=6.8), 9.52 (s, 1H); Anal. C₂₆H₂₉N₅O₇·0.75H₂O: C, H, N.

Example 30

Preparation of Compound 32: trans-(2'S,3'"S,4S)-4-(2'-{3"-[(5'"-Methylisoxazole-3'"-carbonyl)amino]-2"-oxo-2"H-pyridin-1"-yl}-pent-4'-ynoylamino)-5-(2""-oxopyrrolidin-3""-yl)pent-2-enoic acid 2,2-Dimethylpropyl Ester

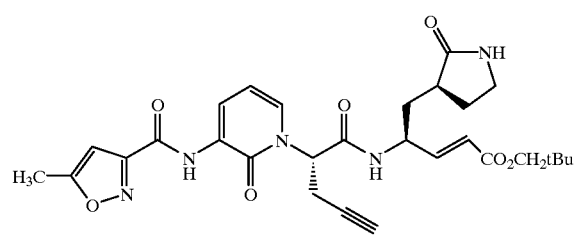

The title compound was prepared from D-propargylalanine by a process analogous to that described in Example 22 for the conversion of D-(4-fluorophenylalanine) to product R2 utilizing intermediates F2 and trans-(3'S,4S)4-tert-butoxycarbonylamino-5-(2'-oxopyrrolidin-3'-yl)pent-2-enoic acid 2,2-dimethylpropyl ester (prepared from K1 in a manner similar to that described for the preparation of X4 in Example 27) and an alternate deprotection of the intermediate corresponding to V1 (LiI in pyridine) where appropriate: IR (cm$^{-1}$) 3295, 1690, 1649, 1596, 1531; $^1$H NMR (CDCl$_3$) δ 0.95 (s, 9H), 1.54–1.80 (m, 2H), 2.05 (t, 1H, J=2.6), 2.10–2.39 (m, 3H), 2.49 (s, 3H), 2.91 (ddd, 1H, J=17.0, 8.2, 2.6), 3.01 (ddd, 1H, J=17.0, 6.8, 2.6), 3.22–3.38 (m, 2H), 3.82 (s, 2H), 4.45–4.56 (m, 1H), 5.72–5.79 (m, 1H), 6.06 (dd, 1H, J=15.7, 1.5), 6.33 (t, 1H, J=7.2), 6.46 (s, 1H), 6.86 (dd, 1H, J=15.7, 5.4), 6.93 (s, 1H), 7.51 (dd, 1H, J=7.2, 1.7), 8.41 (dd, 1H, J=7.2, 1.7), 8.69 (d, 1H, J=6.6), 9.52 (s, 1H); Anal. C$_{29}$H$_{35}$N$_5$O$_7$·0.25H$_2$O: C, H, N.

Example 31

Preparation of Compound 33: trans-(2'S,3''''S,4S)-4-(3'-(3'',4''-Difluorophenyl)-2'-{3'''-[(5''''-methylisoxazole-3''''-carbonyl)amino]-2'''-oxo-2'''H-pyridin-1'''-yl}propionylamino)-5-(2'''''-oxopyrrolidin-3'''''-yl)pent-2-enoic Acid Ethyl Ester

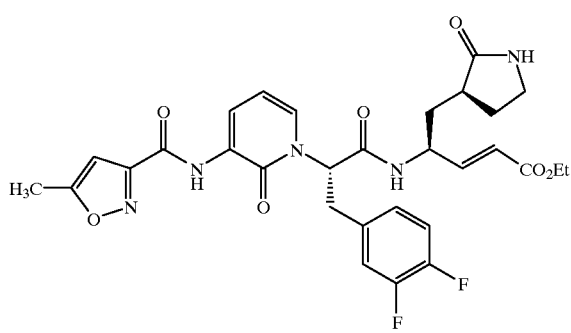

The title compound was prepared by a method analogous to that described in Example 19 for the preparation of specific intermediate R1 utilizing (2R)-3-(3',4'-difluorophenyl)-2-hydroxypropionic acid (synthesized from (2R)-2-tert-butoxycarbonylamino-3-(3',4'-difluorophenyl)propionic acid in analogy to the preparation of intermediate S1 described in Example 22) and triethylphosphonoacetate where appropriate: IR (cm$^{-1}$) 3331, 1690, 1649, 1596, 1531, 1455, 1278; $^1$H NMR (CDCl$_3$) δ 1.30 (t, 3H, J=7.1), 1.44–1.54 (m, 1H), 1.63–1.78 (m, 1H), 2.08–2.29 (m, 3H), 2.49 (d, 3H, J=0.9), 3.05 (dd, 1H, J=13.6, 7.5), 3.20–3.42 (m, 3H), 4.19 (dq, 2H, J=7.1, 1.7), 4.34–4.45 (m, 1H), 5.64 (dd, 1H, J=15.7, 1.4), 6.00 (t, 1H, J=7.8), 6.32 (t, 1H, J=7.3), 6.45 (s, 1H), 6.71 (dd, 1H, J=15.7, 5.6), 6.86–6.91 (m, 1H), 6.98–7.08 (m, 2H), 7.15 (s, 1H), 7.68 (dd, 1H, J=7.3, 1.7), 8.39 (dd, 1H, J=7.3, 1.7), 8.65 (d, 1H, J=6.8), 9.46 (s, 1H); Anal. C$_{30}$H$_{31}$F$_2$N$_5$O$_7$: C, H, N.

Example 32

Preparation of Compound 34: trans-(2'S,3''''S,4S)-4-(2'-{3''-[(5''''-Methylisoxazole-3''''-carbonyl)amino]-2''-oxo-2''H-pyridin-1''-yl}butyrylamino)-5-(2''''-oxopyrrolidin-3''''-yl)pent-2-enoic Acid tert-Butyl Ester

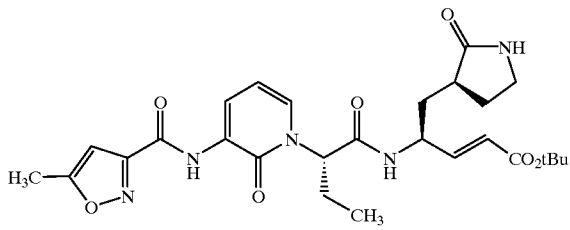

The title compound was prepared by a method analogous to that described for the synthesis of compound R3 in Example 25: IR (cm$^{-1}$) 3331, 3295, 1690, 1649, 1590, 1531, 1455, 1155; $^1$H NMR (CDCl$_3$) δ 0.93 (t, 3H, J=7.3), 1.40–1.60 (m, 1H), 1.49 (s, 9H), 1.62–1.78 (m, 1H), 1.87–2.02 (m, 1H), 2.09–2.36 (m, 4H), 2.50 (s, 3H), 3.26–3.43 (m, 2H), 4.39–4.50 (m, 1H), 5.78 (dd, 1H, J=8.9, 6.7), 5.89 (dd, 1H, J=15.7, 1.3), 6.35 (t, 1H, J=7.3), 6.47 (s, 1H), 6.76 (dd, 1H, J=15.7, 5.9), 7.33 (s, 1H), 7.64 (dd, 1H, J=7.3, 1.8), 8.43 (dd, 1H, J=7.3, 1.8), 8.59 (d, 1H, J=6.8), 9.57 (s, 1H); Anal. C$_{27}$H$_{35}$N$_5$O$_7$·0.5H$_2$O: C, H, N.

Example 33

Preparation of Compound 35: trans-(2S,3''''S,4S)-4-(2'-{3''-[(5''''-Methylisoxazole-3''''-carbonyl)amino]-2''-oxo-2''H-pyridin-1''-yl}butyrylamino)-5-(2''''-oxopyrrolidin-3''''-yl)pent-2-enoic Acid

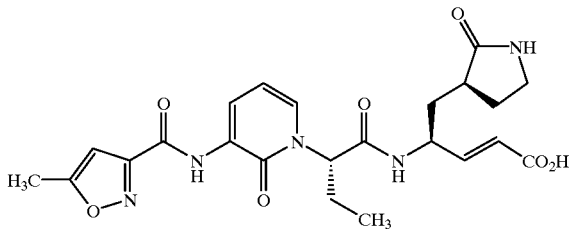

The title compound was prepared from compound 34 by acidic deprotection of the tert-butyl ester moiety present in that compound (following standard literature procedures): IR (cm$^{-1}$) 3319, 1678, 1643, 1590, 1531; $^1$H NMR (CDCl$_3$) δ 0.89 (t, 3H, J=7.2), 1.61–1.99 (m, 3H), 2.08–2.32 (m, 3H), 2.40–2.54 (m, 1H), 2.49 (s, 3H), 3.25–3.41 (m, 2H), 4.58–4.69 (m, 1H), 5.56–5.64 (m, 1H), 5.98 (d, 1H, J=15.6), 6.21 (br, 1H), 6.37 (t, 1H, J=7.3), 6.47 (s, 1H), 6.96 (dd, 1H, J=15.6, 6.6), 7.50 (dd, 1H, J=7.3, 1.6), 7.52 (s, 1H), 8.26 (d, 1H, J=7.7), 8.44 (dd, 1H, J=7.3, 1.6), 8.62 (s, 1H); Anal. C$_{23}$H$_{27}$N$_5$O$_7$·0.75H$_2$O: C, H, N.

Example 34

Preparation of Compound 36: trans-(3'S,4S)-4-[(6'-Benzyloxycarbonylamino-5'-oxo-1',2',3',5'-tetrahydroindolizine-3'-carbonyl)amino]-6-carbamoylhex-2-enoic Acid Ethyl Ester

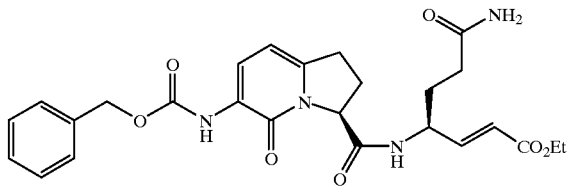

Preparation of Intermediate 6-But-3-enyl-2-hydroxynicotinonitrile (a1)

n-Butyllithium (100 mL of a 1.6 M solution in hexanes, 160 mmol, 2.5 equiv) was added via cannula over 10 min to a solution of diisopropylamine (22.4 mL, 160 mmol, 2.5 equiv) in THF (600 mL) at −78° C. The resulting pale yellow solution was stirred at −78° C. for 5 min, then was warmed to 0° C. for an additional 5 min. 2-Hydroxy-6-methylnicotinonitrile (8) (8.58 g, 64.0 mmol, 1 equiv) was added as a solid in small portions over 15 min and the deep orange solution thus obtained was stirred for 1 h at 0° C. Allyl bromide (8.31 mL, 96.0 mmol, 1.5 equiv) was then added and the reaction mixture was warmed to 23° C., maintained at that temperature for 30 min, and was partitioned between 1.0 M HCl (300 mL) and EtOAc (2×250 mL). The combined organic layers were dried over $Na_2SO_4$ and were concentrated. The resulting orange solid was triturated with boiling $Et_2O$ (100 mL) and subsequently cooled to 23° C., then was filtered through a medium frit, washed with $Et_2O$ (2×50 mL) and air-dried to give a1 (6.42 g, 58%) as a tan solid: mp=122–125° C.; IR (KBr pellet, $cm^{-1}$) 2223, 1654; $^1$H NMR (DMSO-$d_6$) δ 2.32–2.37 (m, 2H), 2.62 (t, 2H, J=7.6), 4.96–5.06 (m, 2H), 5.69–5.83 (m, 1H), 6.23 (d, 1H, J=7.3), 8.03 (d, 1H, J=7.3), 12.55 (s, br, 1H); Anal. $C_{10}H_{10}N_2O·0.10H_2O$: C, H, N.

Preparation of Intermediate 6-But-3-enyl-2-hydroxynicotinamide (b1)

Hydrogen peroxide (30 wt. % solution in water, 45 mL) was added to a solution of a1 (12.13 g, 70.2 mmol) in a mixture of EtOH (150 mL) and 10% aqueous NaOH (280 mL) at 23° C. The reaction mixture was heated to 50° C. for 18 h, then was cooled to 23° C. and the volatiles were removed under reduced pressure. The residue was acidified with 12 M HCl to pH 2–3, and the resulting precipitate was filtered, washed with water (2×50 mL), and air-dried to afford b1 as a yellow solid (13.48 g, 100%): mp=195–198° C.; IR ($cm^{-1}$) 3329, 3134, 1688, 1642; $^1$H NMR (DMSO-$d_6$) δ 2.31–2.38 (m, 2H), 2.64 (t, 2H, J=7.6), 4.96–5.05 (m, 2H), 5.71–5.84 (m, 1H), 6.29 (d, 1H, J=7.3), 7.45 (s, br, 1H), 8.21 (d, 1H, J=7.3), 9.00 (s, br, 1H), 12.37 (s, br, 1H); Anal. $C_{10}H_{12}N_2O_2·0.15H_2O$: C, H, N.

Preparation of Intermediate 6-But-3-enyl-2-hydroxynicotinic Acid (c1)

A solution of b1 (12.38 g, 70.1 mmol) in 10% aqueous KOH (350 mL) was heated to reflux for 20 h and subsequently cooled to room temperature. The reaction mixture was acidified with 12 M HCl to pH 2–3, and the resulting precipitate was filtered, washed with water (2×50 mL), and dried under vacuum to afford c1 as a yellow solid (12.46 g, 92%): mp=151–155° C.; IR($cm^{-1}$) 2905 (br), 1736, 1652; $^1$H NMR (DMSO-$d_6$) δ 2.34–2.29(m, 2H), 2.73 (t, 2H, J=7.6), 4.96–5.07 (m, 2H), 5.72–5.85 (m, 1H), 6.56 (d, 1H, J=7.5), 8.28 (d, 1H, J=7.5), 13.26 (s, br, 1H), 14.64 (s, br, 1H); Anal. $C_{10}H_{11}NO_3·0.10H_2O$: C, H, N.

Preparation of Intermediate (6-But-3-enyl-2-hydroxypyridin-3-yl)carbamic Acid Benzyl Ester (d1)

Triethylamine (13.9 mL, 99.7 mmol, 2.0 equiv) and diphenylphosphoryl azide (16.1 mL, 74.7 mmol, 1.5 equiv) were added sequentially to a suspension of c1 (9.63 g, 49.8 mmol, 1 equiv) in 1,4-dioxane (450 mL) at 23° C. The resulting solution was heated to reflux for 7.5 h, then benzyl alcohol (10.3 mL, 99.5 mmol, 2.0 equiv) was added and reflux was continued for an additional 16 h. The dark brown reaction mixture was cooled to 23° C. and the volatiles were removed under reduced pressure. The resulting dark brown oil was partitioned between water (300 mL) and EtOAc (2×250 mL) and the combined organic layers were dried over $Na_2SO_4$ and concentrated. The solid thus obtained was triturated with $Et_2O$ (150 mL) and was filtered through a medium frit, washed with $Et_2O$ (2×50 mL) and air-dried to give d1 (7.34 g, 49%) as an off-white powder: mp=179–180° C.; IR ($cm^{-1}$) 3386, 1727, 1645; $^1$H NMR (CDCl$_3$) δ 2.39–2.46 (m, 2H), 2.65 (t, 2H, J=7.5), 4.97–5.07 (m, 2H), 5.21 (s, 2H), 5.73–5.87 (m, 1H), 6.10 (d, 1H, J=7.5), 7.32–7.44 (m, 5H), 7.68 (s, br, 1H), 8.06 (s, br, 1H), 12.74 (s, br, 1H); Anal. $C_{17}H_{18}N_2O_3$: C, H, N.

Preparation of Intermediate (6-But-3-enyl-2-methoxypyridin-3-yl)carbamic Acid Benzyl Ester (e1)

Trimethyloxonium tetrafluoroborate (2.0 g, 13.5 mmol, 1.2 equiv) and 2,6-di-tert-butylpyridine (1.52 mL, 6.76 mmol, 0.6 equiv) were added to a solution of d1 (3.36 g, 11.26 mmol, 1 equiv) in $CH_2Cl_2$ (80 mL) at 23° C. The reaction mixture was stirred at that temperature for 65 h, then was partitioned between water (2×50 mL) and $CH_2Cl_2$ (2×200 mL) and combined organic layers were dried over $Na_2SO_4$ and concentrated. The residue was purified by flash column chromatography (5% EtOAc in hexanes) to afford e1 (3.19 g, 91%) as colorless oil: IR ($cm^{-1}$) 3432, 1733; $^1$H NMR (CDCl$_3$) δ 2.42–2.49 (m, 2H), 2.73 (t, 2H, J=7.6), 3.96 (s, 3H), 4.94–5.07 (m, 2H), 5.20 (s, 2H), 5.80–5.94 (m, 1H), 6.71 (d, 1H, J=7.9), 7.11 (s, br, 1H), 7.32–7.43 (m, 5H), 8.16 (s, br, 1H); Anal. $C_{18}H_{20}N_2O_3$: C, H, N.

Preparation of Intermediate (3'R)-[6-(3',4'-Dihydroxybutyl)-2-methoxypyridin-3-yl]carbamic Acid Benzyl Ester (f1)

To a mixture of 1:1 t-BuOH and water (300 mL) at 0° C. was added (DHQD)$_2$AQN (0.148 g, 0.164 mmol, 0.01 equiv), $K_3Fe(CN)_6$ (16.2 g, 49.2 mmol, 3 equiv), $K_2CO_3$ (6.8 g, 49.2 mmol, 3 equiv), potassium osmate dihydrate (0.024 g, 0.066 mmol, 0.004 equiv), and then e1 in t-BuOH (25 mL), sequentially. The resulting mixture was stirred at 0° C. for 20 h, then warmed to room temperature and $Na_2SO_3$ (30 g) was added carefully. The mixture was stirred at room temperature for 2 h, then the volatiles were removed under reduced pressure. The residue was partitioned between water (200 mL) and EtOAc (3×200 mL) and the combined organic layers were dried over $Na_2SO_4$ and concentrated. The residue was purified by flash column chromatography (2% CH₃OH in CH₂Cl₂) to afford f1 (5.57 g, 98%) as pale yellow oil: IR (cm⁻¹) 3427 (br), 1731; ¹H NMR (CDCl₃) δ 1.76–1.87 (m, 2H), 2.07–2.11 (m, 1H), 2.80–2.89 (m, 2H), 3.46–3.53 (m, 1H), 3.60–3.67 (m, 1H), 3.71–3.77 (m, 1H), 3.96 (s, 3H), 4.64 (d, 1H, J=3.2), 5.21 (s, 2H), 6.76 (d, 1H, J=7.8), 7.12 (s, br, 1H), 7.34–7.43 (m, 5H), 8.22 (s, br, 1H); Anal. C₁₈H₂₂N₂O₅: C, H, N.

Preparation of Intermediate (3'R)-{6-[4'-(tert-Butyl-dimethyl-silanyloxy)-3'-hydroxybutyl]-2-methoxypyridin-3-yl}carbamic Acid Benzyl Ester (g1)

Triethylamine (1.55 mL, 11.1 mmol, 2.5 equiv), tert-butyldimethylsilyl chloride (1.07 g, 7.10 mmol, 1.6 equiv), and 4-dimethylaminopyridine (0.025 g, 0.20 mmol, 0.045 equiv) were added sequentially to a solution of f1 (1.54 g, 4.45 mmol, 1 equiv) in CH₂Cl₂ (50 mL) at 23° C. The reaction mixture was stirred for 19 h at 23° C., then was partitioned between 0.5 M HCl (150 mL) and a 1:1 mixture of EtOAc and hexanes (2×150 mL). The combined organic layers were dried over Na₂SO₄ and were concentrated. Purification of the residue by flash column chromatography (20% EtOAc in hexanes) provided g1 (1.69 g, 82%) as a colorless oil: IR (cm⁻¹) 3436, 1734; ¹H NMR (CDCl₃) δ 0.07 (s, 6H), 0.90 (s, 9H), 1.72–1.94 (m, 2H), 2.72–2.88 m, 2H), 3.26 (d, 1H, J=3.1), 3.50 (dd, 1H, J=9.8, 6.9), 3.58–3.63 (m, 1H), 3.65–3.70 (m, 1H), 3.95 (s, 3H), 5.20 (s, 2H), 6.75 (d, 1H, J=8.1), 7.11 (s, br, 1H), 7.33–7.43 (m, 5H), 8.20 (s, br, 1H); Anal. C₂₄H₃₆N₂O₅Si: C, H, N.

Preparation of Intermediate (3S)-(3-Hydroxymethyl-5-oxo-1,2,3,5-tetrahydroindolizin-6-yl)-Carbamic Acid Benzyl Ester (h1)

2,6-Lutidine (2.43 mL, 20.84 mmol, 4.0 equiv) and trifluoromethanesulfonic anhydride (1.31 mL, 7.82 mmol, 1.5 equiv) were added sequentially to a solution of g1 (2.4 g, 5.21 mmol, 1 equiv) in CH₂Cl₂ (100 mL) at −78° C. The colorless reaction mixture was stirred at −78° C. for 45 min, warmed to 23° C. for an additional 15 min, then was partitioned between 0.5 M HCl (150 mL) and CH₂Cl₂ (2×150 mL). The organic layer was dried over Na₂SO₄ and was concentrated. The residue thus obtained was dissolved in THF (120 mL) at 23° C. and tetrabutylammonium fluoride (15.63 mL of a 1.0 M solution in THF, 15.63 mmol, 3.0 equiv) was added. The reaction mixture was stirred at that temperature for 1 h, then was partitioned between 0.5 M HCl (150 mL) and EtOAc (2×150 mL). The organic layers were dried over Na₂SO₄ and were concentrated. The residue thus obtained was purified by flash column chromatography (80% EtOAc in hexanes) to give h1 (0.953 g, 58%) as a colorless oil: IR (cm⁻¹) 3379 (br), 1727, 1649; ¹H NMR (CDCl₃) δ 1.86–1.97 (m, 1H), 2.29–2.41 (m, 1H), 2.90–3.15 (m, 2H), 3.80–3.93 (m, 2H), 4.78–4.86 (m, 1H), 5.11–5.15 (m, 1H), 5.20 (s, 2H), 6.20 (d, 1H, J=7.5), 7.30–7.41 (m, 5 H), 7.75 (s, br, 1H), 8.07 (d, 1H, J=7.5); Anal. C₇H₁₈N₂O₄·0.75H₂O: C, H, N.

Preparation of Intermediate (3S)-6-Benzyloxycarbonylamino-5-oxo-1,2,3,5-tetrahydroindolizine-3-carboxylic Acid (i1)

Dimethylsulfoxide (0.522 mL, 7.36 mmol, 2.6 equiv) was added dropwise to a solution of oxalyl chloride (0.321 mL, 3.68 mmol, 1.3 equiv) in CH₂Cl₂ (80 mL) at −78° C. The reaction mixture was stirred for 20 min at that temperature, then a solution of h1(0.890 g, 2.83 mmol, 1 equiv) in CH₂Cl₂ (20 mL) was added via cannula. After stirring an additional 20 min at −78° C., triethylamine (1.97 mL, 14.15 mmol, 5.0 equiv) was added dropwise. The reaction mixture was maintained at −78° C. for 1.5 h, then acetic acid (15.57 mmol, 0.891 mL, 5.5 equiv) was added. The reaction mixture was warmed to 0° C. for 5 min, then was washed with water (50 mL), saturated NaHCO₃ (50 mL) and brine (50 mL). The organic layer was dried over Na₂SO₄ and concentrated to afford the crude aldehyde product as off-white foam. This material was utilized without further purification.

A solution of NaClO₂ (2.88 g, 25.47 mmol, 9.0 equiv) and NaH₂PO₄ (2.73 g, 19.81 mmol, 7.0 equiv) in water (60 mL) was added dropwise to a solution of the proceeding crude aldehyde (2.83 mmol, 1 equiv) in a mixture of tBuOH (60 mL) and 2-methyl-2-butene (10 mL) over 15 min at 23° C. The resulting mixture was stirred at room temperature for 1 h, then, the volatiles were removed under reduced pressure. The residue thus obtained was partitioned between 0.5 M HCl (150 mL) and 10% CH₃OH in CH₂Cl₂ (2×150 mL). The organic layers were dried over Na₂SO₄ and were concentrated. The resulting residue was purified by flash column chromatography (10% CH₃OH in CH₂Cl₂) to give i1 (0.346 g, 37%) as off-white solid: mp=204–206° C.; IR (cm⁻¹) 3298, 1722, 1564, 1208; ¹H NMR (DMSO-d₆) δ 2.17–2.55 (m, 2H), 2.45–2.59 (m, 2H), 4.98 (dd, 1H, J=9.6, 2.7), 5.16 (s, 2H), 6.23 (d, 1H, J=7.5), 7.34–7.45 (m, 5H), 7.83 (d, 1H, J=7.5), 8.34 (s, 1H); Anal. C₁₇H₁₆N₂O₅: C, H, N.

Preparation of Product k1 (Compound 36)

Intermediate i1 was transformed into compound 36 (via coupling with intermediate AA1) by a process that was analogous to that described in Example 23 for the transformation of W2 to product J2: ¹H NMR (DMSO-d6) δ 1.20 (t, 3H, J=7.1), 1.64–1.84 (m, 2H), 2.01–2.16 (m, 2H), 2.41–2.50 (m, 1H), 3.01–3.06 (m, 2H), 4.11 (q, 2H, J=7.1), 4.41 (m, br, 1H), 5.01 (dd, 1H, J=9.2, 2.7), 5.14 (s, 2H), 5.87 (dd, 1H, J=15.8, 1.4), 6.20 (d, 1H, J=7.6), 6.75 (s, br, 1H), 6.82 (dd, 1H, J=15.8, 5.0), 7.09–7.42 (m, 7H), 7.81 (d, 1H, J=7.6), 8.38 (s, 1H), 8.55 (d, 1H, J=8.4).

Example 35

Preparation of Compound 37: trans-(3'S,3'''S,4S)-4-({6'-[(5''-Methylisoxazole-3''-carbonyl)amino]-5'-oxo-1',2',3',5'-tetrahydroindolizine-3'-carbonyl}amino)-5-(2'''-oxopyrrolidin-3'''-yl)-pent-2-enoic Acid Ethyl Ester

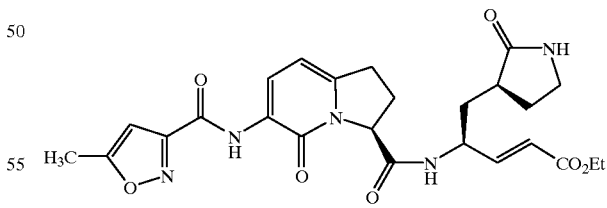

Preparation of Intermediate (3''R)-(5-Methylisoxazole-3-carboxylic Acid {6'-[4''-(tert-butyldimethylsilanyloxy)-3''-hydroxybutyl]-2'-methoxypyridin-3'-yl}amide (g2)

A suspension of intermediate g1 (prepared as described in Example 34) (4.21 g, 9.14 mmol, 1 equiv) and Pd on C (10%, 0.375 g) in EtOAc (120 mL) was stirred under an H₂ atmosphere (balloon) at 23° C. for 1 h. The reaction mixture was filtered through Celite and the filtrate was concentrated under reduced pressure. The residue was dissolved in CH$_3$CN (120 mL), cooled to 0° C., and NMM (1.00 mL, 9.10 mmol, 1.0 equiv) and 5-methylisoxazole-3-carbonyl chloride (1.33 g, 9.14 mmol, 1.0 equiv) were added sequentially. The reaction mixture was stirred at 0° C. for 1 h, then was partitioned between 0.5 M HCl (150 mL) and EtOAc (2×150 mL). The organic layers were dried over Na$_2$SO$_4$ and were concentrated. Trituration of the residue with a 1:3 mixture of Et$_2$O and hexanes (130 mL) provided a white solid which was collected by filtration, washed with hexanes (25 mL), and air-dried (2.61 g, 66%): mp=100–102° C.; IR (cm$^{-1}$) 3390, 1696, 1593, 1536; $^1$H NMR (CDCl$_3$) δ 0.07 (s, 6H), 0.90 (s, 9H), 1.78–1.95 (m, 2H), 2.52 (s, 3H), 2.78–2.90 (m, 2H), 3.45–3.53 (m, 2H), 3.60–3.74 (m, 2H), 4.03 (s, 3H), 6.51 (s, 1H), 6.79 (d, 1H, J=7.9), 8.55 (d, 1H, J=7.9), 8.95 (s, 1H); Anal. C$_{21}$H$_{33}$N$_3$O$_5$Si: C, H, N.

Preparation of Intermediates (3S)-6-[(5'-Methylisoxazole-3'-carbonyl)amino]-5-oxo-1,2,3,5-tetrahydroindolizine-3-carboxylic Acid (i2) and (3S)-8-Chloro-6-[(5'-methylisoxazole-3'-carbonyl)amino]-5-oxo-1,2,3,5-tetrahydroindolizine-3-carboxylic Acid (i3)

The preceding intermediate (g2) was transformed into a 1:4 mixture of intermediates i2 and i3 by a process that was analogous to that described in Example 34 for the transformation of g1 to i1: (i2) IR (cm$^{-1}$) 3343, 2977 (br), 1741, 1688, 1648; $^1$H NMR (CDCl$_3$) δ 2.28–2.74 (m, 2H), 2.50 (s, 3H), 3.04–3.32 (m, 2H), 5.31 (d, 1H, J=7.9), 6.36 (d, 1H, J=7.7), 6.48 (s, 1H), 8.58 (d, 1H, J=7.7), 9.40 (s, 1H); (i3) IR (cm$^{-1}$) 2240, 1652, 1532, 1260; $^1$H NMR (DMSO-d$_6$) δ 1.53–1.63 (m, 2H), 3.11–3.20 (m, 2H), 5.14 (dd, 1H, J=6.9, 2.7), 6.75 (s, 1H), 8.32 (s, 1H), 9.41 (s, br. 1H).

Preparation of Product 11 (Compound 37)

Intermediate i2 was transformed into compound 37 (via coupling with intermediate Y2) by a process that was analogous to that described in Example 25 for the transformation of W3 to product R3: IR (cm$^{-1}$) 3336, 1684, 1651, 1596, 1536; $^1$H NMR (CDCl$_3$) δ 1.28 (t, 3H, J=7.1), 1.63–1.89 (m, 2H), 2.04–2.15 (m, 1H), 2.38–2.64 (m, 3H), 2.50 (s, 3H), 2.98–3.06 (m, 1H), 3.26–3.42 (m, 4H), 4.19 (q, 2H, J=7.1), 4.63–4.65 (m, 1H), 5.15 (dd, 1H, J=8.3, 2.7), 5.97–6.05 (m, 2H), 6.21 (d, 1H, J=7.3), 6.48 (s, 1H), 6.89 (dd, 1H, J=15.6, 5.5), 8.44–8.52 (m, 2H), 9.40 (s, 1H); Anal. C$_{25}$H$_{29}$N$_5$O$_7$·0.6TFA: C, H, N.

Example 36

Preparation of Compound 38: trans-(2"S,3S,3'"S)-6-[(5'-Methylisoxazole-3'-carbonyl)amino]-5-oxo-1,2,3,5-tetrahydroindolizine-3-carboxylic Acid [2"-(2'"-oxodihydrofuran-3'"-ylidene)-1"-(2""-oxopyrrolidin-3""-ylmethyl)ethyl]amide

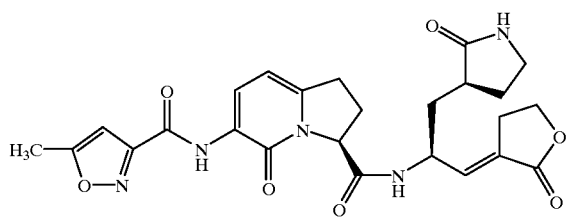

The title compound was prepared from intermediate i2 (via coupling with intermediate Y1) by a process that was analogous to that described in Example 22 for the transformation of W1 to product R2: IR (cm$^{-1}$) 3336, 1752, 1686, 1651, 1594, 1535; $^1$H NMR (CDCl$_3$) δ 1.59–1.68 (m, 1H), 1.77–1.81 (m, 1H), 2.09–1.81 (m, 1H), 2.37–2.45 (m, 2H), 2.50 (s, 3H), 2.58–2.66 (m, 1H), 2.91–3.05 (m, 2H), 3.23–3.44 (m, 4H), 4.39 (t, 2H, J=7.2), 4.60–4.67 (m, 1H), 5.10–5.13 (m, 1H), 6.09 (s, 1H), 6.21 (d, 1H, J=7.9), 6.41–6.48 (m, 2H), 8.45–8.50 (m, 2H), 8.77 (d, 1H, J=6.2), 9.39 (s, 1H).

Example 37

Preparation of Compound 39: trans-(3'S,3'"S,4S)-4-({8'-Chloro-6'-[(5"-methylisoxazole-3"-carbonyl)amino]-5'-oxo-1',2',3',5'-tetrahydroindolizine-3'-carbonyl}amino)-5-(2'"-oxopyrrolidin-3'"-yl)-pent-2-enoic Acid Ethyl Ester

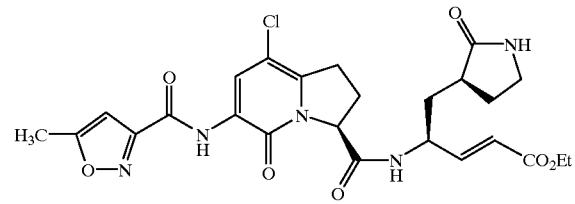

The title compound was prepared from intermediate i3 (via coupling with intermediate Y2) by a process that was analogous to that described in Example 25 for the transformation of W3 to product R3: IR (cm$^{-1}$) 3334, 1683, 1532; $^1$H NMR (CDCl$_3$) δ 1.31 (t, 3H, J=7.2), 1.66–1.89 (m, 4H), 2.33–2.50 (m, 1H), 2.53 (s, 3H), 2.67–2.72 (m, 1H), 3.04–3.20 (m, 2H), 3.27–3.48 (m, 2H), 4.21 (q, 2H, J=7.2), 4.62–4.64 (m, 1H), 5.16–5.20 (m, 1H), 5.94 (s, br. 1H), 5.99 (dd, 1H, J=15.6, 1.5), 6.51 (s, 1H), 6.89 (dd, 1H, J=15.6, 5.7), 8.52 (s, 1H), 8.56 (s, br. 1H), 9.41 (s, br. 1H); Anal. C$_{25}$H$_{28}$ClN$_5$O$_7$·0.50H$_2$O: C, H, N.

Example 38

Compound 40: trans-(2'S,3""S,4S)-4-[2'-(3"-{[1'"-(5""-Methylisoxazol-3""-yl)methanoyl]amino}-2""-oxo-2'"H-pyridin-1'"-yl)pent-4"-ynoylamino]-5-(2'""-oxopyrrolidin-3'""-yl)pent-2-enoic Acid Cyclopentyl Ester

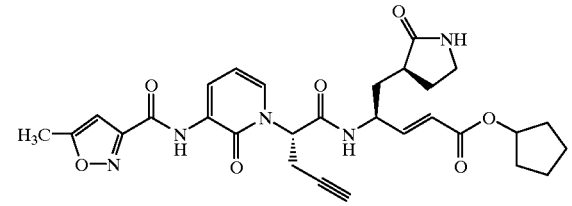

The title compound was prepared from D-propargylalanine by a process analogous to that described in Example 22 for the conversion of D-(4-fluorophenylalanine) to product R2 utilizing intermediates F2 and Y3 and an alternate deprotection of the intermediate corresponding to V1 (LiI in pyridine) where appropriate: IR (cm$^{-1}$) 3302, 1690, 1649, 1632; $^1$H NMR (CDCl$_3$) δ 1.62–1.80 (m, 7H), 1.87–1.92 (m, 2H), 2.01–2.12 (m, 2H), 2.26–2.40 (m, 2H), 2.53 (s, 3H), 2.95–3.12 (m, 2H), 3.26–3.36 (m, 2H), 4.50–4.53 (m, 1H), 5.20–5.25 (m, 1H), 5.54–5.60 (m, 1H), 6.01 (dd, 1H, J=15.6, 1.5), 6.31 (t, 2H, J=7.2), 6.40 (s, br, 1H), 6.49 (s, 1H), 6.83 (dd, 1H, J=15.6, 5.4), 7.43 (dd, 1H, J=6.9, 1.8), 8.44 (dd, 1H, J=6.9, 1.5), 8.58 (d, 1H, J=6.6), 9.56 (s, 1H); Anal. ($C_{29}H_{33}N_5O_7 \cdot 0.75H_2O$) C, H, N.

Example 39

Preparation of Compound 41: trans-(2'S,3'''''S,4S)-4-[2'-(3''-{[1'''-(5''''-Methylisoxazol-3''''-yl)methanoyl]amino}-2'''-oxo-2'''H-pyridin-1'''-yl)pent-4''-ynoylamino]-5-(2'''''-oxopyrrolidin-3'''''-yl)pent-2-enoic Acid tert-Butyl Ester

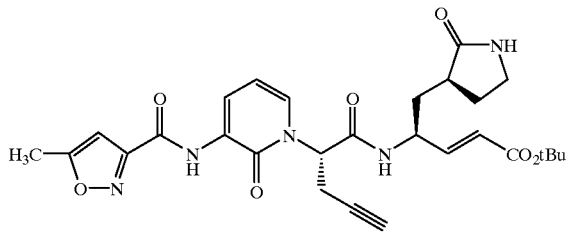

The title compound was prepared from D-propargylalanine by a process analogous to that described in Example 22 for the conversion of D-(4-fluorophenylalanine) to product R2 utilizing intermediates F2, K1, and (triphenyl-1$^5$-phosphanylidene)-acetic acid tert-butyl ester and an alternate deprotection of the intermediate corresponding to V1 (LiI in pyridine) where appropriate: mp=195° C., dec.; IR (cm$^{-1}$) 3295, 1690, 1649; $^1$H NMR (CDCl$_3$) δ 1.47 (s, 9H), 1.50–1.79 (m, 2H), 2.04 (t, 1H, J=2.6), 2.05–2.37 (m, 3H), 2.49 (s, 3H), 2.92 (ddd, 1H, J=17.0, 8.6, 2.6), 3.02 (ddd, 1H, J=17.0, 6.7, 2.6), 3.20–3.37 (m, 2H), 4.41–4.52 (m, 1H), 5.65–5.73 (m, 1H), 5.94 (dd, 1H, J=15.6, 1.4), 6.33 (t, 1H, J=7.3), 6.46 (s, 1H), 6.70 (s, 1H), 6.73 (dd, 1H, J=15.6, 5.3), 7.48 (dd, 1H, J=7.3, 1.7), 8.41 (dd, 1H, J=7.3, 1.7), 8.62 (d, 1 H, J=6.6), 9.53 (s, 1H); Anal. ($C_{28}H_{33}N_5O_7$) C, H, N.

Example 40

Preparation of Compound 42: trans-(2'S,3'''''S,4S)-4-[2'-(3''-{[1'''-(5''''-Methylisoxazol-3''''-yl)methanoyl] amino}-2'''-oxo-2'''H-pyridin-1'''-yl)butanoylamino]-5-(2'''''-oxopyrrolidin-3'''''-yl)pent-2-enoic Acid 2,2-Dimethylpropyl Ester

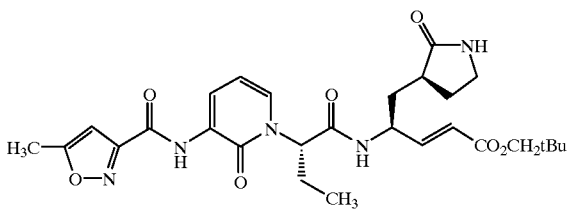

The title compound was prepared by a method analogous to that described in Example 25 for the preparation of specific intermediate R3 utilizing trans-(3'S,4S)4-tert-butoxycarbonylamino-5-(2'-oxopyrrolidin-3'-yl)pent-2-enoic acid 2,2-dimethylpropyl ester (prepared from K1 in a manner similar to that described for the preparation of X4 in Example 27) where appropriate: IR (cm$^{-1}$) 3331, 3295, 1690, 1649; $^1$H NMR (CDCl$_3$) δ 0.87–0.99 (m, 12H), 1.51–1.61 (m, 1H), 1.64–1.79 (m, 1H), 1.83–2.00 (m, 1H), 2.10–2.37 (m, 4H), 2.49 (s, 3H), 3.26–3.43 (m, 2H), 3.83 (s, 2H), 4.43–4.54 (m, 1H), 5.71 (dd, 1H, J=8.7, 6.9), 6.00 (dd, 1H, J=15.7, 1.3), 6.35 (t, 1H, J=7.2), 6.46 (s, 1H), 6.86 (dd, 1H, J=15.7, 5.9), 7.39 (s, 1H), 7.58 (dd, 1H, J=7.2, 1.7), 8.42 (dd, 1H, J=7.2, 1.7), 8.53 (d, 1H, J=7.0), 9.55 (s, 1H); Anal. ($C_{28}H_{37}N_5O_7 \cdot 0.5H_2O$) C, H, N.

Example 41

Preparation of Compound 43: trans-(2'S,3'''''S,4S)-4-[2'-(3''-{[1'''-(5''''-Methylisoxazol-3''''-yl)methanoyl]amino}-2'''-oxo-2'''H-pyridin-1'''-yl)pent-4''-ynoylamino]-5-(2'''''-oxopyrrolidin-3'''''-yl)pent-2-enoic Acid

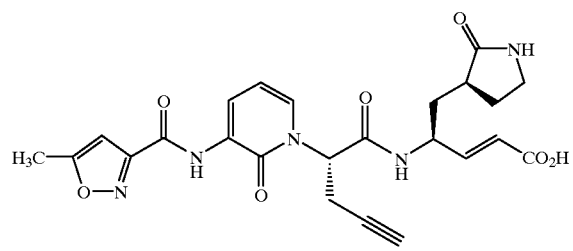

The title compound was prepared from compound 41 by acidic deprotection of the tert-butyl ester moiety present in that compound (following standard literature procedures): R$_f$=0.37 (10% CH$_3$OH in CHCl$_3$); IR (cm$^{-1}$) 3295, 2950 (br), 1696, 1649; $^1$H NMR (CDCl$_3$) δ 1.62–1.85 (m, 2H), 2.05–2.16 (m, 2H), 2.24–2.36 (m, 1H), 2.43–2.56 (m, 1H), 2.52 (s, 3H), 2.92–3.11 (m, 2H), 3.30–3.42 (m, 2H), 4.60–4.71 (m, 1H), 5.65–5.73 (m, 1H), 6.03 (d, 1H, J=15.6), 6.37 (t, 1H, J=7.2), 6.50 (s, 1H), 6.94 (dd, 1H, J=15.6, 6.0), 7.24 (s, 1H), 7.47 (dd, 1H, J=7.2, 1.3), 8.31 (d, 1H, J=7.5), 8.45 (dd, 1H, J=7.2, 1.3), 9.53 (s, 1H); Anal. ($C_{24}H_{25}N_5O_7 \cdot 0.5H_2O$) C, H, N.

Example 42

Compound 44: trans-(2'S,3'''''S,4S)-2-Methyl-4-[2'-(3''-{[1'''-(5''''-methylisoxazol-3''''-yl)methanoyl]amino}-2'''-oxo-2'''H-pyridin-1'''-yl)pent-4''-ynoylamino]-5-(2'''''-oxopyrrolidin-3'''''-yl)pent-2-enoic Acid Ethyl Ester

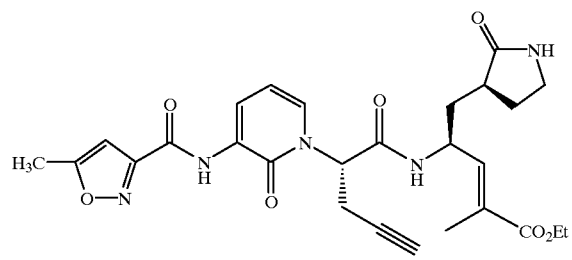

The title compound was prepared from D-propargylalanine by a process analogous to that described in Example 22 for the conversion of D-(4-fluorophenylalanine) to product R2 utilizing intermediates F2 and trans-(3'S,4S)-4-tert-butoxycarbonylamino-2-methyl-5-(2'-oxopyrrolidin-3'-yl)pent-2-enoic acid ethyl ester (prepared from K1 in a manner similar to that described for the preparation of X4 in Example 27) and an alternate deprotection of the intermediate corresponding to V1 (LiI in pyridine) where appropriate: IR (cm$^{-1}$) 3307, 1690, 1649; $^1$H NMR (CDCl$_3$) δ 1.29 (t, 3H, J=7.1), 1.36–1.47 (m, 1H), 1.65–1.80 (m, 1H), 1.95–2.00 (m, 4H), 2.14–2.40 (m, 3H), 2.50 (s, 3H), 2.87–3.03 (m, 2H), 3.23–3.38 (m, 2H), 4.18 (q, 2H, J=7.1), 4.56–4.68 (m, 1H), 5.63–5.72 (m, 1H), 6.34 (t, 1H, J=7.3), 6.47 (s, 1H), 6.52–6.58 (m, 1H), 6.81 (s, 1H), 7.46 (dd, 1H, J=7.3, 1.6), 8.42 (dd, 1H, J=7.3, 1.6), 8.65 (d, 1H, J=6.4), 9.54 (s, 1H).

Example 43

Preparation of Compound 45: 4S-[2S-(3-Methyl-7-oxo-1,4,5,7-tetrahydro-pyrrolo[2,3-c]pyridin-6-yl)3-phenyl-propionylamino]-5-(2-oxo-pyrrolidin-3-yl)pent-2(trans)-enoic acid ethyl ester.

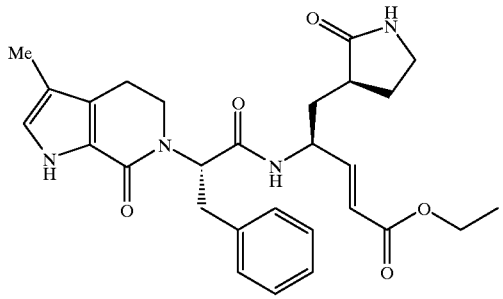

3-(2-Hydroxy-ethyl)-5-iodo-4-methyl-1H-pyrrole-2-carboxylic acid tert-butyl ester (0.34 mmol, 114 mg) in DMSO (2 mL) was treated with o-iodoxybenzoic acid (IBX, 0.51 mmol, 148 mg), then held at room temperature for 3h. The mixture was diluted with ethyl acetate (50 mL), washed with brine (10 mL), then concentrated under reduced pressure to provide 84 mg (75%) of 5-iodo-4-methyl-3-(2-oxo-ethyl)-$^1$H-pyrrole-2-carboxylic acid tert-butyl ester. $^1$H NMR (CDCl$_3$) δ 9.63 (1H, s), 8.91 (1H, br s), 4.09 (2H, s), 2.62 (3H, s), 1.52 (9H, s).

5-Iodo-4-methyl-3-(2-oxo-ethyl)-1H-pyrrole-2-carboxylic acid tert-butyl ester (0.25 mmol, 84 mg) in MeOH (2 mL) was treated with phenylalanine methyl ester (0.25 mmol, 45 mg), then treated with sodium cyanoborohydride (0.25 mmol, 16 mg). The mixture was held at room temperature for 3h, then concentrated under reduced pressure. Purification of the residue by silica gel chromatography gave 80 mg (46%) of 5-iodo-3-[2S-(1-methoxycarbonyl-2-phenyl-ethylamino)-ethyl]-4-methyl-1H-pyrrole-2-carboxylic acid tert-butyl ester. $^1$H NMR (CDCl$_3$) δ 8.81 (1H, br s), 7.30–7.13 (5H, m), 3.61 (3H, s), 3.55 (1H, t, J=6.8), 2.94 (2H, d, J=6.3), 2.90–2.78 (2H, m), 2.76–2.70 (1H, m), 2.62–2.56 (1H, m), 1.94 (3H, s), 1.51 (9H, s).

5-Iodo-3-[2S-(1-methoxycarbonyl-2-phenyl-ethylamino)-ethyl]-4-methyl-1H-pyrrole-2-carboxylic acid tert-butyl ester (0.37 mmol, 0.18 g) in dioxane (2 mL) at 0° C. was treated with HCl (0.37 mmol, 1 mL of 4M in dioxane). The mixture was held at 0° C. for 15 minutes, then concentrated under reduced pressure. The residue was diluted with DMF (3 mL), then treated with HOBT (0.37 mmol, 50 mg), DCC (0.37 mmol, 77 mg), and K$_2$CO$_3$ (0.74 mmol, 0.10 g). The mixture was stirred at room temperature for 30 minutes, then diluted with ethyl acetate (50 mL), washed with brine (10 mL), then concentrated under reduced pressure. The residue was purified by silica gel chromatography to provide 21 mg (13%) of 2S-(3-methyl-7-oxo-1,4,5,7-tetrahydro-pyrrolo[2,3-c]pyridin-6-yl)-3-phenyl propionic acid methyl ester. It was noticed that this material had inadvertently de-iodinated. $^1$H NMR (CDCl$_3$) δ 9.28 (1H, br s), 7.31–7.18 (5H, m), 6.64 (1H, s), 5.33 (1H, dd, J=10.4, 5.6), 3.79–3.74 (1H, m), 3.75 (3H, s), 3.57–3.42 (4H, m), 3.14 (1H, dd, J=14.5, 10.4), 2.59–2.49 (2H, m), 2.00 (3H, s). MS (FAB) 311 (MH$^+$).

2S-(3-methyl-7-oxo-1,4,5,7-tetrahydro-pyrrolo[2,3-c]pyridin-6-yl)-3-phenyl propionic acid methyl ester (0.07 mmol, 21 mg) in 1:1 dioxane-water (3 mL) was treated with lithium hydroxide (0.2 mmol, 5 mg), then heated to reflux for 30 minutes. The solution was acidified with saturated aqueous citric acid (3 mL), then extracted with ethyl acetate (15 mL), washed with brine (5 mL), and concentrated under reduced pressure to provide 15 mg (75%) of 2S-(3-methyl-7-oxo-1,4,5,7-tetrahydro-pyrrolo[2,3-c]pyridin-6-yl)-3-phenyl propionic acid. This material (15 mg, 0.05 mmol) was coupled to 4S-amino-5-(2-oxo-pyrrolidin-3S-yl)-pent-2(trans)-enoic acid ethyl ester (11 mg, 0.05 mmol) in DMF (1 mL) by treatment with diisopropylethyl amine (0.02 mL, 0.01 mmol) and HATU (19 mg, 0.05 mmol) at room temperature for 2 h. The resulting solution was washed with brine (10 mL), and extracted with EtOAc (30 mL). The organics were concentrated under reduced pressure and the residue purified by preparative reverse phase chromatography (CH$_3$CN-H$_2$O) to provide 10 mg (40 %) of 4S-[2S-(3-methyl-7-oxo-1,4,5,7-tetrahydro-pyrrolo[2,3-c]pyridin-6-yl)-3-phenyl-propionylamino]-5-(2-oxo-pyrrolidin-3-yl)pent-2(trans)-enoic acid ethyl ester. $^1$H NMR (CDCl$_3$) δ 10.21 (1H, br s), 7.54 (1H, d, J=7.7), 7.26–7.11 (4H, m), 6.80 (1H, d, J=15.6), 6.62 (1H, br s), 6.23 (1H, br s), 5.82 (1H, dd, J=15.5, 5.4), 5.28 (1H, t, J=8.0), 4.68–4.50 (1H, m), 4.19 (2H, q, J=7.1), 3.67–2.96 (6H, m), 2.56–2.51 (3H, m), 2.21–2.09 (2H, m), 1.96 (3H, s), 1.75–1.64 (1H, m), 1.53–1.43 (3H, m), 1.29 (3H, t, J=7.1). HRMS (FAB) 639.1577 (MCs$^+$, calcd. 639.1584).

Example 44

Preparation of Compound 46: trans-(2'S,3''''S,4S)-4-[3'-(3'',4''-Difluorophenyl)-2'-(3'''-{[1''''-(5''''-methylisoxazol-3''''-yl)methanoyl]amino]}-2''''-oxo-2''''H-pyridin-1''''-yl)propanoylamino]-5-(2''''-oxopyrrolidin-3''''-yl)pent-2-enoic Acid tert-Butyl Ester

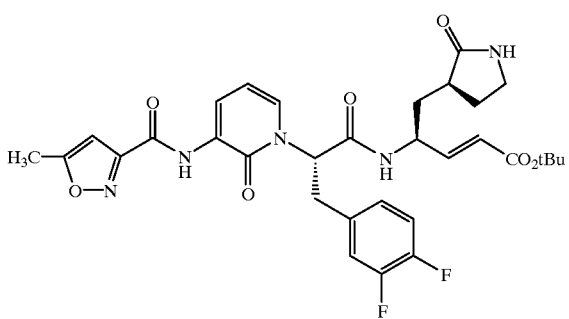

The title compound was prepared from D-(3,4)-difluorophenylalanine by a process analogous to that described in Example 22 for the conversion of D-(4-fluorophenylalanine) to product R2 and Example 19 for the conversion of intermediate L1 to product R1 utilizing tert-butyl diethylphosphonoacetate where appropriate: IR (cm$^{-1}$) 3337, 1693, 1531, 1286, 1155; $^1$H NMR (CDCl$_3$) δ 1.51.(s, 9H), 1.70–1.82 (m, 2H), 2.13–2.28 (m, 2H), 2.51 (s, 3H), 3.07–3.14 (m, 1H), 3.25–3.47 (m, 3H), 4.23 (m, 1H), 5.71 (d, 1H, J=15.9), 5.89–5.98 (m, 1H), 6.33 (t, 1H, J=7.2), 6.48 (s, 1H), 6.66 (dd, 1H, J=15.6, 5.7), 6.87 (m, 2H), 7.01–7.10 (m, 2H), 7.29 (s, 1H), 7.58 (d, 1H, J=5.7), 8.40(dd, 1H, J=7.5, 1.8), 8.55 (d, 1H, J=6.9), 9.48 (s, 1H); Anal. (C$_{32}$H$_{35}$F$_2$N$_5$O$_7$·H$_2$O) C, H, N.

Example 45

Preparation of Compound 47: trans-(2'S,3'''''S,4S)-4-[3'-(3'',4''-Difluorophenyl)-2'-(3'''-{[1''''-(5'''''-methylisoxazol-3'''''-yl)methanoyl]amino}-2''''-oxo-2''''H-pyridin-1''''-yl)propanoylamino]-5-(2'''''-oxopyrrolidin-3'''''-yl)pent-2-enoic Acid 2,2-Dimethylpropyl Ester.

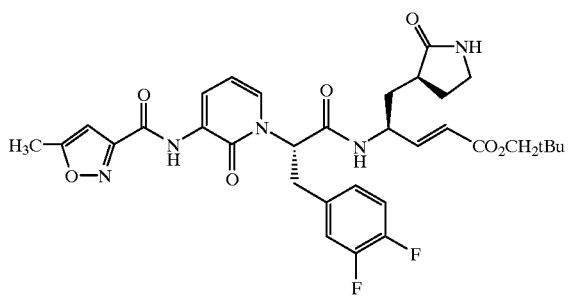

The title compound was prepared from D-(3,4)-difluorophenylalanine by a process analogous to that described in Example 22 for the conversion of D-(4-fluorophenylalanine) to product R2 and trans-(3'S,4S)4-tert-butoxycarbonylamino-5-(2'-oxopyrrolidin-3'-yl)pent-2-enoic acid 2,2-dimethylpropyl ester (prepared from K1 in a manner similar to that described for the preparation of X4 in Example 27) utilizing intermediate F2 where appropriate: IR (cm$^{-1}$) 3335, 1693, 1531, 1248; $^1$H NMR (CDCl$_3$) δ 0.99 (s, 9H), 1.72–1.83 (m, 2H), 2.11–2.29 (m, 2H), 2.52 (s, 3H), 3.09–3.16 (m, 1H), 3.26–3.48 (m, 3H), 3.82–3.92 (m, 2H), 4.48 (m, 1H), 5.86 (d, 1H, J=15.6), 5.91–5.94 (m, 1H), 6.33 (t, 1H, J=8.1), 6.48 (s, 1H), 6.76 (dd, 1H, J=15.6, 6.0), 6.85 (m, 2H), 7.00–7.09 (m, 2H), 7.29 (s, 1H), 7.55 (d, 1H, J=6.9), 8.41 (d, 1H, J=7.5), 8.60 (d, 1H, J=6.9), 9.48 (s, 1H); Anal. (C$_{33}$H$_{37}$F$_2$N$_5$O$_7$·0.5H$_2$O) C, H, N.

Example 46

Preparation of Compound 48: trans-(2'S,3'''''S,4S)-4-[3'-(3'',4''-Difluorophenyl)-2'-(3'''-{[1''''-(5'''''-methylisoxazol-3'''''-yl)methanoyl]amino}-2''''-oxo-2''''H-pyridin-1''''-yl)propanoylamino]-5-(2'''''-oxopyrrolidin-3'''''-yl)pent-2-enoic Acid Isopropyl Ester.

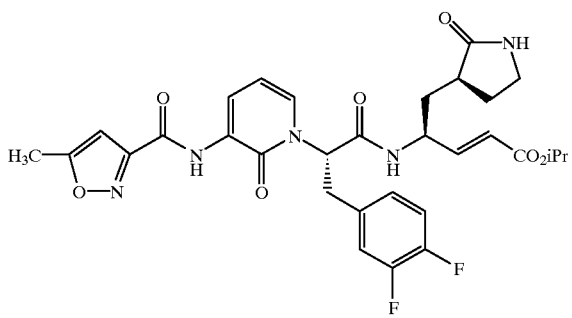

The title compound was prepared from D-(3,4)-difluorophenylalanine by a process analogous to that described in Example 22 for the conversion of D-(4-fluorophenylalanine) to product R2 and trans-(3'S,4S)4-tert-butoxycarbonylamino-5-(2'-oxopyrrolidin-3'-yl)pent-2-enoic acid isopropyl ester (prepared from K1 in a manner similar to that described for the preparation of X4 in Example 27) utilizing intermediate F2 where appropriate: $^1$H NMR (CDCl$_3$) δ 1.27 (d, 3H, J=6.2), 1.28 (d, 3H, J=6.2), 1.45–1.56 (m, 1H), 1.62–1.78 (m, 1H), 2.08–2.29 (m, 3H), 2.49 (s, 3H), 3.06 (dd, 1H, J=13.8, 7.8), 3.21–3.44 (m, 3H), 4.36–4.47 (m, 1H), 4.99–5.12 (m, 1H), 5.66 (dd, 1H, J=15.6, 1.5), 5.96–6.04 (m, 1H), 6.32 (t, 1H, J=7.3), 6.45 (s, 1H), 6.71 (dd, 1H, J=15.6, 5.6), 6.84–6.91 (m, 1H), 6.98–7.17 (m, 3H), 7.66 (dd, 1H, J=7.3, 1.6), 8.39 (dd, 1H, J=7.3, 1.6), 8.64 (d, 1H, J=6.6), 9.45 (s, 1H).

Example 47

Preparation of Compound 49: trans-(2'S,3'''''S,4S)-4-[3'-(3'',4''-Difluorophenyl)-2'-(3'''-{[1''''-(5'''''-methylisoxazol-3'''''-yl)methanoyl]amino}-2''''-oxo-2''''H-pyridin-1''''-yl)propanoylamino]-5-(2'''''-oxopyrrolidin-3'''''-yl)pent-2-enoic Acid Cyclopentyl Ester.

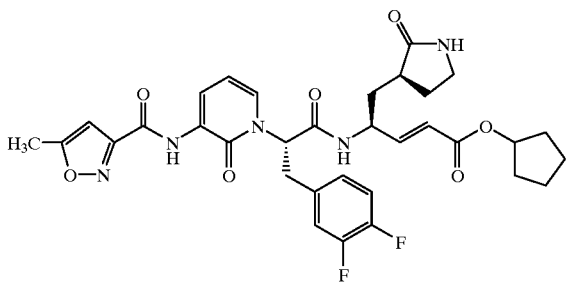

The title compound was prepared from D-(3,4)-difluorophenylalanine by a process analogous to that described in Example 22 for the conversion of D-(4- fluorophenylalanine) to product R2 utilizing intermediates Y3 (Example 27) and F2 where appropriate: ¹H NMR (CDCl₃) δ 1.45–1.98 (m, 10H), 2.08–2.30 (m, 3H), 2.49 (s, 3H), 3.07 (dd, 1H, J=13.7, 8.1), 3.20–3.44 (m, 3H), 4.35–4.47 (m, 1H), 5.18–5.23 (m, 1H), 5.71 (d, 1H, J=15.7), 5.93–6.02 (m, 1H), 6.31 (t, 1H, J=7.2), 6.45 (s, 1H), 6.70 (dd, 1H, J=15.7, 5.8), 6.83–6.89 (m, 1H), 6.97–7.10 (m, 3H), 7.63 (dd, 1H, J=7.2, 1.6), 8.38 (dd, 1H, J=7.2, 1.6), 8.62 (d, 1H, J=6.8), 9.45 (s, 1H).

Example 48

Preparation of Compound 50: trans-(2'S,3''''S,4S)-4-[2'-(3''- {[1'''-(5''''-Methylisoxazol-3'''''-yl)methanoyl]amino }-2'''-oxo-2'''H-pyridin-1'''-yl)pent-4''-ynoylamino]-5-(2'''''-oxopyrrolidin-3'''''-yl)pent-2-enoic Acid Isopropyl Ester

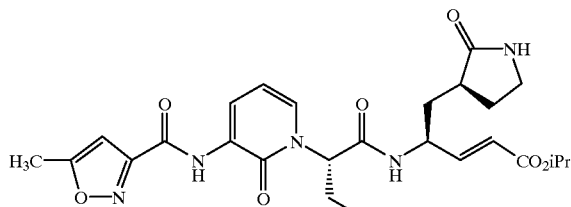

The title compound was prepared from D-propargylalanine by a process analogous to that described in Example 22 for the conversion of D-(4-fluorophenylalanine) to product R2 utilizing intermediates F2 and trans-(3'S,4S)-4-tert-butoxycarbonylamino-2-methyl-5-(2'-oxopyrrolidin-3'-yl)pent-2-enoic acid isopropyl ester (prepared from K1 in a manner similar to that described for the preparation of X4 in Example 27) where appropriate: IR (cm⁻¹) 3304, 1692, 1650; ¹H NMR (CDCl₃) δ 1.25 (d, 6H, J=6.2), 1.54–1.78 (m, 2H), 2.03 (t, 1H, J=2.5), 2.06–2.33 (m, 3H), 2.49 (s, 3H), 2.88–3.07 (m, 2H), 3.21–3.35 (m, 2H), 4.47–4.49 (m, 1H), 5.00–5.08 (m, 1H), 5.66–5.71 (m, 1H), 6.00 (dd, 1H, J=15.7, 1.4), 6.33 (t, 1H, J=7.2), 6.46 (s, 1H), 6.73 (br s, 1H), 6.83 (dd, 1H, J=15.7, 5.4), 7.48 (dd, 1H, J=7.2, 1.7), 8.41 (dd, 1H, J=7.2, 1.7), 8.65 (d, 1H, J=6.6), 9.53 (s, 1H); Anal. (C₂₇H₃₁N₅O₇·0.50H₂O) C, H, N.

Example 49

Preparation of Compound 51: trans-(2'S,3''''S,4S)-4-[3'-(3'',4''-Difluorophenyl)-2'-(3'''-{[1''''-(5'''''-methylisoxazol-3''''''-yl)methanoyl]amino}-2''''-oxo-2''''H-pyridin-1''''-yl)propanoylamino]-5-(2'''''-oxopyrrolidin-3'''''-yl)pent-2-enoic Acid.

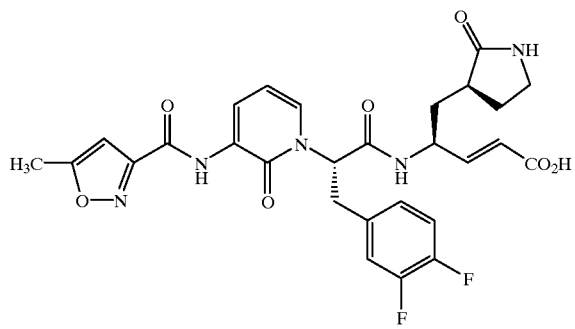

The title compound was prepared by deprotection of the tert-butyl ester present in compound 46 (Example 44) under acidic conditions using standard literature procedures: IR (cm⁻¹) 3413, 1684, 1590, 1519; ¹H NMR (DMSO) δ 1.42–1.54 (m, 1H), 1.59–1.68 (m, 1H), 1.84–1.94 (m, 1H), 2.10–2.16 (m, 1H), 2.51 (s, 3H), 3.05–3.13 (m, 1H), 3.32–3.45 (m, 3H), 4.52 (m, 1H), 5.74 (d, 1H, J=15.9), 5.80–5.82 (m, 1H), 6.36 (t, 1H, J=7.2), 6.71 (s, 1H), 6.77 (dd, 1H, J=15.6, 5.4), 7.04 (m, 1H), 7.28–7.34 (m, 3H), 7.06–7.77 (m, 2H), 8.23 (d, 1H, J=7.5), 8.61 (d, 1H, J=7.2), 9.42 (s, 1H); Anal. (C₂₈H₂₇F₂N₅O₇·H₂O) C, H, N.

Example 50

Preparation of Compound 52: trans-(2'S,3''''S,4S)-4-[2'-(3''-{[1'''-(5''''-Methylisoxazol-3'''''-yl)methanoyl]amino}-2'''oxo-2'''H-pyridin-1'''-yl)butanoylamino]-5-(2'''''-oxopyrrolidin-3'''''-yl)pent-2-enoic Acid Isopropyl Ester.

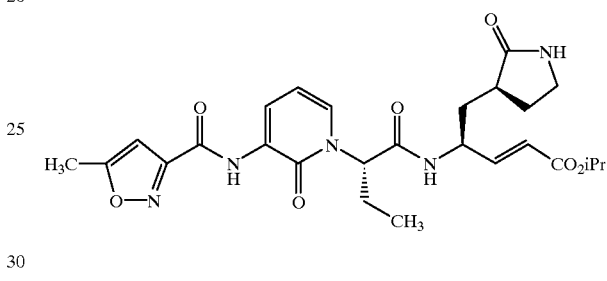

The title compound was prepared by a process analogous to that described in Example 25 for the conversion of intermediate V3 to product R3 utilizing intermediates F2 and trans-(3'S,4S)-4-tert-butoxycarbonylamino-2-methyl-5-(2'-oxopyrrolidin-3'-yl)pent-2-enoic acid isopropyl ester (prepared from K1 in a manner similar to that described for the preparation of X4 in Example 27) where appropriate: IR (cm⁻¹) 3333, 1681, 1531, 1276; ¹H NMR (CDCl₃) δ 0.98 (t, 3H, J=7.2), 1.29 (d, 6H, J=6.6), 1.46–1.73 (m, 1H), 1.89–2.07 (m, 1H), 2.13–2.37 (m, 4H), 2.52 (s, 3H), 3.30–3.43 (m, 3H), 4.48 (m, 1H), 5.02–5.14 (m, 1H), 5.69 (t, 1H, J=6.9), 5.96 (d, 1H, J=15.6), 6.39 (t, 1H, J=7.5), 6.49 (s, 1H), 6.86 (dd, 1H, J=15.6, 6.0), 6.91 (s, br. 1H), 7.56 (d, 1H, J=7.2), 8.44 (d, 1H, J=7.5), 8.53 (d, 1H, J=6.3), 9.59 (s, 1H); Anal. (C₂₆H₃₃N₅O₇·0.5H₂O) C, H, N.

Example 51

Preparation of Compound 53: trans-(2'S,3''''S,4S)-4-[2'-(3''-{[1'''-(5''''-Methylisoxazol-3'''''-yl)methanoyl]amino}-2'''-oxo-2'''H-pyridin-1'''-yl)pent-4''-ynoylamino]-5-(2'''''-oxopyrrolidin-3'''''-yl)pent-2-enoic Acid Cyclobutyl Ester.

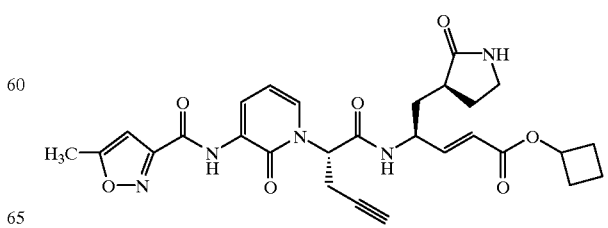

The title compound was prepared from D-propargylalanine by a process analogous to that described in Example 22 for the conversion of D-(4-fluorophenylalanine) to product R2 utilizing intermediates F2 and trans-(3'S,4S)-4-tert-butoxycarbonylamino-2-methyl-5-(2'-oxopyrrolidin-3'-yl)pent-2-enoic acid cyclobutyl ester (prepared from K1 in a manner similar to that described for the preparation of X4 in Example 27) where appropriate: $^1$H NMR (CDCl$_3$) δ 1.52–1.87 (m, 4H), 2.01–2.41 (m, 8H), 2.50 (s, 3H), 2.92 (ddd, 1H, J=17.0, 8.5, 2.6), 3.02 (ddd, 1H, J=17.0, 6.8, 2.6), 3.21–3.37 (m, 2H), 4.43–4.54 (m, 1H), 4.96–5.08 (m, 1H), 5.68–5.76 (m 1H), 6.00 (dd, 1H, J=15.7, 1.5), 6.33 (t, 1H, J=7.3), 6.45–6.48 (m, 1H), 6.83 (s, 1H), 6.84 (dd, 1H, J=15.7, 5.4), 7.49 (dd, 1H, J=7.3, 1.7), 8.41 (dd, 1H, J=7.3, 1.7), 8.68 (d, 1H, J=6.6), 9.52 (s, 1H).

Example 52

Preparation of Compound 54: trans-(2'S,3'''''S,4S)-4-[3'-(3'',4''-Difluorophenyl)-2'-(3'''-{[1''''-(5'''''-methylisoxazol-3'''''-yl)methanoyl]amino}-2''''-oxo-2''''H-pyridin-1''''-yl)propanoylamino]-5-(2'''''-oxopyrrolidin-3'''''-yl)pent-2-enoic Acid Cyclohexyl Ester.

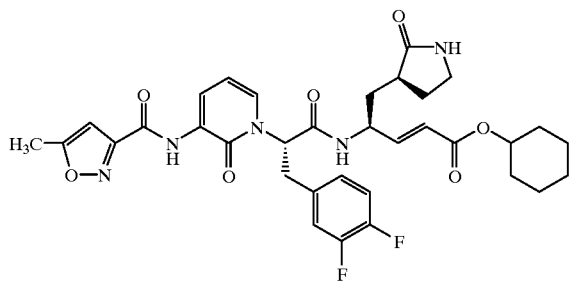

The title compound was prepared from D-(3,4)-difluorophenylalanine by a process analogous to that described in Example 22 for the conversion of D-(4-fluorophenylalanine) to product R2 utilizing intermediates F2 and trans-(3'S,4S)-4-tert-butoxycarbonylamino-2-methyl-5-(2'-oxopyrrolidin-3'-yl)pent-2-enoic acid cyclohexyl ester (prepared from K1 in a manner similar to that described for the preparation of X4 in Example 27) where appropriate: $^1$H NMR (CDCl$_3$) 1.20–1.61 (m, 7H), 1.62–1.79 (m, 3H), 1.82–1.93 (m, 2H), 2.07–2.31 (m, 3H), 2.49 (d, 3H, J=0.7), 3.08 (dd, 1H, J=13.8, 8.2), 3.20–3.45 (m, 3H), 4.36–4.48 (m, 1H), 4.75–4.85 (m, 1H), 5.71 (dd, 1H, J=15.6, 1.4), 5.90–5.98 (m, 1H), 6.31 (t, 1H, J=7.3), 6.44–6.46 (m, 1H), 6.72 (dd, 1H, J=15.6, 5.7), 6.83–6.90 (m, 1H), 6.95–7.08 (m, 3H), 7.59 (dd, 1H, =7.3, 1.6), 8.38 (dd, 1H, J=7.3, 1.6), 8.60 (d, 1H, J=6.6), 9.45 (s, 1H).

Example 53

Preparation of Compound 55: trans-(2'S,3'''''S,4S)-4-[2'-(3''-{[1'''-(5''''-Methylisoxazol-3''''-yl)methanoyl]amino}-2'''-oxo-2'''H-pyridin-1'''-yl)pent-4''-ynoylamino]-5-(2'''''-oxopyrrolidin-3'''''-yl)pent-2-enoic Acid Cyclohexyl Ester.

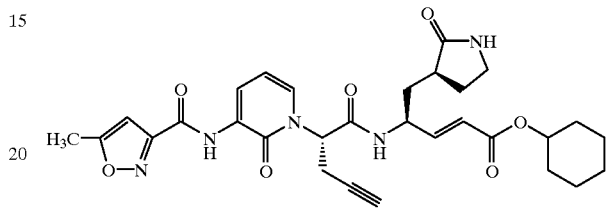

The title compound was prepared from D-propargylalanine by a process analogous to that described in Example 22 for the conversion of D-(4-fluorophenylalanine) to product R2 utilizing intermediates F2 and trans-(3'S,4S)-4-tert-butoxycarbonylamino-2-methyl-5-(2'-oxopyrrolidin-3'-yl)pent-2-enoic acid cyclohexyl ester (prepared from K1 in a manner similar to that described for the preparation of X4 in Example 27) where appropriate: IR (cm$^{-1}$) 3305, 1685, 1650, 1597, 1534; $^1$H NMR (CDCl$_3$) δ 1.24–1.98 (m, 12H), 2.03 (t, 1H, J=2.5), 2.05–2.39 (m, 3H), 2.50 (s, 3H), 2.90–3.09 (m, 2H), 3.20–3.34 (m, 2H), 4.45–4.52 (m, 1H), 4.75–4.83 (m, 1H), 5.59–5.64 (m, 1H), 6.01 (dd, 1H, J=15.6, 1.2), 6.33 (t, 1H, J=7.2), 6.46 (s, 1H), 6.54 (br s, 1H), 6.82 (dd, 1H, J=15.6, 5.3), 7.44 (dd, 1H, J=7.2, 1.7), 8.41 (dd, 1H, J=7.2, 1.7), 8.59 (d, 1H, J=6.6), 9.53 (s, 1H); Anal. (C$_{30}$H$_{35}$N$_5$O$_7$·0.75H$_2$O) C, H, N.

Example 54

Preparation of Compound 56: trans-(2'S,3'''''S,4S)-4-[3'-(3'',4''-Difluorophenyl)-2'-(3'''-{[1''''-(5'''''-methylisoxazol-3'''''-yl)methanoyl]aminol}-2''''-oxo-2''''H-pyridin-1''''-yl)propanoylamino]-5-(2'''''-oxopyrrolidin-3'''''-yl)pent-2-enoic Acid Cycloheptyl Ester.

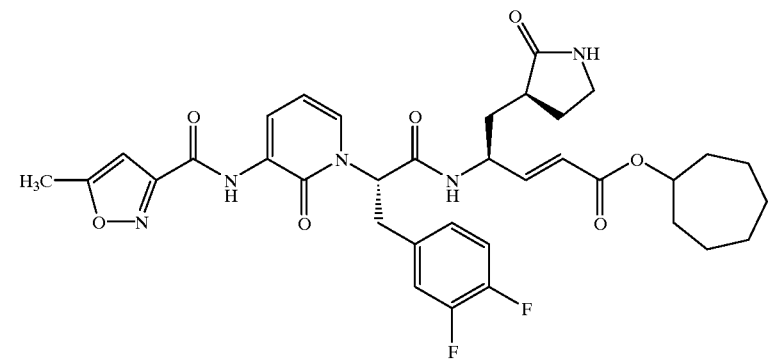

The title compound was prepared from D-(3,4)-difluorophenylalanine by a process analogous to that described in Example 22 for the conversion of D-(4-fluorophenylalanine) to product R2 utilizing intermediates F2 and trans-(3'S,4S)-4-tert-butoxycarbonylamino-2-methyl-5-(2'-oxopyrrolidin-3'-yl)pent-2-enoic acid cycloheptyl ester (prepared from K1 in a manner similar to that described for the preparation of X4 in Example 27) where appropriate: $^1$H NMR (CDCl$_3$) δ 1.40–2.35 (m, 17H), 2.48 (s, 3H), 3.09 (m, 1H), 3.20–3.50 (m, 3H), 4.35–4.50 (m, 1H), 4.90–5.05 (m, 1H), 5.73 (d, 1H, J=15.7), 5.86 (t, 1H, J=7.5), 6.21 (t, 1H, J=7.2), 6.44 (s, 1H), 6.69 (dd, 1H, J=15.6, 7.4), 6.75–6.80 (m, 1H), 6.82–6.89 (m, 1H), 6.95–7.08 (m, 2H), 7.52 (d, 1H, J=6.1), 8.37 (d, 1H, J=6.1), 8.48 (d, 1H, J=6.6), 9.45 (s, 1H); Anal. (C$_{35}$H$_{39}$N$_5$O$_7$F$_3$·0.30H$_2$O) C, H, N.

Example 55

Preparation of Compound 57: trans-(2'S,3''''S,4S)-4-[2'-(3''-{[1'''-(5''''-Methylisoxazol-3''''-yl)methanoyl]amino}-2'''-oxo-2'''H-pyridin-1'''-yl)pent-4''-ynoylamino]-5-(2''''-oxopyrrolidin-3''''-yl)pent-2-enoic Acid Cycloheptyl Ester.

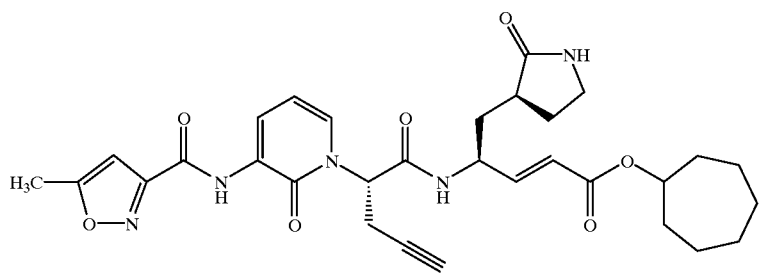

The title compound was prepared from D-propargylalanine by a process analogous to that described in Example 22 for the conversion of D-(4-fluorophenylalanine) to product R2 utilizing intermediates F2 and trans-(3'S,4S)-4-tert-butoxycarbonylamino-2-methyl-5-(2'-oxopyrrolidin-3'-yl)pent-2-enoic acid cycloheptyl ester (prepared from K1 in a manner similar to that described for the preparation of X4 in Example 27) where appropriate: $^1$H NMR (CDCl$_3$) δ 1.40–2.00 (m, 15H), 2.00 (s, 1H), 2.19–2.42 (m, 2H), 2.49 (s, 3H), 2.90–3.13 (m, 2H), 3.14–3.33 (m, 2H), 4.43–4.58 (m, 1H), 4.90–5.05 (m, 1H), 5.48 (t, 1H, J=6.6), 5.98 (d, 1H, J=15.6), 6.21 (s, 1H), 6.33 (t, 1H, J=7.3), 6.46 (s, 1H), 6.80 (dd, 1H, J=15.6, 5.4), 7.36 (d, 1H, J=6.1), 8.35–8.50 (m, 2H), 9.52 (s, 1H); Anal. (C$_{31}$H$_{37}$N$_5$O$_7$) C, H, N.

Example 56

Preparation of Compound 58: trans-(2'S,3''''S,4S)-4-[3'-(3'',4''-Difluorophenyl)-2'-(3'''-{[1''''-(5''''-methylisoxazol-3''''-yl)methanoyl]amino}-2''''-oxo-2''''H-pyridin-1''''-yl)propanoylamino]-5-(2'''''-oxopyrrolidin-3'''''-yl)pent-2-enoic Acid Cyclobutyl Ester.

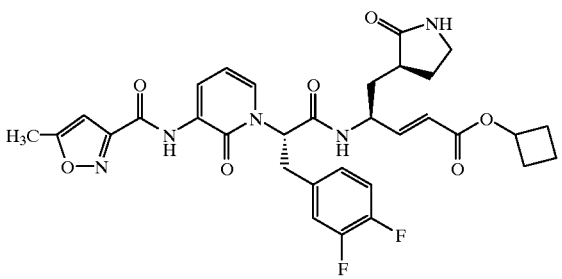

The title compound was prepared from D-(3,4)-difluorophenylalanine by a process analogous to that described in Example 22 for the conversion of D-(4-fluorophenylalanine) to product R2 utilizing intermediatesF2 and trans-(3'S,4S)-4-tert-butoxycarbonylamino-2-methyl-5-(2'-oxopyrrolidin-3'-yl)pent-2-enoic acid cyclobutyl ester (prepared from K1 in a manner similar to that described for the preparation of X4 in Example 27) where appropriate: IR (cm$^{-1}$) 3322, 1682, 1531, 1284; $^1$H NMR (CDCl$_3$) δ 1.50–1.89 (m, 5H), 2.04–2.18 (m, 3H), 2.21–2.31 (m, 2H), 2.34–2.44 (m, 2H), 2.52 (s, 3H), 3.07–3.14 (m, 1H), 3.26–3.46 (m, 3H), 4.43 (m, 1H), 5.00–5.11 (m, 1H), 5.68 (dd, 1H, J=15.9, 1.2), 5.91 (t, 1H, J=7.8), 6.33 (t, 1H, J=7.2), 6.47 (s, 1H), 6.74 (dd, 1H, J=15.6, 5.7), 6.83 (s, br. 1H), 6.89–6.92 (m, 1H), 7.05 (t, 1H, J=8.7), 7.59 (d, 1H, J=7.2), 8.41 (dd, 1H, J=7.5, 1.8), 8.61 (dd, 1H, J=6.6, 1.8), 9.49 (s, 1H); Anal. (C$_{32}$H$_{33}$F$_2$N$_5$O$_7$·H$_2$O) C, H, N.

Example 57

Preparation of Compound 59: trans-(2'S,3''''S,4S)-4-[2'-(3''-{[1'''-(5''''-Methylisoxazol-3''''-yl)methanoyl]amino}-2'''-oxo-2'''H-pyridin-1'''-yl)butanoylamino]-5-(2''''-oxopyrrolidin-3''''-yl)pent-2-enoic Acid Cyclobutyl Ester.

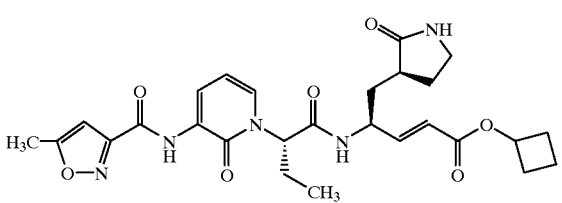

The title compound was prepared by a process analogous to that described in Example 25 for the conversion of intermediate V3 to product R3 utilizing intermediates F2 and trans-(3'S,4S)-4-tert-butoxycarbonylamino-2-methyl-5-(2'-oxopyrrolidin-3'-yl)pent-2-enoic acid cyclobutyl ester (prepared from K1 in a manner similar to that described for the preparation of X4 in Example 27) where appropriate: IR (cm$^{-1}$) 3334, 1690, 1632; $^1$H NMR (CDCl$_3$) δ 0.95 (t, 3H, J=7.5), 1.55–1.85 (m, 5H), 1.88–2.01 (m, 1H), 2.04–2.44 (m, 7H), 2.52 (s, 3H), 3.31–3.41 (m, 2H), 4.48 (m, 1H), 5.01–5.11 (m, 1H), 5.63–5.71 (m, 1H), 5.96 (dd, 1H, J=15.0, 1.5), 6.36 (t, 1H, J=7.5), 6.49 (s, 1H), 6.83–6.90 (m, 2H), 7.54 (d, 1H, J=7.2), 8.45 (dd, 1H, J=7.5, 1.8), 8.53 (dd, 1H, J=6.6, 1.8), 9.59 (s, 1H); Anal. (C$_{27}$H$_{33}$N$_5$O$_7$·0.75H$_2$O) C, H, N.

Example 58

Preparation of Compound 60: trans-(2'S,3''''S,4S)-4-[2'-(3''-{[1'''-(5''''-Methylisoxazol-3''''-yl)methanoyl]amino}-2'''oxo-2'''H-pyridin-1'''-yl)butanoylamino]-5-(2''''-oxopyrrolidin-3''''-yl)pent-2-enoic Acid Cyclohexyl Ester.

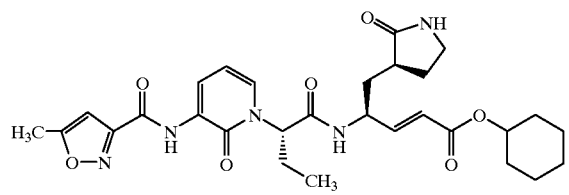

The title compound was prepared by a process analogous to that described in Example 25 for the conversion of intermediate V3 to product R3 utilizing intermediates F2 and trans-(3'S,4S)-4-tert-butoxycarbonylamino-2-methyl-5-(2'-oxopyrrolidin-3'-yl)pent-2-enoic acid cyclohexyl ester (prepared from K1 in a manner similar to that described for the preparation of X4 in Example 27) where appropriate: IR (cm$^{-1}$) 3334, 1687, 1649, 1595, 1532; $^1$H NMR (CDCl$_3$) δ 0.92 (t, 1H, J=7.4), 1.24–1.99 (m, 14H), 2.06–2.30 (m, 3H), 2.49 (s, 3H), 3.28–3.39 (m, 2H), 4.45–4.47 (m, 1H), 4.77–4.84 (m, 1H), 5.65–5.70 (m, 1H), 5.95 (dd, 1H, J=15.7, 1.1), 6.34 (t, 1H, J=7.3), 6.46 (s, 1H), 6.83 (dd, 1H, J=15.7, 5.8), 6.93 (br s, 1H), 7.54 (dd, 1H, J=7.3, 1.7), 8.42 (dd, 1H, J=7.3, 1.7), 8.49 (d, 1H, J=6.8), 9.57 (s, 1H); Anal. (C$_{29}$H$_{37}$N$_5$O$_7$·0.50H$_2$O) C, H, N.

Example 59

Preparation of Compound 61: trans-(2'S,3''''S,4S)-4-[2'-(3''-{[1'''-(5''''-Methylisoxazol-3''''-yl)methanoyl]amino}-2'''oxo-2'''H-pyridin-1'''-yl)butanoylamino]-5-(2''''-oxopyrrolidin-3''''-yl)pent-2-enoic Acid Cycloheptyl Ester.

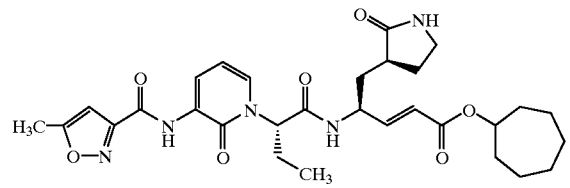

The title compound was prepared by a process analogous to that described in Example 25 for the conversion of intermediate V3 to product R3 utilizing intermediates F2 and trans-(3'S,4S)-4-tert-butoxycarbonylamino-2-methyl-5-(2'-oxopyrrolidin-3'-yl)pent-2-enoic acid cycloheptyl ester (prepared from K1 in a manner similar to that described for the preparation of X4 in Example 27) where appropriate: $^1$H NMR (CDCl$_3$) δ 0.85–2.35 (m, 22H), 2.49 (s, 3H), 3.23–3.38 (m, 2H), 4.46–4.57 (m, 1H), 4.93–5.03 (m, 1H), 5.44–5.52 (m, 1H), 5.93 (dd, 1H, J=15.6, 1.2), 6.12 (s, br, 1H), 6.32 (t, 1H, J=7.2), 6.46 (s, 1H), 6.80 (dd, 1H, J=15.7, 5.7), 7.35 (dd, 1H, J=7.2, 1.7), 8.15 (d, 1H, J=6.8), 8.41 (dd, 1H, J=7.4, 1.6), 9.58 (s, 1H); Anal. (C$_{30}$H$_{39}$N$_5$O$_7$·0.80H$_2$O) C, H, N.

Example 60

Preparation of Compound 62: trans-(2'S,3''''S,4S)-4-[2'-(3''-{[1'''-(5''''-Methylisoxazol-3''''-yl)methanoyl]amino}-2'''oxo-2'''H-pyridin-1'''-yl)butanoylamino]-5-(2''''-oxopyrrolidin-3''''-yl)pent-2-enoic Acid Benzyl Ester.

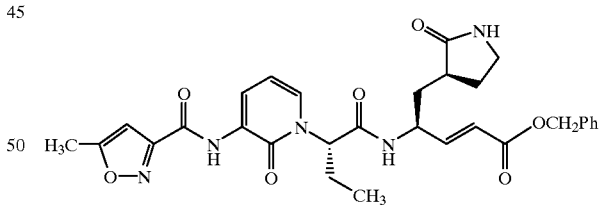

The title compound was prepared by a process analogous to that described in Example 25 for the conversion of intermediate V3 to product R3 utilizing intermediates F2 and trans-(3'S,4S)-4-tert-butoxycarbonylamino-2-methyl-5-(2'-oxopyrrolidin-3'-yl)pent-2-enoic acid benzyl ester (prepared from K1 in a manner similar to that described for the preparation of X4 in Example 27) where appropriate: IR (cm$^{-1}$) 3335, 1685, 1649, 1595, 1533; $^1$H NMR (CDCl$_3$) δ 0.91 (t, 3H, J=7.2), 1.50–1.99 (m, 3H), 2.11–2.31 (m, 4H), 2.48 (s, 3H), 3.27–3.38 (m, 2H), 4.45–4.47 (m, 1H), 5.17 (s, 2H), 5.65–5.70 (m, 1H), 6.01 (dd, 1H, J=15.6, 1.5), 6.33 (t, 1H, J=7.1), 6.46 (s, 1H), 6.90 (dd, 1H, J=15.6, 5.8), 7.00 (br s, 1H), 7.30–7.39 (m, 5H), 7.54 (dd, 1H, J=7.1, 1.8), 8.42 (dd, 1H, J=7.4, 1.8), 8.56 (d, 1H, J=6.8), 9.56 (s, 1H); Anal. ($C_{30}H_{33}N_5O_7 \cdot 0.50H_2O$) C, H, N.

Example 61

Preparation of Compound 63: trans-(2'S,3'''''S,4S)-4-[2'-(3''-{[1'''-(5''''-Methylisoxazol-3''''-yl)methanoyl]amino}-2'''-oxo-2'''H-pyridin-1'''-yl)pent-4''-ynoylamino]-5-(2'''''-oxopyrrolidin-3'''''-yl)pent-2-enoic Acid Benzyl Ester

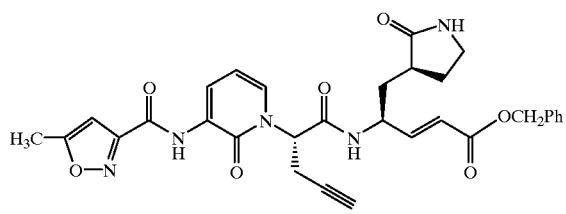

δ 1.55–1.74 (m, 2H), 1.97 (t, 1H, J=2.7), 2.01–2.19 (m, 1H), 2.22–2.39 (m, 2H), 2.49 (s, 3H), 2.88–3.07 (m, 2H), 3.19–3.32 (m, 2H), 4.44–4.52 (m, 1H), 5.16 (s, 2H), 5.55–5.60 (m, 1H), 6.07 (dd, 1H, J=15.7, 1.5), 6.32 (t, 1H, J=7.2), 6.45 (s, 1H), 6.48 (br s, 1H), 6.89 (dd, 1H, J=15.7, 5.3), 7.29–7.41 (m, 5H), 7.44 (dd, 1H, J=6.2, 1.7), 8.40 (dd, 1H, J=7.5, 1.7), 8.61 (d, 1H, J=6.6), 9.52 (s, 1H); Anal. ($C_{31}H_{31}N_5O_7 \cdot 0.50H_2O$) C, H, N.

Example 62

Preparation of Compounds 64 and 65: trans-(2'S,3'''''S,4S)-4-[2'-(3''-{[1'''-(5''''-Methylisoxazol-3''''-yl)methanoyl]amino}-2'''-oxo-2'''H-pyridin-1'''-yl)pent-4''-ynoylamino]-5-(2'''''-oxopyrrolidin-3'''''-yl)pent-2-enoic Acid Pyridin-2-ylmethyl Ester and trans-(2'R,3'''''S,4S)-4-[2'-(3''-{[1'''-(5''''-Methylisoxazol-3''''-yl)methanoyl]amino}-2'''-oxo-2'''H-pyridin-1'''-yl)pent-4''-ynoylamino]-5-(2'''''-oxopyrrolidin-3'''''-yl)pent-2-enoic Acid Pyridin-2-ylmethyl Ester.

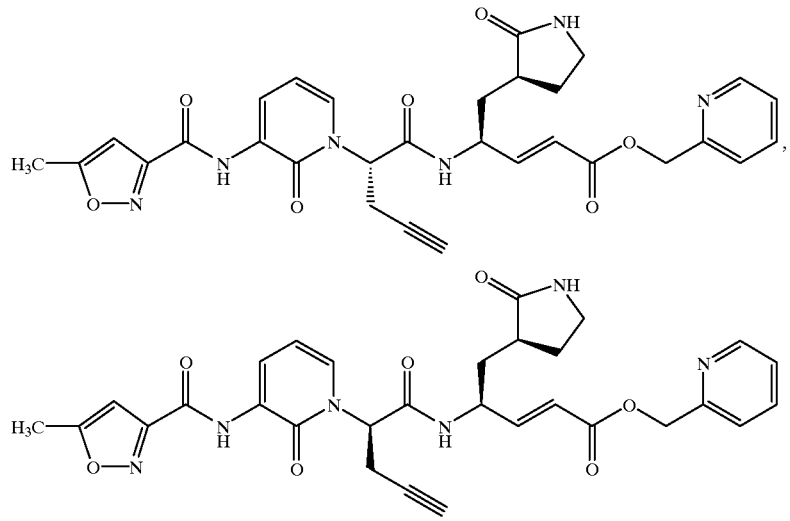

The title compound was prepared from D-propargylalanine by a process analogous to that described in Example 22 for the conversion of D-(4-fluorophenylalanine) to product R2 utilizing intermediates F2 and trans-(3'S,4S)-4-tert-butoxycarbonylamino-2-methyl-5-(2'-oxopyrrolidin-3'-yl)pent-2-enoic acid benzyl ester (prepared from K1 in a manner similar to that described for the preparation of X4 in Example 27) where appropriate: IR (cm$^{-1}$) 3298, 1685, 1650, 1596, 1534; $^1$H NMR (CDCl$_3$)

The title compounds were prepared from D-propargylalanine by a process analogous to that described in Example 22 for the conversion of D-(4-fluorophenylalanine) to product R2 utilizing intermediates F2 and trans-(3'S,4S)-4-tert-butoxycarbonylamino-2-methyl-5-(2'-oxopyrrolidin-3'-yl)pent-2-enoic acid pyridin-2-ylmethyl ester (prepared from K1 in a manner similar to that described for the preparation of X4 in Example 27) where appropriate. They were isolated as a 2:1 mixture of inseparable diasteroemers: IR (cm$^{-1}$) 3297, 1690, 1596, 1273; $^1$H NMR (CDCl$_3$) δ 1.58–1.69 (m), 2.02–2.08 (m), 2.09–2.48 (m), 2.53 (s), 2.81–3.12 (m), 3.24–3.49 (m), 5.26 (s), 5.31 (s), 5.52 (t, J=7.5), 5.82 (t, J=7.5), 5.92 (d, J=15.6), 6.15 (d, J=15.6), 6.36 (t, J=7.2), 6.46 (s), 6.53 (s), 6.87–6.70 (m), 7.24–7.43 (m), 7.68–7.76 (m), 8.43–8.50 (m), 8.61–8.69 (m), 9.56 (s), 9.61 (s); Anal. (C$_{30}$H$_{30}$N$_6$O$_7$·0.5H$_2$O) C, H, N.

Example 63

Preparation of Compound 66: trans-(2'S,3''''S,4S)-4-[2'-(3''-{[1'''-(5''''-Methylisoxazol-3''''-yl)methanoyl]amino}-2''-oxo-2'''H-pyridin-1''-yl)-3''-phenylpropanoylamino]-5-(2'''''-oxopyrrolidin-3'''''-yl)pent-2-enoic Acid Isopropyl Ester.

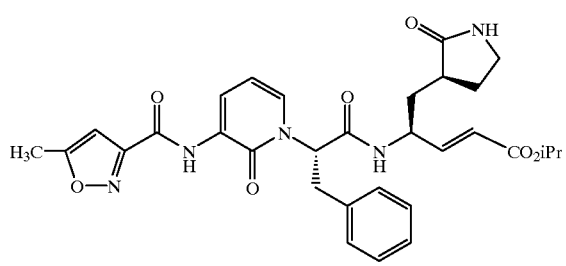

The title compound was prepared from (2R)-2-hydroxy-3-phenylpropionic acid by a process analogous to that described in Example 22 for the conversion of intermediate S1 to product R2 utilizing intermediates F2 and trans-(3'S,4S)-4-tert-butoxycarbonylamino-2-methyl-5-(2'-oxopyrrolidin-3'-yl)pent-2-enoic acid isopropyl ester (prepared from K1 in a manner similar to that described for the preparation of X4 in Example 27) where appropriate: $^1$H NMR (CDCl$_3$) δ 1.27 (d, 3H, J=6.2), 1.28 (d, 3H, J-=6.2), 1.44–1.54 (m, 1H), 1.61–1.75 (m, 1H), 2.09–2.33 (m, 3H), 2.47 (d, 3H, J=0.9), 3.13 (dd, 1H, J=13.7, 8.2), 3.20–3.38 (m, 2H), 3.44 (dd, 1H, J=13.7, 7.7), 4.37–4.48 (m, 1H), 4.99–5.12 (m, 1H), 5.71 (dd, 1H, J=15.6, 1.4), 5.96–6.04 (m, 1H), 6.29 (t, 1H, J=7.3), 6.43–6.45 (m, 1H), 6.69 (dd, 1H, J=15.6, 5.7), 7.19–7.28 (m, 6H), 7.65–7.69 (m, 1H), 8.36 (dd, 1H, J=7.3, 1.6), 8.49 (d, 1H, J=6.8), 9.45 (s, 1H).

Example 64

Preparation of Compound 67: trans-(2'S,3''''''S)-4-[3'-(4''-Fluorophenyl)-2'-(3'''-{[1''''-(5'''''-methylisoxazol-3'''''-yl)methanoyl]amino}-2''''-oxo-2''''H-pyridin-1''''-yl)propanoylamino]-5-(2''''''-oxopyrrolidin-3''''''-yl)pent-2-enoic Acid Isopropyl Ester.

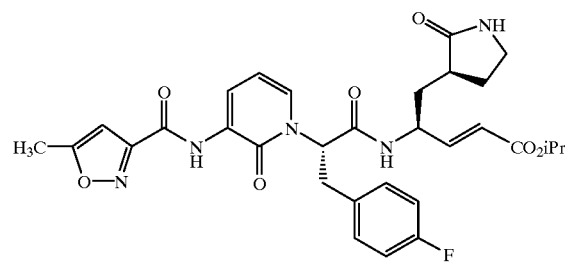

The title compound was prepared from intermediate T1 by a process analogous to that described in Example 22 for the conversion of T1 to product R2 utilizing intermediates F2 and trans-(3'S,4S)-4-tert-butoxycarbonylamino-2-methyl-5-(2'-oxopyrrolidin-3'-yl)pent-2-enoic acid isopropyl ester (prepared from K1 in a manner similar to that described for the preparation of X4 in Example 27) where appropriate: IR (cm$^{-1}$) 3335, 1693, 1649, 1596, 1533; $^1$H NMR (CDCl$_3$) δ 1.27 (d, 3H, J=2.6), 1.29 (d, 3H, J=2.6), 1.59–1.78 (m, 2H), 1.81–1.99 (m, 1H), 2.20–2.29 (m, 1H), 2.47 (s, 3H), 3.13–3.29 (m, 3H), 3.42–3.49 (m, 1H), 4.50–4.52 (m, 1H), 5.02–5.09 (m, 1H), 5.67–5.75 (m, 2H), 6.24 (t, 1H, J=7.3), 6.41 (s, 1H), 6.67–6.74 (m, 2H), 6.92 (t, 2H, J=8.5), 7.10–7.14 (m, 2H), 7.41 (d, 1H, J=7.3), 8.15 (br s, 1H), 8.33 (d, 1H, J=7.7), 9.32 (s, 1H).

Example 65

Preparation of Compound 68: trans-(2'S,3''''S,4S)-4-[2'-({[1''-(5'''-Methylisoxazol-3'''-yl)methanoyl]amino}-oxotrifluoromethyl-2''H-pyridin-1''-yl)butanoylamino]-5-(2''''-oxopyrrolidin-3''''-yl)pent-2-enoic Acid Ethyl Ester.

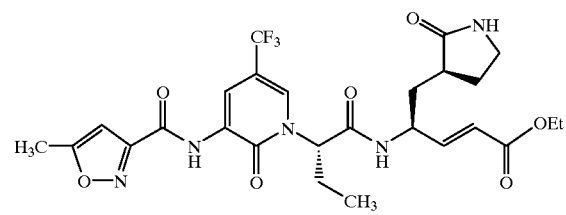

The title compound was prepared from intermediate T3 and by a process analogous to that described in Example 22 for the conversion of D-(4-fluorophenylalanine) to product R2 utilizing nitrotrifluoromethylpyridin-2-ol and intermediate X2 where appropriate: $^1$H NMR (CDCl$_3$) δ 0.93 (t, 3H, J=7.7), 1.28 (t, 3H, J=7.2), 1.60–2.33 (m, 7H), 2.45 (s, 3H), 3.20–3.38 (m, 2H), 4.18 (q, 2H, J=7.0), 4.42–4.53 (m, 1H), 5.68 (t, 1H, J=7.9), 5.98 (d, 1H, J=16.0), 6.40 (s, 1H), 6.60 (s, 1H), 6.84 (dd, 1H, J=16.0, 5.8), 7.92 (s, 1H), 8.50 (d, 1H, J=2.3), 8.86 (d, 1H, J=5.7), 9.39 (s, 1H); Anal. (C$_{26}$H$_{30}$N$_5$O$_7$F$_3$·1.70H$_2$O) C, H, N.

Results of tests conducted using exemplary compounds of the invention are described below.

BIOCHEMICAL AND BIOLOGICAL EVALUATION

Inhibition of Rhinovirus 3C Protease:

Stock solutions (50 mM, in DMSO) of various compounds were prepared; dilutions were in the same solvent. Recombinant rhinovirus 3C proteases (see Birch et al., "Purification of recombinant human rhinovirus 14 3C protease expressed in *Escherichia coli*," *Protein Expr. Pur.* (1995), vol. 6(5), 609–618) from serotypes 14, 16, and 2 were prepared by the following standard chromatographic procedures: (1) ion exchange using Q Sepharose Fast Flow from Pharmacia; (2) affinity chromatography using Affi-Gel Blue from Biorad; and (3) sizing using Sephadex G-100 from Pharmacia. Each assay sample contained 2% DMSO, 50 mM tris pH 7.6, 1 mM EDTA, a test compound at the indicated concentration, approximately 1 $\mu$M substrate, and 50–100 nM protease. The $k_{obs/I}$ values were obtained from reactions initiated by addition of enzyme rather than substrate. RVP activity was measured in the fluorescence resonance energy transfer assay. The substrate was (N-terminal) DABCYL-(Gly-Arg-Ala-Val-Phe-Gln-Gly-Pro-Val-Gly)-EDANS. In the uncleaved peptide, the EDANS fluorescence was quenched by the proximal DABCYL moiety. When the peptide was cleaved, the quenching was relieved, and activity was measured as an increase in fluorescence signal. Data were analyzed using standard non-linear fitting programs (Enzfit), and are shown in the table below. The tabulated data in the column designated $k_{obs}/[I]$ were measured from progress curves in enzyme start experiments.

Antirhinoviral H1-HeLa Cell Culture Assay:

In this cell protection assay, the ability of compounds to protect cells against HRV infection was measured by the XTT dye reduction method, which is described in Weislow et al., *J. Natl. Cancer Inst.* (1989), vol. 81, 577–586. H1-HeLa cells were infected with HRV-14 at a multiplicity of infection (m.o.i.) of 0.13 (virus particles/cell) or mock-infected with medium only. Infected or mock-infected cells were resuspended at 8×10$^5$ cells per mL, and incubated with appropriate concentrations of the compounds to be tested. Two days later, XTT/PMS was added to test plates and the amount of formazan produced was quantified spectrophotometrically at 450/650 nm. The EC$_{50}$ value was calculated as the concentration of compound that increased the percentage of formazan production in compound-treated, virus-infected cells to 50% of that produced by compound-free, mock-infected cells. The 50% cytotoxic dose (CC$_{50}$) was calculated as the concentration of compound that decreased the percentage of formazan produced in compound-treated, mock-infected cells to 50% of that produced by compound-free, mock-infected cells. The therapeutic index (TI) was calculated by dividing the CC$_{50}$ value by the EC$_{50}$ value.

All strains of human rhinovirus (HRV) for use in this assay were purchased from American Type Culture Collection (ATCC), except for HRV serotype-14 (produced from the infectious cDNA clone constructed by Dr. Robert Rueckert, Institute for Molecular Virology, University of Wisconsin, Madison, Wis.). HRV stocks were propagated and viral assays were performed in H1-HeLa cells (ATCC). Cells were grown in minimal essential medium with 10% fetal bovine serum, available from Life Technologies (Gaithersburg, Md.). Test results for the HRV assay are shown in the table below.

Anticoxsackieviral Cell Culture Assay:

Coxsackievirus types A-21 (CAV-21) and B3 (CVB3) were purchased from American Type Culture Collection (ATCC, Rockville, Md.). Virus stocks were propagated and antiviral assays were performed in H1-HeLa cells (ATCC). Cells were grown in minimal essential medium with 10% fetal bovine serum (Life Technologies, Gaithersburg, Md.). The ability of the compounds of this invention to protect cells against either CAV-21 or CVB3 infection was measured by the XTT dye reduction method. This method is described in Weislow et al., *J. Natl. Cancer Inst.* (1989), vol. 81, 577–586. H1-HeLa cells were infected with CAV-21 or CVB3 at a multiplicity of infection (m.o.i.) of 0.025 or 0.075, respectively, or mock-infected with medium only. H1-HeLa cells were plated at 4×10$^4$ cells per well in a 96-well plate and incubated with appropriate concentrations of the test compound. One day (CVB3) or two days (CAV-21) later, XTT/PMS was added to test plates and the amount of formazan produced was quantified spectrophotometrically at 450/650 nm. The EC$_{50}$ was calculated as the concentration of compound that increased the formazan production in compound-treated, virus-infected cells to 50% of that produced by compound-free, uninfected cells. The 50% cytotoxic dose (CC$_{50}$) was calculated as the concentration of compound that decreased formazan production in compound-treated, uninfected cells to 50% of that produced in compound-free, uninfected cells. The therapeutic index (TI) was calculated by dividing the CC$_{50}$ by the EC$_{50}$.

Anti-Echoviral and Anti-Enteroviral Cell Culture Assays

Echovirus type 11 (ECHO 11) was purchased from ATCC (Rockville, Md.). Virus stocks were propagated and antiviral assays were performed in MRC-5 cells (ATCC). Cells were grown in minimal essential medium with 10% fetal bovine serum (Life Technologies, Gaithersburg, Md.). The ability of the compounds of this invention to protect cells against ECHO 11 infection was measured by the XTT dye reduction method (Weislow et al., *J. Natl. Cancer Inst.* (1989), vol. 81, 577–586). MRC-5 cells were infected with ECHO 11 at an m.o.i. of 0.003 or 0.004, respectively, or mock-infected with medium only. Infected or uninfected cells were added at 1×10$^4$ cells per well and incubated with appropriate concentrations of compound. Four days later, XTT/PMS was added to test plates, and the amount of formazan produced was quantified spectrophotometrically at 450/650 nm. The EC$_{50}$ was calculated as the concentration of compound that increased the formazan production in compound-treated, virus-infected cells to 50% of that produced by compound-free, uninfected cells. The 50% cytotoxic dose (CC$_{50}$) was calculated as the concentration of compound that decreased formazan production in compound-treated, uninfected cells to 50% of that produced in compound-free, uninfected cells. The therapeutic index (TI) was calculated by dividing the CC$_{50}$ by the EC$_{50}$. Activity of the compounds against enterovirus type 70 (EV 70) may be measured by the same assay as described above in this section. Enterovirus type 70 (EV 70) may be obtained from the American Type Culture Collection ATCC (Rockville, Md.).

Results obtained for the compounds of the invention may be compared to results obtained in the same manner for control compounds WIN 51711, WIN 52084, and WIN 54954 (obtained from Sterling-Winthrop Pharmaceuticals), Pirodavir (obtained from Janssen Pharmaceuticals), and Pleconaril (prepared according to the method described in Diana et al., *J. Med. Chem.* (1995), vol. 38, 1355). Antiviral data obtained for the test compounds are shown in the table below. The designation "ND" indicates that a value was not determined for that compound, and the designation "NA" means not applicable.

TABLE

| Compd.* | Virus Serotype | $k_{obs}/[I]$ $(M^{-1}s^{-1})^b$ | $EC_{50}(\mu M)$ | $CC_{50}(\mu M)$ | TI |
|---|---|---|---|---|---|
| 1 + 2 (1:1) | HRV-14[a] | 36,900 | 0.179 | 50.1 | 280 |
|  | HRV-1A | ND | 0.825 | 74.1 | 90 |
|  | HRV-10 | ND | 0.145 | 60.3 | 416 |
| 1 | HRV-14 | 114,000 | 0.033 | 50.1 | 1518 |
|  | CAV-21[c] | ND | 1.48 | >10 | >7 |
|  | ECHO-11[d] | ND | 0.16 | >10 | >63 |
|  | CVB3[e] | ND | 0.539 | >10 | >19 |
|  | ENT-70[f] | ND | 0.012 | >10 | >833 |
| 3 | HRV-14 | 2,900 | 1.27 | >10 | >8 |
| 4 | HRV-14 | 574 | ND | ND | ND |
| 5 | HRV-14 | 329,000 | 0.016 | >10 | >625 |
|  | CAV-21 | ND | 1.39 | >10 | >7 |
|  | ECHO-11 | ND | 0.054 | >10 | >185 |
|  | CVB3 | ND | 0.577 | >10 | >17 |
|  | ENT-70 | ND | 0.018 | >10 | >556 |
| 6 | HRV-14 | 37,400 | 0.034 | >10 | >294 |
|  | CAV-21 | ND | 4.68 | >10 | >2 |
|  | ECHO-11 | ND | 0.346 | >10 | >29 |
|  | CVB3 | ND | 2.50 | >10 | >4 |
|  | ENT-70 | ND | 0.061 | >10 | >164 |
| 7 | HRV-14 | 81,000 | 0.014 | >10 | >714 |
| 8 | HRV-14 | 7,660 | 0.888 | >10 | >11 |
| 9 | HRV-14 | 5,040 | 0.518 | >10 | >19 |
| 10 | HRV-14 | 113,300 | 0.104 | >10 | >96 |
|  | HRV-1A | ND | 1.182 | >10 | >9 |
|  | HRV-10 | ND | 1.406 | >10 | >7 |
| 11 | HRV-14 | 193,000 | <0.0032 | >10 | >3125 |
| 12 | HRV-14 | 25,800 | 0.075 | >10 | >133 |
| 13 + 14 (1:1) | HRV-14 | 31,000 | ND | ND | ND |
| 15 | HRV-14 | 6,500 | 0.178 | >10 | >56 |
| 16 | HRV-14 | 74,000 | 0.325 | >10 | >31 |
| 17 | HRV-14 | 348 | >10 | >10 | ND |
| 18 | HRV-14 | 116,000 | 0.125 | >10 | >80 |
| 19 | HRV-14 | 380,000 | 0.003 | >10 | >333 |
| 20 | HRV-14 | 600,000 | 0.015 | >10 | >667 |
| 21 | HRV-14 | 6,340 | 0.469 | >10 | >21 |
| 22 | HRV-14 | 18,500 | 1.0 | >10 | >10 |
| 23 | HRV-14 | 385,000 | 0.064 | >10 | >156 |
| 24 | HRV-14 | 8,800 | ND | ND | ND |
| 25 | HRV-14 | 1,250,000 | 0.002 | >10 | >5000 |
|  | HRV-1A | ND | 0.015 | >10 | >667 |
|  | HRV-10 | ND | 0.004 | >10 | >2500 |
|  | HRV-2 | ND | 0.004 | >10 | >2500 |
|  | HRV-16 | ND | 0.005 | >10 | >2000 |
|  | HRV-3 | ND | 0.004 | >10 | >2500 |
|  | HRV-25 | ND | 0.022 | >10 | >454 |
|  | HRV-9 | ND | 0.01 | >10 | >1000 |
|  | HRV-39 | ND | 0.009 | >10 | >1111 |
|  | HRV-87 | ND | 0.008 | >10 | >1250 |
| 26 | HRV-14 | 170,000 | 0.055 | >10 | >182 |
|  | HRV-1A | ND | 0.014 | >10 | >714 |
|  | HRV-10 | ND | 0.027 | >10 | >370 |
|  | HRV-2 | ND | 0.016 | >10 | >625 |
|  | HRV-16 | ND | 0.050 | >10 | >200 |
|  | HRV-3 | ND | 0.029 | >10 | >344 |
|  | HRV-25 | ND | 0.102 | >10 | >98 |
|  | HRV-9 | ND | 0.045 | >10 | >222 |
|  | HRV-39 | ND | 0.047 | >10 | >212 |
|  | HRV-87 | ND | 0.021 | >10 | >476 |
|  | HRV-13 | ND | 0.058 | >10 | >172 |
|  | HRV-78 | ND | 0.057 | >10 | >175 |
|  | HRV-11 | ND | 0.004 | >10 | >2500 |
|  | HRV-19 | ND | 0.065 | >10 | >153 |
|  | HRV-23 | ND | 0.040 | >10 | >250 |
|  | HRV-Hanks | ND | 0.054 | >10 | >185 |
|  | CAV-21 | ND | 0.121 | >10 | >82 |
|  | ECHO-11 | ND | 0.036 | >10 | >277 |
|  | CVB3 | ND | 0.016 | >10 | >625 |
|  | CVB2[g] | ND | 0.055 | >10 | >181 |
|  | CVB5[h] | ND | 0.018 | >10 | >555 |
|  | ECHO-6[i] | ND | 0.017 | >10 | >588 |
|  | ECHO-9[j] | ND | 0.015 | >10 | >666 |
| 27 + 28 (1:1) | HRV-14 | 3,750 | 1.78 | >10 | >7 |
| 29 | HRV-14 | 148,000 | 0.079 | >10 | >126 |
|  | HRV-1A | ND | 0.046 | >10 | >217 |
|  | HRV-10 | ND | 0.046 | >10 | >217 |
| 30 | HRV-14 | 133,500 | 0.024 | >10 | >416 |
| 31 | HRV-14 | 223,400 | 0.022 | >10 | >454 |
|  | HRV-1A | ND | 0.036 | >10 | >277 |
|  | HRV-10 | ND | 0.048 | >10 | >208 |
|  | HRV-2 | ND | 0.013 | >10 | >769 |
|  | HRV-16 | ND | 0.038 | >10 | >263 |
|  | HRV-3 | ND | 0.021 | >10 | >476 |
|  | HRV-25 | ND | 0.087 | >10 | >114 |
|  | HRV-9 | ND | 0.044 | >10 | >227 |
|  | HRV-39 | ND | 0.043 | >10 | >232 |
|  | HRV-87 | ND | 0.021 | >10 | >476 |
|  | HRV-13 | ND | 0.060 | >10 | >166 |
|  | HRV-78 | ND | 0.061 | >10 | >163 |
|  | HRV-11 | ND | 0.005 | >10 | >2000 |
|  | HRV-19 | ND | 0.050 | >10 | >200 |
|  | HRV-23 | ND | 0.042 | >10 | >238 |
|  | HRV-Hanks | ND | 0.049 | >10 | >204 |
|  | CAV-21 | ND | 0.161 | >10 | >62 |
|  | ECHO-11 | ND | 0.013 | >10 | >769 |
|  | CVB3 | ND | 0.024 | >10 | >416 |
|  | CVB2 | ND | 0.057 | >10 | >175 |
|  | CVB5 | ND | 0.047 | >10 | >212 |
|  | ECHO-6 | ND | 0.021 | >10 | >476 |
|  | ECHO-9 | ND | 0.012 | >10 | >833 |
| 32 | HRV-14 | 127,500 | 0.126 | >10 | >79 |
|  | HRV-1A | ND | 0.179 | >10 | >55 |
|  | HRV-10 | ND | 0.156 | >10 | >64 |
|  | HRV-2 | ND | 0.105 | >10 | >95 |
|  | HRV-16 | ND | 0.184 | >10 | >54 |
|  | HRV-3 | ND | 0.059 | >10 | >169 |
|  | HRV-25 | ND | 0.547 | >10 | >18 |
|  | HRV-9 | ND | 0.500 | >10 | >20 |
|  | HRV-39 | ND | 0.410 | >10 | >24 |
|  | HRV-87 | ND | 0.033 | >10 | >303 |
| 33 | HRV-14 | 1,800,000 | 0.001 | >10 | >10000 |
|  | HRV-2 | ND | 0.003 | >10 | >3333 |
|  | HRV-16 | ND | 0.006 | >10 | >1666 |
|  | HRV-3 | ND | 0.003 | >10 | >3333 |
|  | HRV-25 | ND | 0.028 | >10 | >357 |
|  | HRV-9 | ND | 0.015 | >10 | >666 |
|  | HRV-39 | ND | 0.004 | >10 | >2500 |
|  | HRV-87 | ND | 0.005 | >10 | >2000 |
|  | HRV-13 | ND | 0.014 | >10 | >714 |
|  | HRV-78 | ND | 0.005 | >10 | >2000 |
|  | HRV-11 | ND | 0.003 | >10 | >3333 |
|  | HRV-19 | ND | 0.004 | >10 | >2500 |
|  | HRV-23 | ND | 0.003 | >10 | >3333 |
|  | HRV-Hanks | ND | 0.005 | >10 | >2000 |
|  | CAV-21 | ND | 0.004 | >10 | >2500 |
|  | ECHO-11 | ND | 0.016 | >10 | >625 |
|  | CVB3 | ND | 0.003 | >10 | >3333 |
|  | CVB2 | ND | 0.015 | >10 | >666 |
|  | CVB5 | ND | 0.025 | >10 | >400 |
|  | ECHO-6 | ND | 0.015 | >10 | >666 |
|  | ECHO-9 | ND | 0.003 | >10 | >3333 |
| 34 | HRV-14 | 45,100 | 0.122 | >10 | >81 |
|  | HRV-2 | ND | 0.154 | >10 | >64 |
|  | HRV-16 | ND | 0.543 | >10 | >18 |
|  | HRV-3 | ND | 0.061 | >10 | >163 |
|  | HRV-25 | ND | 0.923 | >10 | >10 |
|  | HRV-9 | ND | 0.593 | >10 | >16 |
|  | HRV-39 | ND | 0.441 | >10 | >22 |
|  | HRV-87 | ND | 0.033 | >10 | >303 |
| 35 | HRV-14 | 220 | >10 | >10 | NA |
| 36 | HRV-14 | 4,540 | 9.0 | >100 | >11 |
| 37 | HRV-14 | 177,000 | 0.162 | >10 | >62 |
|  | HRV-1A | ND | 0.108 | >10 | >93 |

| Compd.* | Virus Serotype | $k_{obs}/[I]$ $(M^{-1}s^{-1})^b$ | $EC_{50}(\mu M)$ | $CC_{50}(\mu M)$ | TI |
|---|---|---|---|---|---|
|  | HRV-10 | ND | 0.041 | >10 | >244 |
|  | HRV-2 | ND | 0.037 | >10 | >270 |
|  | HRV-16 | ND | 0.072 | >10 | >138 |
|  | HRV-3 | ND | 0.043 | >10 | >232 |
|  | HRV-25 | ND | 0.162 | >10 | >61 |
|  | HRV-9 | ND | 0.121 | >10 | >82 |
|  | HRV-39 | ND | 0.016 | >10 | >625 |
|  | HRV-87 | ND | 0.058 | >10 | >172 |
| 38 | HRV-14 | 0.08$^k$ | 16.8 | >100 | >6 |
| 39 | HRV-14 | 200,000 | 0.040 | >10 | >250 |
|  | HRV-1A | ND | 0.042 | >10 | >238 |
|  | HRV-10 | ND | 0.088 | >10 | >113 |
|  | HRV-2 | ND | 0.016 | >10 | >625 |
|  | HRV-16 | ND | 0.057 | >10 | >175 |
|  | HRV-3 | ND | 0.039 | >10 | >256 |
|  | HRV-25 | ND | 0.107 | >10 | >93 |
|  | HRV-9 | ND | 0.048 | >10 | >208 |
|  | HRV-39 | ND | 0.048 | >10 | >208 |
|  | HRV-87 | ND | 0.017 | >10 | >588 |
| 40 | HRV-14 | 186,000 | 0.027 | >10 | >370 |
|  | HRV-2 | ND | 0.052 | >10 | >192 |
|  | HRV-16 | ND | 0.177 | >10 | >56 |
|  | HRV-3 | ND | 0.056 | >10 | >178 |
|  | HRV-25 | ND | 0.490 | >10 | >20 |
|  | HRV-9 | ND | 0.219 | >10 | >46 |
|  | HRV-39 | ND | 0.163 | >10 | >61 |
|  | HRV-87 | ND | 0.083 | >10 | >120 |
|  | HRV-13 | ND | 0.148 | >10 | >67 |
|  | HRV-78 | ND | 0.123 | >10 | >81 |
|  | HRV-11 | ND | 0.006 | >10 | >1666 |
|  | HRV-19 | ND | 0.060 | >10 | >166 |
|  | HRV-23 | ND | 0.055 | >10 | >181 |
|  | HRV-Hanks | ND | 0.115 | >10 | >86 |
| 41 | HRV-14 | 60,500 | 0.062 | >10 | >161 |
|  | HRV-2 | ND | 0.155 | >10 | >64 |
|  | HRV-16 | ND | 0.416 | >10 | >24 |
|  | HRV-3 | ND | 0.054 | >10 | >185 |
|  | HRV-25 | ND | 0.829 | >10 | >12 |
|  | HRV-9 | ND | 0.562 | >10 | >17 |
|  | HRV-39 | ND | 0.445 | >10 | >22 |
|  | HRV-87 | ND | 0.060 | >10 | >166 |
|  | CAV-21 | ND | 0.593 | >10 | >16 |
|  | ECHO-11 | ND | 0.186 | >10 | >53 |
|  | CVB3 | ND | 0.117 | >10 | >85 |
|  | CVB2 | ND | 0.213 | >10 | >46 |
|  | CVB5 | ND | 0.199 | >10 | >50 |
|  | ECHO-6 | ND | 0.147 | >10 | >68 |
|  | ECHO-9 | ND | 0.106 | >10 | >94 |
| 42 | HRV-14 | 38,200 | 0.168 | >10 | >59 |
|  | HRV-2 | ND | 0.161 | >10 | >62 |
|  | HRV-16 | ND | 0.402 | >10 | >24 |
|  | HRV-3 | ND | 0.152 | >10 | >65 |
|  | HRV-25 | ND | 0.611 | >10 | >16 |
|  | HRV-9 | ND | 0.521 | >10 | >19 |
|  | HRV-39 | ND | 0.158 | >10 | >63 |
| 43 | HRV-14 | 382 | >10 | >10 | NA |
| 44 | HRV-14 | 12,500 | 1.46 | >10 | >6 |
|  | HRV-2 | ND | 1.18 | >10 | >8 |
|  | HRV-10 | ND | 0.562 | >10 | >17 |
|  | HRV-16 | ND | 1.09 | >10 | >9 |
|  | HRV-25 | ND | 1.22 | >10 | >8 |
|  | HRV-39 | ND | >1 | >10 | ND |
| 45 | HRV-14 | 673 | ND | ND | ND |
| 46 | HRV-14 | 350,000 | 0.006 | >10 | >1666 |
|  | HRV-1A | ND | 0.182 | >10 | >54 |
|  | HRV-2 | ND | 0.145 | >10 | >68 |
|  | HRV-3 | ND | 0.045 | >10 | >222 |
|  | HRV-9 | ND | 0.151 | >10 | >66 |
|  | HRV-10 | ND | 0.135 | >10 | >74 |
|  | HRV-16 | ND | 0.160 | >10 | >62 |
|  | HRV-25 | ND | 0.188 | >10 | >53 |
|  | HRV-39 | ND | 0.227 | >10 | >44 |
|  | HRV-13 | ND | 0.078 | >10 | >128 |
|  | HRV-78 | ND | 0.025 | >10 | >400 |
|  | HRV-11 | ND | 0.003 | >10 | >3333 |
|  | HRV-19 | ND | 0.020 | >10 | >500 |
|  | HRV-23 | ND | 0.011 | >10 | >909 |
|  | HRV-Hanks | ND | 0.005 | >10 | >2000 |
| 47 | HRV-14 | 1,400,000 | 0.040 | >10 | >250 |
|  | HRV-1A | ND | 0.148 | >10 | >67 |
|  | HRV-2 | ND | 0.133 | >10 | >75 |
|  | HRV-3 | ND | 0.018 | >10 | >555 |
|  | HRV-9 | ND | 0.121 | >10 | >82 |
|  | HRV-10 | ND | 0.114 | >10 | >87 |
|  | HRV-16 | ND | 0.049 | >10 | >204 |
|  | HRV-25 | ND | 0.193 | >10 | >51 |
|  | HRV-39 | ND | 0.168 | >10 | >59 |
| 48 | HRV-14 | 548,000 | 0.003 | >10 | >3333 |
|  | HRV-1A | ND | 0.132 | >10 | >75 |
|  | HRV-2 | ND | 0.048 | >10 | >208 |
|  | HRV-3 | ND | 0.033 | >10 | >333 |
|  | HRV-9 | ND | 0.109 | >10 | >91 |
|  | HRV-10 | ND | 0.085 | >10 | >117 |
|  | HRV-16 | ND | 0.036 | >10 | >277 |
|  | HRV-25 | ND | 0.100 | >10 | >100 |
|  | HRV-39 | ND | 0.044 | >10 | >227 |
|  | HRV-13 | ND | 0.044 | >10 | >227 |
|  | HRV-78 | ND | 0.012 | >10 | >833 |
|  | HRV-11 | ND | 0.003 | >10 | >3333 |
|  | HRV-19 | ND | 0.009 | >10 | >1111 |
|  | HRV-23 | ND | 0.010 | >10 | >1000 |
|  | HRV-Hanks | ND | 0.003 | >10 | >3333 |
|  | CAV21 | ND | 1.120 | >10 | >8 |
|  | CVB2 | ND | 0.162 | >10 | >62 |
|  | CVB3 | ND | 0.187 | >10 | >53 |
|  | CVB5 | ND | 0.178 | >10 | >56 |
|  | ECHO9 | ND | 0.057 | >10 | >175 |
| 49 | HRV-14 | 1,200,000 | 0.004 | >10 | >2500 |
|  | HRV-1A | ND | 0.131 | >10 | >76 |
|  | HRV-2 | ND | 0.083 | >10 | >120 |
|  | HRV-3 | ND | 0.041 | >10 | >243 |
|  | HRV-9 | ND | 0.095 | >10 | >105 |
|  | HRV-10 | ND | 0.076 | >10 | >131 |
|  | HRV-16 | ND | 0.032 | >10 | >312 |
|  | HRV-25 | ND | 0.371 | >10 | >26 |
|  | HRV-39 | ND | 0.145 | >10 | >68 |
| 50 | HRV-14 | 100,000 | 0.068 | >10 | >147 |
|  | HRV-1A | ND | 0.200 | >10 | >50 |
|  | HRV-2 | ND | 0.105 | >10 | >95 |
|  | HRV-3 | ND | 0.117 | >10 | >85 |
|  | HRV-9 | ND | 0.122 | >10 | >81 |
|  | HRV-10 | ND | 0.750 | >10 | >13 |
|  | HRV-16 | ND | 0.185 | >10 | >54 |
|  | HRV-25 | ND | 0.371 | >10 | >26 |
|  | HRV-39 | ND | >1 | >10 | ND |
| 51 | HRV-14 | ND | >10 | >10 | ND |
|  | HRV-9 | ND | >1 | >10 | ND |
|  | HRV-16 | ND | >10 | >10 | ND |
|  | HRV-25 | ND | >10 | >10 | ND |
| 52 | HRV-14 | 36,000 | 0.181 | >10 | >55 |
|  | HRV-9 | ND | 0.473 | >10 | >21 |
|  | HRV-10 | ND | 0.176 | >10 | >56 |
|  | HRV-16 | ND | 0.280 | >10 | >35 |
|  | HRV-25 | ND | 0.109 | >10 | >91 |
|  | HRV-39 | ND | 0.337 | >10 | >29 |
| 53 | HRV-14 | 207,100 | 0.040 | >10 | >250 |
|  | HRV-1A | ND | 0.128 | >10 | >78 |
|  | HRV-2 | ND | 0.078 | >10 | >128 |
|  | HRV-3 | ND | 0.044 | >10 | >227 |
|  | HRV-9 | ND | 0.133 | >10 | >75 |
|  | HRV-10 | ND | 0.037 | >10 | >270 |
|  | HRV-16 | ND | 0.102 | >10 | >98 |
|  | HRV-25 | ND | 0.066 | >10 | >151 |
|  | HRV-39 | ND | 0.125 | >10 | >80 |
|  | HRV-13 | ND | 0.157 | >10 | >63 |
|  | HRV-78 | ND | 0.040 | >10 | >250 |
|  | HRV-11 | ND | 0.020 | >10 | >500 |
|  | HRV-19 | ND | 0.053 | >10 | >188 |
|  | HRV-23 | ND | 0.045 | >10 | >222 |
|  | HRV-Hanks | ND | 0.137 | >10 | >72 |
|  | CAV21 | ND | 0.476 | >10 | >21 |
|  | CVB2 | ND | 0.154 | >10 | >64 |

| Compd.* | Virus Serotype | $k_{obs}/[I]$ $(M^{-1}s^{-1})^b$ | $EC_{50}(\mu M)$ | $CC_{50}(\mu M)$ | TI |
|---|---|---|---|---|---|
| | CVB3 | ND | 0.156 | >10 | >64 |
| | CVB5 | ND | 0.157 | >10 | >63 |
| | ECHO9 | ND | 0.026 | >10 | >384 |
| 54 | HRV-14 | 244,000 | 0.045 | >10 | >222 |
| | HRV-1A | ND | 0.490 | >10 | >20 |
| | HRV-2 | ND | 0.148 | >10 | >67 |
| | HRV-9 | ND | 0.517 | >10 | >19 |
| | HRV-10 | ND | 0.131 | >10 | >76 |
| | HRV-16 | ND | 0.142 | >10 | >70 |
| | HRV-25 | ND | 0.215 | >10 | >46 |
| | HRV-39 | ND | 0.346 | >10 | >28 |
| 55 | HRV-14 | 34,000 | 0.173 | >10 | >57 |
| | HRV-1A | ND | 0.520 | >10 | >19 |
| | HRV-9 | ND | 0.531 | >10 | >18 |
| | HRV-10 | ND | 0.195 | >10 | >51 |
| | HRV-25 | ND | 0.515 | >10 | >19 |
| 56 | HRV-14 | 99,000 | 0.163 | >10 | >61 |
| | HRV-1A | ND | 0.504 | >10 | >19 |
| | HRV-9 | ND | 0.546 | >10 | >18 |
| | HRV-10 | ND | 0.158 | >10 | >63 |
| | HRV-25 | ND | 0.400 | >10 | >25 |
| 57 | HRV-14 | 47,000 | 0.422 | >10 | >23 |
| | HRV-1A | ND | 1.61 | >10 | >6 |
| | HRV-9 | ND | 1.50 | >10 | >6 |
| | HRV-10 | ND | 0.482 | >10 | >20 |
| | HRV-25 | ND | 0.511 | >10 | >1 |
| 58 | HRV-14 | 2,200,000 | 0.003 | >10 | >3333 |
| | HRV-1A | ND | 0.014 | >10 | >714 |
| | HRV-2 | ND | 0.013 | >10 | >769 |
| | HRV-3 | ND | 0.005 | >10 | >2000 |
| | HRV-9 | ND | 0.047 | >10 | >212 |
| | HRV-10 | ND | 0.011 | >10 | >909 |
| | HRV-16 | ND | 0.014 | >10 | >714 |
| | HRV-25 | ND | 0.016 | >10 | >625 |
| | HRV-39 | ND | 0.020 | >10 | >500 |
| | HRV-13 | ND | 0.024 | >10 | >416 |
| | HRV-78 | ND | 0.014 | >10 | >714 |
| | HRV-11 | ND | 0.005 | >10 | >2000 |
| | HRV-19 | ND | 0.017 | >10 | >588 |
| | HRV-23 | ND | 0.008 | >10 | >1250 |
| | HRV-Hanks | ND | 0.021 | >10 | >476 |
| 59 | HRV-14 | 170,000 | 0.020 | >10 | >500 |
| | HRV-1A | ND | 0.084 | >10 | >119 |
| | HRV-2 | ND | 0.049 | >10 | >204 |
| | HRV-3 | ND | 0.033 | >10 | >303 |
| | HRV-9 | ND | 0.070 | >10 | >142 |
| | HRV-10 | ND | 0.058 | >10 | >172 |
| | HRV-16 | ND | 0.105 | >10 | >95 |
| | HRV-25 | ND | 0.042 | >10 | >238 |
| | HRV-39 | ND | 0.122 | >10 | >81 |
| | HRV-13 | ND | 0.012 | >10 | >833 |
| | HRV-78 | ND | 0.073 | >10 | >136 |
| | HRV-11 | ND | 0.014 | >10 | >714 |
| | HRV-19 | ND | 0.044 | >10 | >227 |
| | HRV-23 | ND | 0.037 | >10 | >270 |
| | HRV-Hanks | ND | 0.083 | >10 | >120 |
| | CVB2 | ND | 0.050 | >10 | >200 |
| | CVB5 | ND | 0.040 | >10 | >250 |
| | ECHO9 | ND | 0.040 | >10 | >250 |
| 60 | HRV-14 | 23,000 | 0.173 | >10 | >57 |
| | HRV-1A | ND | 0.558 | >10 | >17 |
| | HRV-9 | ND | 0.516 | >10 | >19 |
| | HRV-10 | ND | 0.368 | >10 | >27 |
| | HRV-25 | ND | 0.251 | >10 | >39 |
| 61 | HRV-14 | 15,000 | ND | ND | ND |
| 62 | HRV-14 | 210,000 | 0.061 | >10 | >163 |
| | HRV-1A | ND | 0.017 | >10 | >588 |
| | HRV-2 | ND | 0.045 | >10 | >222 |
| | HRV-3 | ND | 0.052 | >10 | >192 |
| | HRV-9 | ND | 0.130 | >10 | >76 |
| | HRV-10 | ND | 0.052 | >10 | >192 |
| | HRV-16 | ND | 0.053 | >10 | >188 |
| | HRV-25 | ND | 0.018 | >10 | >555 |
| | HRV-39 | ND | 0.043 | >10 | >232 |
| | HRV-13 | ND | 0.004 | >10 | >2500 |
| | HRV-78 | ND | 0.057 | >10 | >175 |
| | HRV-11 | ND | 0.010 | >10 | >1000 |
| | HRV-19 | ND | 0.021 | >10 | >476 |
| | HRV-23 | ND | 0.032 | >10 | >312 |
| | HRV-Hanks | ND | 0.052 | >10 | >192 |
| | CAV21 | ND | 0.298 | >10 | >33 |
| | CVB2 | ND | 0.016 | >10 | >625 |
| | CVB3 | ND | 0.015 | >10 | >666 |
| | CVB5 | ND | 0.020 | >10 | >500 |
| | ECHO9 | ND | 0.004 | >10 | >2500 |
| 63 | HRV-14 | 300,000 | 0.051 | >10 | >196 |
| | HRV-1A | ND | 0.012 | >10 | >833 |
| | HRV-2 | ND | 0.024 | >10 | >416 |
| | HRV-3 | ND | 0.027 | >10 | >370 |
| | HRV-9 | ND | 0.065 | >10 | >153 |
| | HRV-10 | ND | 0.046 | >10 | >217 |
| | HRV-16 | ND | 0.046 | >10 | >217 |
| | HRV-25 | ND | 0.007 | >10 | >1428 |
| | HRV-39 | ND | 0.035 | >10 | >285 |
| | HRV-13 | ND | 0.045 | >10 | >222 |
| | HRV-78 | ND | 0.034 | >10 | >294 |
| | HRV-11 | ND | 0.017 | >10 | >588 |
| | HRV-19 | ND | 0.014 | >10 | >714 |
| | HRV-23 | ND | 0.037 | >10 | >270 |
| | HRV-Hanks | ND | 0.40 | >10 | >25 |
| | CAV21 | ND | 0.153 | >10 | >65 |
| | CVB2 | ND | 0.012 | >10 | >833 |
| | CVB3 | ND | 0.014 | >10 | >714 |
| | CVB5 | ND | 0.010 | >10 | >1000 |
| | ECHO9 | ND | 0.002 | >10 | >5000 |
| 64 + 65 (2:1) | HRV-14 | 147,500 | 0.572 | >10 | >17 |
| | HRV-3 | ND | 0.455 | >10 | >21 |
| | HRV-9 | ND | 0.550 | >10 | >18 |
| | HRV-10 | ND | 0.458 | >10 | >21 |
| 66 | HRV-14 | 480,000 | 0.155 | >10 | >64 |
| | HRV-3 | ND | 0.056 | >10 | >178 |
| | HRV-9 | ND | 0.196 | >10 | >51 |
| | HRV-16 | ND | 0.011 | >10 | >909 |
| | HRV-39 | ND | 0.022 | >10 | >454 |
| | HRV-13 | ND | 0.057 | >10 | >175 |
| | HRV-78 | ND | 0.015 | >10 | >666 |
| 67 | HRV-14 | 462,500 | 0.057 | >10 | >175 |
| | HRV-3 | ND | 0.019 | >10 | >526 |
| | HRV-9 | ND | 0.162 | >10 | >61 |
| | HRV-16 | ND | 0.033 | >10 | >303 |
| | HRV-39 | ND | 0.038 | >10 | >263 |
| | HRV-13 | ND | 0.162 | >10 | >61 |
| | HRV-78 | ND | 0.048 | >10 | >208 |
| 68 | HRV-14 | 39,500 | ND | ND | ND |
| WIN 51711 | HRV-14 | ND | 0.78 | >60 | >77 |
| WIN 52084 | HRV-14 | ND | 0.07 | >10 | >143 |
| WIN 54954 | HRV-14 | ND | 2.13 | >63 | >30 |
| | CAV-21 | ND | >100 | >100 | NA |
| | CVB3 | ND | >100 | >100 | NA |
| Pirodavir | HRV-14 | ND | 0.03 | >10 | >300 |
| | CAV-21 | ND | >100 | >100 | NA |
| | CVB3 | ND | >100 | >100 | NA |
| | EV-11 | ND | 3.7 | >10 | ta >3 |
| | ENT-70 | ND | 0.06 | >10 | >167 |
| Pleconaril | HRV-14 | ND | 0.01 | >10 | >1000 |
| | CAV-21 | ND | 0.09 | >10 | >107 |
| | CVB3 | ND | >10 | >10 | NA |
| | ECHO-11 | ND | 0.16 | >10 | >62 |

Notes:
[a]HRV human rhinovirus of designated serotype.
[b]3C protease inhibition activity.
[c]CAV-21 = coxsackievirus A21.
[d]ECHO-11 = echovirus 11.
[e]CVB3 = coxsackievirus B3.
[f]ENT-70 = enterovirus 70.
[g]CVB2 = coxsackievirus B2.
[h]CVB5 = coxsackievirus B5.
[i]ECHO-6 = echovirus 6.
[j]ECHO-9 = echovirus 9.
[k]$K_i$ value.

While the invention has been described in terms of preferred embodiments and specific examples, those skilled in the art will recognize through routine experimentation that various changes and modifications can be made without departing from the spirit and scope of the invention. Thus, the invention should be understood as not being limited by the foregoing detailed description, but as being defined by the appended claims and their equivalents.

We claim:

1. A compound having the formula:

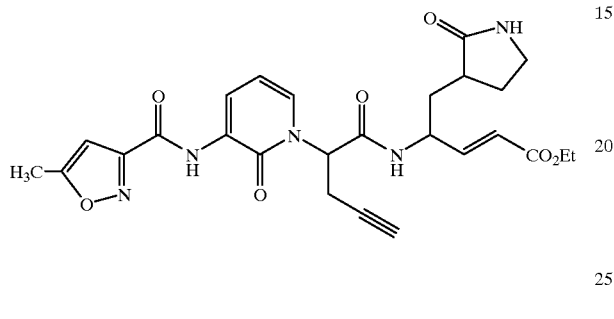

or a prodrug, pharmaceutically acceptable salt, or pharmaceutically acceptable solvate thereof.

2. A stereoisomer of the compound, prodrug, pharmaceutically acceptable salt, or pharmaceutically acceptable solvate according to claim 1, having the formula:

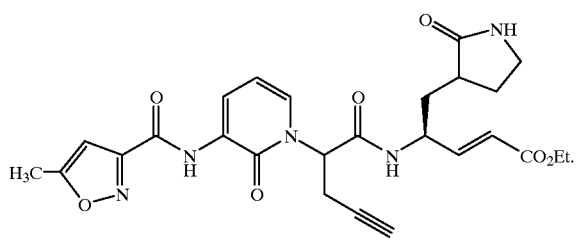

3. A stereoisomer of the compound, prodrug, pharmaceutically acceptable salt, or pharmaceutically acceptable solvate according to claim 1, having the formula:

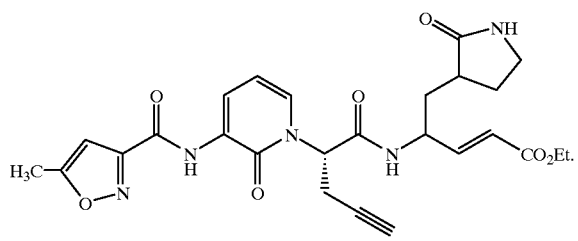

4. A stereoisomer of the compound, prodrug, pharmaceutically acceptable salt, or pharmaceutically acceptable solvate according to claim 1, having the formula:

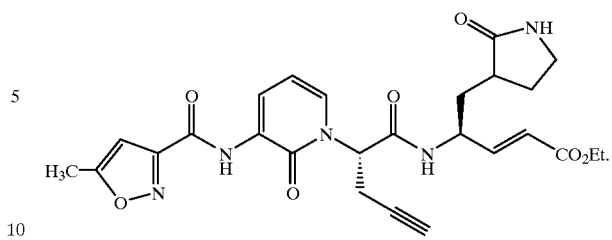

5. A stereoisomer of the compound, prodrug, pharmaceutically acceptable salt, or pharmaceutically acceptable solvate according to claim 1, having the formula:

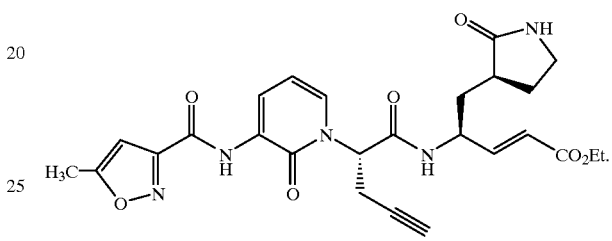

6. A pharmaceutical composition comprising:

a therapeutically effective amount of an antipicornaviral agent selected from the compound, prodrug, pharmaceutically acceptable salt, or pharmaceutically acceptable solvate according to claim 1 or 5; and a pharmaceutically acceptable carrier, diluent, vehicle, or excipient.

7. A method of inhibiting the activity of a picornaviral 3C protease, comprising contacting the picornaviral 3C protease with an effective amount of the compound, prodrug, pharmaceutically acceptable salt, or pharmaceutically acceptable solvate according to claim 1 or 5.

8. The method as defined in claim 7, wherein the picornaviral 3C protease is a rhinoviral protease.

9. A method of treating a mammalian disease condition mediated by picornaviral protease activity, comprising: administering to a mammal in need thereof a therapeutically effective amount of the compound, prodrug, pharmaceutically acceptable salt, or pharmaceutically acceptable solvate as defined in claim 1 or 5.

10. A compound selected from:

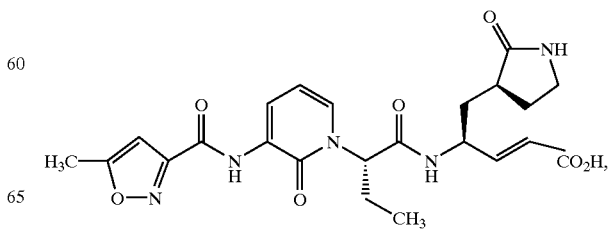

147
-continued
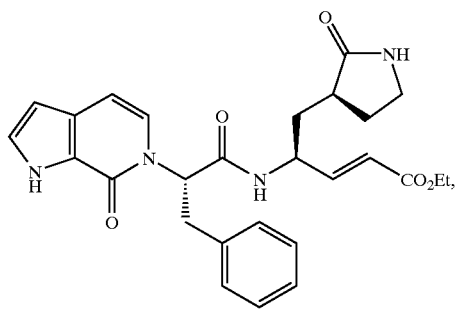
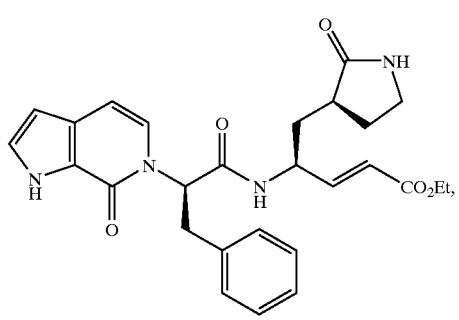
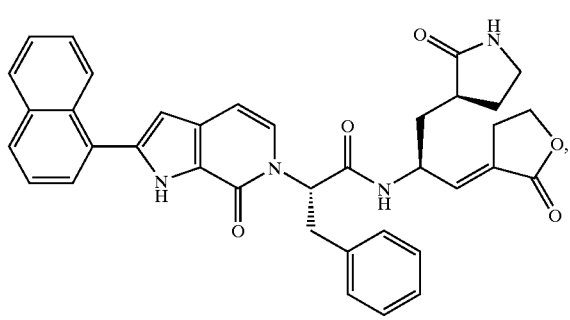
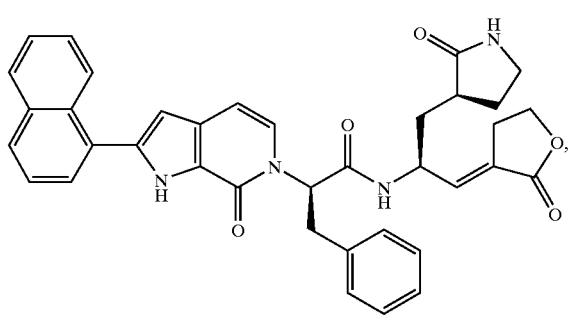
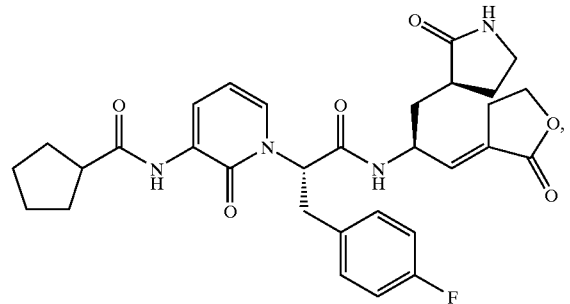
148
-continued
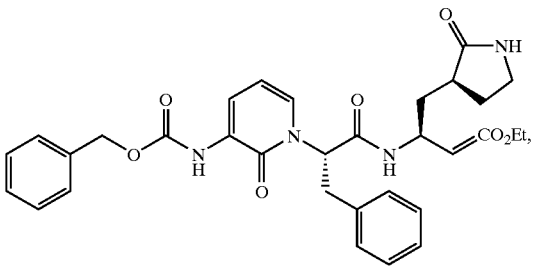
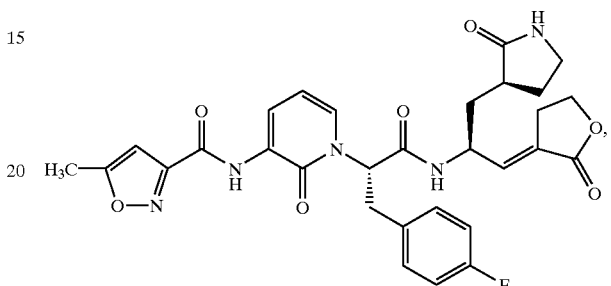
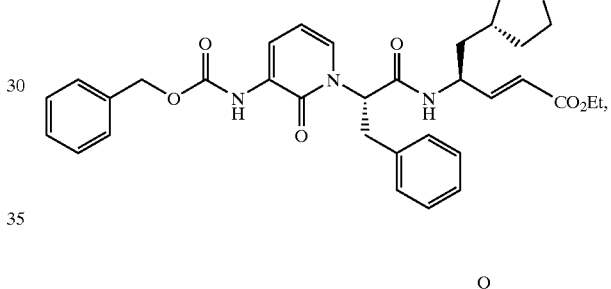
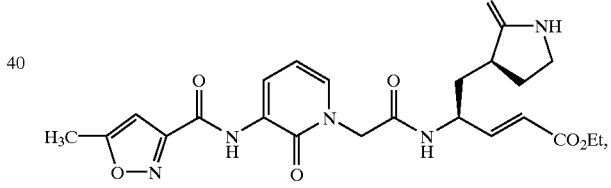
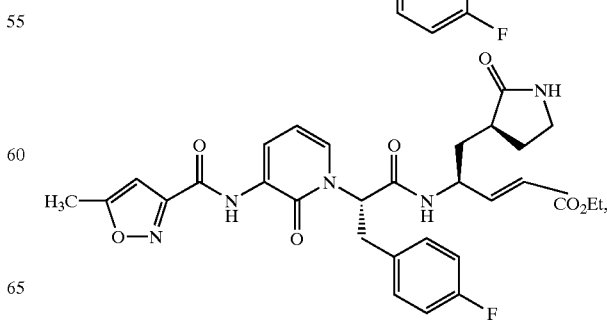

149
-continued
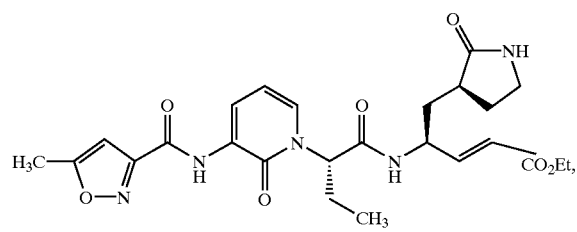
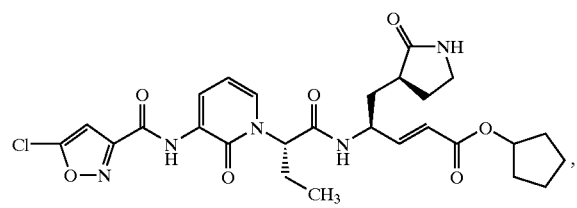
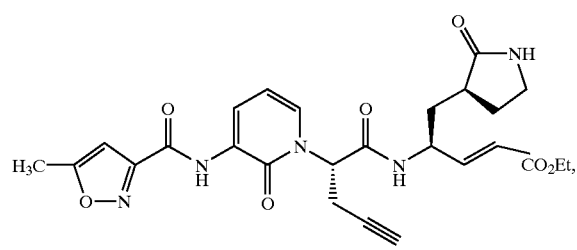
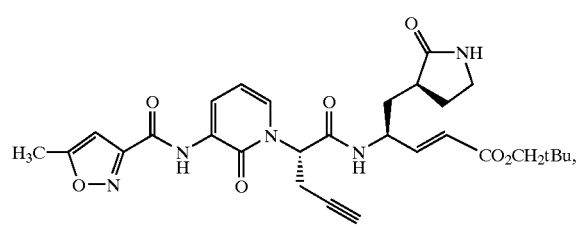
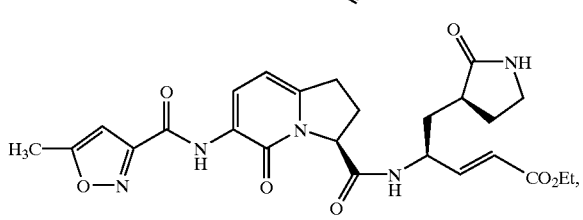
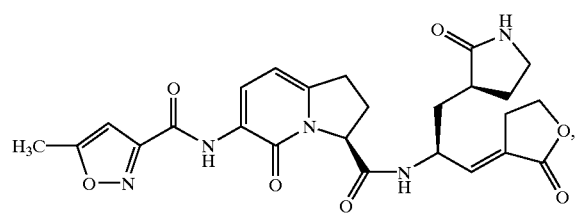
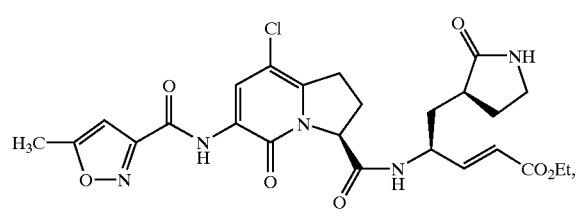
150
-continued
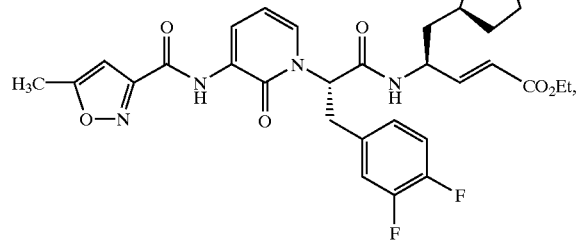
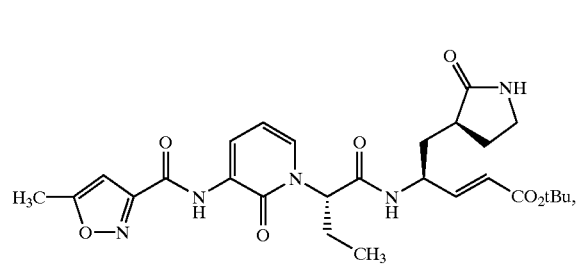
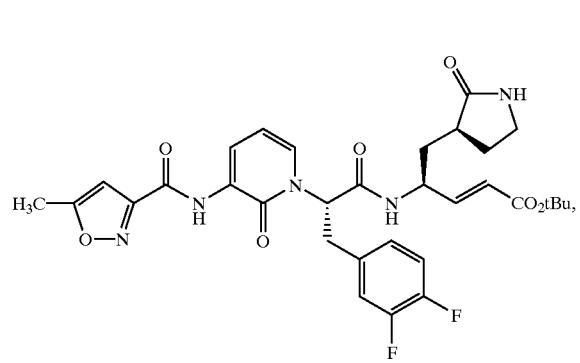
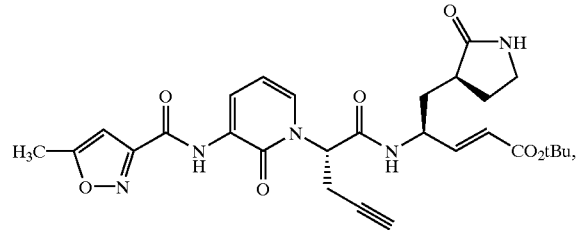
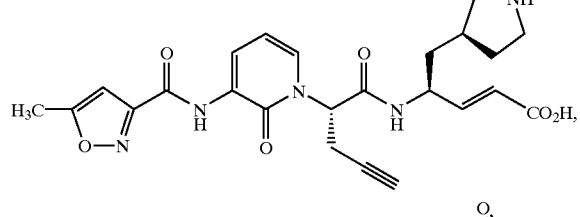
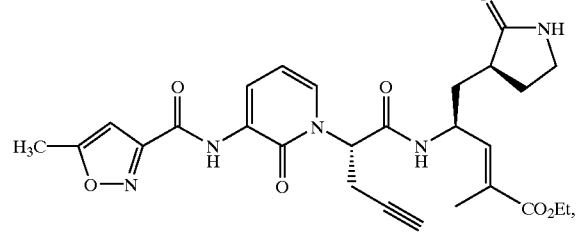

151
-continued
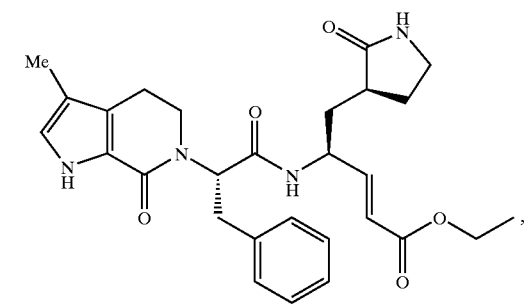
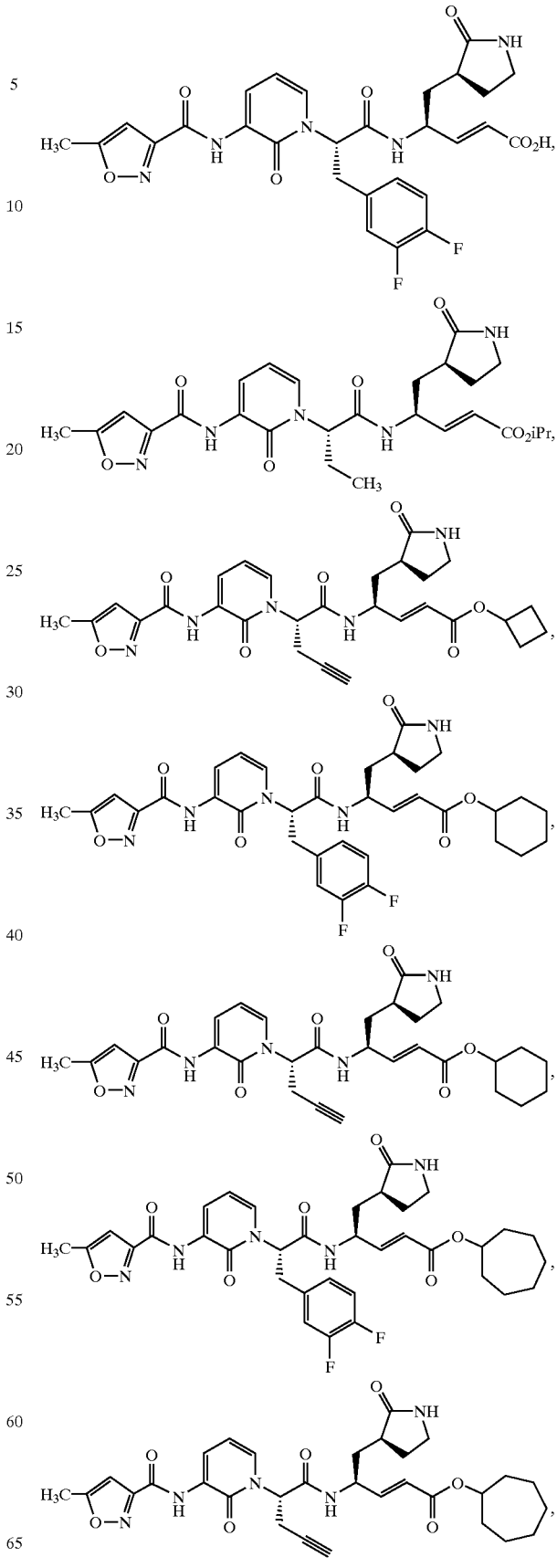

153
-continued
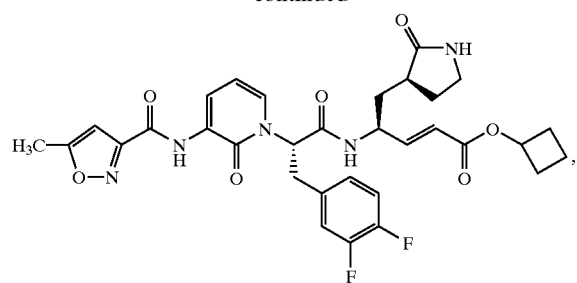
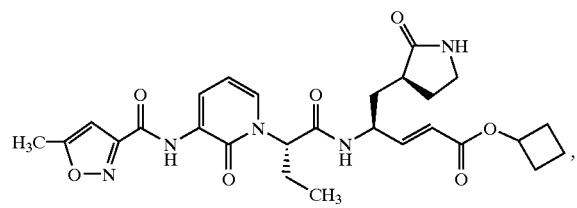
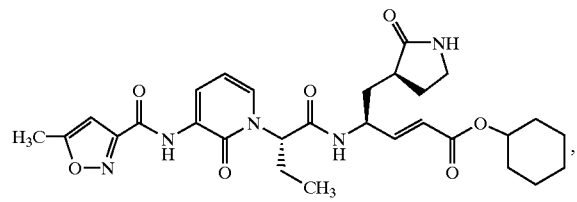
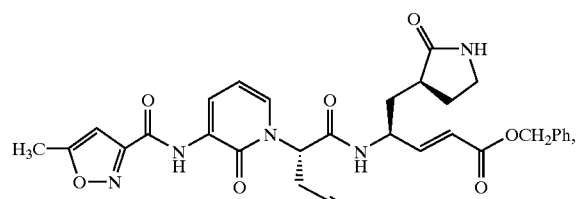
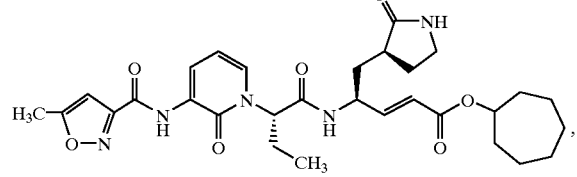
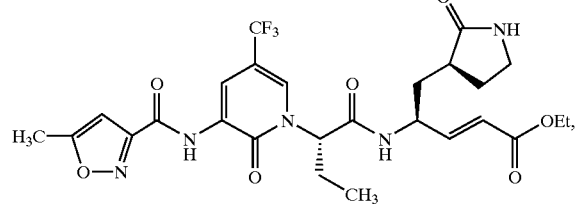
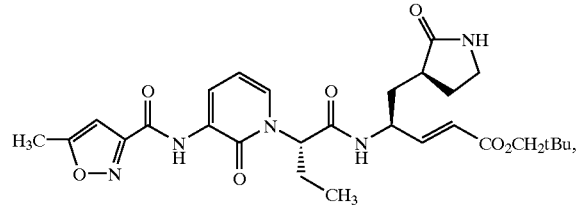
154
-continued
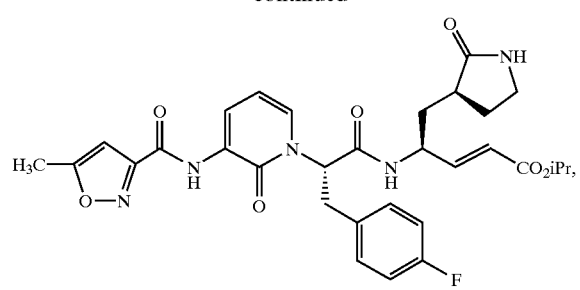
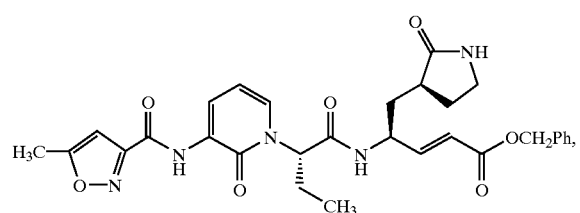
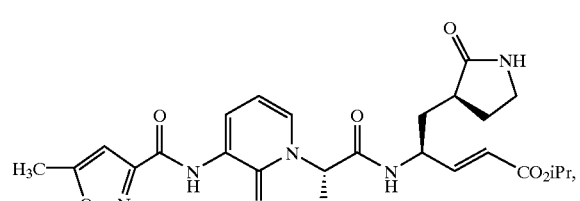
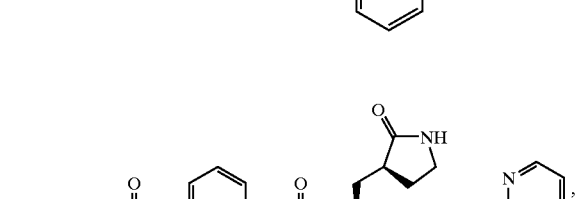
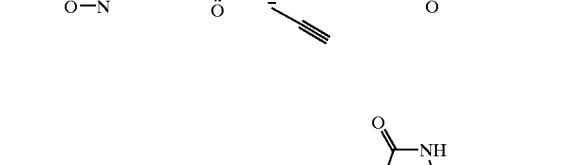
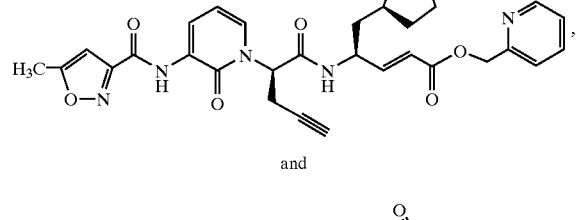
and
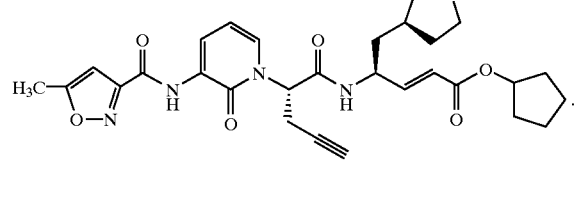

11. A compound selected from claim 10, having the formula:

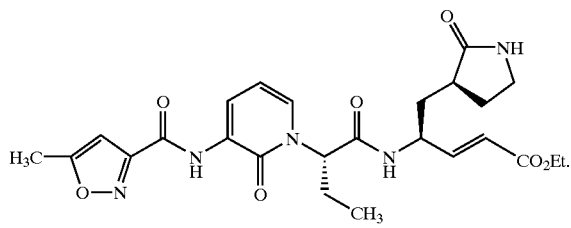

12. A pharmaceutical composition comprising:
   a therapeutically effective amount of the compound of claim 11; and
   a pharmaceutically acceptable carrier, diluent, vehicle or excipient.

13. A method of treating a mammalian disease condition mediated by picornaviral protease activity, comprising: administering to an animal in need thereof a therapeutically effective amount of the compound of claim 11.

14. A compound selected from claim 10, having the formula:

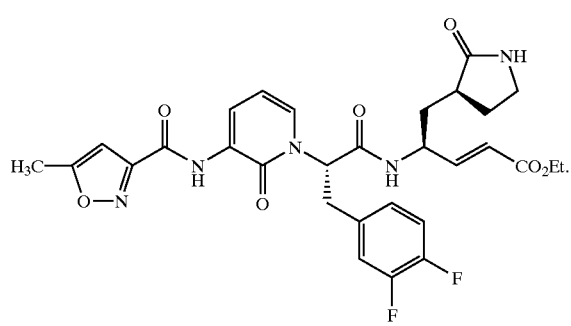

15. A pharmaceutical composition comprising:
   a therapeutically effective amount of the compound of claim 14; and
   a pharmaceutically acceptable carrier, diluent, vehicle or excipient.

16. A method of treating a mammalian disease condition mediated by picornaviral protease activity, comprising: administering to an animal in need thereof a therapeutically effective amount of the compound of claim 14.

17. A compound selected from claim 10, having the formula:

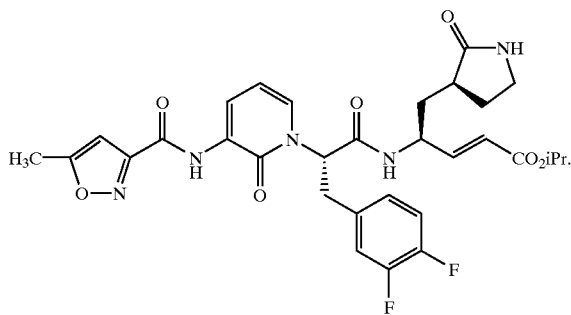

18. A pharmaceutical composition comprising:
   a therapeutically effective amount of the compound of claim 17; and
   a pharmaceutically acceptable carrier, diluent, vehicle or excipient.

19. A method of treating a mammalian disease condition mediated by picornaviral protease activity, comprising: administering to an animal in need thereof a therapeutically effective amount of the compound of claim 17.

20. A compound selected from claim 10 having the formula:

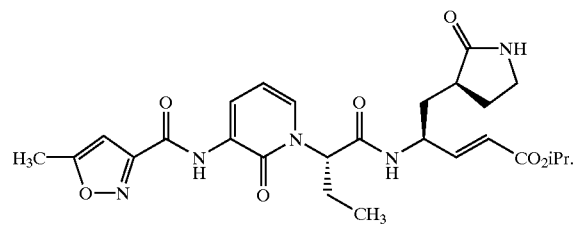

21. A pharmaceutical composition comprising:
   a therapeutically effective amount of the compound of claim 20; and
   a pharmaceutically acceptable carrier, diluent, vehicle or excipient.

22. A method of treating a mammalian disease condition mediated by picornaviral protease activity, comprising: administering to an animal in need thereof a therapeutically effective amount of the compound of claim 20.

23. A compound selected from claim 10 having the formula:

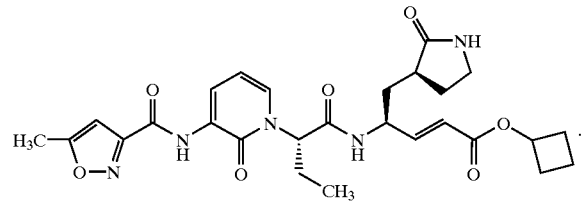

24. A pharmaceutical composition comprising:
   a therapeutically effective amount of the compound of claim 23; and
   a pharmaceutically acceptable carrier, diluent, vehicle or excipient.

25. A method of treating a mammalian disease condition mediated by picornaviral protease activity, comprising: administering to an animal in need thereof a therapeutically effective amount of the compound of claim 23.

26. A compound selected from claim 10 having the formula:

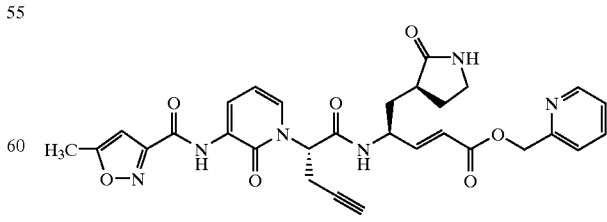

27. A pharmaceutical composition comprising:
   a therapeutically effective amount of the compound of claim 26; and a pharmaceutically acceptable carrier, diluent, vehicle or excipient.

28. A method of treating a mammalian disease condition mediated by picornaviral protease activity, comprising: administering to an animal in need thereof a therapeutically effective amount of the compound of claim 26.

* * * * *